US008084577B2

(12) United States Patent
Herr et al.

(10) Patent No.: US 8,084,577 B2
(45) Date of Patent: Dec. 27, 2011

(54) CRYSTAL OF HUMAN GLYCOPROTEIN VI COLLAGEN BINDING DOMAIN

(75) Inventors: Andrew B. Herr, Cincinnati, OH (US); Katsunori Horii, Hyogo (JP)

(73) Assignee: University of Cincinnati, Cincinnati, OH (US)

( * ) Notice: Subject to any disclaimer, the term of this patent is extended or adjusted under 35 U.S.C. 154(b) by 61 days.

(21) Appl. No.: 12/294,581

(22) PCT Filed: Mar. 28, 2007

(86) PCT No.: PCT/US2007/007900
§ 371 (c)(1),
(2), (4) Date: Aug. 6, 2010

(87) PCT Pub. No.: WO2007/123675
PCT Pub. Date: Nov. 1, 2007

(65) Prior Publication Data
US 2010/0317536 A1    Dec. 16, 2010

Related U.S. Application Data

(60) Provisional application No. 60/786,656, filed on Mar. 28, 2006.

(51) Int. Cl.
*C07K 14/00* (2006.01)
(52) U.S. Cl. ........................................ 530/350
(58) Field of Classification Search .................. None
See application file for complete search history.

(56) References Cited

U.S. PATENT DOCUMENTS
2008/0201123 A1 *  8/2008  Cosgrove ................ 703/11

OTHER PUBLICATIONS

Polayes et al., Focus 16:2-5, 1994.*
Wilson et al., EMBO J. 22:1743-1752, 2003.*
Zheng et al, "Expression of the Platelet Receptor GPVI Confers Signaling via the Fc Receptor gamma-Chain in Response to the Snake Venom Convulxin but not to Collagen," Journal of Biological Chemistry, 276(16): 12999-13006 (Apr. 30, 2001).
International Search Report for PCT/US07/07900, dated Sep. 2, 2008.
Romijn, R. Identification of the Collagen-binding Site of the von Willebrand Factor A3-domain, Journal of Biological Chemistry, 2001, vol. 276, pp. 9985-9991, especially p. 9987, Table 1.
Horii, K., et al. Structural basis for platelet collagen responses by the immune-type receptor glycoprotein VI. Blood, 2006, vol. 108, pp. 936-942.

* cited by examiner

*Primary Examiner* — David J Steadman
(74) *Attorney, Agent, or Firm* — Dinsmore & Shohl LLP

(57) ABSTRACT

A crystal comprising the collagen binding domain of human GPVI is provided and defined by structural atomic coordinates. Employing computer modeling based on the crystal structure, including methods for identifying inhibitors of GPVI collagen binding activity, methods for screening libraries of compounds for potential to bind to the GPVI collagen binding domain, and methods of identifying a compound useful for the treatment of a GPVI-mediated disorder, are also provided.

8 Claims, 5 Drawing Sheets

CRYSTAL OF HUMAN GLYCOPROTEIN VI COLLAGEN BINDING DOMAIN

RELATED APPLICATION

This Application claims priority under 35 U.S.C. §119 to U.S. Provisional Application Ser. No. 60/786,656 filed Mar. 28, 2006.

FIELD OF THE INVENTION

The present invention relates to determining a structural basis for the ability of an immune-type receptor to generate signaling responses to collagen in the context of the pathogenesis of cardiovascular disease, thereby permitting the development of new pharmacological therapies. In particular, the invention provides the crystalline structure of the collagen-binding domain of human GPVI and the characterization of its interaction with a collagen-related peptide.

BACKGROUND OF THE INVENTION

Thrombus formation in the arterial vasculature is a process initiated by the interaction of several platelet receptors with collagen and collagen-associated proteins at the site of vascular injury. Investigators have determined that, initially, platelets are tethered transiently to exposed collagen when the receptor GPIbα interacts with collagen-bound von Willebrand factor (vWF) (Ruggeri et al. 2002). For stable platelet adhesion to occur, the immunoglobulin (Ig)-like receptor GPVI must bind to collagen, triggering the activation of a signaling cascade (Moroi et al. *Thromb Res.* 2004), and Kahn et al. *Semin Thromb Hemost.* 2004). GPVI signaling leads to inside-out activation of the platelet integrins $\alpha_2\beta_1$ and $\alpha_{11b}\beta_3$ (Nieswandt et al. *EMBO J.* 2001, and Chen et al. *Mol Cell Biol.* 2003). Activated $\alpha_2\beta_1$ binds tightly to a specific sequence in collagen to allow firm adhesion of the platelets to the site of injury and activated $\alpha_{11b}\beta_3$ mediates platelet aggregation (Bennett et al. *J Clin Invest.* 2005). In addition, GPVI signaling stimulates secretion of platelet granule contents to activate nearby circulating platelets and propagate thrombus formation. In humans, GPVI deficiency causes a loss of platelet activation in response to collagen, and GPVI polymorphisms have been linked to increased risk of myocardial infarction. Remarkably, loss or inhibition of GPVI prevents arterial thrombus formation in animal models but causes only mildly prolonged bleeding times in mice and humans, suggesting that GPVI could be a prime therapeutic target for prevention of arterial thrombotic diseases such as heart attack and stroke.

The gene for GPVI is found in the leukocyte receptor cluster (LRC) on human chromosome 19. The sequence of the GPVI ectodomain was predicted to form two Ig-like domains comprising the collagen-binding domain followed by a heavily O-glycosylated stalk. Like other LRC receptors, GPVI associates with the FcR γ-chain co-receptor, and signaling is mediated both indirectly through the γ-chain and directly through the GPVI cytoplasmic domain. The quaternary structure of fibrous collagen is required for GPVI activation, although GPVI can also be activated by a synthetic collagen-related peptide (CRP) containing crosslinked strands of the repeating tripeptide $(POG)_n$, where P is proline, O is hydroxyproline, and G is glycine (Farndale et al. *J Thromb Haemost.* 2004). Recently, GPVI has been shown to interact with the ectodomain of GPIbα on the surface of platelets (Arthur et al. *Thromb Haemost.* 2005) and to bind to laminin, a matrix protein exposed at sites of vascular injury (Inoue et al. *Blood.* 2005). Multimeric snake venom proteins such as convulxin can also strongly activate GPVI (Lu et al. *Toxicon.* 2005), suggesting that clustering of GPVI receptors through multiple binding events leads to activation. To better understand the molecular basis for collagen activation of platelets by GPVI, determining the crystal structure of the collagen-binding domain (CBD) of human GPVI and characterizing its interaction with CRP is highly desirable.

SUMMARY OF THE INVENTION

Accordingly, the present inventors determined the crystal structure of the collagen-binding domain of human GPVI and have characterized its interaction with a collagen-related peptide. Like related immune receptors, GPVI contains two immunoglobulin-like domains arranged in a perpendicular orientation. Significantly, GPVI forms a back-to-back dimer in the crystal, an arrangement that could explain data previously obtained from cell-surface GPVI inhibition studies. Docking algorithms identify two parallel grooves on the GPVI dimer surface as collagen-binding sites, and the orientation and spacing of these grooves precisely match the dimensions of an intact collagen fiber. Based on these findings, the present invention provides a structural basis for the ability of an immune-type receptor to generate signaling responses to collagen and for the development of GPVI inhibitors as new therapies for human cardiovascular disease.

One embodiment is directed to a crystal comprising the collagen binding domain of human GPVI having an amino acid sequence substantially similar to the sequence designated SEQ ID NO: 1. The crystal diffracts X-rays for determination of atomic coordinates to provide resolution of better than about 5.0 Angstroms. The crystal has a three-dimensional structure comprising main chain and side chain atoms and atomic coordinates set forth in Table 2. One aspect includes a computer readable storage device or article encoded with computer readable data comprising the atomic coordinates set forth in Table 2.

Another embodiment provides a method of identifying an inhibitor of GPVI collagen binding activity. The method comprises: (1) designing or selecting a potential inhibitor using a three-dimensional structure of the GPVI collagen binding domain comprising main chain and side chain atoms and as defined by atomic coordinates set forth in Table 2, plus or minus a root mean square deviation for the main chain atoms of not greater than 3 Angstroms; (2) synthesizing or obtaining the potential inhibitor; and (3) determining whether the potential inhibitor inhibits the activity of GPVI, wherein designing or selecting a potential inhibitor employs computer modeling.

An embodiment directed to a method of screening a library of compounds for potential to bind to the GPVI collagen binding domain is also provided. The method comprises: using at least some of the atomic coordinates set forth Table 2 to perform computational docking of the library of compounds to the GPVI collagen binding domain.

A further embodiment is directed to a method of identifying a compound useful for the treatment of a GPVI-mediated disorder. The method comprises the steps of: (a) using a three-dimensional structure of the GPVI collagen binding domain as defined by at least some of the atomic coordinates set forth in Table 2, and (b) employing the structure to design, modify, or select a compound that modulates GPVI activity.

DETAILED DESCRIPTION OF THE PREFERRED EMBODIMENTS

The following abbreviations apply throughout this disclosure: GPVI, glycoprotein VI; Ig, immunoglobulin; LRC, leukocyte receptor cluster; CRP, collagen-related peptide; CBD, collagen-binding domain; polyproline type II, PPII. The atomic coordinates set forth in Table 2 have been deposited at the RCSB protein data bank (PDB 2GI7).

Activation of circulating platelets by exposed vessel wall collagen is a primary step in the pathogenesis of heart attack and stroke, and drugs to block platelet activation have successfully reduced cardiovascular morbidity and mortality. Platelet interaction with a damaged vessel wall initiates thrombus formation. Collagen is the primary component of the subendothelial matrix permitting platelet adhesion and activation. In humans and mice, collagen activation of platelets is mediated by glycoprotein VI (GPVI), a receptor that is homologous to immune receptors but bears little sequence similarity to known matrix protein adhesion receptors.

The receptor GPVI is central to the process of collagen-mediated platelet activation and subsequent thrombus formation. The atomic structure of GPVI is therefore of interest in terms of understanding how an immune-type receptor can recognize fibrous collagen. Furthermore, the structure allows the identification of potential regions responsible for interacting with collagen, which may serve as desirable targets for inhibitory drugs. The present invention provides a crystalline structure of the GPVI collagen binding domain, and the crystallographic data presently disclosed reveals that the GPVI CBD adopts a fold previously seen in related immune receptors of the leukocyte receptor cluster, but an 11-residue deletion in the sequence of GPVI relative to other LRC receptors creates a shallow groove on the surface of D1 that forms a putative collagen-binding site, based on docking algorithms and mutagenesis data.

The CBD forms a back-to-back dimer in the crystal in which the two putative collagen-binding grooves are nearly parallel and separated by 55 Angstroms, a configuration that matches the orientation and dimensions of triple helices within fibrous collagen. The dimeric GPVI conformation observed in the crystal is intriguing and may well represent the physiologically relevant form of GPVI on the platelet surface. Previous studies have shown that soluble GPVI-Fc fusions, but not monomeric soluble GPVI, inhibited platelet activation, suggesting that either a dimeric conformation or the higher avidity conferred by the Fc fusion was required to effectively compete with cell-surface GPVI for binding to collagen. This is further supported by surface plasmon resonance assays showing that the GPVI-Fc fusion bound collagen nearly 200-fold more tightly than monomeric GPVI did (Miura et al. *J Biol Chem.* (2002)).

Figure 3:
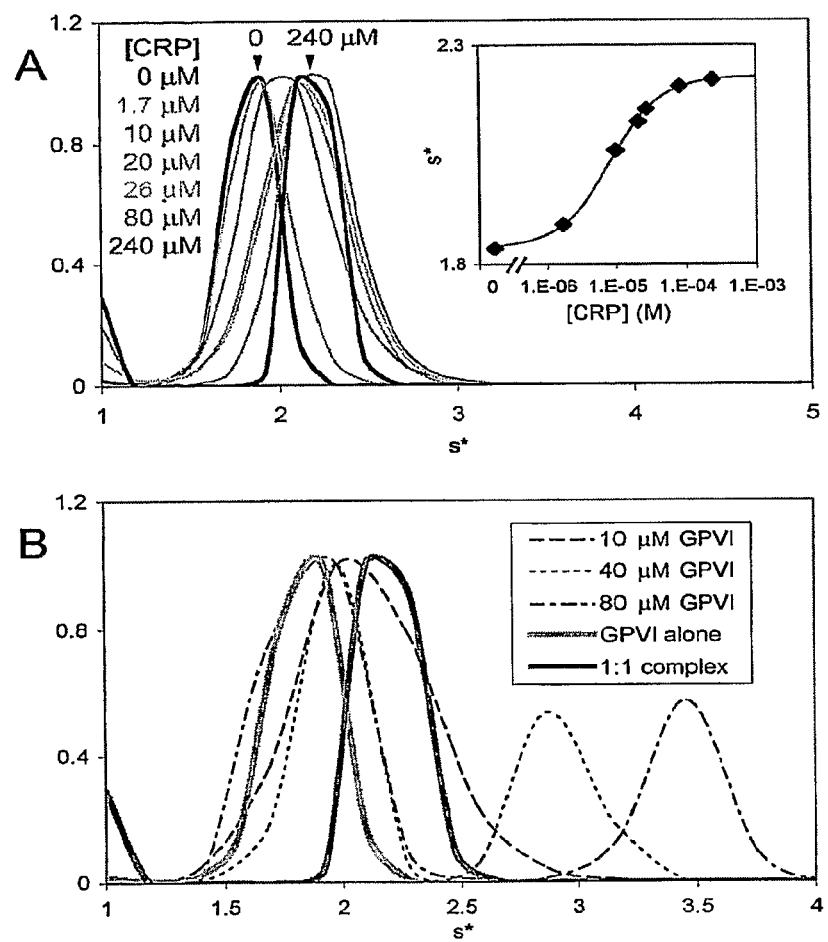
FIG. 3. GPVI-CRP binding affinity and stoichiometry. A. Normalized sedimentation velocity size distribution from a titration of 6.7 μM GPVI with CRP (1.7 to 240 μM). The two extreme cases (unligated GPVI at 0 μM CRP and fully ligated GPVI at 240 μM) are illustrated with thick lines and labeled. All other curves are shown by varying shades of gray. Inset: fitting the $s_w$ values as a function of CRP concentration to a binding isotherm yields a $K_D$ of 5 μM. B. Normalized sedimentation velocity size distributions for 1:1, 4:1, and 8:1 GPVI:CRP mixtures (dashed lines), with the free GPVI and final 1:1 complex from panel A included for comparison (solid thick lines). Note that the mixtures with 4- and 8-fold molar excess of GPVI form complexes larger than a 1:1 complex (thick dark gray line).

The data presented herein suggest that GPVI dimerization is a rather weak interaction that nonetheless could occur on the platelet surface. Analytical ultracentrifugation experiments indicated that the soluble GPVI CBD construct used for crystallization remained monomeric in solution at up to 100 μM (FIG. 3A and data not shown). However, the construct crystallized according to the present invention lacks the stalk region, which could help stabilize a dimeric conformation, as seen for CD94 (Boyington et al. *Protein Expr Purif.* (2000)). Furthermore, the high density of GPVI at the platelet surface favors dimer formation. It is well established that weak protein-protein interactions in solution occur to a significant extent when the components are restricted to two-dimensional diffusion in a lipid bilayer. For example, if the $K_D$ for GPVI dimerization in solution were 420 μM (~8.5 mg/ml), this would correspond to a 2D $K_D$ of 1260 receptors per μm², which is equivalent to the GPVI density on platelets. Thus even very weak dimerization of the CBD in solution would be sufficient to allow significant dimerization of GPVI at the platelet surface. Interestingly, activation of GPVI signaling by collagen is critically dependent on GPVI surface density; RBL cells transfected with GPVI were unresponsive to collagen unless expressed at a surface density approximating that observed on platelets (Zheng et al. *J Biol Chem.* (2001), Chen et al. *J Biol Chem.* (2002)). These studies, like the inhibition studies using GPVI-Fc fusion proteins, suggest that increased avidity of GPVI—or potentially the dimeric GPVI conformation described here—are required for effective interaction with collagen.

These present invention establishes a structural basis for the ability of platelets to recognize and be activated by the vessel wall matrix protein collagen. Platelet activation is a critical step in the pathogenesis of human vascular diseases and new anti-platelet agents have revolutionized the immediate treatment of myocardial infarction. The early role of GPVI in arterial thrombus formation and the relative lack of bleeding associated with human GPVI-deficiency states suggest that new therapies aimed at inhibiting GPVI function might provide an ideal long-term treatment approach to these diseases. A structural understanding of collagen recognition by GPVI provides a foundation for the development of novel therapeutic agents.

One embodiment of the present invention is directed to a crystal comprising the collagen binding domain of human GPVI having an amino acid sequence substantially similar to the sequence designated SEQ ID NO: 1. The crystal diffracts X-rays for determination of atomic coordinates to provide resolution of better than about 5.0 Angstroms. In more specific embodiments, the crystal diffracts to provide resolution of better than about 3 Angstroms or better than about 2.4 Angstroms. According to one embodiment, the GPVI collagen binding domain of the novel crystal is in a dimeric form.

A person of ordinary skill in the art understands that the amino acid sequence of the collagen binding domain designated as SEQ ID NO: 1 may comprise certain deletions, additions, mutations, or other differences and still retain substantive functionality. As used herein, therefore, the term "substantially similar" is intended to encompass sequences that encode polypeptides that retain structure and functionality, regardless of the presence of mutations. An amino acid sequence may, for example, differ from that set forth as SEQ ID NO: 1 by conservative substitutions and still be within the scope contemplated by reference to SEQ ID NO: 1. For purposes of defining the scope of the present invention, "conservative substitution" is used herein to mean amino acid substitutions which are functionally equivalent to the substituted amino acid residue. The substitution may have similar polarity, steric arrangement, or belong to the same class (e.g.: the nonpolar (hydrophobic) amino acids include alanine, glycine, leucine, isoleucine, valine, proline, phenylalanine, tryptophan and methionine; amino acids containing aromatic ring structures are phenylalanine, tryptophan, and tyrosine; the polar neutral amino acids include serine, threonine, cysteine, tyrosine, asparagine, and glutamine; the positively charged (basic) amino acids include arginine, lysine, and histidine; the negatively charged (acidic) amino acids include aspartic acid and glutamic acid) as the substituted residue, and includes substitutions that have an inconsequential effect on the three dimensional structure of GPVI with respect to the use of that structure for the design and/or selection of agents which interact with GPVI, as well as other proteins, peptides, molecules or molecular complexes comprising a substrate binding site, for molecular docking or computer modeling.

In another specific embodiment, the inventive crystal has an orthorhombic space group symmetry $P2_12_12$ and unit cell dimensions of a=114.06 Angstroms b=45.29 Angstroms, and c=75.13 Angstroms, with a unit cell variability of 5% in all dimensions. A unit cell of a crystal is the smallest divisible unit of the crystal that possesses the symmetry and properties of the crystal. It is a group of atoms that have a fixed geometry relative to one another. The unit cell is a "box" arrangement repeated by simple translation to make up the crystal where the atoms of the crystal may be at the corners, edges, on the faces or enclosed in the box giving the crystal its ordered internal arrangement.

According to another specific embodiment, the crystal comprises main chain and side chain atoms having a three dimensional structure defined by structural coordinates, which are the atomic coordinates set forth in Table 2. Structural coordinates, as used herein, refers to the Cartesian coordinates corresponding to an atom's spatial relationship to other atoms in a molecule or molecular complex. The coordinates are derived from mathematical equations related to the experimentally measured intensities obtained upon diffraction of a mono- or polychromatic beam of X-rays by the atoms (scattering centers) of a crystal. The diffraction data may be used to calculate an electron density map of the repeating unit of the crystal. The electron density maps can be used to establish the positions of the individual atoms within the unit cell of the crystal. Alternatively, computer programs such as CNS can be used to establish and refine the positions of individual atoms. Software programs are known in the art which permit graphical representation of a set of structural coordinates in order to obtain a three dimensional representation of a molecule or molecular complex. The structural coordinates of the present invention may be modified from the original sets provided Table 2 by, for example, various algebraic manipulations. Structural coordinates according to the present invention are relative, and are in no way specifically limited by the actual x, y, z coordinates set forth in Table 2. Those of skill in the art understand that a set of structure coordinates determined by X-ray crystallography has a degree of error. For the purposes of the invention, any set of structure coordinates having a root mean square deviation of equivalent protein main chain atoms (N, CA, C and O) of less than about 3.0 Angstroms or, more specifically less than about 2.0 Angstroms, 1.0 Angstroms, and 0.50 Angstroms, when superimposed, using main chain atoms, on the structure coordinates listed herein shall be considered within the scope of the invention.

As used herein, root mean square deviation refers to a statistical term defined as the square root of the arithmetic mean of the squares of the deviations from the mean. It represents deviation or variation from the structural coordinates set forth. The present invention is contemplated as including within its scope all embodiments comprising conservative substitutions of the noted amino acid residues resulting in the same structural coordinates within the stated root mean square deviation. It will be obvious to the skilled practitioner that the numbering of the amino acid residues may be different than that set forth herein, and may contain certain conservative amino acid substitutions that yield the same three dimensional structures as that defined by the Figures. Corresponding amino acids and conservative substitutions in other isoforms or analogues are easily identified by visual inspection of the relevant amino acid sequences or by using commercially available homology software programs (e.g., MODELLER, MSI, San Diego, Calif.) A person of skill in the art will recognize that the atomic coordinates set forth in Table 2, herein, may be encoded on a computer readable storage device or article. The data may be uploaded into a computer device and used to perform computer modeling using various computer drug design software products known in the art.

One method of screening a compound library or database that is useful for certain aspects of the present invention employs the well-known technique of molecular docking. "Docking" refers to placing candidate molecules from a library into the active site of the protein and evaluating how well the compound "fits" to the receptor or enzyme. Docking involves determinations of how best to fit the potential ligands into the active site, and how to rank the "fitting" of the compounds in the library in order to conduct meaningful comparisons. Algorithms and hardware are known in the art which permit docking with a consideration of conformation flexibility. "Virtual screening" is a term understood in the art to refer to computational processes that select molecules likely to have activity against a known biological target. Docking is a form of virtual screening since the molecules identified by a docking scan are compared directly with the requirements of the target.

Numerous computer programs are available and suitable for computer aided drug design, computer modeling, molecular docking, and computationally designing, identifying, selecting and evaluating potential inhibitors via computer programs according to the present invention. Known exemplary computer software designed for computer aided drug design include, but are not limited to, GRID (available from Oxford University, UK), MCSS (available from Molecular Simulations Inc., Burlington, Mass.), AUTODOCK (available from Oxford Molecular Group), FLEX X (available from Tripos, St. Louis. Mo.), DOCK (available from University of California, San Francisco), CAVEAT (available from University of California, Berkeley), HOOK (available from Molecular Simulations Inc., Burlington, Mass.), and 3D database systems such as MACCS-3D (available from MDL Information Systems, San Leandro, Calif.), UNITY (available from Tripos, St. Louis. Mo.), and CATALYST (available from Molecular Simulations Inc., Burlington, Mass.). Any of these software systems may be suitably employed in the presently inventive methods. Software including LUDI (available from Biosym Technologies, San Diego, Calif.), LEGEND (available from Molecular Simulations Inc., Burlington, Mass.), and LEAPFROG (Tripos Associates, St. Louis, Mo.), enable the ground-up synthesis of potential inhibitors rather than a means to screen existing molecules. Compound deformation energy and electrostatic repulsion, may be evaluated using programs such as GAUSSIAN 92, AMBER, QUANTA/CHARMM, AND INSIGHT II/DISCOVER. These computer modeling techniques may be performed on any suitable hardware including for example, workstations available from Silicon Graphics, Sun Microsystems, and the like. Other modeling techniques known in the art may also be employed in accordance with this invention. See for example, N.C. Cohen, Molecular Modeling in Drug Design, Academic Press (1996) (and references therein), and software identified at internet sites including the CMBI Cheminformatics site and the NIH Molecular Modeling site.

Another embodiment of the present invention provides a method of identifying an inhibitor of GPVI collagen binding activity. The method comprises: (1) designing or selecting a potential inhibitor using a three-dimensional structure of the GPVI collagen binding domain comprising main chain and atoms and as defined by atomic coordinates set forth in Table 2, plus or minus a root mean square deviation for the main chain atoms of not greater than 3 Angstroms; (2) synthesizing or obtaining the potential inhibitor; and (3) determining whether the potential inhibitor inhibits the activity of GPVI, wherein designing or selecting a potential inhibitor employs computer modeling. Various assays known in the art, including, but not limited to, protein binding assays, inhibitor assays and cellular-based assays, may be employed to determine whether the potential inhibitor inhibits the activity of GPVI. In some embodiments, determining whether the potential inhibitor inhibits the activity of GPVI comprises contacting the potential inhibitor with GPVI in the presence of a known ligand, determining the ability of the potential inhibitor to compete with the known GPVI collagen binding domain ligand and screening the potential inhibitor of GPVI in an assay for efficacy in inhibiting GPVI. Exemplary known ligands include collagen, CRP and convulxin.

In a further method embodiment, the atomic coordinates set forth in Table 2 may be used to design or select binding agents to interact with the GPVI collagen binding domain, employing, for example, any of the software products designed for computer aided drug design set forth above. Other embodiments are directed to methods of screening a library of compounds for potential to bind to the GPVI collagen binding domain. These methods comprise using at least some of the atomic coordinates set forth Table 2 to perform computational docking of the library of compounds to the GPVI collagen binding domain. Still other embodiments are directed to methods of identifying a compound useful for the treatment of a GPVI-mediated disorder. The methods comprise: (a) using a three-dimensional structure of the GPVI collagen binding domain as defined by at least some of the atomic coordinates set forth in Table 2, and (b) employing the structure to design, modify, or select a compound that modulates GPVI activity. GPVI modulators derived according to the present inventive methods may be useful in the prevention or treatment of vascular disorders, including, but not limited to thrombotic disorders.

Figure 4:
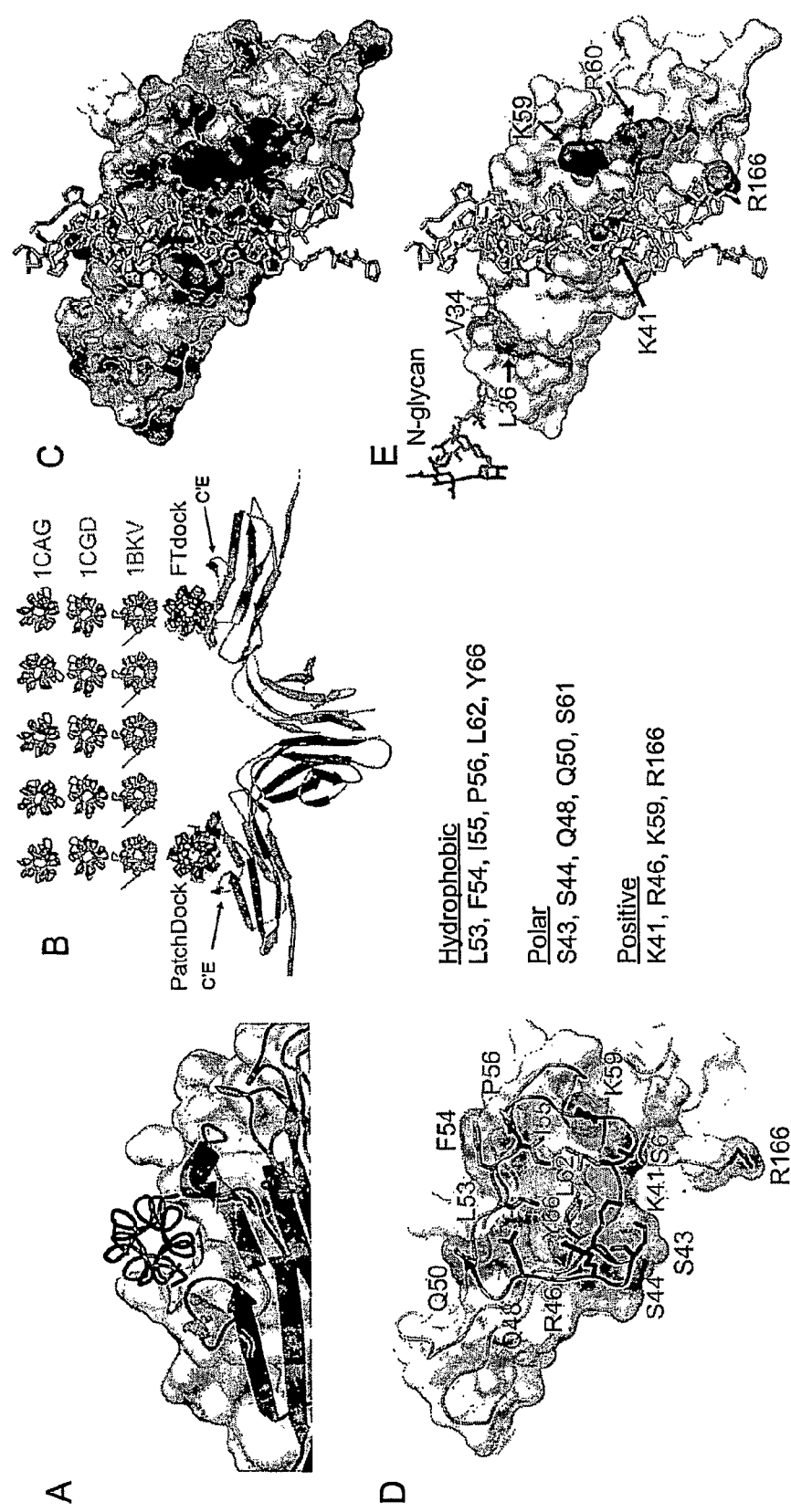
FIG. 4. Computational docking of CRP onto GPVI. A. Side view of the surface of D1, illustrating the predicted binding of CRP within the binding groove. Two distinct docking algorithms placed CRP within the groove in D1 adjacent to the C'E region. B. Model of the GPVI-CRP complex predicted by the Patchdock and FTDock algorithms. The docking prediction for CRP determined by each program is shown with the C'E loop labeled for reference. Three crystal structures of CRP variants with their PDB IDs are illustrated above the predicted GPVI-CRP complex to show that the spacing and orientation of the docked CRP triple helices match the conserved ~14 Angstrom spacing observed in the CRP crystal structures, which itself is similar to that observed in intact collagen fibers. Of note, although collagen fibers have circular cross-sections, within a blood vessel the average fiber diameter is very large (~300-400 Angstroms) relative to the spacing between individual collagen triple helices (~14 Angstroms), such that the surface recognized by GPVI would be approximately planar. C. Electrostatic potential of GPVI D1 mapped onto its surface, with the Patchdock CRP model superimposed. D. Stereo view of the residues in D1 that contact CRP in one or both of the docked models. The GPVI side chains contacting CRP are listed in the adjacent table according to their chemical properties of being hydrophobic, polar, and positively charged. E. Residues implicated in collagen or CRP binding are shown on the GPVI D1 surface after adding a modeled N-glycan. Darkly shaded residues (V34, K41, K59, and N-glycan) have been implicated in both collagen and CRP binding (O'Connor et al. J Thromb Haemost. 2005, Smethurst et al. Blood., 2004, Lecut et al. J Biol Chem., 2004, Kunicki et al. Blood. 2005), and moderately shaded residues (L36, R60, R166) have been implicated in collagen binding only (O'Connor et al. J Thromb Haemost. 2005, and Lecut et al. J Biol Chem. 2004).

Two specific agonists in addition to collagen are typically used to study GPVI function: collagen-related peptide (CRP), which is a class of triple helical synthetic peptides based on a repeated Glycine-Proline-Hydroxyproline (GPO) motif; and convulxin, a multimeric lectin-like toxin derived from rattlesnake venom. The GPVI structural data disclosed herein provides a framework for understanding the interaction between GPVI and collagen or CRP by allowing accurate mapping of mutagenesis results onto the surface of the GPVI dimer. The residues implicated in collagen or CRP binding fall into two clusters: the primary region includes basic residues on the surface of D1 including K41, K59, R60, and R166 (FIG. 4E). Mutation of K41 or K59 affects binding to both collagen and CRP; a K41A mutation increases the affinity of GPVI for both ligands, whereas mutation of residue K59 to the mouse equivalent (K59E) decreases affinity for both collagen and CRP. The R60A and R166A mutations reduce collagen affinity but have no effect on CRP binding. A second cluster of residues implicated in collagen or CRP binding is found at the distal end of D1; these residues include L36, implicated in collagen (but not CRP) binding, and both V34 and the N-glycan attached to N72, both of which are involved in collagen and CRP binding (Lecut et al. *J Biol Chem*. (2004), Kunicki et al. *Blood*. (2005)). The GPVI structure shows that the side chain of V34 is buried and its mutation is likely to alter the conformation of the BC loop in D1, which includes L36 and is immediately adjacent to N72.

In the presently disclosed computational model of CRP docked to GPVI, the CRP binding groove is located within the primary cluster of basic residues (K41, K59, R60, and R166). K41 is centrally positioned within the floor of the putative binding groove and contacts CRP directly. Furthermore, the docked CRP interacts with the side chain of R166 and is within reach of the K59 and R60 side chains. The docking predictions were based strictly on geometric and energetic criteria and did not take into account any mutagenesis data. Therefore, the correlation between the docking prediction and mutagenesis results suggests that the predicted CRP binding mode is a reasonable approximation of the physiological interaction of GPVI with CRP and collagen.

Figure 5:
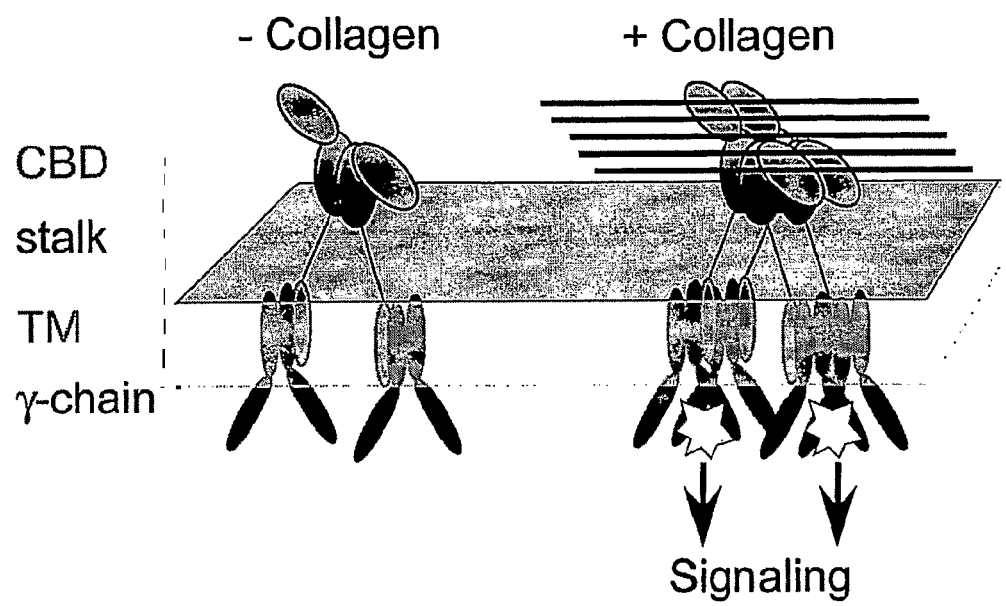
FIG. 5. Implications for GPVI signaling. Model for signaling by receptor clustering, in which clustering triggers a signaling cascade via the FcR γ-chain co-receptor. This would resemble TCR signaling via the related ζ-chain co-receptor, which occurs upon clustering at least two TCR complexes in an orientation-independent manner, with the proximity of the TCR complexes correlating to the strength of the signal (Cochran et al. J Biol Chem. 2001). An individual GPVI dimer would not necessarily allow the γ-chains to approach closely enough to trigger signaling, due to the long GPVI stalk region. However, multiple GPVI molecules bound to a collagen fiber would bring several γ-chains into close proximity, triggering activation. Although GPVI in the model is illustrated as a dimer, the proposed mechanism of GPVI clustering by fibrous collagen would also apply if GPVI were monomeric at the platelet surface.

The cluster of residues including V34, L36 and the N-glycan at N72 may form a secondary binding site for CRP or collagen triple helices. Residue L36 is located on the surface of D1 approximately 14 Angstroms from the putative binding groove, and these secondary residues are positioned such that they could interact with adjacent triple helices within an intact collagen fibril. The mutagenesis results are therefore consistent with the mode of interaction between GPVI and a collagen fibril illustrated in FIG. 4B, in which a GPVI dimer binds simultaneously to several triple helices within the collagen fibril. This binding mode also suggests a model for the initiation of signal transduction triggered by receptor clustering that accompanies collagen binding (FIG. 5).

According to more specific embodiments of the present invention, the GPVI collagen binding domain comprises at least some or all of residues K41, S43, S44, R46, Q48, Q50, L53, F54, I55, P56, K59, S61, L62, Y66, and R166. Molecular docking-based modeling or computer aided drug design may be performed using the structural atomic coordinates of all or some of these specific residues. One may, for example, computationally dock a ligand to the binding site defined specifically by these residues, keep that binding site computationally locked, and delete any portion of the polypeptide remaining outside the locked coordinates. The computationally locked portion is then released and a fusion protein may be designed by fusing the released polypeptide to any other suitable polypeptide. Fusion proteins formed in this manner may be useful as GPVI modulators. According to this embodiment, the atomic coordinates of the subset of residues selected to define the binding site may vary by a root mean square deviation of not more than about 3.0 Angstroms, or, in more specific embodiments of not more than about 2.0, 1.0 and 0.5 Angstroms, and still be considered within the scope of the coordinates, regardless of the root mean square deviation of the main chain atoms of the entire fusion protein.

According to another specific embodiment, the dimeric form of the collagen binding domain is used to select or design agents via computer modeling or computer aided drug design according to the present invention, whereby two ligands for the binding site are designed or selected, wherein the two ligands may be the same or different, and are connected by a crosslinker of appropriate length to permit bivalent binding to the dimeric form of GPVI observed in the crystal.

The following Examples are provided to illustrate specific embodiments and aspects of the present invention and should not be construed as limiting the scope of the invention as defined by the claims.

EXAMPLES

1. Cloning, Expression, Refolding and Purification of GPVI

Human GPVI cDNA was prepared as described in Zheng et al. *J. Biol Chem*. (2001). The DNA sequence encoding the CBD (residues Q1-T183) was amplified by PCR using CACC GAAAACCTGTATTTTCAGGGCCAGAGTGGACCGCT CCCC (SEQ ID NO: 3) (the tobacco etch virus protease (TEVp) cleavage site is underlined) and CTATGTGACCA-CAAGCTCCAGCGGGTCGCTGGG (SEQ ID NO: 4) as the sense and antisense primers, respectively. The PCR product was inserted into the pDEST17 vector encoding an N-terminal (His)$_6$-tag using the GATEWAY system (Invitrogen), and transformed into *Escherichia coli* strain Tuner(DE3) (Novagen). Cultures were grown to an $A_{600}$ of 0.8 and induced for 4 hours at 37° C. with 0.1 mM isopropyl β-D-thiogalactopyranoside. The recombinant GPVI CBD was solubilized from inclusion bodies using denaturant buffer (6 M guanidine hydrochloride, 20 mM $NaH_2PO_4$, 10 mM imidazole, 1 mM dithiothreitol, pH 7.3) and purified under denaturing conditions by immobilized-metal affinity chromatography (IMAC) using Ni-NTA agarose (QIAGEN).

The denatured and reduced protein was refolded by rapid dilution with vigorous stirring in refolding buffer (1 M L-arginine, 2 mM EDTA, 5 mM reduced L-glutathione, 0.5 mM oxidized L-glutathione and 100 mM Tris-HCl, pH 8.8) at 4° C. for 16 hours. The refolded protein was dialyzed against TEVp cleavage buffer (100 mM NaCl, 2 mM $CaCl_2$ and 20 mM Tris-HCl, pH 8.0), cleaved overnight at room temperature, and further purified by IMAC and size exclusion chromatography using a HiLoad™ 26/60 Superdex 75 column (Amersham Biosciences) equilibrated with TBS buffer (150 mM NaCl, 20 mM Tris-HCl, pH 7.4). The recombinant GPVI was judged to be >90% pure by SDS-PAGE with a yield of 0.5-1.0 mg per 1 L of LB. CRP used for binding experiments was purchased from Peptide International (Louisville, Ky.) as a non-crosslinked $(POG)_{10}$ polypeptide.

2. Crystallization and Structure Determination

Purified GPVI was crystallized by mixing 0.4 μl GPVI (5 mg/ml in TBS) with 0.4 μl of crystallization buffer (1 M ammonium sulfate and 5% MPD) in sitting drop crystallization plates. Small needle-shaped crystals appeared in 3 days and were improved by micro- and macro-seeding techniques. For seeding, 2 μl of protein solution (10 mg/ml in TBS) was mixed with 2 μl of crystallization buffer (0.9 M ammonium sulfate, 8% MPD and 20% glycerol). After seeding, diamond-shaped plate-like crystals grew to a maximum size of ~150× 150×20 μm³ in one month. The crystals belong to the space group $P2_12_12$ with two GPVI molecules in the asymmetric unit. Data were collected at 110 K with an R-AXIS IV++ image-plate area detector (Rigaku MSC) using CuKα radiation generated by a rotating anode generator (Micromax-007). A complete data set was collected to 2.4 Angstrom resolution from 176 images (0.5° oscillation with 5 minutes exposure time), processed by Mosflm, and scaled by SCALA from the CCP4 suite (Collaborative Computational Project No. 4. The CCP4 suite: programs for protein crystallography. *Acta Crystallogr D*. (1994)).

The structure was solved by molecular replacement using Phaser1.3.1 (McCoy et al. *Acta Crystallogr D Biol Crystallogr*. (2005)). The search model used was LIR-1 (pdb 1G0X (Chapman et al. *Immunity* (2000)) after truncating loops, which yielded two clear solutions. All crystallographic refinements were performed with CNS (Brunger et al. AT, *Acta Crystallogr D Biol Crystallogr* (1998)) using the maximum-likelihood target function. Rigid body refinement was followed by several cycles of torsion-angle simulated annealing, positional refinement, individual B-factor refinement, and manual model rebuilding. $2F_o-F_c$ and $F_o-F_c$ electron density maps were used to manually rebuild the model with XtalView (McRee et al. *J Struct Biol*. (1999)). When the value of the R-factor dropped to 24%, solvent molecules and ions were gradually included. The electron density was well defined for the overall structure except for two residues of the N-terminus for molecule A and residues 99-107 and 130-137 for molecule B. The final model contained 182 and 167 residues for molecules A and B, respectively. Criteria for inclusion of solvent and ion molecules included height and shape of the electron density peaks and appropriate coordination by GPVI residues. Data collection and refinement statistics are reported in Table 1.

3. Analytical Ultracentrifugation

Sedimentation velocity and equilibrium experiments were carried out at 20° C. in a Beckman XL-I ProteomeLab analytical ultracentrifuge using absorbance optics, as described in (Herr et al. *J Mol. Biol*. (2003)). For sedimentation velocity experiments, samples of GPVI or mixtures with CRP were spun at 48,000 rpm. Sedimentation coefficients were determined using the program SEDFIT (Schuck et al. *Biophys J*. (2000)). For sedimentation equilibrium experiments, mixtures of 10 μM CRP and 10, 40, and 80 μM GPVI were spun at speeds of 16,000, 19,000, 29,000, 35,000, and 48,000 rpm. Data files were trimmed and analyzed by global fitting using the programs WinREEDIT and WinNONLIN (Jeff Lary, University of Connecticut, Storrs, Conn.). Values of $s_w$, the weight-average sedimentation coefficient determined by SEDFIT, were fitted to a single-site binding isotherm using SEDPHAT (Schuck et al. *Anal Biochem*. (2003)).

4. Docking of CRP to GPVI

The Patchdock server (Schneidman-Duhovny et al. *Proteins* (2003)) was used to predict the binding orientation of CRP on GPVI. A truncated CRP with the sequence $(POG)_5$ was created from the crystal structure of $(POG)_4POA(POG)_5$ (pdb 1CAG (Bella et al. *Science* (1994)) and used as the ligand, with GPVI D1 as the receptor. Six of the top 10 solutions showed CRP bound in a putative binding groove adjacent to the C'E loop and neighboring several residues implicated in collagen and CRP binding (K41, K59, R60, and R166 (O'Connor et al. *J Thromb Haemost*. (2005), Smethurst et al. *Blood*. (2004)). Three of these solutions bound in one orientation (i.e., with the N-termini of CRP closer to GPVI residue F54), and the other three solutions bound in the opposite orientation (i.e., with the C-termini closer to F54), consistent with the pseudo-two-fold symmetry within CRP.

The FTDock program from the 3D-Dock software package was also used to dock CRP to GPVI (Katchalski-Katzir et al. *Proc Natl Acad Sci USA*. (1992)). Because FTDock does not recognize hydroxyproline, a modified CRP with the sequence $(PPG)_5$ was created from the crystal structure of $(PPG)_{10}$, (pdb 1K6F (Berisio et al. *Protein Sci*. (2002)). The grid-based shape complementarity search was performed using 148 grid units in each dimension (grid point spacing: 0.7 Angstrom). The docking solutions were sorted by surface complementarity and the top solution was also found in the same surface groove in D1 identified by Patchdock. Furthermore, filtering the solutions by proximity to K59 reveals a second solution within the binding groove, but in the opposite orientation.

5. Calculation of Estimated 2D $K_D$ at Platelet Surface

Correlating the reported GPVI receptor density on the platelet surface (Chen et al. *J Biol Chem*. (2002)) with an estimated $K_D$ for dimerization of soluble GPVI CBD was carried out according the approach of Dustin et al. (Dustin et al. *J Cell Biol*. (1996), Dustin et al. *J Biol Chem*. (1997)). The interaction of two membrane-embedded receptors is estimated to occur with a loss of 3 degrees of freedom (compared to their interaction as soluble receptors), due to their restriction to 2-dimensional diffusion within the plane of a lipid bilayer (Bromley et al. *Nat Immunol*. (2001)). The 3D $K_D$ was converted into $\Delta G$ and corrected by a factor of $-1.5RT$ to account for the 2D restriction of the receptors. The corrected 3D $K_D^*$ was then converted from molar units to receptors per $\mu m^3$. Finally, the 2D $K_D$ was estimated based on the equation 2D $K_D = \sigma$ (3D $K_D^*$), where σ is the confinement region corresponding to the distance the receptor extends outward from the membrane. For GPVI, the confinement region was calculated to be 22 nm by adding the height of the CBD (52 Angstroms) and the estimated height of the 65-residue O-glycosylated stalk (169 Angstroms, based on the reported dimensions of 2.6 Angstroms per residue for the O-glycosylated stalk of CD8 (Merry et al. *J Biol Chem*. (2003)).

6. Other Computational Methods

Generation of collagen fiber models was carried out by applying crystallographic symmetry to the CRP structures (pdb 1CAG, 1CGD, and 1BKV) using the program O (Jones et al. *Acta Crystallogr A*. (1991)). Analysis of buried surface areas and interdomain angles were calculated using Areaimol from the CCP4 suite (Collaborative Computational Project No. 4. The CCP4 suite: programs for protein crystallography. *Acta Crystallogr D*. (1994), and Dom_Angle, respectively (Su et al. *Science*. (1998)). Domain boundaries were defined as residues 0-89 for D1 and residues 90-183 for D2. Figures were generated with PyMOL (DeLano et al. *DeLano Scientific* (2002), Molscript (Kraulis et al. *J Appl Crystallogr*. (1991), and Raster3D (Merritt et al. *Acta Cryst D*. (1994)).

7. Crystal Structure of the Collagen-Binding Domain of GPVI

Figure 1:
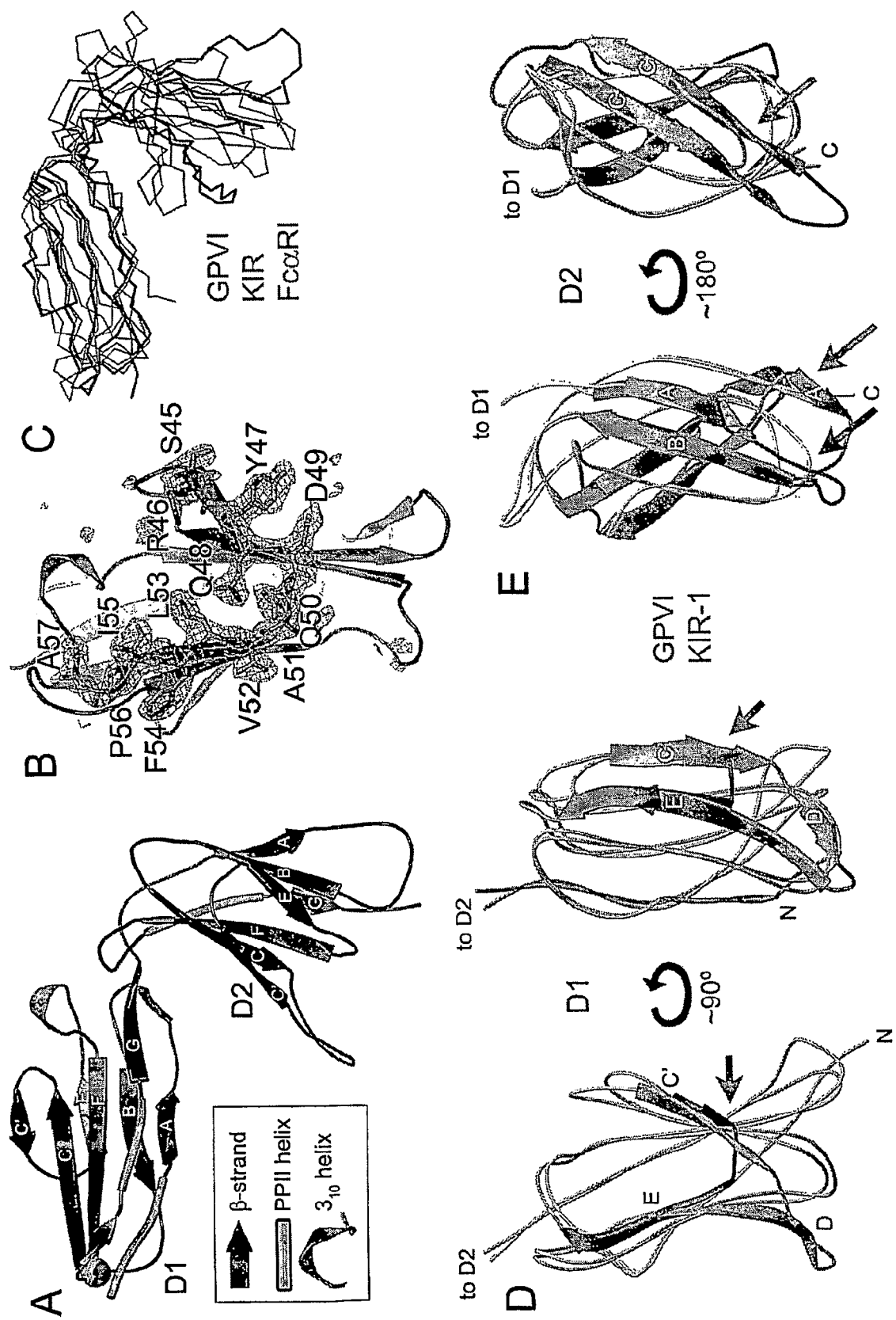
FIG. 1. Structure of the GPVI CBD. A. Ribbon diagram of GPVI. The N-terminal domain is labeled D1, and the C-terminal domain is D2. The predicted N-glycosylation site at N72 is shown by a ball. B. Simulated annealing electron density omit map showing the C'E region of the CBD that differs from related immune receptors, with a ball-and-stick model of the deleted region superimposed. C. Superposition of GPVI (thick lines), p58 KIR (Fan et al. Nature 1997), and FcαRI (Herr et al. Nature 2003) (thin lines). The orientation is similar to that shown in panel A. D. Superposition of D1 of GPVI and p58 KIR (Fan et al. Nature 1997) shown in two orientations, highlighting the unusual C'E region in GPVI (arrows). E. Superposition of D2 of GPVI (darker gray) and p58 KIR (Fan et al. Nature 1997) (lighter gray) in two orientations, highlighting the lack of an A' strand and the extended CC' hairpin in GPVI (note arrows).

The crystal structure of the GPVI CBD was solved by molecular replacement using data to a resolution of 2.4 Angstroms. The CBD is composed of two Ig-like domains oriented 90° apart, similar to other LRC receptors such as FcαRI and the leukocyte Ig-like (LILR or LIR) and killer-cell Ig-like (KIR) receptor families (FIG. 1A, C). Both the N-terminal and C-terminal domains (D1 and D2, respectively) of GPVI most closely resemble the domains of p58 KIR (Fan et al. *Nature* (1997)), with rms deviations of 1.7 and 1.6 Angstroms over 83 and 82 residues, respectively. There were two GPVI molecules per asymmetric unit, with D1-D2 interdomain angles ranging from 90-92° and with D1-D2 interfaces that buried 855-877 square Angstroms. These interdomain angles and interface areas are comparable to those observed for FcαRI, LIR-1, and p58 KIR, although the interface area for GPVI is somewhat less extensive. As in many LRC receptors, a conserved cis proline in D1 (P14) introduces a bend after the first β strand, creating a distinct A' strand that forms hydrogen bonds with the G strand. As a result, the Ig fold of D1 is I-type, formed by two β sheets composed of the ABE and A 'GFCC' strands. D1 also contains a short $3_{10}$ helix and two stretches of polyproline type II (PPII) helix. Within D1, the most significant differences between GPVI and other LRC receptors occur in the C' and E strands and intervening C'E loop, which adopt unusual conformations due to an 11-residue deletion in GPVI (FIG. 1B, D). This deletion creates a shallow, primarily hydrophobic groove on the surface of D1 bordered by charged and polar residues including K41, K59, R60, and R166, which have been implicated in collagen or CRP binding. There is a single predicted N-glycosylation site at residue N72 in the FG loop of D1; the N-glycan would be expected to extend outward from the end of D1, as seen for FcαRI (Herr et al. *Nature* (2003)).

GPVI D2, like D1, contains the conserved proline (P100) at the end of the A strand, but in D2 it adopts the trans rather than cis conformation. As a result, there is no sharp bend in the protein backbone, the A' strand does not form, and the architecture of the subsequent AB loop is significantly altered (FIG. 1E). The topology of the D2 domain is therefore a C2-type Ig fold with ABE and GFCC' β sheets, rather than the typical I-type fold. GPVI D2 diverges somewhat from the canonical C2 fold, which features a very short C' strand of three residues. Instead, GPVI D2 has significantly elongated C and C' strands, each containing 10 residues. Both the unusual AB loop and CC' β hairpin extend outward from the main body of D2 and appear to be quite flexible, given the lack of clear electron density for these regions in a second independent molecule within the asymmetric unit.

8. The GPVI CBD Forms a Dimer in the Crystal

Figure 2:
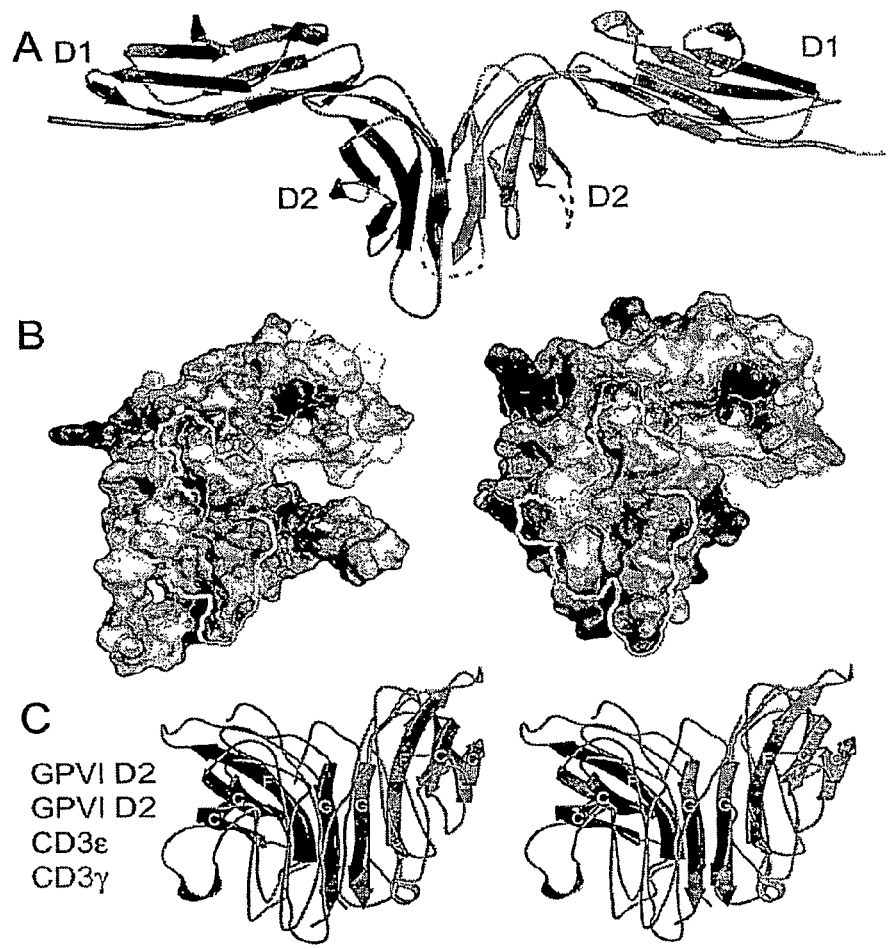
FIG. 2. Dimeric conformation of GPVI in the crystal. A. Structure of the GPVI dimer in the asymmetric unit. B. Electrostatic potential of GPVI mapped onto the surface of each GPVI protomer, shown in an "open-book" view. Residues contributing to the dimer interface on each protomer have been outlined in light gray. The potential map has been contoured from −100 to +100 kT. C. Left, Stereoview of a superposition of the dimers formed by GPVI D2 and the CD3εγ heterodimer (Kjer-Nielsen et al. Proc Natl Acad Sci USA. 2004). For clarity, only those β-strands in the continuous β-sheet are shown as ribbons; all others are shown as coils.

The asymmetric unit of the crystal contains a parallel, back-to-back dimer formed by the D2 domains of the two GPVI molecules (FIG. 2A). The G strands of the D2 domains interact to create a continuous β sheet across the dimer interface. The unusual D2 architecture lacking an A' strand is necessary for dimer formation, since the presence of A' strands would sterically block the G strands from forming a continuous β sheet. The dimer interface buries 1,046 square Angstroms of accessible surface area, which is within the range expected for dimeric proteins, although lower than average for a protein of this size (Jones et al. *Proc Natl Acad Sci USA*. (1996)). The dimer interface shows excellent surface complementarity, with a shape complementarity index of 0.73, comparable to oligomeric proteins ($S_c$=0.70-0.74) and protease-inhibitor complexes ($S_c$=0.71-0.76) (Lawrence et al. *J Mol Biol*. (1993)). The interface is dominated by hydrophobic interactions along with hydrogen bonds contributed by the peptide backbone in the parallel G strands of both D2 domains (FIG. 2B). Interestingly, the GPVI dimerization mode is essentially identical to that observed for CD3εδ and CD3εδ receptor heterodimers in the T-cell receptor (TCR) complex (Sun et al. *Cell* (2001), Sun et al. *Proc Natl Acad Sci USA*. (2004), Kjer-Nielsen et al. *Proc Natl Acad Sci USA*. (2004)). Like GPV1, CD3εδ and CD3εδ form back-to-back dimers with the G strands forming a continuous β sheet (FIG. 2C). Indeed, the CD3εδ dimer (Kjer-Nielsen et al. *Proc Natl Acad Sci USA*. (2004)) superimposes on the GPVI D2 dimer with an rms deviation of only 2.0 Angstroms over 55 residues, which is remarkable given the low sequence identity between GPVI and the CD3 receptors (20% or 14% identity between GPVI and CD3ε or γ, respectively).

9. Interaction of GPVI CBD and Collagen-Related Peptide in Solution

To understand how GPVI associates with the macromolecule collagen, the interactions between the GPVI, CBD and CRP, which functionally mimics collagen in biological assays, were studied. To analyze the affinity of the interaction under conditions favoring a 1:1 complex, sedimentation velocity analytical ultracentrifugation experiments were carried out by titrating GPVI with CRP (a non-crosslinked (POG)$_{10}$ triple helix) at up to 35-fold molar excess (FIG. 3A). The weight-averaged sedimentation coefficient ($s_w$) of each dataset was plotted as a function of CRP concentration and fitted to a single-site binding isotherm, yielding a $K_D$ of 5 μM (FIG. 3A, inset). This affinity is significantly tighter than that determined by surface plasmon resonance (SPR) (Miura et al. *J Biol Chem*. (2002)); however, the SPR experiment measured binding of GPVI to immobilized, cross-linked CRP with a different sequence than the non-crosslinked CRP described here.

Additional sedimentation velocity and sedimentation equilibrium experiments conducted using 1:1, 4:1, or 8:1 molar ratios mixtures of GPVI:CRP indicated that multiple GPVI molecules can bind to a single CRP triple helix, consistent with the presence of multiple overlapping sites for GPVI within the repeating tripeptide sequence of the CRP triple helix. The $s_w$ values indicated formation of a 1:1 complex in the first sample and formation of higher-order complexes in the 4:1 and 8:1 mixtures (FIG. 3B). Sedimentation equilibrium experiments conducted in parallel on similar mixtures indicated that two or three molecules of GPVI could bind simultaneously to a CRP triple helix (data not shown).

10. Computational Determination of CRP Binding Sites on the GPVI Dimer

Unfortunately, complexes of GPVI with CRP were found to be resistant to crystallization, most likely due to excessive heterogeneity of the complexes, which results from the ability of GPVI to bind at multiple overlapping sites along the triple helix. In order to identify collagen-binding sites on GPVI, two different computational algorithms, PatchDock (Schneidman-Duhovny et al. *Proteins* (2003)) and FTDock (Katchalski-Katzir et al. *Proc Natl Acad Sci USA*. (1992)), were employed to dock CRP onto GPVI. Both docking programs positioned CRP within the shallow groove on D1 adjacent to the C'E loop (FIG. 4A, B). The floor of the putative binding groove is formed by several hydrophobic residues (L53, F54, P56, L62, and Y66 and the aliphatic portion of K41), with several polar (S43, S44, Q48, Q50, S61) and basic (K41, R46, K59, R166) residues around the periphery (FIG. 4C-E). This groove is unique to GPVI among LRC receptors, as it results from the 11-residue deletion in GPVI. The binding of CRP to this groove provides a structural explanation for how an immune-type receptor has evolved to bind vessel wall collagen. In these models, CRP is immediately adjacent to GPVI residues K41, K59, R60, and R166, which have been implicated as collagen and CRP-binding residues by mutational analysis, as described below (FIG. 4E). Furthermore, previously described GPVI mutations having no effect on CRP affinity are not located within the putative binding groove. The docked CRP solutions from each program are evenly distributed between two nearly opposite orientations within the groove. This is consistent with the pseudo-two fold symmetry present in CRP, caused by its imino groups (prolines and hydroxyprolines) occupying similar positions in both orientations.

Native collagen fibers are composed of a pseudo-hexagonal array of parallel CRP-like triple helices separated by 13-14 Angstroms, an arrangement that is also conserved in crystal structures of soluble CRP-like peptides (FIG. 4B, top). Interestingly, the two putative CRP-binding grooves within a GPVI dimer are essentially parallel and are separated by ~55 Angstroms, which is equivalent to the distance between the n and n+4 helices in a collagen fiber. The geometric compatibility of the binding grooves with collagen helices would allow the GPVI dimer to bind simultaneously to two triple helices within a collagen fiber.

TABLE 1

Crystallographic data processing and refinement statistics

Data Collection

| | |
|---|---|
| Wavelength (Angstroms) | 1.5418 |
| Space group | $P2_12_12$ |
| Cell dimensions (Angstroms) | a = 114.06 b = 45.29 c = 75.13 |
| Resolution range (Angstroms)* | 20.0-2.4 (2.52-2.40) |
| Measured reflections | 50,335 |
| Unique reflections | 15,739 |
| Average I/σ(I) | 6.6 (2.1) |
| Completeness (%) | 99.3 (97.4) |
| $R_{sym}$ (%)† | 7.9 (34.8) |

Refinement statistics

| | |
|---|---|
| Resolution range used in refinement (Angstroms) | 10-2.4 |
| R factor (%)‡ | 22.3 |
| $R_{free}$ (%)∥ | 27.6 |
| Number of heavy atoms | |
| Molecule A (Residues: 2-183) | 1412 |
| Molecule B (Residues: 0-98, 108-129, 138-183) | 1309 |
| Water molecules | 177 |
| Glycerol (2), $SO_4^{2-}$ (2), $Cl^-$ (1) | 23 |
| Average B factor (square Angstroms) | |
| Molecule A | 44.3 |
| Molecule B | 50.9 |
| Solvent | 51.3 |
| Ramachandran plot | |
| Residues in most favored | 252 |
| Residues in additional allowed | 33 |
| Residues in generously allowed | 1 |
| Residues in disallowed | 0 |
| rms deviations from ideal | |
| Bond lengths (Angstroms) | 0.006 |
| Bond angles (°) | 1.50 |

*Values in parentheses refer to the highest resolution shell.
†$R_{sym} = \Sigma_i | I_{hi} - \langle I_{hi} \rangle | / \Sigma_i | I_{hi} |$, where h specifies unique reflection indices, i indicates symmetry equivalent observations of h.
‡R factor = $\Sigma | |F_{obs}| - |F_{calc}| | / |F_{obs}|$, where $|F_{obs}|$ and $|F_{calc}|$ are the observed and calculated structure factor amplitudes, respectively.
∥$R_{free}$ is the same as R factor, but was calculated for a test set containing 5% randomly chosen reflections that were not included in the refinement.

TABLE 2

| | | | | | | | | | | |
|---|---|---|---|---|---|---|---|---|---|---|
| CRYST1 | | 114.057 | | 45.286 | 75.131 | 90.00 | 90.00 | 90.00 | P 21 21 2 | |
| ATOM | 1 | N | SER | A | 2 | 18.171 | 29.819 | 66.736 | 1.00 49.43 | N |
| ATOM | 2 | CA | SER | A | 2 | 17.428 | 28.818 | 65.924 | 1.00 49.76 | C |
| ATOM | 3 | C | SER | A | 2 | 18.155 | 28.559 | 64.607 | 1.00 48.33 | C |
| ATOM | 4 | O | SER | A | 2 | 18.657 | 29.486 | 63.969 | 1.00 49.56 | O |
| ATOM | 5 | CB | SER | A | 2 | 16.003 | 29.316 | 65.670 | 1.00 51.80 | C |
| ATOM | 6 | OG | SER | A | 2 | 15.999 | 30.700 | 65.351 | 1.00 55.27 | O |
| ATOM | 7 | N | GLY | A | 3 | 18.211 | 27.291 | 64.209 | 1.00 46.47 | N |
| ATOM | 8 | CA | GLY | A | 3 | 18.905 | 26.917 | 62.990 | 1.00 43.11 | C |
| ATOM | 9 | C | GLY | A | 3 | 18.191 | 27.192 | 61.678 | 1.00 41.71 | C |
| ATOM | 10 | O | GLY | A | 3 | 17.077 | 27.719 | 61.662 | 1.00 40.69 | O |
| ATOM | 11 | N | PRO | A | 4 | 18.830 | 26.843 | 60.548 | 1.00 39.53 | N |
| ATOM | 12 | CA | PRO | A | 4 | 18.310 | 27.027 | 59.195 | 1.00 39.01 | C |
| ATOM | 13 | C | PRO | A | 4 | 17.226 | 26.018 | 58.809 | 1.00 39.56 | C |
| ATOM | 14 | O | PRO | A | 4 | 17.117 | 24.935 | 59.390 | 1.00 38.22 | O |
| ATOM | 15 | CB | PRO | A | 4 | 19.560 | 26.906 | 58.333 | 1.00 38.63 | C |
| ATOM | 16 | CG | PRO | A | 4 | 20.361 | 25.891 | 59.065 | 1.00 38.24 | C |
| ATOM | 17 | CD | PRO | A | 4 | 20.211 | 26.324 | 60.507 | 1.00 38.96 | C |
| ATOM | 18 | N | LEU | A | 5 | 16.444 | 26.391 | 57.804 | 1.00 39.25 | N |
| ATOM | 19 | CA | LEU | A | 5 | 15.339 | 25.584 | 57.308 | 1.00 40.47 | C |
| ATOM | 20 | C | LEU | A | 5 | 15.742 | 24.657 | 56.166 | 1.00 40.51 | C |
| ATOM | 21 | O | LEU | A | 5 | 16.743 | 24.881 | 55.494 | 1.00 42.63 | O |
| ATOM | 22 | CB | LEU | A | 5 | 14.223 | 26.521 | 56.830 | 1.00 40.35 | C |
| ATOM | 23 | CG | LEU | A | 5 | 13.756 | 27.536 | 57.876 | 1.00 39.58 | C |
| ATOM | 24 | CD1 | LEU | A | 5 | 12.845 | 28.585 | 57.259 | 1.00 39.37 | C |
| ATOM | 25 | CD2 | LEU | A | 5 | 13.040 | 26.789 | 58.978 | 1.00 40.29 | C |
| ATOM | 26 | N | PRO | A | 6 | 14.963 | 23.595 | 55.930 | 1.00 40.62 | N |
| ATOM | 27 | CA | PRO | A | 6 | 15.317 | 22.689 | 54.835 | 1.00 39.86 | C |
| ATOM | 28 | C | PRO | A | 6 | 15.379 | 23.426 | 53.487 | 1.00 39.04 | C |
| ATOM | 29 | O | PRO | A | 6 | 14.706 | 24.433 | 53.290 | 1.00 38.95 | O |
| ATOM | 30 | CB | PRO | A | 6 | 14.221 | 21.618 | 54.904 | 1.00 40.12 | C |
| ATOM | 31 | CG | PRO | A | 6 | 13.089 | 22.302 | 55.615 | 1.00 40.90 | C |
| ATOM | 32 | CD | PRO | A | 6 | 13.782 | 23.110 | 56.662 | 1.00 39.95 | C |
| ATOM | 33 | N | LYS | A | 7 | 16.204 | 22.939 | 52.565 | 1.00 38.90 | N |
| ATOM | 34 | CA | LYS | A | 7 | 16.343 | 23.595 | 51.266 | 1.00 36.61 | C |
| ATOM | 35 | C | LYS | A | 7 | 15.151 | 23.348 | 50.354 | 1.00 34.96 | C |
| ATOM | 36 | O | LYS | A | 7 | 14.530 | 22.283 | 50.381 | 1.00 35.59 | O |

TABLE 2-continued

| | | | | | | | | | | | |
|---|---|---|---|---|---|---|---|---|---|---|---|
| ATOM | 37 | CB | LYS | A | 7 | 17.618 | 23.126 | 50.553 | 1.00 | 36.94 | C |
| ATOM | 38 | CG | LYS | A | 7 | 17.486 | 21.786 | 49.868 | 1.00 | 36.31 | C |
| ATOM | 39 | CD | LYS | A | 7 | 18.829 | 21.249 | 49.433 | 1.00 | 38.26 | C |
| ATOM | 40 | CE | LYS | A | 7 | 18.681 | 19.824 | 48.931 | 1.00 | 39.11 | C |
| ATOM | 41 | NZ | LYS | A | 7 | 19.998 | 19.151 | 48.737 | 1.00 | 45.99 | N |
| ATOM | 42 | N | PRO | A | 8 | 14.834 | 24.331 | 49.510 | 1.00 | 32.67 | N |
| ATOM | 43 | CA | PRO | A | 8 | 13.711 | 24.208 | 48.587 | 1.00 | 30.96 | C |
| ATOM | 44 | C | PRO | A | 8 | 14.149 | 23.476 | 47.329 | 1.00 | 34.27 | C |
| ATOM | 45 | O | PRO | A | 8 | 15.331 | 23.198 | 47.131 | 1.00 | 33.75 | O |
| ATOM | 46 | CB | PRO | A | 8 | 13.362 | 25.649 | 48.301 | 1.00 | 29.43 | C |
| ATOM | 47 | CG | PRO | A | 8 | 14.753 | 26.282 | 48.216 | 1.00 | 32.03 | C |
| ATOM | 48 | CD | PRO | A | 8 | 15.515 | 25.632 | 49.359 | 1.00 | 29.78 | C |
| ATOM | 49 | N | SER | A | 9 | 13.188 | 23.163 | 46.477 | 1.00 | 34.49 | N |
| ATOM | 50 | CA | SER | A | 9 | 13.500 | 22.493 | 45.241 | 1.00 | 34.88 | C |
| ATOM | 51 | C | SER | A | 9 | 13.551 | 23.600 | 44.202 | 1.00 | 35.14 | C |
| ATOM | 52 | O | SER | A | 9 | 12.967 | 24.670 | 44.391 | 1.00 | 34.19 | O |
| ATOM | 53 | CB | SER | A | 9 | 12.396 | 21.486 | 44.889 | 1.00 | 37.58 | C |
| ATOM | 54 | OG | SER | A | 9 | 11.145 | 22.141 | 44.701 | 1.00 | 37.99 | O |
| ATOM | 55 | N | LEU | A | 10 | 14.271 | 23.352 | 43.118 | 1.00 | 34.40 | N |
| ATOM | 56 | CA | LEU | A | 10 | 14.363 | 24.314 | 42.038 | 1.00 | 35.58 | C |
| ATOM | 57 | C | LEU | A | 10 | 14.329 | 23.476 | 40.779 | 1.00 | 36.49 | C |
| ATOM | 58 | O | LEU | A | 10 | 15.282 | 22.763 | 40.473 | 1.00 | 39.59 | O |
| ATOM | 59 | CB | LEU | A | 10 | 15.660 | 25.117 | 42.127 | 1.00 | 32.11 | C |
| ATOM | 60 | CG | LEU | A | 10 | 15.820 | 26.207 | 41.066 | 1.00 | 29.39 | C |
| ATOM | 61 | CD1 | LEU | A | 10 | 14.567 | 27.065 | 41.005 | 1.00 | 29.82 | C |
| ATOM | 62 | CD2 | LEU | A | 10 | 17.047 | 27.055 | 41.383 | 1.00 | 30.57 | C |
| ATOM | 63 | N | GLN | A | 11 | 13.221 | 23.558 | 40.056 | 1.00 | 38.36 | N |
| ATOM | 64 | CA | GLN | A | 11 | 13.043 | 22.759 | 38.854 | 1.00 | 40.01 | C |
| ATOM | 65 | C | GLN | A | 11 | 12.611 | 23.583 | 37.645 | 1.00 | 38.19 | C |
| ATOM | 66 | O | GLN | A | 11 | 11.903 | 24.577 | 37.780 | 1.00 | 37.77 | O |
| ATOM | 67 | CB | GLN | A | 11 | 12.031 | 21.653 | 39.167 | 1.00 | 42.44 | C |
| ATOM | 68 | CG | GLN | A | 11 | 12.401 | 20.910 | 40.455 | 1.00 | 49.56 | C |
| ATOM | 69 | CD | GLN | A | 11 | 11.405 | 19.829 | 40.866 | 1.00 | 55.23 | C |
| ATOM | 70 | OE1 | GLN | A | 11 | 10.201 | 20.083 | 40.988 | 1.00 | 57.58 | O |
| ATOM | 71 | NE2 | GLN | A | 11 | 11.912 | 18.618 | 41.104 | 1.00 | 55.37 | N |
| ATOM | 72 | N | ALA | A | 12 | 13.072 | 23.182 | 36.465 | 1.00 | 36.79 | N |
| ATOM | 73 | CA | ALA | A | 12 | 12.732 | 23.879 | 35.232 | 1.00 | 35.95 | C |
| ATOM | 74 | C | ALA | A | 12 | 11.693 | 23.044 | 34.491 | 1.00 | 36.46 | C |
| ATOM | 75 | O | ALA | A | 12 | 11.715 | 21.813 | 34.581 | 1.00 | 36.19 | O |
| ATOM | 76 | CB | ALA | A | 12 | 13.983 | 24.062 | 34.371 | 1.00 | 33.53 | C |
| ATOM | 77 | N | LEU | A | 13 | 10.788 | 23.708 | 33.771 | 1.00 | 36.07 | N |
| ATOM | 78 | CA | LEU | A | 13 | 9.735 | 23.017 | 33.026 | 1.00 | 36.02 | C |
| ATOM | 79 | C | LEU | A | 13 | 9.375 | 23.702 | 31.710 | 1.00 | 37.40 | C |
| ATOM | 80 | O | LEU | A | 13 | 9.337 | 24.933 | 31.624 | 1.00 | 40.32 | O |
| ATOM | 81 | CB | LEU | A | 13 | 8.474 | 22.880 | 33.881 | 1.00 | 35.04 | C |
| ATOM | 82 | CG | LEU | A | 13 | 8.463 | 21.787 | 34.948 | 1.00 | 34.87 | C |
| ATOM | 83 | CD1 | LEU | A | 13 | 7.179 | 21.862 | 35.761 | 1.00 | 34.39 | C |
| ATOM | 84 | CD2 | LEU | A | 13 | 8.585 | 20.428 | 34.272 | 1.00 | 35.61 | C |
| ATOM | 85 | N | PRO | A | 14 | 9.083 | 22.906 | 30.666 | 1.00 | 36.36 | N |
| ATOM | 86 | CA | PRO | A | 14 | 9.082 | 21.435 | 30.705 | 1.00 | 36.31 | C |
| ATOM | 87 | C | PRO | A | 14 | 10.443 | 20.750 | 30.963 | 1.00 | 36.47 | C |
| ATOM | 88 | O | PRO | A | 14 | 10.489 | 19.613 | 31.441 | 1.00 | 35.62 | O |
| ATOM | 89 | CB | PRO | A | 14 | 8.475 | 21.062 | 29.353 | 1.00 | 35.66 | C |
| ATOM | 90 | CG | PRO | A | 14 | 8.946 | 22.178 | 28.455 | 1.00 | 35.35 | C |
| ATOM | 91 | CD | PRO | A | 14 | 8.760 | 23.404 | 29.317 | 1.00 | 35.80 | C |
| ATOM | 92 | N | SER | A | 15 | 11.543 | 21.439 | 30.669 | 1.00 | 35.85 | N |
| ATOM | 93 | CA | SER | A | 15 | 12.869 | 20.860 | 30.878 | 1.00 | 36.71 | C |
| ATOM | 94 | C | SER | A | 15 | 13.958 | 21.895 | 31.182 | 1.00 | 36.67 | C |
| ATOM | 95 | O | SER | A | 15 | 13.795 | 23.084 | 30.911 | 1.00 | 36.15 | O |
| ATOM | 96 | CB | SER | A | 15 | 13.275 | 20.057 | 29.634 | 1.00 | 36.92 | C |
| ATOM | 97 | OG | SER | A | 15 | 14.626 | 19.625 | 29.703 | 1.00 | 38.10 | O |
| ATOM | 98 | N | SER | A | 16 | 15.073 | 21.430 | 31.741 | 1.00 | 36.81 | N |
| ATOM | 99 | CA | SER | A | 16 | 16.198 | 22.311 | 32.041 | 1.00 | 37.01 | C |
| ATOM | 100 | C | SER | A | 16 | 17.031 | 22.454 | 30.769 | 1.00 | 37.99 | C |
| ATOM | 101 | O | SER | A | 16 | 17.932 | 23.294 | 30.682 | 1.00 | 37.37 | O |
| ATOM | 102 | CB | SER | A | 16 | 17.046 | 21.730 | 33.170 | 1.00 | 37.32 | C |
| ATOM | 103 | OG | SER | A | 16 | 17.429 | 20.410 | 32.865 | 1.00 | 40.96 | O |
| ATOM | 104 | N | LEU | A | 17 | 16.733 | 21.606 | 29.787 | 1.00 | 39.64 | N |
| ATOM | 105 | CA | LEU | A | 17 | 17.405 | 21.665 | 28.492 | 1.00 | 41.01 | C |
| ATOM | 106 | C | LEU | A | 17 | 16.420 | 22.410 | 27.606 | 1.00 | 40.76 | C |
| ATOM | 107 | O | LEU | A | 17 | 15.349 | 21.894 | 27.265 | 1.00 | 40.45 | O |
| ATOM | 108 | CB | LEU | A | 17 | 17.661 | 20.269 | 27.923 | 1.00 | 42.49 | C |
| ATOM | 109 | CG | LEU | A | 17 | 18.708 | 19.407 | 28.630 | 1.00 | 45.34 | C |
| ATOM | 110 | CD1 | LEU | A | 17 | 18.971 | 18.178 | 27.792 | 1.00 | 44.53 | C |
| ATOM | 111 | CD2 | LEU | A | 17 | 19.996 | 20.188 | 28.832 | 1.00 | 44.60 | C |
| ATOM | 112 | N | VAL | A | 18 | 16.779 | 23.631 | 27.247 | 1.00 | 40.13 | N |
| ATOM | 113 | CA | VAL | A | 18 | 15.897 | 24.454 | 26.444 | 1.00 | 39.21 | C |
| ATOM | 114 | C | VAL | A | 18 | 16.491 | 24.888 | 25.127 | 1.00 | 38.82 | C |
| ATOM | 115 | O | VAL | A | 18 | 17.560 | 25.503 | 25.085 | 1.00 | 36.71 | O |
| ATOM | 116 | CB | VAL | A | 18 | 15.500 | 25.741 | 27.195 | 1.00 | 39.72 | C |

TABLE 2-continued

| | | | | | | | | | | | |
|---|---|---|---|---|---|---|---|---|---|---|---|
| ATOM | 117 | CG1 | VAL | A | 18 | 14.308 | 26.409 | 26.488 | 1.00 | 40.26 | C |
| ATOM | 118 | CG2 | VAL | A | 18 | 15.202 | 25.428 | 28.660 | 1.00 | 39.06 | C |
| ATOM | 119 | N | PRO | A | 19 | 15.813 | 24.551 | 24.024 | 1.00 | 40.10 | N |
| ATOM | 120 | CA | PRO | A | 19 | 16.339 | 24.968 | 22.723 | 1.00 | 41.53 | C |
| ATOM | 121 | C | PRO | A | 19 | 16.079 | 26.472 | 22.567 | 1.00 | 42.12 | C |
| ATOM | 122 | O | PRO | A | 19 | 15.038 | 26.974 | 23.002 | 1.00 | 42.23 | O |
| ATOM | 123 | CB | PRO | A | 19 | 15.558 | 24.097 | 21.733 | 1.00 | 39.86 | C |
| ATOM | 124 | CG | PRO | A | 19 | 14.330 | 23.729 | 22.465 | 1.00 | 39.66 | C |
| ATOM | 125 | CD | PRO | A | 19 | 14.780 | 23.513 | 23.873 | 1.00 | 39.16 | C |
| ATOM | 126 | N | LEU | A | 20 | 17.041 | 27.191 | 21.996 | 1.00 | 42.89 | N |
| ATOM | 127 | CA | LEU | A | 20 | 16.905 | 28.632 | 21.808 | 1.00 | 44.13 | C |
| ATOM | 128 | C | LEU | A | 20 | 15.560 | 28.964 | 21.189 | 1.00 | 46.58 | C |
| ATOM | 129 | O | LEU | A | 20 | 15.047 | 28.201 | 20.372 | 1.00 | 46.40 | O |
| ATOM | 130 | CB | LEU | A | 20 | 18.024 | 29.155 | 20.912 | 1.00 | 44.08 | C |
| ATOM | 131 | CG | LEU | A | 20 | 19.419 | 29.101 | 21.536 | 1.00 | 44.71 | C |
| ATOM | 132 | CD1 | LEU | A | 20 | 20.477 | 29.347 | 20.478 | 1.00 | 42.64 | C |
| ATOM | 133 | CD2 | LEU | A | 20 | 19.506 | 30.132 | 22.652 | 1.00 | 44.19 | C |
| ATOM | 134 | N | GLU | A | 21 | 14.995 | 30.104 | 21.585 | 1.00 | 48.92 | N |
| ATOM | 135 | CA | GLU | A | 21 | 13.695 | 30.552 | 21.081 | 1.00 | 50.54 | C |
| ATOM | 136 | C | GLU | A | 21 | 12.540 | 29.852 | 21.790 | 1.00 | 49.68 | C |
| ATOM | 137 | O | GLU | A | 21 | 11.403 | 30.314 | 21.727 | 1.00 | 49.37 | O |
| ATOM | 138 | CB | GLU | A | 21 | 13.588 | 30.310 | 19.568 | 1.00 | 52.65 | C |
| ATOM | 139 | CG | GLU | A | 21 | 14.000 | 31.484 | 18.684 | 1.00 | 58.03 | C |
| ATOM | 140 | CD | GLU | A | 21 | 15.235 | 32.228 | 19.185 | 1.00 | 62.13 | C |
| ATOM | 141 | OE1 | GLU | A | 21 | 15.123 | 32.958 | 20.199 | 1.00 | 63.55 | O |
| ATOM | 142 | OE2 | GLU | A | 21 | 16.316 | 32.086 | 18.565 | 1.00 | 63.56 | O |
| ATOM | 143 | N | LYS | A | 22 | 12.828 | 28.743 | 22.466 | 1.00 | 48.20 | N |
| ATOM | 144 | CA | LYS | A | 22 | 11.784 | 28.010 | 23.172 | 1.00 | 47.26 | C |
| ATOM | 145 | C | LYS | A | 22 | 11.614 | 28.504 | 24.603 | 1.00 | 47.34 | C |
| ATOM | 146 | O | LYS | A | 22 | 12.518 | 29.120 | 25.171 | 1.00 | 47.20 | O |
| ATOM | 147 | CB | LYS | A | 22 | 12.096 | 26.517 | 23.155 | 1.00 | 48.86 | C |
| ATOM | 148 | CG | LYS | A | 22 | 12.199 | 25.945 | 21.756 | 1.00 | 49.81 | C |
| ATOM | 149 | CD | LYS | A | 22 | 10.898 | 26.118 | 21.002 | 1.00 | 52.62 | C |
| ATOM | 150 | CE | LYS | A | 22 | 10.953 | 25.480 | 19.622 | 1.00 | 54.06 | C |
| ATOM | 151 | NZ | LYS | A | 22 | 9.655 | 25.654 | 18.903 | 1.00 | 56.10 | N |
| ATOM | 152 | N | PRO | A | 23 | 10.444 | 28.244 | 25.208 | 1.00 | 46.88 | N |
| ATOM | 153 | CA | PRO | A | 23 | 10.167 | 28.680 | 26.581 | 1.00 | 46.01 | C |
| ATOM | 154 | C | PRO | A | 23 | 10.570 | 27.714 | 27.696 | 1.00 | 45.25 | C |
| ATOM | 155 | O | PRO | A | 23 | 10.641 | 26.495 | 27.495 | 1.00 | 43.07 | O |
| ATOM | 156 | CB | PRO | A | 23 | 8.662 | 28.905 | 26.563 | 1.00 | 45.81 | C |
| ATOM | 157 | CG | PRO | A | 23 | 8.204 | 27.760 | 25.728 | 1.00 | 47.25 | C |
| ATOM | 158 | CD | PRO | A | 23 | 9.209 | 27.759 | 24.564 | 1.00 | 46.65 | C |
| ATOM | 159 | N | VAL | A | 24 | 10.824 | 28.291 | 28.872 | 1.00 | 43.43 | N |
| ATOM | 160 | CA | VAL | A | 24 | 11.187 | 27.544 | 30.068 | 1.00 | 40.67 | C |
| ATOM | 161 | C | VAL | A | 24 | 10.838 | 28.377 | 31.292 | 1.00 | 39.39 | C |
| ATOM | 162 | O | VAL | A | 24 | 11.071 | 29.583 | 31.323 | 1.00 | 39.49 | O |
| ATOM | 163 | CB | VAL | A | 24 | 12.711 | 27.183 | 30.106 | 1.00 | 39.78 | C |
| ATOM | 164 | CG1 | VAL | A | 24 | 13.571 | 28.443 | 30.027 | 1.00 | 38.40 | C |
| ATOM | 165 | CG2 | VAL | A | 24 | 13.020 | 26.408 | 31.380 | 1.00 | 34.09 | C |
| ATOM | 166 | N | THR | A | 25 | 10.263 | 27.725 | 32.293 | 1.00 | 38.24 | N |
| ATOM | 167 | CA | THR | A | 25 | 9.892 | 28.399 | 33.524 | 1.00 | 38.20 | C |
| ATOM | 168 | C | THR | A | 25 | 10.545 | 27.729 | 34.735 | 1.00 | 38.61 | C |
| ATOM | 169 | O | THR | A | 25 | 10.428 | 26.520 | 34.923 | 1.00 | 38.06 | O |
| ATOM | 170 | CB | THR | A | 25 | 8.357 | 28.429 | 33.709 | 1.00 | 37.31 | C |
| ATOM | 171 | OG1 | THR | A | 25 | 8.049 | 28.601 | 35.097 | 1.00 | 38.56 | O |
| ATOM | 172 | CG2 | THR | A | 25 | 7.729 | 27.150 | 33.212 | 1.00 | 35.98 | C |
| ATOM | 173 | N | LEU | A | 26 | 11.244 | 28.529 | 35.538 | 1.00 | 38.95 | N |
| ATOM | 174 | CA | LEU | A | 26 | 11.922 | 28.036 | 36.728 | 1.00 | 40.70 | C |
| ATOM | 175 | C | LEU | A | 26 | 11.023 | 28.236 | 37.937 | 1.00 | 41.86 | C |
| ATOM | 176 | O | LEU | A | 26 | 10.373 | 29.270 | 38.084 | 1.00 | 42.93 | O |
| ATOM | 177 | CB | LEU | A | 26 | 13.253 | 28.771 | 36.941 | 1.00 | 38.62 | C |
| ATOM | 178 | CG | LEU | A | 26 | 14.187 | 28.879 | 35.730 | 1.00 | 38.76 | C |
| ATOM | 179 | CD1 | LEU | A | 26 | 15.574 | 29.324 | 36.182 | 1.00 | 38.28 | C |
| ATOM | 180 | CD2 | LEU | A | 26 | 14.272 | 27.547 | 35.033 | 1.00 | 38.07 | C |
| ATOM | 181 | N | ARG | A | 27 | 10.999 | 27.244 | 38.814 | 1.00 | 42.50 | N |
| ATOM | 182 | CA | ARG | A | 27 | 10.157 | 27.320 | 39.986 | 1.00 | 43.14 | C |
| ATOM | 183 | C | ARG | A | 27 | 10.897 | 26.915 | 41.253 | 1.00 | 42.14 | C |
| ATOM | 184 | O | ARG | A | 27 | 11.492 | 25.836 | 41.316 | 1.00 | 40.72 | O |
| ATOM | 185 | CB | ARG | A | 27 | 8.943 | 26.409 | 39.794 | 1.00 | 46.31 | C |
| ATOM | 186 | CG | ARG | A | 27 | 7.846 | 26.573 | 40.837 | 1.00 | 52.43 | C |
| ATOM | 187 | CD | ARG | A | 27 | 6.581 | 27.132 | 40.188 | 1.00 | 58.55 | C |
| ATOM | 188 | NE | ARG | A | 27 | 5.466 | 27.236 | 41.125 | 1.00 | 63.04 | N |
| ATOM | 189 | CZ | ARG | A | 27 | 4.239 | 27.631 | 40.788 | 1.00 | 65.77 | C |
| ATOM | 190 | NH1 | ARG | A | 27 | 3.963 | 27.964 | 39.531 | 1.00 | 65.24 | N |
| ATOM | 191 | NH2 | ARG | A | 27 | 3.283 | 27.687 | 41.709 | 1.00 | 66.11 | N |
| ATOM | 192 | N | CYS | A | 28 | 10.861 | 27.790 | 42.256 | 1.00 | 40.19 | N |
| ATOM | 193 | CA | CYS | A | 28 | 11.480 | 27.503 | 43.541 | 1.00 | 41.99 | C |
| ATOM | 194 | C | CYS | A | 28 | 10.323 | 27.006 | 44.413 | 1.00 | 42.73 | C |
| ATOM | 195 | O | CYS | A | 28 | 9.216 | 27.535 | 44.328 | 1.00 | 45.70 | O |
| ATOM | 196 | CB | CYS | A | 28 | 12.098 | 28.773 | 44.125 | 1.00 | 40.17 | C |

TABLE 2-continued

| | | | | | | | | | | | |
|---|---|---|---|---|---|---|---|---|---|---|---|
| ATOM | 197 | SG | CYS | A | 28 | 13.155 | 28.487 | 45.581 | 1.00 | 41.89 | S |
| ATOM | 198 | N | GLN | A | 29 | 10.547 | 25.984 | 45.230 | 1.00 | 42.82 | N |
| ATOM | 199 | CA | GLN | A | 29 | 9.461 | 25.478 | 46.063 | 1.00 | 43.47 | C |
| ATOM | 200 | C | GLN | A | 29 | 9.940 | 24.905 | 47.381 | 1.00 | 43.85 | C |
| ATOM | 201 | O | GLN | A | 29 | 10.655 | 23.904 | 47.409 | 1.00 | 45.20 | O |
| ATOM | 202 | CB | GLN | A | 29 | 8.670 | 24.403 | 45.311 | 1.00 | 44.89 | C |
| ATOM | 203 | CG | GLN | A | 29 | 7.389 | 23.969 | 46.013 | 1.00 | 45.62 | C |
| ATOM | 204 | CD | GLN | A | 29 | 6.262 | 24.994 | 45.872 | 1.00 | 47.19 | C |
| ATOM | 205 | OE1 | GLN | A | 29 | 5.669 | 25.140 | 44.801 | 1.00 | 48.71 | O |
| ATOM | 206 | NE2 | GLN | A | 29 | 5.971 | 25.711 | 46.956 | 1.00 | 47.18 | N |
| ATOM | 207 | N | GLY | A | 30 | 9.539 | 25.545 | 48.474 | 1.00 | 44.09 | N |
| ATOM | 208 | CA | GLY | A | 30 | 9.928 | 25.075 | 49.791 | 1.00 | 44.88 | C |
| ATOM | 209 | C | GLY | A | 30 | 8.674 | 24.699 | 50.551 | 1.00 | 46.67 | C |
| ATOM | 210 | O | GLY | A | 30 | 7.590 | 24.713 | 49.967 | 1.00 | 47.06 | O |
| ATOM | 211 | N | PRO | A | 31 | 8.774 | 24.370 | 51.851 | 1.00 | 46.66 | N |
| ATOM | 212 | CA | PRO | A | 31 | 7.582 | 24.001 | 52.627 | 1.00 | 45.84 | C |
| ATOM | 213 | C | PRO | A | 31 | 6.437 | 25.017 | 52.513 | 1.00 | 43.97 | C |
| ATOM | 214 | O | PRO | A | 31 | 6.638 | 26.166 | 52.120 | 1.00 | 40.31 | O |
| ATOM | 215 | CB | PRO | A | 31 | 8.121 | 23.875 | 54.054 | 1.00 | 45.53 | C |
| ATOM | 216 | CG | PRO | A | 31 | 9.310 | 24.791 | 54.060 | 1.00 | 46.87 | C |
| ATOM | 217 | CD | PRO | A | 31 | 9.949 | 24.505 | 52.729 | 1.00 | 47.25 | C |
| ATOM | 218 | N | PRO | A | 32 | 5.213 | 24.590 | 52.840 | 1.00 | 44.06 | N |
| ATOM | 219 | CA | PRO | A | 32 | 4.080 | 25.511 | 52.751 | 1.00 | 45.57 | C |
| ATOM | 220 | C | PRO | A | 32 | 4.173 | 26.667 | 53.739 | 1.00 | 45.58 | C |
| ATOM | 221 | O | PRO | A | 32 | 4.629 | 26.491 | 54.871 | 1.00 | 45.24 | O |
| ATOM | 222 | CB | PRO | A | 32 | 2.873 | 24.603 | 53.009 | 1.00 | 45.74 | C |
| ATOM | 223 | CG | PRO | A | 32 | 3.440 | 23.517 | 53.878 | 1.00 | 45.95 | C |
| ATOM | 224 | CD | PRO | A | 32 | 4.770 | 23.239 | 53.227 | 1.00 | 44.88 | C |
| ATOM | 225 | N | GLY | A | 33 | 3.770 | 27.854 | 53.284 | 1.00 | 45.42 | N |
| ATOM | 226 | CA | GLY | A | 33 | 3.774 | 29.029 | 54.135 | 1.00 | 45.46 | C |
| ATOM | 227 | C | GLY | A | 33 | 5.040 | 29.840 | 54.368 | 1.00 | 46.44 | C |
| ATOM | 228 | O | GLY | A | 33 | 5.157 | 30.484 | 55.407 | 1.00 | 48.63 | O |
| ATOM | 229 | N | VAL | A | 34 | 5.988 | 29.846 | 53.442 | 1.00 | 47.14 | N |
| ATOM | 230 | CA | VAL | A | 34 | 7.197 | 30.640 | 53.673 | 1.00 | 47.91 | C |
| ATOM | 231 | C | VAL | A | 34 | 6.934 | 32.126 | 53.383 | 1.00 | 46.22 | C |
| ATOM | 232 | O | VAL | A | 34 | 6.032 | 32.463 | 52.621 | 1.00 | 43.32 | O |
| ATOM | 233 | CB | VAL | A | 34 | 8.397 | 30.125 | 52.815 | 1.00 | 48.47 | C |
| ATOM | 234 | CG1 | VAL | A | 34 | 8.550 | 28.624 | 53.006 | 1.00 | 48.22 | C |
| ATOM | 235 | CG2 | VAL | A | 34 | 8.209 | 30.475 | 51.351 | 1.00 | 47.13 | C |
| ATOM | 236 | N | ASP | A | 35 | 7.722 | 33.005 | 53.998 | 1.00 | 47.88 | N |
| ATOM | 237 | CA | ASP | A | 35 | 7.549 | 34.445 | 53.816 | 1.00 | 50.42 | C |
| ATOM | 238 | C | ASP | A | 35 | 8.126 | 35.028 | 52.532 | 1.00 | 51.68 | C |
| ATOM | 239 | O | ASP | A | 35 | 7.454 | 35.791 | 51.837 | 1.00 | 53.57 | O |
| ATOM | 240 | CB | ASP | A | 35 | 8.159 | 35.216 | 54.986 | 1.00 | 52.59 | C |
| ATOM | 241 | CG | ASP | A | 35 | 7.563 | 34.828 | 56.323 | 1.00 | 56.56 | C |
| ATOM | 242 | OD1 | ASP | A | 35 | 6.344 | 34.545 | 56.382 | 1.00 | 57.95 | O |
| ATOM | 243 | OD2 | ASP | A | 35 | 8.318 | 34.826 | 57.320 | 1.00 | 56.86 | O |
| ATOM | 244 | N | LEU | A | 36 | 9.376 | 34.690 | 52.228 | 1.00 | 50.43 | N |
| ATOM | 245 | CA | LEU | A | 36 | 10.036 | 35.217 | 51.039 | 1.00 | 47.88 | C |
| ATOM | 246 | C | LEU | A | 36 | 10.804 | 34.160 | 50.272 | 1.00 | 45.79 | C |
| ATOM | 247 | O | LEU | A | 36 | 11.325 | 33.200 | 50.844 | 1.00 | 45.41 | O |
| ATOM | 248 | CB | LEU | A | 36 | 11.015 | 36.327 | 51.426 | 1.00 | 49.31 | C |
| ATOM | 249 | CG | LEU | A | 36 | 11.900 | 36.856 | 50.293 | 1.00 | 51.03 | C |
| ATOM | 250 | CD1 | LEU | A | 36 | 11.122 | 37.898 | 49.522 | 1.00 | 53.68 | C |
| ATOM | 251 | CD2 | LEU | A | 36 | 13.183 | 37.463 | 50.842 | 1.00 | 51.00 | C |
| ATOM | 252 | N | TYR | A | 37 | 10.877 | 34.357 | 48.964 | 1.00 | 43.09 | N |
| ATOM | 253 | CA | TYR | A | 37 | 11.608 | 33.456 | 48.083 | 1.00 | 40.09 | C |
| ATOM | 254 | C | TYR | A | 37 | 12.697 | 34.279 | 47.423 | 1.00 | 37.71 | C |
| ATOM | 255 | O | TYR | A | 37 | 12.498 | 35.462 | 47.144 | 1.00 | 34.88 | O |
| ATOM | 256 | CB | TYR | A | 37 | 10.681 | 32.889 | 47.003 | 1.00 | 39.80 | C |
| ATOM | 257 | CG | TYR | A | 37 | 10.011 | 31.593 | 47.375 | 1.00 | 40.48 | C |
| ATOM | 258 | CD1 | TYR | A | 37 | 10.750 | 30.423 | 47.494 | 1.00 | 40.94 | C |
| ATOM | 259 | CD2 | TYR | A | 37 | 8.640 | 31.529 | 47.593 | 1.00 | 39.67 | C |
| ATOM | 260 | CE1 | TYR | A | 37 | 10.145 | 29.216 | 47.816 | 1.00 | 42.03 | C |
| ATOM | 261 | CE2 | TYR | A | 37 | 8.022 | 30.326 | 47.919 | 1.00 | 41.98 | C |
| ATOM | 262 | CZ | TYR | A | 37 | 8.782 | 29.172 | 48.030 | 1.00 | 43.11 | C |
| ATOM | 263 | OH | TYR | A | 37 | 8.194 | 27.971 | 48.370 | 1.00 | 44.98 | O |
| ATOM | 264 | N | ARG | A | 38 | 13.853 | 33.666 | 47.194 | 1.00 | 35.91 | N |
| ATOM | 265 | CA | ARG | A | 38 | 14.941 | 34.363 | 46.522 | 1.00 | 34.57 | C |
| ATOM | 266 | C | ARG | A | 38 | 15.574 | 33.461 | 45.463 | 1.00 | 35.68 | C |
| ATOM | 267 | O | ARG | A | 38 | 16.147 | 32.413 | 45.767 | 1.00 | 34.07 | O |
| ATOM | 268 | CB | ARG | A | 38 | 15.984 | 34.832 | 47.528 | 1.00 | 34.34 | C |
| ATOM | 269 | CG | ARG | A | 38 | 17.031 | 35.732 | 46.909 | 1.00 | 34.46 | C |
| ATOM | 270 | CD | ARG | A | 38 | 17.759 | 36.532 | 47.978 | 1.00 | 37.79 | C |
| ATOM | 271 | NE | ARG | A | 38 | 16.949 | 37.641 | 48.479 | 1.00 | 36.62 | N |
| ATOM | 272 | CZ | ARG | A | 38 | 17.299 | 38.428 | 49.492 | 1.00 | 35.61 | C |
| ATOM | 273 | NH1 | ARG | A | 38 | 18.447 | 38.236 | 50.129 | 1.00 | 35.44 | N |
| ATOM | 274 | NH2 | ARG | A | 38 | 16.501 | 39.416 | 49.862 | 1.00 | 37.22 | N |
| ATOM | 275 | N | LEU | A | 39 | 15.448 | 33.883 | 44.208 | 1.00 | 36.80 | N |
| ATOM | 276 | CA | LEU | A | 39 | 15.960 | 33.133 | 43.069 | 1.00 | 36.94 | C |

TABLE 2-continued

| | | | | | | | | | | | |
|---|---|---|---|---|---|---|---|---|---|---|---|
| ATOM | 277 | C | LEU | A | 39 | 17.096 | 33.903 | 42.408 | 1.00 | 37.01 | C |
| ATOM | 278 | O | LEU | A | 39 | 16.911 | 35.028 | 41.951 | 1.00 | 37.30 | O |
| ATOM | 279 | CB | LEU | A | 39 | 14.813 | 32.889 | 42.071 | 1.00 | 34.67 | C |
| ATOM | 280 | CG | LEU | A | 39 | 15.011 | 32.050 | 40.804 | 1.00 | 35.32 | C |
| ATOM | 281 | CD1 | LEU | A | 39 | 15.738 | 32.860 | 39.755 | 1.00 | 37.79 | C |
| ATOM | 282 | CD2 | LEU | A | 39 | 15.774 | 30.772 | 41.130 | 1.00 | 33.19 | C |
| ATOM | 283 | N | GLU | A | 40 | 18.270 | 33.287 | 42.345 | 1.00 | 37.09 | N |
| ATOM | 284 | CA | GLU | A | 40 | 19.421 | 33.945 | 41.752 | 1.00 | 38.13 | C |
| ATOM | 285 | C | GLU | A | 40 | 20.091 | 33.170 | 40.627 | 1.00 | 39.04 | C |
| ATOM | 286 | O | GLU | A | 40 | 19.930 | 31.957 | 40.494 | 1.00 | 38.42 | O |
| ATOM | 287 | CB | GLU | A | 40 | 20.477 | 34.217 | 42.826 | 1.00 | 36.49 | C |
| ATOM | 288 | CG | GLU | A | 40 | 20.930 | 32.955 | 43.538 | 1.00 | 37.50 | C |
| ATOM | 289 | CD | GLU | A | 40 | 22.310 | 33.076 | 44.168 | 1.00 | 37.73 | C |
| ATOM | 290 | OE1 | GLU | A | 40 | 22.641 | 34.156 | 44.688 | 1.00 | 38.96 | O |
| ATOM | 291 | OE2 | GLU | A | 40 | 23.057 | 32.078 | 44.158 | 1.00 | 37.88 | O |
| ATOM | 292 | N | LYS | A | 41 | 20.851 | 33.905 | 39.822 | 1.00 | 40.49 | N |
| ATOM | 293 | CA | LYS | A | 41 | 21.629 | 33.334 | 38.739 | 1.00 | 41.35 | C |
| ATOM | 294 | C | LYS | A | 41 | 23.048 | 33.579 | 39.224 | 1.00 | 41.89 | C |
| ATOM | 295 | O | LYS | A | 41 | 23.397 | 34.711 | 39.545 | 1.00 | 43.48 | O |
| ATOM | 296 | CB | LYS | A | 41 | 21.376 | 34.082 | 37.426 | 1.00 | 41.18 | C |
| ATOM | 297 | CG | LYS | A | 41 | 22.056 | 33.427 | 36.232 | 1.00 | 41.99 | C |
| ATOM | 298 | CD | LYS | A | 41 | 21.451 | 33.847 | 34.904 | 1.00 | 42.93 | C |
| ATOM | 299 | CE | LYS | A | 41 | 22.060 | 33.042 | 33.751 | 1.00 | 42.44 | C |
| ATOM | 300 | NZ | LYS | A | 41 | 23.532 | 33.264 | 33.631 | 1.00 | 39.72 | N |
| ATOM | 301 | N | LEU | A | 42 | 23.862 | 32.534 | 39.300 | 1.00 | 42.73 | N |
| ATOM | 302 | CA | LEU | A | 42 | 25.230 | 32.685 | 39.792 | 1.00 | 44.77 | C |
| ATOM | 303 | C | LEU | A | 42 | 26.161 | 33.582 | 38.970 | 1.00 | 47.34 | C |
| ATOM | 304 | O | LEU | A | 42 | 27.075 | 34.192 | 39.522 | 1.00 | 48.33 | O |
| ATOM | 305 | CB | LEU | A | 42 | 25.875 | 31.310 | 39.961 | 1.00 | 44.18 | C |
| ATOM | 306 | CG | LEU | A | 42 | 25.597 | 30.528 | 41.250 | 1.00 | 46.39 | C |
| ATOM | 307 | CD1 | LEU | A | 42 | 24.102 | 30.436 | 41.531 | 1.00 | 47.52 | C |
| ATOM | 308 | CD2 | LEU | A | 42 | 26.197 | 29.139 | 41.116 | 1.00 | 45.89 | C |
| ATOM | 309 | N | SER | A | 43 | 25.928 | 33.678 | 37.662 | 1.00 | 50.78 | N |
| ATOM | 310 | CA | SER | A | 43 | 26.784 | 34.485 | 36.781 | 1.00 | 52.46 | C |
| ATOM | 311 | C | SER | A | 43 | 26.719 | 35.984 | 37.034 | 1.00 | 53.08 | C |
| ATOM | 312 | O | SER | A | 43 | 27.706 | 36.692 | 36.858 | 1.00 | 53.09 | O |
| ATOM | 313 | CB | SER | A | 43 | 26.429 | 34.235 | 35.318 | 1.00 | 54.08 | C |
| ATOM | 314 | OG | SER | A | 43 | 25.235 | 34.918 | 34.969 | 1.00 | 57.23 | O |
| ATOM | 315 | N | SER | A | 44 | 25.549 | 36.470 | 37.424 | 1.00 | 53.69 | N |
| ATOM | 316 | CA | SER | A | 44 | 25.384 | 37.890 | 37.691 | 1.00 | 54.44 | C |
| ATOM | 317 | C | SER | A | 44 | 25.152 | 38.117 | 39.174 | 1.00 | 54.36 | C |
| ATOM | 318 | O | SER | A | 44 | 25.174 | 39.256 | 39.642 | 1.00 | 55.26 | O |
| ATOM | 319 | CB | SER | A | 44 | 24.194 | 38.452 | 36.907 | 1.00 | 54.40 | C |
| ATOM | 320 | OG | SER | A | 44 | 22.965 | 37.996 | 37.446 | 1.00 | 52.76 | O |
| ATOM | 321 | N | SER | A | 45 | 24.931 | 37.028 | 39.906 | 1.00 | 54.21 | N |
| ATOM | 322 | CA | SER | A | 45 | 24.670 | 37.100 | 41.339 | 1.00 | 55.36 | C |
| ATOM | 323 | C | SER | A | 45 | 23.398 | 37.942 | 41.581 | 1.00 | 56.77 | C |
| ATOM | 324 | O | SER | A | 45 | 23.005 | 38.211 | 42.726 | 1.00 | 57.29 | O |
| ATOM | 325 | CB | SER | A | 45 | 25.874 | 37.714 | 42.059 | 1.00 | 54.86 | C |
| ATOM | 326 | OG | SER | A | 45 | 25.744 | 37.588 | 43.465 | 1.00 | 55.22 | O |
| ATOM | 327 | N | ARG | A | 46 | 22.760 | 38.338 | 40.481 | 1.00 | 55.68 | N |
| ATOM | 328 | CA | ARG | A | 46 | 21.537 | 39.139 | 40.498 | 1.00 | 54.87 | C |
| ATOM | 329 | C | ARG | A | 46 | 20.390 | 38.198 | 40.850 | 1.00 | 53.65 | C |
| ATOM | 330 | O | ARG | A | 46 | 20.383 | 37.037 | 40.422 | 1.00 | 54.29 | O |
| ATOM | 331 | CB | ARG | A | 46 | 21.323 | 39.748 | 39.115 | 1.00 | 55.68 | C |
| ATOM | 332 | CG | ARG | A | 46 | 20.245 | 40.788 | 39.003 | 1.00 | 58.65 | C |
| ATOM | 333 | CD | ARG | A | 46 | 20.437 | 41.566 | 37.700 | 1.00 | 61.22 | C |
| ATOM | 334 | NE | ARG | A | 46 | 19.379 | 42.543 | 37.445 | 1.00 | 64.20 | N |
| ATOM | 335 | CZ | ARG | A | 46 | 18.099 | 42.231 | 37.259 | 1.00 | 65.46 | C |
| ATOM | 336 | NH1 | ARG | A | 46 | 17.705 | 40.962 | 37.302 | 1.00 | 66.82 | N |
| ATOM | 337 | NH2 | ARG | A | 46 | 17.212 | 43.187 | 37.018 | 1.00 | 65.80 | N |
| ATOM | 338 | N | TYR | A | 47 | 19.424 | 38.693 | 41.621 | 1.00 | 48.93 | N |
| ATOM | 339 | CA | TYR | A | 47 | 18.307 | 37.860 | 42.043 | 1.00 | 44.13 | C |
| ATOM | 340 | C | TYR | A | 47 | 16.954 | 38.548 | 41.921 | 1.00 | 42.46 | C |
| ATOM | 341 | O | TYR | A | 47 | 16.856 | 39.697 | 41.505 | 1.00 | 41.50 | O |
| ATOM | 342 | CB | TYR | A | 47 | 18.521 | 37.419 | 43.498 | 1.00 | 42.44 | C |
| ATOM | 343 | CG | TYR | A | 47 | 18.368 | 38.530 | 44.522 | 1.00 | 40.22 | C |
| ATOM | 344 | CD1 | TYR | A | 47 | 17.100 | 38.955 | 44.938 | 1.00 | 40.83 | C |
| ATOM | 345 | CD2 | TYR | A | 47 | 19.483 | 39.166 | 45.060 | 1.00 | 40.63 | C |
| ATOM | 346 | CE1 | TYR | A | 47 | 16.942 | 39.981 | 45.861 | 1.00 | 39.17 | C |
| ATOM | 347 | CE2 | TYR | A | 47 | 19.343 | 40.205 | 45.993 | 1.00 | 41.62 | C |
| ATOM | 348 | CZ | TYR | A | 47 | 18.064 | 40.607 | 46.389 | 1.00 | 42.71 | C |
| ATOM | 349 | OH | TYR | A | 47 | 17.905 | 41.624 | 47.313 | 1.00 | 40.68 | O |
| ATOM | 350 | N | GLN | A | 48 | 15.913 | 37.812 | 42.287 | 1.00 | 40.15 | N |
| ATOM | 351 | CA | GLN | A | 48 | 14.551 | 38.311 | 42.265 | 1.00 | 40.50 | C |
| ATOM | 352 | C | GLN | A | 48 | 13.897 | 37.659 | 43.481 | 1.00 | 42.10 | C |
| ATOM | 353 | O | GLN | A | 48 | 14.161 | 36.487 | 43.767 | 1.00 | 43.31 | O |
| ATOM | 354 | CB | GLN | A | 48 | 13.834 | 37.885 | 40.979 | 1.00 | 36.35 | C |
| ATOM | 355 | CG | GLN | A | 48 | 13.610 | 36.390 | 40.843 | 1.00 | 35.27 | C |
| ATOM | 356 | CD | GLN | A | 48 | 12.717 | 36.020 | 39.658 | 1.00 | 34.35 | C |

TABLE 2-continued

| | | | | | | | | | | | |
|---|---|---|---|---|---|---|---|---|---|---|---|
| ATOM | 357 | OE1 | GLN | A | 48 | 12.964 | 36.437 | 38.524 | 1.00 | 30.96 | O |
| ATOM | 358 | NE2 | GLN | A | 48 | 11.678 | 35.224 | 39.921 | 1.00 | 30.08 | N |
| ATOM | 359 | N | ASP | A | 49 | 13.064 | 38.407 | 44.203 | 1.00 | 42.67 | N |
| ATOM | 360 | CA | ASP | A | 49 | 12.416 | 37.863 | 45.387 | 1.00 | 42.99 | C |
| ATOM | 361 | C | ASP | A | 49 | 11.067 | 37.201 | 45.143 | 1.00 | 42.96 | C |
| ATOM | 362 | O | ASP | A | 49 | 10.090 | 37.495 | 45.826 | 1.00 | 43.87 | O |
| ATOM | 363 | CB | ASP | A | 49 | 12.274 | 38.941 | 46.463 | 1.00 | 46.87 | C |
| ATOM | 364 | CG | ASP | A | 49 | 13.508 | 39.044 | 47.356 | 1.00 | 53.22 | C |
| ATOM | 365 | OD1 | ASP | A | 49 | 14.113 | 37.990 | 47.653 | 1.00 | 56.74 | O |
| ATOM | 366 | OD2 | ASP | A | 49 | 13.865 | 40.170 | 47.782 | 1.00 | 56.49 | O |
| ATOM | 367 | N | GLN | A | 50 | 11.026 | 36.297 | 44.168 | 1.00 | 43.17 | N |
| ATOM | 368 | CA | GLN | A | 50 | 9.815 | 35.546 | 43.827 | 1.00 | 42.42 | C |
| ATOM | 369 | C | GLN | A | 50 | 10.270 | 34.150 | 43.409 | 1.00 | 40.92 | C |
| ATOM | 370 | O | GLN | A | 50 | 11.393 | 33.974 | 42.938 | 1.00 | 41.96 | O |
| ATOM | 371 | CB | GLN | A | 50 | 9.065 | 36.220 | 42.678 | 1.00 | 43.36 | C |
| ATOM | 372 | CG | GLN | A | 50 | 8.727 | 37.671 | 42.953 | 1.00 | 47.38 | C |
| ATOM | 373 | CD | GLN | A | 50 | 8.339 | 38.436 | 41.701 | 1.00 | 49.06 | C |
| ATOM | 374 | OE1 | GLN | A | 50 | 7.226 | 38.295 | 41.191 | 1.00 | 49.34 | O |
| ATOM | 375 | NE2 | GLN | A | 50 | 9.268 | 39.248 | 41.193 | 1.00 | 49.25 | N |
| ATOM | 376 | N | ALA | A | 51 | 9.394 | 33.167 | 43.567 | 1.00 | 38.06 | N |
| ATOM | 377 | CA | ALA | A | 51 | 9.725 | 31.791 | 43.238 | 1.00 | 36.47 | C |
| ATOM | 378 | C | ALA | A | 51 | 9.690 | 31.415 | 41.758 | 1.00 | 36.25 | C |
| ATOM | 379 | O | ALA | A | 51 | 10.347 | 30.463 | 41.345 | 1.00 | 36.75 | O |
| ATOM | 380 | CB | ALA | A | 51 | 8.814 | 30.853 | 44.023 | 1.00 | 34.79 | C |
| ATOM | 381 | N | VAL | A | 52 | 8.940 | 32.142 | 40.944 | 1.00 | 34.58 | N |
| ATOM | 382 | CA | VAL | A | 52 | 8.869 | 31.765 | 39.544 | 1.00 | 35.03 | C |
| ATOM | 383 | C | VAL | A | 52 | 9.476 | 32.745 | 38.559 | 1.00 | 36.34 | C |
| ATOM | 384 | O | VAL | A | 52 | 9.241 | 33.947 | 38.638 | 1.00 | 36.38 | O |
| ATOM | 385 | CB | VAL | A | 52 | 7.411 | 31.494 | 39.109 | 1.00 | 34.36 | C |
| ATOM | 386 | CG1 | VAL | A | 52 | 7.379 | 31.044 | 37.649 | 1.00 | 34.41 | C |
| ATOM | 387 | CG2 | VAL | A | 52 | 6.789 | 30.441 | 40.004 | 1.00 | 32.40 | C |
| ATOM | 388 | N | LEU | A | 53 | 10.271 | 32.205 | 37.638 | 1.00 | 36.79 | N |
| ATOM | 389 | CA | LEU | A | 53 | 10.902 | 32.988 | 36.581 | 1.00 | 38.89 | C |
| ATOM | 390 | C | LEU | A | 53 | 10.425 | 32.386 | 35.264 | 1.00 | 40.26 | C |
| ATOM | 391 | O | LEU | A | 53 | 10.562 | 31.192 | 35.034 | 1.00 | 40.57 | O |
| ATOM | 392 | CB | LEU | A | 53 | 12.432 | 32.911 | 36.654 | 1.00 | 37.28 | C |
| ATOM | 393 | CG | LEU | A | 53 | 13.179 | 33.484 | 35.434 | 1.00 | 36.25 | C |
| ATOM | 394 | CD1 | LEU | A | 53 | 12.703 | 34.895 | 35.168 | 1.00 | 34.47 | C |
| ATOM | 395 | CD2 | LEU | A | 53 | 14.691 | 33.466 | 35.660 | 1.00 | 33.31 | C |
| ATOM | 396 | N | PHE | A | 54 | 9.834 | 33.208 | 34.411 | 1.00 | 44.05 | N |
| ATOM | 397 | CA | PHE | A | 54 | 9.358 | 32.722 | 33.126 | 1.00 | 45.97 | C |
| ATOM | 398 | C | PHE | A | 54 | 10.245 | 33.266 | 32.028 | 1.00 | 46.61 | C |
| ATOM | 399 | O | PHE | A | 54 | 10.545 | 34.460 | 31.986 | 1.00 | 46.74 | O |
| ATOM | 400 | CB | PHE | A | 54 | 7.921 | 33.170 | 32.863 | 1.00 | 47.72 | C |
| ATOM | 401 | CG | PHE | A | 54 | 7.419 | 32.798 | 31.498 | 1.00 | 49.53 | C |
| ATOM | 402 | CD1 | PHE | A | 54 | 7.126 | 31.474 | 31.188 | 1.00 | 50.51 | C |
| ATOM | 403 | CD2 | PHE | A | 54 | 7.265 | 33.770 | 30.510 | 1.00 | 52.23 | C |
| ATOM | 404 | CE1 | PHE | A | 54 | 6.686 | 31.119 | 29.911 | 1.00 | 51.59 | C |
| ATOM | 405 | CE2 | PHE | A | 54 | 6.825 | 33.429 | 29.224 | 1.00 | 52.07 | C |
| ATOM | 406 | CZ | PHE | A | 54 | 6.536 | 32.100 | 28.926 | 1.00 | 52.46 | C |
| ATOM | 407 | N | ILE | A | 55 | 10.684 | 32.379 | 31.150 | 1.00 | 47.45 | N |
| ATOM | 408 | CA | ILE | A | 55 | 11.511 | 32.783 | 30.033 | 1.00 | 48.36 | C |
| ATOM | 409 | C | ILE | A | 55 | 10.720 | 32.436 | 28.774 | 1.00 | 50.14 | C |
| ATOM | 410 | O | ILE | A | 55 | 10.659 | 31.275 | 28.364 | 1.00 | 51.51 | O |
| ATOM | 411 | CB | ILE | A | 55 | 12.866 | 32.050 | 30.049 | 1.00 | 47.42 | C |
| ATOM | 412 | CG1 | ILE | A | 55 | 13.654 | 32.465 | 31.301 | 1.00 | 48.91 | C |
| ATOM | 413 | CG2 | ILE | A | 55 | 13.646 | 32.363 | 28.786 | 1.00 | 46.22 | C |
| ATOM | 414 | CD1 | ILE | A | 55 | 15.057 | 31.856 | 31.417 | 1.00 | 46.40 | C |
| ATOM | 415 | N | PRO | A | 56 | 10.074 | 33.446 | 28.161 | 1.00 | 50.85 | N |
| ATOM | 416 | CA | PRO | A | 56 | 9.284 | 33.227 | 26.946 | 1.00 | 50.59 | C |
| ATOM | 417 | C | PRO | A | 56 | 10.118 | 32.634 | 25.812 | 1.00 | 50.00 | C |
| ATOM | 418 | O | PRO | A | 56 | 9.685 | 31.711 | 25.129 | 1.00 | 51.30 | O |
| ATOM | 419 | CB | PRO | A | 56 | 8.748 | 34.627 | 26.629 | 1.00 | 49.33 | C |
| ATOM | 420 | CG | PRO | A | 56 | 9.793 | 35.532 | 27.193 | 1.00 | 49.27 | C |
| ATOM | 421 | CD | PRO | A | 56 | 10.112 | 34.880 | 28.508 | 1.00 | 49.80 | C |
| ATOM | 422 | N | ALA | A | 57 | 11.319 | 33.168 | 25.627 | 1.00 | 49.28 | N |
| ATOM | 423 | CA | ALA | A | 57 | 12.218 | 32.693 | 24.587 | 1.00 | 47.75 | C |
| ATOM | 424 | C | ALA | A | 57 | 13.628 | 32.555 | 25.159 | 1.00 | 47.57 | C |
| ATOM | 425 | O | ALA | A | 57 | 14.267 | 33.541 | 25.533 | 1.00 | 47.50 | O |
| ATOM | 426 | CB | ALA | A | 57 | 12.211 | 33.659 | 23.406 | 1.00 | 47.04 | C |
| ATOM | 427 | N | MET | A | 58 | 14.100 | 31.316 | 25.219 | 1.00 | 46.93 | N |
| ATOM | 428 | CA | MET | A | 58 | 15.415 | 30.994 | 25.749 | 1.00 | 47.22 | C |
| ATOM | 429 | C | MET | A | 58 | 16.552 | 31.707 | 25.007 | 1.00 | 47.84 | C |
| ATOM | 430 | O | MET | A | 58 | 16.658 | 31.626 | 23.784 | 1.00 | 48.95 | O |
| ATOM | 431 | CB | MET | A | 58 | 15.608 | 29.475 | 25.692 | 1.00 | 46.57 | C |
| ATOM | 432 | CG | MET | A | 58 | 16.918 | 28.971 | 26.255 | 1.00 | 46.65 | C |
| ATOM | 433 | SD | MET | A | 58 | 17.113 | 29.353 | 27.990 | 1.00 | 47.35 | S |
| ATOM | 434 | CE | MET | A | 58 | 18.894 | 29.486 | 28.106 | 1.00 | 46.29 | C |
| ATOM | 435 | N | LYS | A | 59 | 17.397 | 32.411 | 25.753 | 1.00 | 47.43 | N |
| ATOM | 436 | CA | LYS | A | 59 | 18.529 | 33.119 | 25.163 | 1.00 | 48.57 | C |

TABLE 2-continued

| | | | | | | | | | | | |
|---|---|---|---|---|---|---|---|---|---|---|---|
| ATOM | 437 | C | LYS | A | 59 | 19.846 | 32.562 | 25.682 | 1.00 | 48.47 | C |
| ATOM | 438 | O | LYS | A | 59 | 19.913 | 32.006 | 26.779 | 1.00 | 48.00 | O |
| ATOM | 439 | CB | LYS | A | 59 | 18.453 | 34.623 | 25.459 | 1.00 | 50.26 | C |
| ATOM | 440 | CG | LYS | A | 59 | 17.358 | 35.337 | 24.687 | 1.00 | 52.84 | C |
| ATOM | 441 | CD | LYS | A | 59 | 17.272 | 36.805 | 25.043 | 1.00 | 56.18 | C |
| ATOM | 442 | CE | LYS | A | 59 | 16.178 | 37.494 | 24.229 | 1.00 | 58.39 | C |
| ATOM | 443 | NZ | LYS | A | 59 | 15.939 | 38.902 | 24.663 | 1.00 | 60.23 | N |
| ATOM | 444 | N | ARG | A | 60 | 20.889 | 32.717 | 24.878 | 1.00 | 48.60 | N |
| ATOM | 445 | CA | ARG | A | 60 | 22.216 | 32.232 | 25.218 | 1.00 | 49.42 | C |
| ATOM | 446 | C | ARG | A | 60 | 22.651 | 32.754 | 26.584 | 1.00 | 49.30 | C |
| ATOM | 447 | O | ARG | A | 60 | 23.099 | 31.987 | 27.439 | 1.00 | 50.29 | O |
| ATOM | 448 | CB | ARG | A | 60 | 23.202 | 32.676 | 24.137 | 1.00 | 52.04 | C |
| ATOM | 449 | CG | ARG | A | 60 | 22.706 | 32.380 | 22.720 | 1.00 | 57.97 | C |
| ATOM | 450 | CD | ARG | A | 60 | 23.377 | 33.244 | 21.651 | 1.00 | 60.53 | C |
| ATOM | 451 | NE | ARG | A | 60 | 24.440 | 32.540 | 20.939 | 1.00 | 64.59 | N |
| ATOM | 452 | CZ | ARG | A | 60 | 25.611 | 32.203 | 21.471 | 1.00 | 66.72 | C |
| ATOM | 453 | NH1 | ARG | A | 60 | 25.884 | 32.507 | 22.737 | 1.00 | 67.54 | N |
| ATOM | 454 | NH2 | ARG | A | 60 | 26.515 | 31.565 | 20.733 | 1.00 | 66.76 | N |
| ATOM | 455 | N | SER | A | 61 | 22.500 | 34.059 | 26.788 | 1.00 | 48.75 | N |
| ATOM | 456 | CA | SER | A | 61 | 22.889 | 34.700 | 28.042 | 1.00 | 47.51 | C |
| ATOM | 457 | C | SER | A | 61 | 22.035 | 34.264 | 29.225 | 1.00 | 46.65 | C |
| ATOM | 458 | O | SER | A | 61 | 22.355 | 34.576 | 30.372 | 1.00 | 46.25 | O |
| ATOM | 459 | CB | SER | A | 61 | 22.801 | 36.212 | 27.901 | 1.00 | 46.42 | C |
| ATOM | 460 | OG | SER | A | 61 | 21.474 | 36.588 | 27.580 | 1.00 | 48.36 | O |
| ATOM | 461 | N | LEU | A | 62 | 20.945 | 33.554 | 28.948 | 1.00 | 44.98 | N |
| ATOM | 462 | CA | LEU | A | 62 | 20.063 | 33.088 | 30.009 | 1.00 | 42.71 | C |
| ATOM | 463 | C | LEU | A | 62 | 20.442 | 31.687 | 30.467 | 1.00 | 42.89 | C |
| ATOM | 464 | O | LEU | A | 62 | 19.861 | 31.159 | 31.417 | 1.00 | 43.62 | O |
| ATOM | 465 | CB | LEU | A | 62 | 18.604 | 33.094 | 29.542 | 1.00 | 42.46 | C |
| ATOM | 466 | CG | LEU | A | 62 | 17.898 | 34.441 | 29.333 | 1.00 | 42.16 | C |
| ATOM | 467 | CD1 | LEU | A | 62 | 16.433 | 34.190 | 28.989 | 1.00 | 40.12 | C |
| ATOM | 468 | CD2 | LEU | A | 62 | 18.002 | 35.294 | 30.593 | 1.00 | 39.63 | C |
| ATOM | 469 | N | ALA | A | 63 | 21.405 | 31.076 | 29.783 | 1.00 | 41.51 | N |
| ATOM | 470 | CA | ALA | A | 63 | 21.849 | 29.740 | 30.159 | 1.00 | 40.31 | C |
| ATOM | 471 | C | ALA | A | 63 | 22.768 | 29.920 | 31.349 | 1.00 | 38.78 | C |
| ATOM | 472 | O | ALA | A | 63 | 23.254 | 31.023 | 31.591 | 1.00 | 37.40 | O |
| ATOM | 473 | CB | ALA | A | 63 | 22.598 | 29.087 | 29.019 | 1.00 | 41.16 | C |
| ATOM | 474 | N | GLY | A | 64 | 23.000 | 28.844 | 32.093 | 1.00 | 38.07 | N |
| ATOM | 475 | CA | GLY | A | 64 | 23.869 | 28.925 | 33.255 | 1.00 | 34.77 | C |
| ATOM | 476 | C | GLY | A | 64 | 23.247 | 28.348 | 34.516 | 1.00 | 35.87 | C |
| ATOM | 477 | O | GLY | A | 64 | 22.182 | 27.719 | 34.478 | 1.00 | 34.05 | O |
| ATOM | 478 | N | ARG | A | 65 | 23.916 | 28.575 | 35.644 | 1.00 | 35.75 | N |
| ATOM | 479 | CA | ARG | A | 65 | 23.456 | 28.072 | 36.930 | 1.00 | 36.32 | C |
| ATOM | 480 | C | ARG | A | 65 | 22.507 | 29.002 | 37.695 | 1.00 | 35.62 | C |
| ATOM | 481 | O | ARG | A | 65 | 22.688 | 30.214 | 37.722 | 1.00 | 36.12 | O |
| ATOM | 482 | CB | ARG | A | 65 | 24.663 | 27.749 | 37.805 | 1.00 | 36.14 | C |
| ATOM | 483 | CG | ARG | A | 65 | 25.539 | 26.654 | 37.245 | 1.00 | 39.20 | C |
| ATOM | 484 | CD | ARG | A | 65 | 26.743 | 26.435 | 38.135 | 1.00 | 40.84 | C |
| ATOM | 485 | NE | ARG | A | 65 | 27.683 | 27.548 | 38.049 | 1.00 | 46.60 | N |
| ATOM | 486 | CZ | ARG | A | 65 | 28.566 | 27.852 | 38.998 | 1.00 | 49.97 | C |
| ATOM | 487 | NH1 | ARG | A | 65 | 28.621 | 27.123 | 40.110 | 1.00 | 51.95 | N |
| ATOM | 488 | NH2 | ARG | A | 65 | 29.395 | 28.878 | 38.838 | 1.00 | 48.38 | N |
| ATOM | 489 | N | TYR | A | 66 | 21.488 | 28.412 | 38.312 | 1.00 | 36.03 | N |
| ATOM | 490 | CA | TYR | A | 66 | 20.520 | 29.154 | 39.112 | 1.00 | 35.66 | C |
| ATOM | 491 | C | TYR | A | 66 | 20.399 | 28.471 | 40.474 | 1.00 | 35.44 | C |
| ATOM | 492 | O | TYR | A | 66 | 20.623 | 27.262 | 40.600 | 1.00 | 32.48 | O |
| ATOM | 493 | CB | TYR | A | 66 | 19.139 | 29.195 | 38.439 | 1.00 | 33.94 | C |
| ATOM | 494 | CG | TYR | A | 66 | 19.073 | 30.040 | 37.187 | 1.00 | 35.26 | C |
| ATOM | 495 | CD1 | TYR | A | 66 | 19.664 | 29.607 | 35.997 | 1.00 | 35.29 | C |
| ATOM | 496 | CD2 | TYR | A | 66 | 18.403 | 31.269 | 37.186 | 1.00 | 35.38 | C |
| ATOM | 497 | CE1 | TYR | A | 66 | 19.586 | 30.376 | 34.835 | 1.00 | 38.15 | C |
| ATOM | 498 | CE2 | TYR | A | 66 | 18.318 | 32.049 | 36.031 | 1.00 | 35.82 | C |
| ATOM | 499 | CZ | TYR | A | 66 | 18.913 | 31.597 | 34.861 | 1.00 | 37.67 | C |
| ATOM | 500 | OH | TYR | A | 66 | 18.865 | 32.361 | 33.721 | 1.00 | 36.06 | O |
| ATOM | 501 | N | ARG | A | 67 | 20.023 | 29.250 | 41.484 | 1.00 | 33.50 | N |
| ATOM | 502 | CA | ARG | A | 67 | 19.898 | 28.736 | 42.829 | 1.00 | 33.44 | C |
| ATOM | 503 | C | ARG | A | 67 | 18.835 | 29.543 | 43.560 | 1.00 | 34.55 | C |
| ATOM | 504 | O | ARG | A | 67 | 18.542 | 30.677 | 43.194 | 1.00 | 33.17 | O |
| ATOM | 505 | CB | ARG | A | 67 | 21.261 | 28.863 | 43.513 | 1.00 | 35.35 | C |
| ATOM | 506 | CG | ARG | A | 67 | 21.391 | 28.297 | 44.917 | 1.00 | 35.74 | C |
| ATOM | 507 | CD | ARG | A | 67 | 22.847 | 28.419 | 45.384 | 1.00 | 34.82 | C |
| ATOM | 508 | NE | ARG | A | 67 | 23.412 | 29.753 | 45.142 | 1.00 | 34.51 | N |
| ATOM | 509 | CZ | ARG | A | 67 | 24.720 | 30.023 | 45.130 | 1.00 | 36.05 | C |
| ATOM | 510 | NH1 | ARG | A | 67 | 25.606 | 29.056 | 45.354 | 1.00 | 35.08 | N |
| ATOM | 511 | NH2 | ARG | A | 67 | 25.151 | 31.247 | 44.863 | 1.00 | 33.21 | N |
| ATOM | 512 | N | CYS | A | 68 | 18.237 | 28.963 | 44.591 | 1.00 | 36.11 | N |
| ATOM | 513 | CA | CYS | A | 68 | 17.231 | 29.708 | 45.324 | 1.00 | 36.23 | C |
| ATOM | 514 | C | CYS | A | 68 | 17.143 | 29.295 | 46.779 | 1.00 | 34.77 | C |
| ATOM | 515 | O | CYS | A | 68 | 17.493 | 28.167 | 47.151 | 1.00 | 32.91 | O |
| ATOM | 516 | CB | CYS | A | 68 | 15.852 | 29.574 | 44.646 | 1.00 | 38.97 | C |

TABLE 2-continued

| | | | | | | | | | | |
|---|---|---|---|---|---|---|---|---|---|---|
| ATOM | 517 | SG | CYS | A | 68 | 14.977 | 27.974 | 44.819 | 1.00 | 43.57 | S |
| ATOM | 518 | N | SER | A | 69 | 16.697 | 30.244 | 47.597 | 1.00 | 34.26 | N |
| ATOM | 519 | CA | SER | A | 69 | 16.496 | 30.041 | 49.027 | 1.00 | 32.89 | C |
| ATOM | 520 | C | SER | A | 69 | 15.223 | 30.764 | 49.427 | 1.00 | 31.99 | C |
| ATOM | 521 | O | SER | A | 69 | 14.726 | 31.621 | 48.698 | 1.00 | 31.96 | O |
| ATOM | 522 | CB | SER | A | 69 | 17.665 | 30.614 | 49.834 | 1.00 | 32.13 | C |
| ATOM | 523 | OG | SER | A | 69 | 18.824 | 29.818 | 49.706 | 1.00 | 33.70 | O |
| ATOM | 524 | N | TYR | A | 70 | 14.680 | 30.413 | 50.582 | 1.00 | 32.97 | N |
| ATOM | 525 | CA | TYR | A | 70 | 13.488 | 31.090 | 51.062 | 1.00 | 32.08 | C |
| ATOM | 526 | C | TYR | A | 70 | 13.722 | 31.525 | 52.496 | 1.00 | 34.30 | C |
| ATOM | 527 | O | TYR | A | 70 | 14.528 | 30.923 | 53.223 | 1.00 | 32.97 | O |
| ATOM | 528 | CB | TYR | A | 70 | 12.254 | 30.181 | 50.976 | 1.00 | 30.90 | C |
| ATOM | 529 | CG | TYR | A | 70 | 12.342 | 28.912 | 51.792 | 1.00 | 28.11 | C |
| ATOM | 530 | CD1 | TYR | A | 70 | 12.878 | 27.741 | 51.255 | 1.00 | 27.08 | C |
| ATOM | 531 | CD2 | TYR | A | 70 | 11.900 | 28.890 | 53.106 | 1.00 | 27.48 | C |
| ATOM | 532 | CE1 | TYR | A | 70 | 12.964 | 26.572 | 52.018 | 1.00 | 26.37 | C |
| ATOM | 533 | CE2 | TYR | A | 70 | 11.983 | 27.740 | 53.873 | 1.00 | 28.63 | C |
| ATOM | 534 | CZ | TYR | A | 70 | 12.513 | 26.586 | 53.330 | 1.00 | 26.47 | C |
| ATOM | 535 | OH | TYR | A | 70 | 12.588 | 25.463 | 54.125 | 1.00 | 28.38 | O |
| ATOM | 536 | N | GLN | A | 71 | 13.027 | 32.584 | 52.896 | 1.00 | 36.17 | N |
| ATOM | 537 | CA | GLN | A | 71 | 13.146 | 33.101 | 54.250 | 1.00 | 39.39 | C |
| ATOM | 538 | C | GLN | A | 71 | 11.792 | 33.030 | 54.960 | 1.00 | 42.07 | C |
| ATOM | 539 | O | GLN | A | 71 | 10.820 | 33.647 | 54.519 | 1.00 | 43.73 | O |
| ATOM | 540 | CB | GLN | A | 71 | 13.632 | 34.553 | 54.215 | 1.00 | 38.37 | C |
| ATOM | 541 | CG | GLN | A | 71 | 14.301 | 35.009 | 55.505 | 1.00 | 40.71 | C |
| ATOM | 542 | CD | GLN | A | 71 | 14.639 | 36.489 | 55.519 | 1.00 | 39.69 | C |
| ATOM | 543 | OE1 | GLN | A | 71 | 15.440 | 36.939 | 56.331 | 1.00 | 41.69 | O |
| ATOM | 544 | NE2 | GLN | A | 71 | 14.023 | 37.251 | 54.628 | 1.00 | 43.75 | N |
| ATOM | 545 | N | ASN | A | 72 | 11.713 | 32.260 | 56.040 | 1.00 | 44.13 | N |
| ATOM | 546 | CA | ASN | A | 72 | 10.469 | 32.169 | 56.796 | 1.00 | 47.20 | C |
| ATOM | 547 | C | ASN | A | 72 | 10.764 | 32.776 | 58.153 | 1.00 | 49.17 | C |
| ATOM | 548 | O | ASN | A | 72 | 11.674 | 32.333 | 58.858 | 1.00 | 50.48 | O |
| ATOM | 549 | CB | ASN | A | 72 | 10.018 | 30.730 | 56.976 | 1.00 | 49.67 | C |
| ATOM | 550 | CG | ASN | A | 72 | 8.616 | 30.643 | 57.531 | 1.00 | 53.91 | C |
| ATOM | 551 | OD1 | ASN | A | 72 | 8.308 | 29.781 | 58.362 | 1.00 | 55.73 | O |
| ATOM | 552 | ND2 | ASN | A | 72 | 7.749 | 31.540 | 57.070 | 1.00 | 53.55 | N |
| ATOM | 553 | N | GLY | A | 73 | 9.990 | 33.781 | 58.535 | 1.00 | 49.93 | N |
| ATOM | 554 | CA | GLY | A | 73 | 10.273 | 34.444 | 59.790 | 1.00 | 51.94 | C |
| ATOM | 555 | C | GLY | A | 73 | 11.516 | 35.238 | 59.439 | 1.00 | 52.46 | C |
| ATOM | 556 | O | GLY | A | 73 | 11.486 | 36.038 | 58.501 | 1.00 | 54.47 | O |
| ATOM | 557 | N | SER | A | 74 | 12.612 | 35.019 | 60.154 | 1.00 | 51.39 | N |
| ATOM | 558 | CA | SER | A | 74 | 13.843 | 35.730 | 59.832 | 1.00 | 50.19 | C |
| ATOM | 559 | C | SER | A | 74 | 14.915 | 34.697 | 59.528 | 1.00 | 49.05 | C |
| ATOM | 560 | O | SER | A | 74 | 16.081 | 35.036 | 59.331 | 1.00 | 49.81 | O |
| ATOM | 561 | CB | SER | A | 74 | 14.302 | 36.600 | 61.002 | 1.00 | 50.65 | C |
| ATOM | 562 | OG | SER | A | 74 | 14.955 | 35.816 | 61.987 | 1.00 | 52.99 | O |
| ATOM | 563 | N | LEU | A | 75 | 14.509 | 33.432 | 59.488 | 1.00 | 46.78 | N |
| ATOM | 564 | CA | LEU | A | 75 | 15.440 | 32.345 | 59.227 | 1.00 | 44.10 | C |
| ATOM | 565 | C | LEU | A | 75 | 15.540 | 31.968 | 57.751 | 1.00 | 41.29 | C |
| ATOM | 566 | O | LEU | A | 75 | 14.532 | 31.866 | 57.055 | 1.00 | 41.53 | O |
| ATOM | 567 | CB | LEU | A | 75 | 15.033 | 31.101 | 60.025 | 1.00 | 44.88 | C |
| ATOM | 568 | CG | LEU | A | 75 | 14.920 | 31.150 | 61.551 | 1.00 | 45.09 | C |
| ATOM | 569 | CD1 | LEU | A | 75 | 14.461 | 29.789 | 62.028 | 1.00 | 44.50 | C |
| ATOM | 570 | CD2 | LEU | A | 75 | 16.254 | 31.507 | 62.198 | 1.00 | 44.43 | C |
| ATOM | 571 | N | TRP | A | 76 | 16.768 | 31.762 | 57.283 | 1.00 | 37.58 | N |
| ATOM | 572 | CA | TRP | A | 76 | 17.010 | 31.355 | 55.906 | 1.00 | 34.46 | C |
| ATOM | 573 | C | TRP | A | 76 | 17.068 | 29.840 | 55.835 | 1.00 | 34.34 | C |
| ATOM | 574 | O | TRP | A | 76 | 17.255 | 29.160 | 56.848 | 1.00 | 33.43 | O |
| ATOM | 575 | CB | TRP | A | 76 | 18.331 | 31.922 | 55.382 | 1.00 | 32.31 | C |
| ATOM | 576 | CG | TRP | A | 76 | 18.210 | 33.329 | 54.926 | 1.00 | 33.41 | C |
| ATOM | 577 | CD1 | TRP | A | 76 | 18.568 | 34.456 | 55.612 | 1.00 | 31.26 | C |
| ATOM | 578 | CD2 | TRP | A | 76 | 17.640 | 33.772 | 53.693 | 1.00 | 32.98 | C |
| ATOM | 579 | NE1 | TRP | A | 76 | 18.251 | 35.575 | 54.880 | 1.00 | 30.99 | N |
| ATOM | 580 | CE2 | TRP | A | 76 | 17.680 | 35.184 | 53.697 | 1.00 | 33.15 | C |
| ATOM | 581 | CE3 | TRP | A | 76 | 17.095 | 33.112 | 52.582 | 1.00 | 32.76 | C |
| ATOM | 582 | CZ2 | TRP | A | 76 | 17.198 | 35.950 | 52.629 | 1.00 | 33.35 | C |
| ATOM | 583 | CZ3 | TRP | A | 76 | 16.615 | 33.873 | 51.521 | 1.00 | 32.91 | C |
| ATOM | 584 | CH2 | TRP | A | 76 | 16.672 | 35.280 | 51.554 | 1.00 | 32.34 | C |
| ATOM | 585 | N | SER | A | 77 | 16.912 | 29.318 | 54.626 | 1.00 | 33.46 | N |
| ATOM | 586 | CA | SER | A | 77 | 16.952 | 27.882 | 54.393 | 1.00 | 32.01 | C |
| ATOM | 587 | C | SER | A | 77 | 18.271 | 27.582 | 53.730 | 1.00 | 31.41 | C |
| ATOM | 588 | O | SER | A | 77 | 18.934 | 28.487 | 53.229 | 1.00 | 29.92 | O |
| ATOM | 589 | CB | SER | A | 77 | 15.835 | 27.468 | 53.438 | 1.00 | 30.61 | C |
| ATOM | 590 | OG | SER | A | 77 | 16.023 | 28.071 | 52.155 | 1.00 | 30.27 | O |
| ATOM | 591 | N | LEU | A | 78 | 18.660 | 26.315 | 53.733 | 1.00 | 32.01 | N |
| ATOM | 592 | CA | LEU | A | 78 | 19.884 | 25.939 | 53.052 | 1.00 | 31.48 | C |
| ATOM | 593 | C | LEU | A | 78 | 19.532 | 26.302 | 51.608 | 1.00 | 31.37 | C |
| ATOM | 594 | O | LEU | A | 78 | 18.345 | 26.407 | 51.269 | 1.00 | 29.32 | O |
| ATOM | 595 | CB | LEU | A | 78 | 20.134 | 24.440 | 53.193 | 1.00 | 29.42 | C |
| ATOM | 596 | CG | LEU | A | 78 | 20.251 | 23.936 | 54.639 | 1.00 | 30.75 | C |

TABLE 2-continued

| | | | | | | | | | | | |
|---|---|---|---|---|---|---|---|---|---|---|---|
| ATOM | 597 | CD1 | LEU | A | 78 | 20.426 | 22.426 | 54.650 | 1.00 | 28.45 | C |
| ATOM | 598 | CD2 | LEU | A | 78 | 21.435 | 24.606 | 55.332 | 1.00 | 28.78 | C |
| ATOM | 599 | N | PRO | A | 79 | 20.544 | 26.535 | 50.752 | 1.00 | 30.45 | N |
| ATOM | 600 | CA | PRO | A | 79 | 20.272 | 26.887 | 49.357 | 1.00 | 29.21 | C |
| ATOM | 601 | C | PRO | A | 79 | 19.825 | 25.654 | 48.585 | 1.00 | 30.07 | C |
| ATOM | 602 | O | PRO | A | 79 | 20.242 | 24.542 | 48.915 | 1.00 | 28.80 | O |
| ATOM | 603 | CB | PRO | A | 79 | 21.613 | 27.420 | 48.881 | 1.00 | 27.28 | C |
| ATOM | 604 | CG | PRO | A | 79 | 22.579 | 26.562 | 49.633 | 1.00 | 26.60 | C |
| ATOM | 605 | CD | PRO | A | 79 | 21.995 | 26.523 | 51.018 | 1.00 | 28.42 | C |
| ATOM | 606 | N | SER | A | 80 | 18.973 | 25.836 | 47.577 | 1.00 | 29.26 | N |
| ATOM | 607 | CA | SER | A | 80 | 18.517 | 24.690 | 46.791 | 1.00 | 30.42 | C |
| ATOM | 608 | C | SER | A | 80 | 19.706 | 24.196 | 46.007 | 1.00 | 30.66 | C |
| ATOM | 609 | O | SER | A | 80 | 20.740 | 24.865 | 45.949 | 1.00 | 31.82 | O |
| ATOM | 610 | CB | SER | A | 80 | 17.426 | 25.082 | 45.788 | 1.00 | 30.12 | C |
| ATOM | 611 | OG | SER | A | 80 | 17.982 | 25.792 | 44.688 | 1.00 | 31.17 | O |
| ATOM | 612 | N | ASP | A | 81 | 19.566 | 23.016 | 45.418 | 1.00 | 32.95 | N |
| ATOM | 613 | CA | ASP | A | 81 | 20.626 | 22.475 | 44.587 | 1.00 | 33.94 | C |
| ATOM | 614 | C | ASP | A | 81 | 20.673 | 23.405 | 43.389 | 1.00 | 34.67 | C |
| ATOM | 615 | O | ASP | A | 81 | 19.671 | 24.036 | 43.045 | 1.00 | 35.97 | O |
| ATOM | 616 | CB | ASP | A | 81 | 20.291 | 21.061 | 44.109 | 1.00 | 32.96 | C |
| ATOM | 617 | CG | ASP | A | 81 | 20.410 | 20.031 | 45.208 | 1.00 | 34.99 | C |
| ATOM | 618 | OD1 | ASP | A | 81 | 21.137 | 20.298 | 46.190 | 1.00 | 32.41 | O |
| ATOM | 619 | OD2 | ASP | A | 81 | 19.789 | 18.950 | 45.079 | 1.00 | 37.82 | O |
| ATOM | 620 | N | GLN | A | 82 | 21.833 | 23.497 | 42.757 | 1.00 | 36.07 | N |
| ATOM | 621 | CA | GLN | A | 82 | 21.983 | 24.357 | 41.597 | 1.00 | 36.17 | C |
| ATOM | 622 | C | GLN | A | 82 | 21.218 | 23.787 | 40.400 | 1.00 | 34.51 | C |
| ATOM | 623 | O | GLN | A | 82 | 21.231 | 22.583 | 40.152 | 1.00 | 32.73 | O |
| ATOM | 624 | CB | GLN | A | 82 | 23.475 | 24.524 | 41.278 | 1.00 | 37.74 | C |
| ATOM | 625 | CG | GLN | A | 82 | 24.207 | 25.350 | 42.338 | 1.00 | 45.98 | C |
| ATOM | 626 | CD | GLN | A | 82 | 25.728 | 25.267 | 42.247 | 1.00 | 50.85 | C |
| ATOM | 627 | OE1 | GLN | A | 82 | 26.325 | 25.562 | 41.205 | 1.00 | 52.48 | O |
| ATOM | 628 | NE2 | GLN | A | 82 | 26.364 | 24.872 | 43.351 | 1.00 | 52.90 | N |
| ATOM | 629 | N | LEU | A | 83 | 20.509 | 24.657 | 39.691 | 1.00 | 34.25 | N |
| ATOM | 630 | CA | LEU | A | 83 | 19.765 | 24.250 | 38.506 | 1.00 | 33.95 | C |
| ATOM | 631 | C | LEU | A | 83 | 20.645 | 24.716 | 37.359 | 1.00 | 34.00 | C |
| ATOM | 632 | O | LEU | A | 83 | 21.021 | 25.893 | 37.294 | 1.00 | 31.52 | O |
| ATOM | 633 | CB | LEU | A | 83 | 18.391 | 24.940 | 38.454 | 1.00 | 34.85 | C |
| ATOM | 634 | CG | LEU | A | 83 | 17.344 | 24.594 | 37.368 | 1.00 | 37.20 | C |
| ATOM | 635 | CD1 | LEU | A | 83 | 17.692 | 25.232 | 36.035 | 1.00 | 36.69 | C |
| ATOM | 636 | CD2 | LEU | A | 83 | 17.246 | 23.096 | 37.215 | 1.00 | 36.48 | C |
| ATOM | 637 | N | GLU | A | 84 | 21.005 | 23.783 | 36.481 | 1.00 | 33.45 | N |
| ATOM | 638 | CA | GLU | A | 84 | 21.847 | 24.099 | 35.334 | 1.00 | 33.81 | C |
| ATOM | 639 | C | GLU | A | 84 | 20.975 | 24.285 | 34.095 | 1.00 | 33.82 | C |
| ATOM | 640 | O | GLU | A | 84 | 20.643 | 23.319 | 33.406 | 1.00 | 34.73 | O |
| ATOM | 641 | CB | GLU | A | 84 | 22.856 | 22.973 | 35.107 | 1.00 | 35.20 | C |
| ATOM | 642 | CG | GLU | A | 84 | 23.553 | 22.520 | 36.380 | 1.00 | 40.56 | C |
| ATOM | 643 | CD | GLU | A | 84 | 24.639 | 21.497 | 36.129 | 1.00 | 43.89 | C |
| ATOM | 644 | OE1 | GLU | A | 84 | 25.743 | 21.885 | 35.690 | 1.00 | 46.61 | O |
| ATOM | 645 | OE2 | GLU | A | 84 | 24.386 | 20.298 | 36.364 | 1.00 | 49.53 | O |
| ATOM | 646 | N | LEU | A | 85 | 20.587 | 25.528 | 33.828 | 1.00 | 32.84 | N |
| ATOM | 647 | CA | LEU | A | 85 | 19.755 | 25.827 | 32.672 | 1.00 | 32.86 | C |
| ATOM | 648 | C | LEU | A | 85 | 20.625 | 25.776 | 31.415 | 1.00 | 33.20 | C |
| ATOM | 649 | O | LEU | A | 85 | 21.542 | 26.588 | 31.240 | 1.00 | 32.62 | O |
| ATOM | 650 | CB | LEU | A | 85 | 19.121 | 27.208 | 32.827 | 1.00 | 30.55 | C |
| ATOM | 651 | CG | LEU | A | 85 | 17.902 | 27.454 | 31.936 | 1.00 | 31.78 | C |
| ATOM | 652 | CD1 | LEU | A | 85 | 16.818 | 26.398 | 32.220 | 1.00 | 27.87 | C |
| ATOM | 653 | CD2 | LEU | A | 85 | 17.367 | 28.862 | 32.199 | 1.00 | 30.81 | C |
| ATOM | 654 | N | VAL | A | 86 | 20.330 | 24.815 | 30.545 | 1.00 | 34.28 | N |
| ATOM | 655 | CA | VAL | A | 86 | 21.100 | 24.623 | 29.318 | 1.00 | 34.06 | C |
| ATOM | 656 | C | VAL | A | 86 | 20.383 | 25.115 | 28.070 | 1.00 | 35.59 | C |
| ATOM | 657 | O | VAL | A | 86 | 19.181 | 24.910 | 27.911 | 1.00 | 36.81 | O |
| ATOM | 658 | CB | VAL | A | 86 | 21.414 | 23.121 | 29.113 | 1.00 | 36.33 | C |
| ATOM | 659 | CG1 | VAL | A | 86 | 22.250 | 22.913 | 27.845 | 1.00 | 33.73 | C |
| ATOM | 660 | CG2 | VAL | A | 86 | 22.106 | 22.557 | 30.356 | 1.00 | 32.81 | C |
| ATOM | 661 | N | ALA | A | 87 | 21.128 | 25.769 | 27.187 | 1.00 | 36.51 | N |
| ATOM | 662 | CA | ALA | A | 87 | 20.582 | 26.243 | 25.920 | 1.00 | 36.59 | C |
| ATOM | 663 | C | ALA | A | 87 | 21.090 | 25.292 | 24.827 | 1.00 | 36.85 | C |
| ATOM | 664 | O | ALA | A | 87 | 22.299 | 25.136 | 24.649 | 1.00 | 35.69 | O |
| ATOM | 665 | CB | ALA | A | 87 | 21.053 | 27.666 | 25.636 | 1.00 | 36.89 | C |
| ATOM | 666 | N | THR | A | 88 | 20.164 | 24.641 | 24.123 | 1.00 | 37.07 | N |
| ATOM | 667 | CA | THR | A | 88 | 20.524 | 23.723 | 23.046 | 1.00 | 36.28 | C |
| ATOM | 668 | C | THR | A | 88 | 20.221 | 24.408 | 21.718 | 1.00 | 37.73 | C |
| ATOM | 669 | O | THR | A | 88 | 19.390 | 25.328 | 21.640 | 1.00 | 36.08 | O |
| ATOM | 670 | CB | THR | A | 88 | 19.716 | 22.408 | 23.094 | 1.00 | 37.11 | C |
| ATOM | 671 | OG1 | THR | A | 88 | 18.355 | 22.670 | 22.734 | 1.00 | 40.73 | O |
| ATOM | 672 | CG2 | THR | A | 88 | 19.750 | 21.801 | 24.484 | 1.00 | 34.19 | C |
| ATOM | 673 | N | GLY | A | 89 | 20.898 | 23.953 | 20.673 | 1.00 | 37.63 | N |
| ATOM | 674 | CA | GLY | A | 89 | 20.703 | 24.532 | 19.363 | 1.00 | 36.54 | C |
| ATOM | 675 | C | GLY | A | 89 | 21.611 | 25.727 | 19.195 | 1.00 | 36.33 | C |
| ATOM | 676 | O | GLY | A | 89 | 21.334 | 26.608 | 18.387 | 1.00 | 37.37 | O |

TABLE 2-continued

| | | | | | | | | | | |
|---|---|---|---|---|---|---|---|---|---|---|
| ATOM | 677 | N | VAL | A | 90 | 22.692 | 25.767 | 19.964 | 1.00 | 34.75 | N |
| ATOM | 678 | CA | VAL | A | 90 | 23.627 | 26.877 | 19.878 | 1.00 | 36.82 | C |
| ATOM | 679 | C | VAL | A | 90 | 24.683 | 26.613 | 18.814 | 1.00 | 38.27 | C |
| ATOM | 680 | O | VAL | A | 90 | 25.295 | 27.541 | 18.285 | 1.00 | 37.79 | O |
| ATOM | 681 | CB | VAL | A | 90 | 24.316 | 27.124 | 21.231 | 1.00 | 36.86 | C |
| ATOM | 682 | CG1 | VAL | A | 90 | 25.440 | 28.131 | 21.079 | 1.00 | 36.51 | C |
| ATOM | 683 | CG2 | VAL | A | 90 | 23.297 | 27.625 | 22.231 | 1.00 | 36.33 | C |
| ATOM | 684 | N | PHE | A | 91 | 24.878 | 25.337 | 18.496 | 1.00 | 39.84 | N |
| ATOM | 685 | CA | PHE | A | 91 | 25.855 | 24.929 | 17.495 | 1.00 | 39.69 | C |
| ATOM | 686 | C | PHE | A | 91 | 25.239 | 23.905 | 16.563 | 1.00 | 39.97 | C |
| ATOM | 687 | O | PHE | A | 91 | 24.156 | 23.374 | 16.833 | 1.00 | 40.06 | O |
| ATOM | 688 | CB | PHE | A | 91 | 27.064 | 24.306 | 18.181 | 1.00 | 41.06 | C |
| ATOM | 689 | CG | PHE | A | 91 | 27.650 | 25.165 | 19.248 | 1.00 | 45.64 | C |
| ATOM | 690 | CD1 | PHE | A | 91 | 28.353 | 26.318 | 18.920 | 1.00 | 47.20 | C |
| ATOM | 691 | CD2 | PHE | A | 91 | 27.495 | 24.831 | 20.586 | 1.00 | 47.80 | C |
| ATOM | 692 | CE1 | PHE | A | 91 | 28.895 | 27.128 | 19.911 | 1.00 | 48.30 | C |
| ATOM | 693 | CE2 | PHE | A | 91 | 28.033 | 25.635 | 21.584 | 1.00 | 49.88 | C |
| ATOM | 694 | CZ | PHE | A | 91 | 28.734 | 26.787 | 21.246 | 1.00 | 49.48 | C |
| ATOM | 695 | N | ALA | A | 92 | 25.943 | 23.624 | 15.471 | 1.00 | 39.46 | N |
| ATOM | 696 | CA | ALA | A | 92 | 25.495 | 22.638 | 14.496 | 1.00 | 38.27 | C |
| ATOM | 697 | C | ALA | A | 92 | 25.477 | 21.278 | 15.173 | 1.00 | 37.48 | C |
| ATOM | 698 | O | ALA | A | 92 | 26.419 | 20.912 | 15.870 | 1.00 | 37.07 | O |
| ATOM | 699 | CB | ALA | A | 92 | 26.436 | 22.614 | 13.311 | 1.00 | 38.81 | C |
| ATOM | 700 | N | LYS | A | 93 | 24.396 | 20.538 | 14.963 | 1.00 | 37.09 | N |
| ATOM | 701 | CA | LYS | A | 93 | 24.221 | 19.219 | 15.556 | 1.00 | 37.36 | C |
| ATOM | 702 | C | LYS | A | 93 | 25.330 | 18.236 | 15.177 | 1.00 | 37.95 | C |
| ATOM | 703 | O | LYS | A | 93 | 25.854 | 18.271 | 14.064 | 1.00 | 40.00 | O |
| ATOM | 704 | CB | LYS | A | 93 | 22.880 | 18.632 | 15.109 | 1.00 | 36.45 | C |
| ATOM | 705 | CG | LYS | A | 93 | 22.804 | 18.387 | 13.617 | 1.00 | 34.19 | C |
| ATOM | 706 | CD | LYS | A | 93 | 21.501 | 17.736 | 13.232 | 1.00 | 35.79 | C |
| ATOM | 707 | CE | LYS | A | 93 | 21.336 | 17.687 | 11.717 | 1.00 | 38.64 | C |
| ATOM | 708 | NZ | LYS | A | 93 | 20.028 | 17.101 | 11.306 | 1.00 | 40.23 | N |
| ATOM | 709 | N | PRO | A | 94 | 25.718 | 17.354 | 16.109 | 1.00 | 36.28 | N |
| ATOM | 710 | CA | PRO | A | 94 | 26.766 | 16.396 | 15.751 | 1.00 | 35.49 | C |
| ATOM | 711 | C | PRO | A | 94 | 26.077 | 15.225 | 15.056 | 1.00 | 35.71 | C |
| ATOM | 712 | O | PRO | A | 94 | 24.846 | 15.222 | 14.908 | 1.00 | 33.82 | O |
| ATOM | 713 | CB | PRO | A | 94 | 27.353 | 16.005 | 17.105 | 1.00 | 34.75 | C |
| ATOM | 714 | CG | PRO | A | 94 | 26.164 | 16.040 | 17.995 | 1.00 | 32.91 | C |
| ATOM | 715 | CD | PRO | A | 94 | 25.449 | 17.321 | 17.558 | 1.00 | 35.55 | C |
| ATOM | 716 | N | SER | A | 95 | 26.858 | 14.240 | 14.626 | 1.00 | 34.49 | N |
| ATOM | 717 | CA | SER | A | 95 | 26.294 | 13.072 | 13.979 | 1.00 | 33.34 | C |
| ATOM | 718 | C | SER | A | 95 | 26.581 | 11.847 | 14.825 | 1.00 | 32.98 | C |
| ATOM | 719 | O | SER | A | 95 | 27.721 | 11.584 | 15.199 | 1.00 | 33.16 | O |
| ATOM | 720 | CB | SER | A | 95 | 26.859 | 12.914 | 12.567 | 1.00 | 37.77 | C |
| ATOM | 721 | OG | SER | A | 95 | 28.267 | 13.047 | 12.563 | 1.00 | 46.35 | O |
| ATOM | 722 | N | LEU | A | 96 | 25.521 | 11.105 | 15.125 | 1.00 | 32.83 | N |
| ATOM | 723 | CA | LEU | A | 96 | 25.586 | 9.908 | 15.953 | 1.00 | 30.98 | C |
| ATOM | 724 | C | LEU | A | 96 | 25.614 | 8.619 | 15.126 | 1.00 | 30.36 | C |
| ATOM | 725 | O | LEU | A | 96 | 24.748 | 8.390 | 14.291 | 1.00 | 29.22 | O |
| ATOM | 726 | CB | LEU | A | 96 | 24.379 | 9.906 | 16.902 | 1.00 | 30.85 | C |
| ATOM | 727 | CG | LEU | A | 96 | 24.165 | 8.777 | 17.910 | 1.00 | 30.98 | C |
| ATOM | 728 | CD1 | LEU | A | 96 | 25.417 | 8.597 | 18.759 | 1.00 | 32.84 | C |
| ATOM | 729 | CD2 | LEU | A | 96 | 22.968 | 9.115 | 18.802 | 1.00 | 32.70 | C |
| ATOM | 730 | N | SER | A | 97 | 26.614 | 7.775 | 15.361 | 1.00 | 30.24 | N |
| ATOM | 731 | CA | SER | A | 97 | 26.715 | 6.524 | 14.627 | 1.00 | 30.38 | C |
| ATOM | 732 | C | SER | A | 97 | 27.099 | 5.390 | 15.553 | 1.00 | 33.14 | C |
| ATOM | 733 | O | SER | A | 97 | 27.611 | 5.621 | 16.648 | 1.00 | 33.20 | O |
| ATOM | 734 | CB | SER | A | 97 | 27.749 | 6.636 | 13.507 | 1.00 | 30.12 | C |
| ATOM | 735 | OG | SER | A | 97 | 29.036 | 6.936 | 14.011 | 1.00 | 29.03 | O |
| ATOM | 736 | N | ALA | A | 98 | 26.823 | 4.165 | 15.116 | 1.00 | 35.13 | N |
| ATOM | 737 | CA | ALA | A | 98 | 27.161 | 2.981 | 15.889 | 1.00 | 37.77 | C |
| ATOM | 738 | C | ALA | A | 98 | 28.562 | 2.553 | 15.481 | 1.00 | 38.73 | C |
| ATOM | 739 | O | ALA | A | 98 | 28.945 | 2.678 | 14.322 | 1.00 | 40.05 | O |
| ATOM | 740 | CB | ALA | A | 98 | 26.168 | 1.863 | 15.604 | 1.00 | 37.56 | C |
| ATOM | 741 | N | GLN | A | 99 | 29.331 | 2.062 | 16.439 | 1.00 | 41.22 | N |
| ATOM | 742 | CA | GLN | A | 99 | 30.687 | 1.617 | 16.164 | 1.00 | 44.62 | C |
| ATOM | 743 | C | GLN | A | 99 | 30.794 | 0.106 | 16.326 | 1.00 | 45.05 | C |
| ATOM | 744 | O | GLN | A | 99 | 30.053 | −0.505 | 17.093 | 1.00 | 43.74 | O |
| ATOM | 745 | CB | GLN | A | 99 | 31.667 | 2.319 | 17.104 | 1.00 | 45.98 | C |
| ATOM | 746 | CG | GLN | A | 99 | 31.713 | 3.832 | 16.919 | 1.00 | 50.14 | C |
| ATOM | 747 | CD | GLN | A | 99 | 32.265 | 4.235 | 15.562 | 1.00 | 53.05 | C |
| ATOM | 748 | OE1 | GLN | A | 99 | 33.348 | 3.799 | 15.171 | 1.00 | 55.27 | O |
| ATOM | 749 | NE2 | GLN | A | 99 | 31.525 | 5.073 | 14.838 | 1.00 | 51.64 | N |
| ATOM | 750 | N | PRO | A | 100 | 31.727 | −0.517 | 15.599 | 1.00 | 46.07 | N |
| ATOM | 751 | CA | PRO | A | 100 | 31.927 | −1.967 | 15.666 | 1.00 | 46.03 | C |
| ATOM | 752 | C | PRO | A | 100 | 32.283 | −2.471 | 17.056 | 1.00 | 44.15 | C |
| ATOM | 753 | O | PRO | A | 100 | 33.120 | −1.888 | 17.733 | 1.00 | 45.12 | O |
| ATOM | 754 | CB | PRO | A | 100 | 33.050 | −2.210 | 14.654 | 1.00 | 47.20 | C |
| ATOM | 755 | CG | PRO | A | 100 | 33.829 | −0.928 | 14.694 | 1.00 | 48.59 | C |
| ATOM | 756 | CD | PRO | A | 100 | 32.730 | 0.115 | 14.724 | 1.00 | 47.87 | C |

TABLE 2-continued

| | | | | | | | | | | |
|---|---|---|---|---|---|---|---|---|---|---|
| ATOM | 757 | N | GLY | A | 101 | 31.636 | −3.552 | 17.478 | 1.00 | 44.40 | N |
| ATOM | 758 | CA | GLY | A | 101 | 31.924 | −4.125 | 18.783 | 1.00 | 46.25 | C |
| ATOM | 759 | C | GLY | A | 101 | 32.770 | −5.378 | 18.648 | 1.00 | 47.05 | C |
| ATOM | 760 | O | GLY | A | 101 | 32.889 | −5.910 | 17.550 | 1.00 | 46.79 | O |
| ATOM | 761 | N | PRO | A | 102 | 33.384 | −5.876 | 19.731 | 1.00 | 48.92 | N |
| ATOM | 762 | CA | PRO | A | 102 | 34.197 | −7.089 | 19.580 | 1.00 | 50.65 | C |
| ATOM | 763 | C | PRO | A | 102 | 33.386 | −8.302 | 19.135 | 1.00 | 51.50 | C |
| ATOM | 764 | O | PRO | A | 102 | 32.262 | −8.515 | 19.591 | 1.00 | 48.93 | O |
| ATOM | 765 | CB | PRO | A | 102 | 34.835 | −7.262 | 20.961 | 1.00 | 50.45 | C |
| ATOM | 766 | CG | PRO | A | 102 | 33.891 | −6.560 | 21.874 | 1.00 | 50.94 | C |
| ATOM | 767 | CD | PRO | A | 102 | 33.488 | −5.339 | 21.095 | 1.00 | 49.51 | C |
| ATOM | 768 | N | ALA | A | 103 | 33.971 | −9.080 | 18.229 | 1.00 | 54.06 | N |
| ATOM | 769 | CA | ALA | A | 103 | 33.329 | −10.270 | 17.676 | 1.00 | 57.29 | C |
| ATOM | 770 | C | ALA | A | 103 | 32.886 | −11.261 | 18.747 | 1.00 | 59.40 | C |
| ATOM | 771 | O | ALA | A | 103 | 31.910 | −11.985 | 18.565 | 1.00 | 60.71 | O |
| ATOM | 772 | CB | ALA | A | 103 | 34.272 | −10.957 | 16.685 | 1.00 | 57.06 | C |
| ATOM | 773 | N | VAL | A | 104 | 33.605 | −11.299 | 19.860 | 1.00 | 61.39 | N |
| ATOM | 774 | CA | VAL | A | 104 | 33.252 | −12.203 | 20.940 | 1.00 | 65.15 | C |
| ATOM | 775 | C | VAL | A | 104 | 32.233 | −11.493 | 21.841 | 1.00 | 66.48 | C |
| ATOM | 776 | O | VAL | A | 104 | 31.973 | −10.304 | 21.665 | 1.00 | 67.47 | O |
| ATOM | 777 | CB | VAL | A | 104 | 34.511 | −12.604 | 21.750 | 1.00 | 66.47 | C |
| ATOM | 778 | CG1 | VAL | A | 104 | 34.972 | −11.435 | 22.619 | 1.00 | 67.09 | C |
| ATOM | 779 | CG2 | VAL | A | 104 | 34.225 | −13.849 | 22.582 | 1.00 | 67.98 | C |
| ATOM | 780 | N | SER | A | 105 | 31.657 | −12.216 | 22.797 | 1.00 | 67.85 | N |
| ATOM | 781 | CA | SER | A | 105 | 30.660 | −11.638 | 23.697 | 1.00 | 69.86 | C |
| ATOM | 782 | C | SER | A | 105 | 31.082 | −10.268 | 24.238 | 1.00 | 71.04 | C |
| ATOM | 783 | O | SER | A | 105 | 32.275 | −9.976 | 24.353 | 1.00 | 71.90 | O |
| ATOM | 784 | CB | SER | A | 105 | 30.386 | −12.591 | 24.867 | 1.00 | 68.81 | C |
| ATOM | 785 | OG | SER | A | 105 | 29.262 | −12.156 | 25.614 | 1.00 | 65.88 | O |
| ATOM | 786 | N | SER | A | 106 | 30.100 | −9.431 | 24.570 | 1.00 | 71.39 | N |
| ATOM | 787 | CA | SER | A | 106 | 30.394 | −8.098 | 25.090 | 1.00 | 71.25 | C |
| ATOM | 788 | C | SER | A | 106 | 29.433 | −7.637 | 26.195 | 1.00 | 70.10 | C |
| ATOM | 789 | O | SER | A | 106 | 29.501 | −6.493 | 26.643 | 1.00 | 69.80 | O |
| ATOM | 790 | CB | SER | A | 106 | 30.393 | −7.081 | 23.944 | 1.00 | 71.68 | C |
| ATOM | 791 | OG | SER | A | 106 | 30.968 | −5.854 | 24.357 | 1.00 | 72.39 | O |
| ATOM | 792 | N | GLY | A | 107 | 28.546 | −8.530 | 26.629 | 1.00 | 68.65 | N |
| ATOM | 793 | CA | GLY | A | 107 | 27.604 | −8.198 | 27.688 | 1.00 | 65.20 | C |
| ATOM | 794 | C | GLY | A | 107 | 26.628 | −7.069 | 27.398 | 1.00 | 63.24 | C |
| ATOM | 795 | O | GLY | A | 107 | 26.363 | −6.232 | 28.262 | 1.00 | 62.37 | O |
| ATOM | 796 | N | GLY | A | 108 | 26.086 | −7.040 | 26.186 | 1.00 | 61.45 | N |
| ATOM | 797 | CA | GLY | A | 108 | 25.137 | −6.000 | 25.836 | 1.00 | 60.53 | C |
| ATOM | 798 | C | GLY | A | 108 | 25.756 | −4.634 | 25.579 | 1.00 | 59.27 | C |
| ATOM | 799 | O | GLY | A | 108 | 25.053 | −3.697 | 25.188 | 1.00 | 58.91 | O |
| ATOM | 800 | N | ASP | A | 109 | 27.061 | −4.506 | 25.808 | 1.00 | 56.39 | N |
| ATOM | 801 | CA | ASP | A | 109 | 27.739 | −3.238 | 25.573 | 1.00 | 53.46 | C |
| ATOM | 802 | C | ASP | A | 109 | 27.481 | −2.775 | 24.148 | 1.00 | 50.24 | C |
| ATOM | 803 | O | ASP | A | 109 | 27.337 | −3.589 | 23.237 | 1.00 | 49.64 | O |
| ATOM | 804 | CB | ASP | A | 109 | 29.248 | −3.381 | 25.789 | 1.00 | 54.43 | C |
| ATOM | 805 | CG | ASP | A | 109 | 29.629 | −3.407 | 27.253 | 1.00 | 55.56 | C |
| ATOM | 806 | OD1 | ASP | A | 109 | 28.708 | −3.414 | 28.101 | 1.00 | 56.20 | O |
| ATOM | 807 | OD2 | ASP | A | 109 | 30.848 | −3.420 | 27.550 | 1.00 | 54.70 | O |
| ATOM | 808 | N | VAL | A | 110 | 7.4062 | −1.461 | 23.971 | 1.00 | 47.84 | N |
| ATOM | 809 | CA | VAL | A | 110 | 27.185 | −0.851 | 22.658 | 1.00 | 44.51 | C |
| ATOM | 810 | C | VAL | A | 110 | 28.009 | 0.429 | 22.615 | 1.00 | 41.04 | C |
| ATOM | 811 | O | VAL | A | 110 | 27.969 | 1.230 | 23.541 | 1.00 | 39.49 | O |
| ATOM | 812 | CB | VAL | A | 110 | 25.693 | −0.488 | 22.425 | 1.00 | 44.38 | C |
| ATOM | 813 | CG1 | VAL | A | 110 | 25.544 | 0.269 | 21.119 | 1.00 | 44.92 | C |
| ATOM | 814 | CG2 | VAL | A | 110 | 24.842 | −1.752 | 22.385 | 1.00 | 44.42 | C |
| ATOM | 815 | N | THR | A | 111 | 28.768 | 0.611 | 21.544 | 1.00 | 38.79 | N |
| ATOM | 816 | CA | THR | A | 111 | 29.593 | 1.797 | 21.406 | 1.00 | 34.46 | C |
| ATOM | 817 | C | THR | A | 111 | 29.018 | 2.716 | 20.355 | 1.00 | 32.73 | C |
| ATOM | 818 | O | THR | A | 111 | 28.788 | 2.310 | 19.224 | 1.00 | 29.50 | O |
| ATOM | 819 | CB | THR | A | 111 | 31.024 | 1.439 | 21.000 | 1.00 | 34.45 | C |
| ATOM | 820 | OG1 | THR | A | 111 | 31.602 | 0.604 | 22.012 | 1.00 | 37.92 | O |
| ATOM | 821 | CG2 | THR | A | 111 | 31.873 | 2.704 | 20.849 | 1.00 | 34.66 | C |
| ATOM | 822 | N | LEU | A | 112 | 28.767 | 3.957 | 20.746 | 1.00 | 31.45 | N |
| ATOM | 823 | CA | LEU | A | 112 | 28.241 | 4.945 | 19.829 | 1.00 | 31.16 | C |
| ATOM | 824 | C | LEU | A | 112 | 29.278 | 6.055 | 19.692 | 1.00 | 31.87 | C |
| ATOM | 825 | O | LEU | A | 112 | 30.099 | 6.266 | 20.589 | 1.00 | 30.87 | O |
| ATOM | 826 | CB | LEU | A | 112 | 26.928 | 5.515 | 20.362 | 1.00 | 31.16 | C |
| ATOM | 827 | CG | LEU | A | 112 | 25.784 | 4.530 | 20.658 | 1.00 | 33.27 | C |
| ATOM | 828 | CD1 | LEU | A | 112 | 24.524 | 5.323 | 21.052 | 1.00 | 30.61 | C |
| ATOM | 829 | CD2 | LEU | A | 112 | 25.492 | 3.659 | 19.427 | 1.00 | 29.56 | C |
| ATOM | 830 | N | GLN | A | 113 | 29.260 | 6.749 | 18.562 | 1.00 | 32.28 | N |
| ATOM | 831 | CA | GLN | A | 113 | 30.194 | 7.850 | 18.342 | 1.00 | 31.23 | C |
| ATOM | 832 | C | GLN | A | 113 | 29.418 | 9.129 | 18.098 | 1.00 | 29.93 | C |
| ATOM | 833 | O | GLN | A | 113 | 28.521 | 9.173 | 17.248 | 1.00 | 28.95 | O |
| ATOM | 834 | CB | GLN | A | 113 | 31.094 | 7.570 | 17.135 | 1.00 | 32.30 | C |
| ATOM | 835 | CG | GLN | A | 113 | 32.126 | 8.661 | 16.852 | 1.00 | 34.40 | C |
| ATOM | 836 | CD | GLN | A | 113 | 32.968 | 8.363 | 15.616 | 1.00 | 37.32 | C |

TABLE 2-continued

| | | | | | | | | | | |
|---|---|---|---|---|---|---|---|---|---|---|
| ATOM | 837 | OE1 | GLN | A | 113 | 32.632 | 8.774 | 14.505 | 1.00 | 40.75 | O |
| ATOM | 838 | NE2 | GLN | A | 113 | 34.056 | 7.629 | 15.804 | 1.00 | 38.14 | N |
| ATOM | 839 | N | CYS | A | 114 | 29.747 | 10.162 | 18.863 | 1.00 | 30.63 | N |
| ATOM | 840 | CA | CYS | A | 114 | 29.101 | 11.452 | 18.707 | 1.00 | 34.04 | C |
| ATOM | 841 | C | CYS | A | 114 | 30.154 | 12.345 | 18.069 | 1.00 | 36.19 | C |
| ATOM | 842 | O | CYS | A | 114 | 30.998 | 12.912 | 18.759 | 1.00 | 35.54 | O |
| ATOM | 843 | CB | CYS | A | 114 | 28.657 | 12.003 | 20.060 | 1.00 | 33.21 | C |
| ATOM | 844 | SG | CYS | A | 114 | 27.592 | 13.482 | 19.911 | 1.00 | 34.65 | S |
| ATOM | 845 | N | GLN | A | 115 | 30.098 | 12.455 | 16.745 | 1.00 | 39.55 | N |
| ATOM | 846 | CA | GLN | A | 115 | 31.081 | 13.223 | 15.991 | 1.00 | 44.93 | C |
| ATOM | 847 | C | GLN | A | 115 | 30.691 | 14.617 | 15.553 | 1.00 | 46.86 | C |
| ATOM | 848 | O | GLN | A | 115 | 29.678 | 14.819 | 14.893 | 1.00 | 46.91 | O |
| ATOM | 849 | CB | GLN | A | 115 | 31.524 | 12.426 | 14.761 | 1.00 | 47.47 | C |
| ATOM | 850 | CG | GLN | A | 115 | 32.404 | 13.202 | 13.795 | 1.00 | 51.63 | C |
| ATOM | 851 | CD | GLN | A | 115 | 32.736 | 12.404 | 12.547 | 1.00 | 54.20 | C |
| ATOM | 852 | OE1 | GLN | A | 115 | 33.584 | 11.509 | 12.574 | 1.00 | 56.59 | O |
| ATOM | 853 | NE2 | GLN | A | 115 | 32.056 | 12.714 | 11.447 | 1.00 | 53.04 | N |
| ATOM | 854 | N | THR | A | 116 | 31.534 | 15.570 | 15.923 | 1.00 | 50.64 | N |
| ATOM | 855 | CA | THR | A | 116 | 31.356 | 16.974 | 15.581 | 1.00 | 55.43 | C |
| ATOM | 856 | C | THR | A | 116 | 32.749 | 17.463 | 15.195 | 1.00 | 58.52 | C |
| ATOM | 857 | O | THR | A | 116 | 33.718 | 16.724 | 15.353 | 1.00 | 59.65 | O |
| ATOM | 858 | CB | THR | A | 116 | 30.840 | 17.768 | 16.796 | 1.00 | 56.06 | C |
| ATOM | 859 | OG1 | THR | A | 116 | 30.726 | 19.154 | 16.449 | 1.00 | 58.03 | O |
| ATOM | 860 | CG2 | THR | A | 116 | 31.783 | 17.605 | 17.979 | 1.00 | 52.57 | C |
| ATOM | 861 | N | ARG | A | 117 | 32.878 | 18.681 | 14.683 | 1.00 | 63.02 | N |
| ATOM | 862 | CA | ARG | A | 117 | 34.215 | 19.144 | 14.324 | 1.00 | 67.76 | C |
| ATOM | 863 | C | ARG | A | 117 | 34.647 | 20.430 | 15.021 | 1.00 | 68.99 | C |
| ATOM | 864 | O | ARG | A | 117 | 35.822 | 20.805 | 14.960 | 1.00 | 70.47 | O |
| ATOM | 865 | CB | ARG | A | 117 | 34.351 | 19.298 | 12.801 | 1.00 | 70.81 | C |
| ATOM | 866 | CG | ARG | A | 117 | 35.809 | 19.302 | 12.334 | 1.00 | 74.35 | C |
| ATOM | 867 | CD | ARG | A | 117 | 35.963 | 18.991 | 10.850 | 1.00 | 76.88 | C |
| ATOM | 868 | NE | ARG | A | 117 | 37.378 | 18.921 | 10.476 | 1.00 | 80.96 | N |
| ATOM | 869 | CZ | ARG | A | 117 | 37.832 | 18.668 | 9.248 | 1.00 | 81.03 | C |
| ATOM | 870 | NH1 | ARG | A | 117 | 36.985 | 18.454 | 8.248 | 1.00 | 81.45 | N |
| ATOM | 871 | NH2 | ARG | A | 117 | 39.140 | 18.638 | 9.020 | 1.00 | 79.59 | N |
| ATOM | 872 | N | TYR | A | 118 | 33.707 | 21.092 | 15.694 | 1.00 | 69.11 | N |
| ATOM | 873 | CA | TYR | A | 118 | 33.997 | 22.338 | 16.410 | 1.00 | 68.84 | C |
| ATOM | 874 | C | TYR | A | 118 | 35.221 | 22.214 | 17.327 | 1.00 | 68.24 | C |
| ATOM | 875 | O | TYR | A | 118 | 35.807 | 23.217 | 17.737 | 1.00 | 69.13 | O |
| ATOM | 876 | CB | TYR | A | 118 | 32.789 | 22.760 | 17.259 | 1.00 | 68.53 | C |
| ATOM | 877 | CG | TYR | A | 118 | 31.623 | 23.364 | 16.494 | 1.00 | 68.16 | C |
| ATOM | 878 | CD1 | TYR | A | 118 | 31.728 | 24.620 | 15.898 | 1.00 | 66.95 | C |
| ATOM | 879 | CD2 | TYR | A | 118 | 30.396 | 22.699 | 16.414 | 1.00 | 67.66 | C |
| ATOM | 880 | CE1 | TYR | A | 118 | 30.636 | 25.203 | 15.249 | 1.00 | 66.11 | C |
| ATOM | 881 | CE2 | TYR | A | 118 | 29.302 | 23.270 | 15.766 | 1.00 | 66.16 | C |
| ATOM | 882 | CZ | TYR | A | 118 | 29.426 | 24.522 | 15.188 | 1.00 | 65.72 | C |
| ATOM | 883 | OH | TYR | A | 118 | 28.337 | 25.095 | 14.564 | 1.00 | 63.03 | O |
| ATOM | 884 | N | GLY | A | 119 | 35.602 | 20.983 | 17.647 | 1.00 | 67.26 | N |
| ATOM | 885 | CA | GLY | A | 119 | 36.730 | 20.770 | 18.535 | 1.00 | 64.40 | C |
| ATOM | 886 | C | GLY | A | 119 | 36.262 | 20.702 | 19.982 | 1.00 | 62.33 | C |
| ATOM | 887 | O | GLY | A | 119 | 37.064 | 20.843 | 20.910 | 1.00 | 64.13 | O |
| ATOM | 888 | N | PHE | A | 120 | 34.961 | 20.483 | 20.175 | 1.00 | 57.70 | N |
| ATOM | 889 | CA | PHE | A | 120 | 34.374 | 20.402 | 21.510 | 1.00 | 52.21 | C |
| ATOM | 890 | C | PHE | A | 120 | 34.933 | 19.244 | 22.323 | 1.00 | 48.15 | C |
| ATOM | 891 | O | PHE | A | 120 | 35.418 | 18.265 | 21.766 | 1.00 | 48.97 | O |
| ATOM | 892 | CB | PHE | A | 120 | 32.853 | 20.288 | 21.411 | 1.00 | 52.96 | C |
| ATOM | 893 | CG | PHE | A | 120 | 32.190 | 21.521 | 20.869 | 1.00 | 54.64 | C |
| ATOM | 894 | CD1 | PHE | A | 120 | 32.790 | 22.773 | 21.010 | 1.00 | 55.67 | C |
| ATOM | 895 | CD2 | PHE | A | 120 | 30.950 | 21.442 | 20.244 | 1.00 | 57.25 | C |
| ATOM | 896 | CE1 | PHE | A | 120 | 32.160 | 23.930 | 20.534 | 1.00 | 57.52 | C |
| ATOM | 897 | CE2 | PHE | A | 120 | 30.308 | 22.592 | 19.764 | 1.00 | 57.97 | C |
| ATOM | 898 | CZ | PHE | A | 120 | 30.915 | 23.839 | 19.910 | 1.00 | 58.31 | C |
| ATOM | 899 | N | ASP | A | 121 | 34.849 | 19.351 | 23.644 | 1.00 | 44.10 | N |
| ATOM | 900 | CA | ASP | A | 121 | 35.395 | 18.323 | 24.521 | 1.00 | 41.01 | C |
| ATOM | 901 | C | ASP | A | 121 | 34.387 | 17.727 | 25.498 | 1.00 | 39.84 | C |
| ATOM | 902 | O | ASP | A | 121 | 34.764 | 17.128 | 26.499 | 1.00 | 41.13 | O |
| ATOM | 903 | CB | ASP | A | 121 | 36.562 | 18.909 | 25.310 | 1.00 | 38.52 | C |
| ATOM | 904 | CG | ASP | A | 121 | 36.104 | 19.897 | 26.362 | 1.00 | 38.95 | C |
| ATOM | 905 | OD1 | ASP | A | 121 | 34.940 | 20.359 | 26.271 | 1.00 | 38.56 | O |
| ATOM | 906 | OD2 | ASP | A | 121 | 36.904 | 20.216 | 27.271 | 1.00 | 37.45 | O |
| ATOM | 907 | N | GLN | A | 122 | 33.107 | 17.891 | 25.228 | 1.00 | 37.82 | N |
| ATOM | 908 | CA | GLN | A | 122 | 32.110 | 17.331 | 26.120 | 1.00 | 38.02 | C |
| ATOM | 909 | C | GLN | A | 122 | 30.958 | 16.787 | 25.292 | 1.00 | 38.39 | C |
| ATOM | 910 | O | GLN | A | 122 | 30.546 | 17.398 | 24.307 | 1.00 | 40.52 | O |
| ATOM | 911 | CB | GLN | A | 122 | 31.634 | 18.397 | 27.105 | 1.00 | 39.33 | C |
| ATOM | 912 | CG | GLN | A | 122 | 32.675 | 18.761 | 28.157 | 1.00 | 40.99 | C |
| ATOM | 913 | CD | GLN | A | 122 | 32.769 | 17.720 | 29.260 | 1.00 | 43.10 | C |
| ATOM | 914 | OE1 | GLN | A | 122 | 31.898 | 17.641 | 30.127 | 1.00 | 47.15 | O |
| ATOM | 915 | NE2 | GLN | A | 122 | 33.815 | 16.907 | 29.224 | 1.00 | 42.14 | N |
| ATOM | 916 | N | PHE | A | 123 | 30.449 | 15.628 | 25.684 | 1.00 | 36.42 | N |

TABLE 2-continued

| | | | | | | | | | | |
|---|---|---|---|---|---|---|---|---|---|---|
| ATOM | 917 | CA | PHE | A | 123 | 29.370 | 15.004 | 24.948 | 1.00 | 36.68 | C |
| ATOM | 918 | C | PHE | A | 123 | 28.305 | 14.455 | 25.873 | 1.00 | 36.67 | C |
| ATOM | 919 | O | PHE | A | 123 | 28.605 | 13.856 | 26.896 | 1.00 | 37.81 | O |
| ATOM | 920 | CB | PHE | A | 123 | 29.924 | 13.875 | 24.074 | 1.00 | 36.21 | C |
| ATOM | 921 | CG | PHE | A | 123 | 31.104 | 14.286 | 23.238 | 1.00 | 36.09 | C |
| ATOM | 922 | CD1 | PHE | A | 123 | 32.376 | 14.377 | 23.803 | 1.00 | 34.80 | C |
| ATOM | 923 | CD2 | PHE | A | 123 | 30.937 | 14.638 | 21.899 | 1.00 | 35.65 | C |
| ATOM | 924 | CE1 | PHE | A | 123 | 33.465 | 14.813 | 23.055 | 1.00 | 31.85 | C |
| ATOM | 925 | CE2 | PHE | A | 123 | 32.018 | 15.075 | 21.142 | 1.00 | 34.13 | C |
| ATOM | 926 | CZ | PHE | A | 123 | 33.284 | 15.163 | 21.723 | 1.00 | 34.38 | C |
| ATOM | 927 | N | ALA | A | 124 | 27.051 | 14.666 | 25.510 | 1.00 | 35.78 | N |
| ATOM | 928 | CA | ALA | A | 124 | 25.961 | 14.161 | 26.314 | 1.00 | 35.02 | C |
| ATOM | 929 | C | ALA | A | 124 | 25.133 | 13.272 | 25.417 | 1.00 | 34.92 | C |
| ATOM | 930 | O | ALA | A | 124 | 24.517 | 13.732 | 24.465 | 1.00 | 35.69 | O |
| ATOM | 931 | CB | ALA | A | 124 | 25.118 | 15.312 | 26.844 | 1.00 | 35.11 | C |
| ATOM | 932 | N | LEU | A | 125 | 25.128 | 11.989 | 25.716 | 1.00 | 33.89 | N |
| ATOM | 933 | CA | LEU | A | 125 | 24.367 | 11.038 | 24.924 | 1.00 | 35.58 | C |
| ATOM | 934 | C | LEU | A | 125 | 23.135 | 10.606 | 25.704 | 1.00 | 37.95 | C |
| ATOM | 935 | O | LEU | A | 125 | 23.199 | 10.420 | 26.926 | 1.00 | 37.76 | O |
| ATOM | 936 | CB | LEU | A | 125 | 25.236 | 9.817 | 24.619 | 1.00 | 33.63 | C |
| ATOM | 937 | CG | LEU | A | 125 | 24.523 | 8.567 | 24.119 | 1.00 | 34.49 | C |
| ATOM | 938 | CD1 | LEU | A | 125 | 23.913 | 8.815 | 22.750 | 1.00 | 34.80 | C |
| ATOM | 939 | CD2 | LEU | A | 125 | 25.529 | 7.427 | 24.054 | 1.00 | 35.30 | C |
| ATOM | 940 | N | TYR | A | 126 | 22.003 | 10.458 | 25.026 | 1.00 | 38.39 | N |
| ATOM | 941 | CA | TYR | A | 126 | 20.827 | 10.014 | 25.753 | 1.00 | 40.68 | C |
| ATOM | 942 | C | TYR | A | 126 | 19.834 | 9.172 | 24.967 | 1.00 | 40.47 | C |
| ATOM | 943 | O | TYR | A | 126 | 19.668 | 9.305 | 23.754 | 1.00 | 39.03 | O |
| ATOM | 944 | CB | TYR | A | 126 | 20.107 | 11.203 | 26.416 | 1.00 | 40.84 | C |
| ATOM | 945 | CG | TYR | A | 126 | 19.072 | 11.907 | 25.562 | 1.00 | 43.26 | C |
| ATOM | 946 | CD1 | TYR | A | 126 | 19.443 | 12.682 | 24.467 | 1.00 | 44.00 | C |
| ATOM | 947 | CD2 | TYR | A | 126 | 17.714 | 11.802 | 25.861 | 1.00 | 45.53 | C |
| ATOM | 948 | CE1 | TYR | A | 126 | 18.485 | 13.336 | 23.689 | 1.00 | 45.48 | C |
| ATOM | 949 | CE2 | TYR | A | 126 | 16.749 | 12.450 | 25.095 | 1.00 | 45.13 | C |
| ATOM | 950 | CZ | TYR | A | 126 | 17.139 | 13.214 | 24.011 | 1.00 | 45.98 | C |
| ATOM | 951 | OH | TYR | A | 126 | 16.182 | 13.842 | 23.240 | 1.00 | 47.24 | O |
| ATOM | 952 | N | LYS | A | 127 | 19.207 | 8.263 | 25.696 | 1.00 | 43.00 | N |
| ATOM | 953 | CA | LYS | A | 127 | 18.191 | 7.389 | 25.153 | 1.00 | 45.17 | C |
| ATOM | 954 | C | LYS | A | 127 | 16.863 | 8.022 | 25.551 | 1.00 | 47.19 | C |
| ATOM | 955 | O | LYS | A | 127 | 16.598 | 8.234 | 26.735 | 1.00 | 44.93 | O |
| ATOM | 956 | CB | LYS | A | 127 | 18.287 | 5.996 | 25.769 | 1.00 | 44.85 | C |
| ATOM | 957 | CG | LYS | A | 127 | 17.015 | 5.186 | 25.584 | 1.00 | 44.80 | C |
| ATOM | 958 | CD | LYS | A | 127 | 16.901 | 4.076 | 26.601 | 1.00 | 45.02 | C |
| ATOM | 959 | CE | LYS | A | 127 | 15.439 | 3.818 | 26.925 | 1.00 | 47.23 | C |
| ATOM | 960 | NZ | LYS | A | 127 | 14.764 | 5.050 | 27.451 | 1.00 | 46.07 | N |
| ATOM | 961 | N | GLU | A | 128 | 16.048 | 8.342 | 24.555 | 1.00 | 50.47 | N |
| ATOM | 962 | CA | GLU | A | 128 | 14.747 | 8.929 | 24.802 | 1.00 | 55.42 | C |
| ATOM | 963 | C | GLU | A | 128 | 13.895 | 7.966 | 25.616 | 1.00 | 57.21 | C |
| ATOM | 964 | O | GLU | A | 128 | 13.965 | 6.747 | 25.435 | 1.00 | 56.72 | O |
| ATOM | 965 | CB | GLU | A | 128 | 14.043 | 9.231 | 23.481 | 1.00 | 56.79 | C |
| ATOM | 966 | CG | GLU | A | 128 | 14.542 | 10.477 | 22.780 | 1.00 | 61.95 | C |
| ATOM | 967 | CD | GLU | A | 128 | 13.968 | 10.609 | 21.386 | 1.00 | 64.50 | C |
| ATOM | 968 | OE1 | GLU | A | 128 | 12.779 | 10.257 | 21.206 | 1.00 | 64.51 | O |
| ATOM | 969 | OE2 | GLU | A | 128 | 14.702 | 11.067 | 20.478 | 1.00 | 64.33 | O |
| ATOM | 970 | N | GLY | A | 129 | 13.097 | 8.525 | 26.515 | 1.00 | 59.19 | N |
| ATOM | 971 | CA | GLY | A | 129 | 12.226 | 7.709 | 27.327 | 1.00 | 63.88 | C |
| ATOM | 972 | C | GLY | A | 129 | 10.802 | 7.873 | 26.839 | 1.00 | 67.81 | C |
| ATOM | 973 | O | GLY | A | 129 | 10.244 | 8.967 | 26.903 | 1.00 | 69.11 | O |
| ATOM | 974 | N | ASP | A | 130 | 10.218 | 6.792 | 26.335 | 1.00 | 70.85 | N |
| ATOM | 975 | CA | ASP | A | 130 | 8.844 | 6.823 | 25.844 | 1.00 | 73.82 | C |
| ATOM | 976 | C | ASP | A | 130 | 7.843 | 6.884 | 27.004 | 1.00 | 75.00 | C |
| ATOM | 977 | O | ASP | A | 130 | 8.124 | 6.408 | 28.105 | 1.00 | 74.29 | O |
| ATOM | 978 | CB | ASP | A | 130 | 8.571 | 5.588 | 24.974 | 1.00 | 74.95 | C |
| ATOM | 979 | CG | ASP | A | 130 | 9.288 | 4.344 | 25.481 | 1.00 | 76.54 | C |
| ATOM | 980 | OD1 | ASP | A | 130 | 10.534 | 4.292 | 25.380 | 1.00 | 76.21 | O |
| ATOM | 981 | OD2 | ASP | A | 130 | 8.609 | 3.421 | 25.984 | 1.00 | 77.14 | O |
| ATOM | 982 | N | PRO | A | 131 | 6.664 | 7.491 | 26.772 | 1.00 | 76.14 | N |
| ATOM | 983 | CA | PRO | A | 131 | 5.620 | 7.614 | 27.795 | 1.00 | 76.71 | C |
| ATOM | 984 | C | PRO | A | 131 | 4.814 | 6.327 | 28.001 | 1.00 | 77.71 | C |
| ATOM | 985 | O | PRO | A | 131 | 5.099 | 5.298 | 27.380 | 1.00 | 77.97 | O |
| ATOM | 986 | CB | PRO | A | 131 | 4.766 | 8.762 | 27.266 | 1.00 | 76.62 | C |
| ATOM | 987 | CG | PRO | A | 131 | 4.841 | 8.560 | 25.794 | 1.00 | 75.47 | C |
| ATOM | 988 | CD | PRO | A | 131 | 6.306 | 8.269 | 25.571 | 1.00 | 75.94 | C |
| ATOM | 989 | N | ALA | A | 132 | 3.813 | 6.395 | 28.880 | 1.00 | 78.98 | N |
| ATOM | 990 | CA | ALA | A | 132 | 2.949 | 5.250 | 29.181 | 1.00 | 79.98 | C |
| ATOM | 991 | C | ALA | A | 132 | 1.948 | 5.007 | 28.050 | 1.00 | 80.88 | C |
| ATOM | 992 | O | ALA | A | 132 | 1.711 | 5.892 | 27.221 | 1.00 | 81.43 | O |
| ATOM | 993 | CB | ALA | A | 132 | 2.209 | 5.491 | 30.492 | 1.00 | 79.92 | C |
| ATOM | 994 | N | PRO | A | 133 | 1.307 | 3.823 | 28.019 | 1.00 | 81.31 | N |
| ATOM | 995 | CA | PRO | A | 133 | 1.366 | 2.646 | 28.899 | 1.00 | 81.90 | C |
| ATOM | 996 | C | PRO | A | 133 | 2.703 | 1.905 | 28.969 | 1.00 | 82.36 | C |

TABLE 2-continued

| | | | | | | | | | | |
|---|---|---|---|---|---|---|---|---|---|---|
| ATOM | 997 | O | PRO | A | 133 | 2.734 | 0.701 | 29.242 | 1.00 | 82.84 | O |
| ATOM | 998 | CB | PRO | A | 133 | 0.265 | 1.739 | 28.341 | 1.00 | 81.84 | C |
| ATOM | 999 | CG | PRO | A | 133 | −0.667 | 2.687 | 27.662 | 1.00 | 82.09 | C |
| ATOM | 1000 | CD | PRO | A | 133 | 0.284 | 3.624 | 26.979 | 1.00 | 81.54 | C |
| ATOM | 1001 | N | TYR | A | 134 | 3.803 | 2.613 | 28.738 | 1.00 | 81.85 | N |
| ATOM | 1002 | CA | TYR | A | 134 | 5.116 | 1.980 | 28.767 | 1.00 | 81.17 | C |
| ATOM | 1003 | C | TYR | A | 134 | 6.073 | 2.679 | 29.724 | 1.00 | 79.59 | C |
| ATOM | 1004 | O | TYR | A | 134 | 6.902 | 2.035 | 30.369 | 1.00 | 79.58 | O |
| ATOM | 1005 | CB | TYR | A | 134 | 5.676 | 1.955 | 27.349 | 1.00 | 82.82 | C |
| ATOM | 1006 | CG | TYR | A | 134 | 4.700 | 1.323 | 26.383 | 1.00 | 83.68 | C |
| ATOM | 1007 | CD1 | TYR | A | 134 | 4.486 | −0.057 | 26.385 | 1.00 | 83.92 | C |
| ATOM | 1008 | CD2 | TYR | A | 134 | 3.934 | 2.109 | 25.517 | 1.00 | 83.49 | C |
| ATOM | 1009 | CE1 | TYR | A | 134 | 3.529 | −0.641 | 25.552 | 1.00 | 83.81 | C |
| ATOM | 1010 | CE2 | TYR | A | 134 | 2.973 | 1.535 | 24.680 | 1.00 | 82.91 | C |
| ATOM | 1011 | CZ | TYR | A | 134 | 2.777 | 0.160 | 24.704 | 1.00 | 82.88 | C |
| ATOM | 1012 | OH | TYR | A | 134 | 1.832 | −0.417 | 23.886 | 1.00 | 81.06 | O |
| ATOM | 1013 | N | LYS | A | 135 | 5.940 | 3.997 | 29.816 | 1.00 | 77.68 | N |
| ATOM | 1014 | CA | LYS | A | 135 | 6.766 | 4.812 | 30.699 | 1.00 | 75.24 | C |
| ATOM | 1015 | C | LYS | A | 135 | 8.186 | 4.280 | 30.830 | 1.00 | 73.74 | C |
| ATOM | 1016 | O | LYS | A | 135 | 8.492 | 3.515 | 31.743 | 1.00 | 73.88 | O |
| ATOM | 1017 | CB | LYS | A | 135 | 6.123 | 4.902 | 32.088 | 1.00 | 75.02 | C |
| ATOM | 1018 | CG | LYS | A | 135 | 5.925 | 6.327 | 32.604 | 1.00 | 74.72 | C |
| ATOM | 1019 | CD | LYS | A | 135 | 7.254 | 7.047 | 32.808 | 1.00 | 74.09 | C |
| ATOM | 1020 | CE | LYS | A | 135 | 7.052 | 8.494 | 33.250 | 1.00 | 73.39 | C |
| ATOM | 1021 | NZ | LYS | A | 135 | 6.342 | 8.617 | 34.554 | 1.00 | 71.23 | N |
| ATOM | 1022 | N | ASN | A | 136 | 9.046 | 4.681 | 29.902 | 1.00 | 71.59 | N |
| ATOM | 1023 | CA | ASN | A | 136 | 10.437 | 4.268 | 29.922 | 1.00 | 68.38 | C |
| ATOM | 1024 | C | ASN | A | 136 | 11.234 | 5.510 | 30.276 | 1.00 | 65.84 | C |
| ATOM | 1025 | O | ASN | A | 136 | 11.081 | 6.551 | 29.651 | 1.00 | 65.50 | O |
| ATOM | 1026 | CB | ASN | A | 136 | 10.859 | 3.754 | 28.552 | 1.00 | 69.89 | C |
| ATOM | 1027 | CG | ASN | A | 136 | 12.066 | 2.850 | 28.624 | 1.00 | 70.50 | C |
| ATOM | 1028 | OD1 | ASN | A | 136 | 13.088 | 3.199 | 29.219 | 1.00 | 71.47 | O |
| ATOM | 1029 | ND2 | ASN | A | 136 | 11.958 | 1.678 | 28.013 | 1.00 | 71.37 | N |
| ATOM | 1030 | N | PRO | A | 137 | 12.104 | 5.417 | 31.281 | 1.00 | 64.28 | N |
| ATOM | 1031 | CA | PRO | A | 137 | 12.903 | 6.576 | 31.685 | 1.00 | 61.92 | C |
| ATOM | 1032 | C | PRO | A | 137 | 13.966 | 6.963 | 30.677 | 1.00 | 58.77 | C |
| ATOM | 1033 | O | PRO | A | 137 | 14.429 | 6.124 | 29.900 | 1.00 | 57.09 | O |
| ATOM | 1034 | CB | PRO | A | 137 | 13.533 | 6.107 | 32.986 | 1.00 | 63.33 | C |
| ATOM | 1035 | CG | PRO | A | 137 | 13.825 | 4.660 | 32.671 | 1.00 | 64.28 | C |
| ATOM | 1036 | CD | PRO | A | 137 | 12.518 | 4.211 | 32.023 | 1.00 | 64.36 | C |
| ATOM | 1037 | N | GLU | A | 138 | 14.338 | 8.242 | 30.687 | 1.00 | 56.31 | N |
| ATOM | 1038 | CA | GLU | A | 138 | 15.405 | 8.719 | 29.818 | 1.00 | 53.37 | C |
| ATOM | 1039 | C | GLU | A | 138 | 16.657 | 8.212 | 30.513 | 1.00 | 51.27 | C |
| ATOM | 1040 | O | GLU | A | 138 | 16.657 | 8.008 | 31.729 | 1.00 | 51.66 | O |
| ATOM | 1041 | CB | GLU | A | 138 | 15.492 | 10.249 | 29.770 | 1.00 | 52.56 | C |
| ATOM | 1042 | CG | GLU | A | 138 | 14.350 | 10.981 | 29.107 | 1.00 | 54.92 | C |
| ATOM | 1043 | CD | GLU | A | 138 | 14.743 | 12.400 | 28.704 | 1.00 | 56.83 | C |
| ATOM | 1044 | OE1 | GLU | A | 138 | 15.460 | 13.066 | 29.481 | 1.00 | 57.06 | O |
| ATOM | 1045 | OE2 | GLU | A | 138 | 14.332 | 12.855 | 27.612 | 1.00 | 57.94 | O |
| ATOM | 1046 | N | ARG | A | 139 | 17.715 | 8.001 | 29.748 | 1.00 | 49.57 | N |
| ATOM | 1047 | CA | ARG | A | 139 | 18.970 | 7.544 | 30.312 | 1.00 | 47.63 | C |
| ATOM | 1048 | C | ARG | A | 139 | 20.076 | 8.385 | 29.710 | 1.00 | 45.43 | C |
| ATOM | 1049 | O | ARG | A | 139 | 20.325 | 8.333 | 28.510 | 1.00 | 45.40 | O |
| ATOM | 1050 | CB | ARG | A | 139 | 19.174 | 6.065 | 30.008 | 1.00 | 49.79 | C |
| ATOM | 1051 | CG | ARG | A | 139 | 18.146 | 5.196 | 30.702 | 1.00 | 53.91 | C |
| ATOM | 1052 | CD | ARG | A | 139 | 18.157 | 3.777 | 30.177 | 1.00 | 58.48 | C |
| ATOM | 1053 | NE | ARG | A | 139 | 17.145 | 2.960 | 30.842 | 1.00 | 63.23 | N |
| ATOM | 1054 | CZ | ARG | A | 139 | 17.150 | 2.684 | 32.143 | 1.00 | 65.59 | C |
| ATOM | 1055 | NH1 | ARG | A | 139 | 18.118 | 3.162 | 32.921 | 1.00 | 65.48 | N |
| ATOM | 1056 | NH2 | ARG | A | 139 | 16.188 | 1.930 | 32.666 | 1.00 | 65.15 | N |
| ATOM | 1057 | N | TRP | A | 140 | 20.716 | 9.184 | 30.554 | 1.00 | 43.40 | N |
| ATOM | 1058 | CA | TRP | A | 140 | 21.791 | 10.055 | 30.119 | 1.00 | 40.75 | C |
| ATOM | 1059 | C | TRP | A | 140 | 23.183 | 9.446 | 30.282 | 1.00 | 39.92 | C |
| ATOM | 1060 | O | TRP | A | 140 | 23.439 | 8.667 | 31.200 | 1.00 | 39.08 | O |
| ATOM | 1061 | CB | TRP | A | 140 | 21.699 | 11.393 | 30.858 | 1.00 | 40.25 | C |
| ATOM | 1062 | CG | TRP | A | 140 | 20.565 | 12.218 | 30.361 | 1.00 | 41.67 | C |
| ATOM | 1063 | CD1 | TRP | A | 140 | 19.252 | 12.142 | 30.751 | 1.00 | 39.88 | C |
| ATOM | 1064 | CD2 | TRP | A | 140 | 20.607 | 13.152 | 29.274 | 1.00 | 41.67 | C |
| ATOM | 1065 | NE1 | TRP | A | 140 | 18.476 | 12.962 | 29.966 | 1.00 | 40.11 | N |
| ATOM | 1066 | CE2 | TRP | A | 140 | 19.279 | 13.594 | 29.050 | 1.00 | 41.25 | C |
| ATOM | 1067 | CE3 | TRP | A | 140 | 21.640 | 13.653 | 28.458 | 1.00 | 41.06 | C |
| ATOM | 1068 | CZ2 | TRP | A | 140 | 18.955 | 14.515 | 28.044 | 1.00 | 39.75 | C |
| ATOM | 1069 | CZ3 | TRP | A | 140 | 21.319 | 14.567 | 27.456 | 1.00 | 39.51 | C |
| ATOM | 1070 | CH2 | TRP | A | 140 | 19.984 | 14.987 | 27.259 | 1.00 | 41.49 | C |
| ATOM | 1071 | N | TYR | A | 141 | 24.072 | 9.821 | 29.368 | 1.00 | 39.14 | N |
| ATOM | 1072 | CA | TYR | A | 141 | 25.446 | 9.352 | 29.340 | 1.00 | 37.18 | C |
| ATOM | 1073 | C | TYR | A | 141 | 26.339 | 10.524 | 28.989 | 1.00 | 37.42 | C |
| ATOM | 1074 | O | TYR | A | 141 | 26.165 | 11.150 | 27.949 | 1.00 | 40.57 | O |
| ATOM | 1075 | CB | TYR | A | 141 | 25.583 | 8.277 | 28.276 | 1.00 | 38.05 | C |
| ATOM | 1076 | CG | TYR | A | 141 | 24.740 | 7.070 | 28.559 | 1.00 | 39.37 | C |

TABLE 2-continued

| | | | | | | | | | | |
|---|---|---|---|---|---|---|---|---|---|---|
| ATOM | 1077 | CD1 | TYR | A | 141 | 25.049 | 6.229 | 29.621 | 1.00 | 39.49 | C |
| ATOM | 1078 | CD2 | TYR | A | 141 | 23.609 | 6.786 | 27.799 | 1.00 | 38.61 | C |
| ATOM | 1079 | CE1 | TYR | A | 141 | 24.257 | 5.140 | 29.922 | 1.00 | 40.45 | C |
| ATOM | 1080 | CE2 | TYR | A | 141 | 22.807 | 5.696 | 28.095 | 1.00 | 39.59 | C |
| ATOM | 1081 | CZ | TYR | A | 141 | 23.140 | 4.876 | 29.161 | 1.00 | 40.84 | C |
| ATOM | 1082 | OH | TYR | A | 141 | 22.363 | 3.789 | 29.484 | 1.00 | 43.71 | O |
| ATOM | 1083 | N | ARG | A | 142 | 27.300 | 10.832 | 29.842 | 1.00 | 38.22 | N |
| ATOM | 1084 | CA | ARG | A | 142 | 28.186 | 11.951 | 29.559 | 1.00 | 39.57 | C |
| ATOM | 1085 | C | ARG | A | 142 | 29.611 | 11.453 | 29.389 | 1.00 | 37.41 | C |
| ATOM | 1086 | O | ARG | A | 142 | 30.044 | 10.561 | 30.104 | 1.00 | 40.52 | O |
| ATOM | 1087 | CB | ARG | A | 142 | 28.094 | 12.972 | 30.696 | 1.00 | 45.76 | C |
| ATOM | 1088 | CG | ARG | A | 142 | 28.655 | 14.359 | 30.386 | 1.00 | 52.24 | C |
| ATOM | 1089 | CD | ARG | A | 142 | 27.944 | 15.400 | 31.245 | 1.00 | 57.25 | C |
| ATOM | 1090 | NE | ARG | A | 142 | 28.747 | 16.594 | 31.498 | 1.00 | 60.32 | N |
| ATOM | 1091 | CZ | ARG | A | 142 | 28.290 | 17.673 | 32.130 | 1.00 | 62.56 | C |
| ATOM | 1092 | NH1 | ARG | A | 142 | 27.033 | 17.707 | 32.565 | 1.00 | 62.55 | N |
| ATOM | 1093 | NH2 | ARG | A | 142 | 29.092 | 18.712 | 32.342 | 1.00 | 63.25 | N |
| ATOM | 1094 | N | ALA | A | 143 | 30.331 | 12.009 | 28.424 | 1.00 | 35.00 | N |
| ATOM | 1095 | CA | ALA | A | 143 | 31.711 | 11.608 | 28.179 | 1.00 | 34.15 | C |
| ATOM | 1096 | C | ALA | A | 143 | 32.581 | 12.811 | 27.822 | 1.00 | 34.01 | C |
| ATOM | 1097 | O | ALA | A | 143 | 32.084 | 13.846 | 27.376 | 1.00 | 32.26 | O |
| ATOM | 1098 | CB | ALA | A | 143 | 31.771 | 10.571 | 27.065 | 1.00 | 33.88 | C |
| ATOM | 1099 | N | SER | A | 144 | 33.886 | 12.664 | 28.026 | 1.00 | 33.61 | N |
| ATOM | 1100 | CA | SER | A | 144 | 34.836 | 13.730 | 27.731 | 1.00 | 34.57 | C |
| ATOM | 1101 | C | SER | A | 144 | 35.482 | 13.478 | 26.378 | 1.00 | 33.54 | C |
| ATOM | 1102 | O | SER | A | 144 | 36.471 | 14.127 | 26.016 | 1.00 | 33.18 | O |
| ATOM | 1103 | CB | SER | A | 144 | 35.913 | 13.797 | 28.817 | 1.00 | 34.41 | C |
| ATOM | 1104 | OG | SER | A | 144 | 35.352 | 14.206 | 30.051 | 1.00 | 38.94 | O |
| ATOM | 1105 | N | PHE | A | 145 | 34.920 | 12.518 | 25.649 | 1.00 | 30.61 | N |
| ATOM | 1106 | CA | PHE | A | 145 | 35.399 | 12.157 | 24.323 | 1.00 | 31.20 | C |
| ATOM | 1107 | C | PHE | A | 145 | 34.216 | 11.645 | 23.493 | 1.00 | 30.37 | C |
| ATOM | 1108 | O | PHE | A | 145 | 33.271 | 11.088 | 24.038 | 1.00 | 31.72 | O |
| ATOM | 1109 | CB | PHE | A | 145 | 36.532 | 11.124 | 24.427 | 1.00 | 30.76 | C |
| ATOM | 1110 | CG | PHE | A | 145 | 36.544 | 10.364 | 25.718 | 1.00 | 30.44 | C |
| ATOM | 1111 | CD1 | PHE | A | 145 | 35.525 | 9.469 | 26.025 | 1.00 | 29.77 | C |
| ATOM | 1112 | CD2 | PHE | A | 145 | 37.574 | 10.546 | 26.630 | 1.00 | 31.35 | C |
| ATOM | 1113 | CE1 | PHE | A | 145 | 35.534 | 8.772 | 27.219 | 1.00 | 26.54 | C |
| ATOM | 1114 | CE2 | PHE | A | 145 | 37.593 | 9.849 | 27.830 | 1.00 | 30.53 | C |
| ATOM | 1115 | CZ | PHE | A | 145 | 36.571 | 8.961 | 28.123 | 1.00 | 30.11 | C |
| ATOM | 1116 | N | PRO | A | 146 | 34.261 | 11.828 | 22.159 | 1.00 | 31.31 | N |
| ATOM | 1117 | CA | PRO | A | 146 | 33.206 | 11.422 | 21.221 | 1.00 | 31.52 | C |
| ATOM | 1118 | C | PRO | A | 146 | 32.816 | 9.957 | 21.126 | 1.00 | 32.34 | C |
| ATOM | 1119 | O | PRO | A | 146 | 31.737 | 9.642 | 20.649 | 1.00 | 33.45 | O |
| ATOM | 1120 | CB | PRO | A | 146 | 33.709 | 11.965 | 19.888 | 1.00 | 30.08 | C |
| ATOM | 1121 | CG | PRO | A | 146 | 35.176 | 11.781 | 20.011 | 1.00 | 29.98 | C |
| ATOM | 1122 | CD | PRO | A | 146 | 35.466 | 12.252 | 21.420 | 1.00 | 30.27 | C |
| ATOM | 1123 | N | ILE | A | 147 | 33.681 | 9.052 | 21.553 | 1.00 | 33.80 | N |
| ATOM | 1124 | CA | ILE | A | 147 | 33.329 | 7.645 | 21.466 | 1.00 | 34.25 | C |
| ATOM | 1125 | C | ILE | A | 147 | 32.887 | 7.115 | 22.832 | 1.00 | 35.43 | C |
| ATOM | 1126 | O | ILE | A | 147 | 33.669 | 7.076 | 23.787 | 1.00 | 35.48 | O |
| ATOM | 1127 | CB | ILE | A | 147 | 34.507 | 6.849 | 20.873 | 1.00 | 33.47 | C |
| ATOM | 1128 | CG1 | ILE | A | 147 | 34.747 | 7.352 | 19.442 | 1.00 | 32.17 | C |
| ATOM | 1129 | CG2 | ILE | A | 147 | 34.208 | 5.345 | 20.896 | 1.00 | 33.09 | C |
| ATOM | 1130 | CD1 | ILE | A | 147 | 35.916 | 6.709 | 18.712 | 1.00 | 31.86 | C |
| ATOM | 1131 | N | ILE | A | 148 | 31.619 | 6.713 | 22.907 | 1.00 | 35.31 | N |
| ATOM | 1132 | CA | ILE | A | 148 | 31.033 | 6.231 | 24.151 | 1.00 | 36.97 | C |
| ATOM | 1133 | C | ILE | A | 148 | 30.448 | 4.821 | 24.101 | 1.00 | 36.51 | C |
| ATOM | 1134 | O | ILE | A | 148 | 29.607 | 4.511 | 23.259 | 1.00 | 37.91 | O |
| ATOM | 1135 | CB | ILE | A | 148 | 29.906 | 7.183 | 24.604 | 1.00 | 39.00 | C |
| ATOM | 1136 | CG1 | ILE | A | 148 | 30.394 | 8.628 | 24.563 | 1.00 | 41.02 | C |
| ATOM | 1137 | CG2 | ILE | A | 148 | 29.455 | 6.840 | 26.002 | 1.00 | 38.82 | C |
| ATOM | 1138 | CD1 | ILE | A | 148 | 29.267 | 9.634 | 24.725 | 1.00 | 43.91 | C |
| ATOM | 1139 | N | THR | A | 149 | 30.878 | 3.975 | 25.027 | 1.00 | 35.37 | N |
| ATOM | 1140 | CA | THR | A | 149 | 30.377 | 2.614 | 25.100 | 1.00 | 36.42 | C |
| ATOM | 1141 | C | THR | A | 149 | 29.272 | 2.539 | 26.132 | 1.00 | 38.18 | C |
| ATOM | 1142 | O | THR | A | 149 | 29.479 | 2.886 | 27.289 | 1.00 | 41.96 | O |
| ATOM | 1143 | CB | THR | A | 149 | 31.469 | 1.625 | 25.522 | 1.00 | 35.18 | C |
| ATOM | 1144 | OG1 | THR | A | 149 | 32.478 | 1.566 | 24.508 | 1.00 | 37.20 | O |
| ATOM | 1145 | CG2 | THR | A | 149 | 30.876 | 0.236 | 25.725 | 1.00 | 35.81 | C |
| ATOM | 1146 | N | VAL | A | 150 | 28.095 | 2.093 | 25.721 | 1.00 | 39.70 | N |
| ATOM | 1147 | CA | VAL | A | 150 | 26.984 | 1.971 | 26.652 | 1.00 | 41.38 | C |
| ATOM | 1148 | C | VAL | A | 150 | 26.886 | 0.518 | 27.095 | 1.00 | 43.32 | C |
| ATOM | 1149 | O | VAL | A | 150 | 26.596 | −0.369 | 26.291 | 1.00 | 43.29 | O |
| ATOM | 1150 | CB | VAL | A | 150 | 25.649 | 2.400 | 26.010 | 1.00 | 41.16 | C |
| ATOM | 1151 | CG1 | VAL | A | 150 | 24.512 | 2.194 | 27.004 | 1.00 | 37.79 | C |
| ATOM | 1152 | CG2 | VAL | A | 150 | 25.727 | 3.866 | 25.581 | 1.00 | 38.75 | C |
| ATOM | 1153 | N | THR | A | 151 | 27.147 | 0.284 | 28.377 | 1.00 | 46.15 | N |
| ATOM | 1154 | CA | THR | A | 151 | 27.105 | −1.061 | 28.934 | 1.00 | 48.28 | C |
| ATOM | 1155 | C | THR | A | 151 | 25.673 | −1.555 | 29.044 | 1.00 | 47.82 | C |
| ATOM | 1156 | O | THR | A | 151 | 24.794 | −0.834 | 29.520 | 1.00 | 47.53 | O |

TABLE 2-continued

| | | | | | | | | | | |
|---|---|---|---|---|---|---|---|---|---|---|
| ATOM | 1157 | CB | THR | A | 151 | 27.777 | −1.098 | 30.321 | 1.00 | 49.34 | C |
| ATOM | 1158 | OG1 | THR | A | 151 | 27.266 | −0.027 | 31.124 | 1.00 | 51.82 | O |
| ATOM | 1159 | CG2 | THR | A | 151 | 29.292 | −0.928 | 30.182 | 1.00 | 50.70 | C |
| ATOM | 1160 | N | ALA | A | 152 | 25.447 | −2.783 | 28.584 | 1.00 | 48.69 | N |
| ATOM | 1161 | CA | ALA | A | 152 | 24.122 | −3.391 | 28.620 | 1.00 | 48.78 | C |
| ATOM | 1162 | C | ALA | A | 152 | 23.109 | −2.343 | 28.179 | 1.00 | 48.57 | C |
| ATOM | 1163 | O | ALA | A | 152 | 22.193 | −1.983 | 28.922 | 1.00 | 48.02 | O |
| ATOM | 1164 | CB | ALA | A | 152 | 23.812 | −3.876 | 30.035 | 1.00 | 48.90 | C |
| ATOM | 1165 | N | ALA | A | 153 | 23.294 | −1.849 | 26.960 | 1.00 | 48.11 | N |
| ATOM | 1166 | CA | ALA | A | 153 | 22.424 | −0.822 | 26.412 | 1.00 | 47.17 | C |
| ATOM | 1167 | C | ALA | A | 153 | 20.991 | −1.298 | 26.231 | 1.00 | 47.15 | C |
| ATOM | 1168 | O | ALA | A | 153 | 20.743 | −2.442 | 25.841 | 1.00 | 43.93 | O |
| ATOM | 1169 | CB | ALA | A | 153 | 22.978 | −0.327 | 25.087 | 1.00 | 45.52 | C |
| ATOM | 1170 | N | HIS | A | 154 | 20.053 | −0.403 | 26.528 | 1.00 | 47.04 | N |
| ATOM | 1171 | CA | HIS | A | 154 | 18.636 | −0.698 | 26.388 | 1.00 | 47.98 | C |
| ATOM | 1172 | C | HIS | A | 154 | 18.189 | −0.279 | 24.998 | 1.00 | 46.98 | C |
| ATOM | 1173 | O | HIS | A | 154 | 18.701 | 0.696 | 24.447 | 1.00 | 47.17 | O |
| ATOM | 1174 | CB | HIS | A | 154 | 17.818 | 0.084 | 27.423 | 1.00 | 49.75 | C |
| ATOM | 1175 | CG | HIS | A | 154 | 18.102 | −0.304 | 28.841 | 1.00 | 52.68 | C |
| ATOM | 1176 | ND1 | HIS | A | 154 | 17.717 | −1.515 | 29.372 | 1.00 | 53.39 | N |
| ATOM | 1177 | CD2 | HIS | A | 154 | 18.745 | 0.355 | 29.833 | 1.00 | 52.52 | C |
| ATOM | 1178 | CE1 | HIS | A | 154 | 18.111 | −1.584 | 30.632 | 1.00 | 54.90 | C |
| ATOM | 1179 | NE2 | HIS | A | 154 | 18.737 | −0.462 | 30.936 | 1.00 | 51.96 | N |
| ATOM | 1180 | N | SER | A | 155 | 17.246 | −1.020 | 24.428 | 1.00 | 44.32 | N |
| ATOM | 1181 | CA | SER | A | 155 | 16.714 | −0.674 | 23.119 | 1.00 | 41.98 | C |
| ATOM | 1182 | C | SER | A | 155 | 16.073 | 0.700 | 23.246 | 1.00 | 40.45 | C |
| ATOM | 1183 | O | SER | A | 155 | 15.484 | 1.024 | 24.275 | 1.00 | 39.06 | O |
| ATOM | 1184 | CB | SER | A | 155 | 15.648 | −1.679 | 22.688 | 1.00 | 41.32 | C |
| ATOM | 1185 | OG | SER | A | 155 | 16.212 | −2.947 | 22.436 | 1.00 | 41.20 | O |
| ATOM | 1186 | N | GLY | A | 156 | 16.190 | 1.515 | 22.203 | 1.00 | 40.20 | N |
| ATOM | 1187 | CA | GLY | A | 156 | 15.592 | 2.834 | 22.261 | 1.00 | 36.66 | C |
| ATOM | 1188 | C | GLY | A | 156 | 16.134 | 3.784 | 21.215 | 1.00 | 36.30 | C |
| ATOM | 1189 | O | GLY | A | 156 | 16.962 | 3.410 | 20.388 | 1.00 | 33.59 | O |
| ATOM | 1190 | N | THR | A | 157 | 15.647 | 5.020 | 21.264 | 1.00 | 34.60 | N |
| ATOM | 1191 | CA | THR | A | 157 | 16.066 | 6.059 | 20.349 | 1.00 | 33.87 | C |
| ATOM | 1192 | C | THR | A | 157 | 17.138 | 6.880 | 21.043 | 1.00 | 33.63 | C |
| ATOM | 1193 | O | THR | A | 157 | 16.934 | 7.364 | 22.156 | 1.00 | 29.86 | O |
| ATOM | 1194 | CB | THR | A | 157 | 14.901 | 6.982 | 20.005 | 1.00 | 34.28 | C |
| ATOM | 1195 | OG1 | THR | A | 157 | 13.839 | 6.206 | 19.450 | 1.00 | 35.53 | O |
| ATOM | 1196 | CG2 | THR | A | 157 | 15.339 | 8.044 | 19.006 | 1.00 | 34.53 | C |
| ATOM | 1197 | N | TYR | A | 158 | 18.279 | 7.044 | 20.382 | 1.00 | 33.94 | N |
| ATOM | 1198 | CA | TYR | A | 158 | 19.376 | 7.800 | 20.970 | 1.00 | 34.34 | C |
| ATOM | 1199 | C | TYR | A | 158 | 19.707 | 9.074 | 20.206 | 1.00 | 34.29 | C |
| ATOM | 1200 | O | TYR | A | 158 | 19.522 | 9.150 | 18.997 | 1.00 | 36.03 | O |
| ATOM | 1201 | CB | TYR | A | 158 | 20.627 | 6.931 | 21.049 | 1.00 | 34.08 | C |
| ATOM | 1202 | CG | TYR | A | 158 | 20.557 | 5.809 | 22.057 | 1.00 | 35.09 | C |
| ATOM | 1203 | CD1 | TYR | A | 158 | 19.676 | 4.741 | 21.889 | 1.00 | 36.16 | C |
| ATOM | 1204 | CD2 | TYR | A | 158 | 21.410 | 5.794 | 23.156 | 1.00 | 36.44 | C |
| ATOM | 1205 | CE1 | TYR | A | 158 | 19.653 | 3.681 | 22.786 | 1.00 | 37.45 | C |
| ATOM | 1206 | CE2 | TYR | A | 158 | 21.398 | 4.746 | 24.060 | 1.00 | 38.59 | C |
| ATOM | 1207 | CZ | TYR | A | 158 | 20.525 | 3.688 | 23.870 | 1.00 | 40.56 | C |
| ATOM | 1208 | OH | TYR | A | 158 | 20.572 | 2.618 | 24.744 | 1.00 | 43.47 | O |
| ATOM | 1209 | N | ARG | A | 159 | 20.195 | 10.073 | 20.930 | 1.00 | 33.49 | N |
| ATOM | 1210 | CA | ARG | A | 159 | 20.593 | 11.340 | 20.337 | 1.00 | 34.57 | C |
| ATOM | 1211 | C | ARG | A | 159 | 21.716 | 11.853 | 21.207 | 1.00 | 34.13 | C |
| ATOM | 1212 | O | ARG | A | 159 | 21.809 | 11.482 | 22.369 | 1.00 | 33.01 | O |
| ATOM | 1213 | CB | ARG | A | 159 | 19.441 | 12.341 | 20.357 | 1.00 | 35.99 | C |
| ATOM | 1214 | CG | ARG | A | 159 | 18.302 | 12.034 | 19.395 | 1.00 | 38.36 | C |
| ATOM | 1215 | CD | ARG | A | 159 | 17.155 | 12.986 | 19.632 | 1.00 | 40.80 | C |
| ATOM | 1216 | NE | ARG | A | 159 | 16.031 | 12.720 | 18.750 | 1.00 | 49.08 | N |
| ATOM | 1217 | CZ | ARG | A | 159 | 15.894 | 13.242 | 17.535 | 1.00 | 54.07 | C |
| ATOM | 1218 | NH1 | ARG | A | 159 | 16.819 | 14.070 | 17.050 | 1.00 | 53.77 | N |
| ATOM | 1219 | NH2 | ARG | A | 159 | 14.827 | 12.933 | 16.804 | 1.00 | 55.63 | N |
| ATOM | 1220 | N | CYS | A | 160 | 22.570 | 12.705 | 20.656 | 1.00 | 34.26 | N |
| ATOM | 1221 | CA | CYS | A | 160 | 23.670 | 13.244 | 21.440 | 1.00 | 32.33 | C |
| ATOM | 1222 | C | CYS | A | 160 | 23.865 | 14.726 | 21.175 | 1.00 | 31.75 | C |
| ATOM | 1223 | O | CYS | A | 160 | 23.377 | 15.273 | 20.169 | 1.00 | 30.91 | O |
| ATOM | 1224 | CB | CYS | A | 160 | 24.976 | 12.474 | 21.155 | 1.00 | 32.71 | C |
| ATOM | 1225 | SG | CYS | A | 160 | 25.732 | 12.729 | 19.510 | 1.00 | 37.58 | S |
| ATOM | 1226 | N | TYR | A | 161 | 24.576 | 15.364 | 22.104 | 1.00 | 29.38 | N |
| ATOM | 1227 | CA | TYR | A | 161 | 24.896 | 16.782 | 22.043 | 1.00 | 26.89 | C |
| ATOM | 1228 | C | TYR | A | 161 | 26.372 | 16.926 | 22.314 | 1.00 | 25.54 | C |
| ATOM | 1229 | O | TYR | A | 161 | 26.945 | 16.146 | 23.068 | 1.00 | 25.45 | O |
| ATOM | 1230 | CB | TYR | A | 161 | 24.187 | 17.576 | 23.138 | 1.00 | 26.43 | C |
| ATOM | 1231 | CG | TYR | A | 161 | 22.696 | 17.546 | 23.111 | 1.00 | 29.65 | C |
| ATOM | 1232 | CD1 | TYR | A | 161 | 21.987 | 16.454 | 23.633 | 1.00 | 27.22 | C |
| ATOM | 1233 | CD2 | TYR | A | 161 | 21.974 | 18.639 | 22.616 | 1.00 | 28.67 | C |
| ATOM | 1234 | CE1 | TYR | A | 161 | 20.598 | 16.458 | 23.668 | 1.00 | 27.33 | C |
| ATOM | 1235 | CE2 | TYR | A | 161 | 20.589 | 18.650 | 22.644 | 1.00 | 28.77 | C |
| ATOM | 1236 | CZ | TYR | A | 161 | 19.906 | 17.563 | 23.168 | 1.00 | 30.33 | C |

TABLE 2-continued

| | | | | | | | | | | | |
|---|---|---|---|---|---|---|---|---|---|---|---|
| ATOM | 1237 | OH | TYR | A | 161 | 18.528 | 17.584 | 23.172 | 1.00 | 33.99 | O |
| ATOM | 1238 | N | SER | A | 162 | 26.981 | 17.944 | 21.725 | 1.00 | 26.05 | N |
| ATOM | 1239 | CA | SER | A | 162 | 28.391 | 18.202 | 21.962 | 1.00 | 29.18 | C |
| ATOM | 1240 | C | SER | A | 162 | 28.505 | 19.627 | 22.459 | 1.00 | 30.26 | C |
| ATOM | 1241 | O | SER | A | 162 | 27.682 | 20.480 | 22.117 | 1.00 | 31.81 | O |
| ATOM | 1242 | CB | SER | A | 162 | 29.206 | 18.063 | 20.686 | 1.00 | 28.23 | C |
| ATOM | 1243 | OG | SER | A | 162 | 29.006 | 19.183 | 19.839 | 1.00 | 34.19 | O |
| ATOM | 1244 | N | PHE | A | 163 | 29.514 | 19.878 | 23.280 | 1.00 | 32.26 | N |
| ATOM | 1245 | CA | PHE | A | 163 | 29.738 | 21.206 | 23.809 | 1.00 | 33.82 | C |
| ATOM | 1246 | C | PHE | A | 163 | 31.105 | 21.304 | 24.440 | 1.00 | 35.42 | C |
| ATOM | 1247 | O | PHE | A | 163 | 31.805 | 20.309 | 24.583 | 1.00 | 36.76 | O |
| ATOM | 1248 | CB | PHE | A | 163 | 28.659 | 21.602 | 24.829 | 1.00 | 33.09 | C |
| ATOM | 1249 | CG | PHE | A | 163 | 28.608 | 20.736 | 26.062 | 1.00 | 32.65 | C |
| ATOM | 1250 | CD1 | PHE | A | 163 | 27.852 | 19.565 | 26.081 | 1.00 | 34.62 | C |
| ATOM | 1251 | CD2 | PHE | A | 163 | 29.233 | 21.146 | 27.240 | 1.00 | 32.10 | C |
| ATOM | 1252 | CE1 | PHE | A | 163 | 27.709 | 18.817 | 27.262 | 1.00 | 34.01 | C |
| ATOM | 1253 | CE2 | PHE | A | 163 | 29.099 | 20.412 | 28.426 | 1.00 | 30.01 | C |
| ATOM | 1254 | CZ | PHE | A | 163 | 28.336 | 19.250 | 28.440 | 1.00 | 33.04 | C |
| ATOM | 1255 | N | SER | A | 164 | 31.471 | 22.522 | 24.813 | 1.00 | 38.01 | N |
| ATOM | 1256 | CA | SER | A | 164 | 32.761 | 22.817 | 25.407 | 1.00 | 38.05 | C |
| ATOM | 1257 | C | SER | A | 164 | 32.683 | 23.024 | 26.911 | 1.00 | 40.11 | C |
| ATOM | 1258 | O | SER | A | 164 | 31.719 | 23.603 | 27.424 | 1.00 | 38.23 | O |
| ATOM | 1259 | CB | SER | A | 164 | 33.340 | 24.063 | 24.751 | 1.00 | 36.65 | C |
| ATOM | 1260 | OG | SER | A | 164 | 34.231 | 24.713 | 25.632 | 1.00 | 44.07 | O |
| ATOM | 1261 | N | SER | A | 165 | 33.711 | 22.552 | 27.612 | 1.00 | 40.90 | N |
| ATOM | 1262 | CA | SER | A | 165 | 33.777 | 22.687 | 29.064 | 1.00 | 43.06 | C |
| ATOM | 1263 | C | SER | A | 165 | 33.951 | 24.146 | 29.474 | 1.00 | 43.08 | C |
| ATOM | 1264 | O | SER | A | 165 | 33.824 | 24.486 | 30.640 | 1.00 | 44.41 | O |
| ATOM | 1265 | CB | SER | A | 165 | 34.931 | 21.849 | 29.614 | 1.00 | 42.13 | C |
| ATOM | 1266 | OG | SER | A | 165 | 36.142 | 22.175 | 28.960 | 1.00 | 42.79 | O |
| ATOM | 1267 | N | ARG | A | 166 | 34.242 | 24.995 | 28.498 | 1.00 | 45.93 | N |
| ATOM | 1268 | CA | ARG | A | 166 | 34.431 | 26.428 | 28.703 | 1.00 | 48.47 | C |
| ATOM | 1269 | C | ARG | A | 166 | 33.076 | 27.132 | 28.890 | 1.00 | 47.71 | C |
| ATOM | 1270 | O | ARG | A | 166 | 32.975 | 28.142 | 29.584 | 1.00 | 47.37 | O |
| ATOM | 1271 | CB | ARG | A | 166 | 35.176 | 27.002 | 27.490 | 1.00 | 51.75 | C |
| ATOM | 1272 | CG | ARG | A | 166 | 34.946 | 28.482 | 27.218 | 1.00 | 57.18 | C |
| ATOM | 1273 | CD | ARG | A | 166 | 35.276 | 28.817 | 25.759 | 1.00 | 62.36 | C |
| ATOM | 1274 | NE | ARG | A | 166 | 34.969 | 30.206 | 25.408 | 1.00 | 66.58 | N |
| ATOM | 1275 | CZ | ARG | A | 166 | 35.620 | 31.268 | 25.882 | 1.00 | 67.43 | C |
| ATOM | 1276 | NH1 | ARG | A | 166 | 36.630 | 31.110 | 26.732 | 1.00 | 66.05 | N |
| ATOM | 1277 | NH2 | ARG | A | 166 | 35.253 | 32.491 | 25.513 | 1.00 | 67.07 | N |
| ATOM | 1278 | N | ASP | A | 167 | 32.049 | 26.593 | 28.243 | 1.00 | 46.07 | N |
| ATOM | 1279 | CA | ASP | A | 167 | 30.685 | 27.110 | 28.319 | 1.00 | 45.06 | C |
| ATOM | 1280 | C | ASP | A | 167 | 29.792 | 25.872 | 28.350 | 1.00 | 42.37 | C |
| ATOM | 1281 | O | ASP | A | 167 | 29.050 | 25.610 | 27.407 | 1.00 | 43.51 | O |
| ATOM | 1282 | CB | ASP | A | 167 | 30.349 | 27.944 | 27.074 | 1.00 | 48.79 | C |
| ATOM | 1283 | CG | ASP | A | 167 | 31.124 | 29.248 | 27.011 | 1.00 | 54.18 | C |
| ATOM | 1284 | OD1 | ASP | A | 167 | 30.910 | 30.106 | 27.895 | 1.00 | 56.62 | O |
| ATOM | 1285 | OD2 | ASP | A | 167 | 31.946 | 29.417 | 26.082 | 1.00 | 55.65 | O |
| ATOM | 1286 | N | PRO | A | 168 | 29.856 | 25.096 | 29.442 | 1.00 | 39.52 | N |
| ATOM | 1287 | CA | PRO | A | 168 | 29.098 | 23.862 | 29.670 | 1.00 | 37.72 | C |
| ATOM | 1288 | C | PRO | A | 168 | 27.584 | 23.944 | 29.563 | 1.00 | 37.47 | C |
| ATOM | 1289 | O | PRO | A | 168 | 26.903 | 22.917 | 29.536 | 1.00 | 36.03 | O |
| ATOM | 1290 | CB | PRO | A | 168 | 29.539 | 23.453 | 31.062 | 1.00 | 37.69 | C |
| ATOM | 1291 | CG | PRO | A | 168 | 29.763 | 24.765 | 31.724 | 1.00 | 37.62 | C |
| ATOM | 1292 | CD | PRO | A | 168 | 30.542 | 25.505 | 30.677 | 1.00 | 38.85 | C |
| ATOM | 1293 | N | TYR | A | 169 | 27.056 | 25.160 | 29.494 | 1.00 | 37.62 | N |
| ATOM | 1294 | CA | TYR | A | 169 | 25.614 | 25.345 | 29.412 | 1.00 | 37.00 | C |
| ATOM | 1295 | C | TYR | A | 169 | 25.094 | 25.746 | 28.036 | 1.00 | 36.98 | C |
| ATOM | 1296 | O | TYR | A | 169 | 23.897 | 25.975 | 27.858 | 1.00 | 37.18 | O |
| ATOM | 1297 | CB | TYR | A | 169 | 25.190 | 26.336 | 30.496 | 1.00 | 34.19 | C |
| ATOM | 1298 | CG | TYR | A | 169 | 25.609 | 25.826 | 31.856 | 1.00 | 34.53 | C |
| ATOM | 1299 | CD1 | TYR | A | 169 | 25.178 | 24.577 | 32.302 | 1.00 | 32.17 | C |
| ATOM | 1300 | CD2 | TYR | A | 169 | 26.533 | 26.525 | 32.641 | 1.00 | 32.21 | C |
| ATOM | 1301 | CE1 | TYR | A | 169 | 25.660 | 24.027 | 33.474 | 1.00 | 29.98 | C |
| ATOM | 1302 | CE2 | TYR | A | 169 | 27.018 | 25.982 | 33.822 | 1.00 | 30.03 | C |
| ATOM | 1303 | CZ | TYR | A | 169 | 26.582 | 24.729 | 34.230 | 1.00 | 32.02 | C |
| ATOM | 1304 | OH | TYR | A | 169 | 27.084 | 24.151 | 35.378 | 1.00 | 30.21 | O |
| ATOM | 1305 | N | LEU | A | 170 | 26.005 | 25.817 | 27.068 | 1.00 | 36.47 | N |
| ATOM | 1306 | CA | LEU | A | 170 | 25.656 | 26.149 | 25.694 | 1.00 | 37.51 | C |
| ATOM | 1307 | C | LEU | A | 170 | 25.925 | 24.903 | 24.860 | 1.00 | 37.28 | C |
| ATOM | 1308 | O | LEU | A | 170 | 27.051 | 24.639 | 24.454 | 1.00 | 38.78 | O |
| ATOM | 1309 | CB | LEU | A | 170 | 26.498 | 27.320 | 25.180 | 1.00 | 37.64 | C |
| ATOM | 1310 | CG | LEU | A | 170 | 26.301 | 28.673 | 25.867 | 1.00 | 39.51 | C |
| ATOM | 1311 | CD1 | LEU | A | 170 | 27.204 | 29.710 | 25.202 | 1.00 | 39.46 | C |
| ATOM | 1312 | CD2 | LEU | A | 170 | 24.835 | 29.097 | 25.778 | 1.00 | 38.49 | C |
| ATOM | 1313 | N | TRP | A | 171 | 24.874 | 24.139 | 24.615 | 1.00 | 35.54 | N |
| ATOM | 1314 | CA | TRP | A | 171 | 24.987 | 22.906 | 23.866 | 1.00 | 34.40 | C |
| ATOM | 1315 | C | TRP | A | 171 | 24.604 | 23.089 | 22.416 | 1.00 | 35.74 | C |
| ATOM | 1316 | O | TRP | A | 171 | 23.951 | 24.062 | 22.046 | 1.00 | 37.22 | O |

TABLE 2-continued

| | | | | | | | | | | |
|---|---|---|---|---|---|---|---|---|---|---|
| ATOM | 1317 | CB | TRP | A | 171 | 24.077 | 21.839 | 24.489 | 1.00 | 32.13 | C |
| ATOM | 1318 | CG | TRP | A | 171 | 24.524 | 21.332 | 25.846 | 1.00 | 29.75 | C |
| ATOM | 1319 | CD1 | TRP | A | 171 | 25.487 | 21.872 | 26.659 | 1.00 | 27.15 | C |
| ATOM | 1320 | CD2 | TRP | A | 171 | 24.020 | 20.183 | 26.530 | 1.00 | 26.04 | C |
| ATOM | 1321 | NE1 | TRP | A | 171 | 25.613 | 21.121 | 27.803 | 1.00 | 25.53 | N |
| ATOM | 1322 | CE2 | TRP | A | 171 | 24.724 | 20.081 | 27.750 | 1.00 | 25.57 | C |
| ATOM | 1323 | CE3 | TRP | A | 171 | 23.043 | 19.227 | 26.229 | 1.00 | 25.82 | C |
| ATOM | 1324 | CZ2 | TRP | A | 171 | 24.482 | 19.062 | 28.668 | 1.00 | 24.53 | C |
| ATOM | 1325 | CZ3 | TRP | A | 171 | 22.804 | 18.214 | 27.138 | 1.00 | 27.49 | C |
| ATOM | 1326 | CH2 | TRP | A | 171 | 23.522 | 18.139 | 28.347 | 1.00 | 26.03 | C |
| ATOM | 1327 | N | SER | A | 172 | 25.026 | 22.131 | 21.600 | 1.00 | 35.34 | N |
| ATOM | 1328 | CA | SER | A | 172 | 24.714 | 22.115 | 20.182 | 1.00 | 32.85 | C |
| ATOM | 1329 | C | SER | A | 172 | 23.250 | 21.704 | 20.057 | 1.00 | 32.82 | C |
| ATOM | 1330 | O | SER | A | 172 | 22.555 | 21.504 | 21.052 | 1.00 | 31.10 | O |
| ATOM | 1331 | CB | SER | A | 172 | 25.545 | 21.041 | 19.491 | 1.00 | 33.39 | C |
| ATOM | 1332 | OG | SER | A | 172 | 25.057 | 19.749 | 19.855 | 1.00 | 29.71 | O |
| ATOM | 1333 | N | ALA | A | 173 | 22.787 | 21.574 | 18.822 | 1.00 | 33.17 | N |
| ATOM | 1334 | CA | ALA | A | 173 | 21.433 | 21.105 | 18.585 | 1.00 | 33.25 | C |
| ATOM | 1335 | C | ALA | A | 173 | 21.585 | 19.585 | 18.708 | 1.00 | 33.08 | C |
| ATOM | 1336 | O | ALA | A | 173 | 22.698 | 19.057 | 18.603 | 1.00 | 33.09 | O |
| ATOM | 1337 | CB | ALA | A | 173 | 20.976 | 21.475 | 17.185 | 1.00 | 32.36 | C |
| ATOM | 1338 | N | PRO | A | 174 | 20.481 | 18.865 | 18.941 | 1.00 | 32.46 | N |
| ATOM | 1339 | CA | PRO | A | 174 | 20.548 | 17.408 | 19.074 | 1.00 | 31.07 | C |
| ATOM | 1340 | C | PRO | A | 174 | 20.871 | 16.729 | 17.759 | 1.00 | 31.03 | C |
| ATOM | 1341 | O | PRO | A | 174 | 20.418 | 17.165 | 16.717 | 1.00 | 33.46 | O |
| ATOM | 1342 | CB | PRO | A | 174 | 19.154 | 17.052 | 19.576 | 1.00 | 33.36 | C |
| ATOM | 1343 | CG | PRO | A | 174 | 18.296 | 18.097 | 18.910 | 1.00 | 31.14 | C |
| ATOM | 1344 | CD | PRO | A | 174 | 19.099 | 19.353 | 19.117 | 1.00 | 30.60 | C |
| ATOM | 1345 | N | SER | A | 175 | 21.657 | 15.662 | 17.802 | 1.00 | 31.24 | N |
| ATOM | 1346 | CA | SER | A | 175 | 22.006 | 14.943 | 16.579 | 1.00 | 33.10 | C |
| ATOM | 1347 | C | SER | A | 175 | 20.768 | 14.236 | 16.014 | 1.00 | 32.35 | C |
| ATOM | 1348 | O | SER | A | 175 | 19.721 | 14.196 | 16.658 | 1.00 | 30.56 | O |
| ATOM | 1349 | CB | SER | A | 175 | 23.077 | 13.888 | 16.876 | 1.00 | 32.61 | C |
| ATOM | 1350 | OG | SER | A | 175 | 22.513 | 12.818 | 17.619 | 1.00 | 32.49 | O |
| ATOM | 1351 | N | ASP | A | 175 | 20.890 | 13.677 | 14.814 | 1.00 | 32.66 | N |
| ATOM | 1352 | CA | ASP | A | 176 | 19.768 | 12.940 | 14.233 | 1.00 | 34.79 | C |
| ATOM | 1353 | C | ASP | A | 176 | 19.631 | 11.673 | 15.069 | 1.00 | 34.58 | C |
| ATOM | 1354 | O | ASP | A | 176 | 20.619 | 11.135 | 15.564 | 1.00 | 35.45 | O |
| ATOM | 1355 | CB | ASP | A | 176 | 20.025 | 12.590 | 12.761 | 1.00 | 35.48 | C |
| ATOM | 1356 | CG | ASP | A | 176 | 20.135 | 13.821 | 11.876 | 1.00 | 34.91 | C |
| ATOM | 1357 | OD1 | ASP | A | 176 | 19.310 | 14.751 | 12.037 | 1.00 | 34.44 | O |
| ATOM | 1358 | OD2 | ASP | A | 176 | 21.043 | 13.850 | 11.018 | 1.00 | 35.38 | O |
| ATOM | 1359 | N | PRO | A | 177 | 18.405 | 11.165 | 15.223 | 1.00 | 35.14 | N |
| ATOM | 1360 | CA | PRO | A | 177 | 18.152 | 9.961 | 16.022 | 1.00 | 34.29 | C |
| ATOM | 1361 | C | PRO | A | 177 | 18.722 | 8.628 | 15.530 | 1.00 | 34.03 | C |
| ATOM | 1362 | O | PRO | A | 177 | 18.828 | 8.374 | 14.330 | 1.00 | 33.49 | O |
| ATOM | 1363 | CB | PRO | A | 177 | 16.634 | 9.931 | 16.092 | 1.00 | 34.76 | C |
| ATOM | 1364 | CG | PRO | A | 177 | 16.268 | 10.382 | 14.718 | 1.00 | 30.92 | C |
| ATOM | 1365 | CD | PRO | A | 177 | 17.185 | 11.581 | 14.512 | 1.00 | 33.15 | C |
| ATOM | 1366 | N | LEU | A | 178 | 19.081 | 7.779 | 16.485 | 1.00 | 32.99 | N |
| ATOM | 1367 | CA | LEU | A | 178 | 19.593 | 6.455 | 16.187 | 1.00 | 33.07 | C |
| ATOM | 1368 | C | LEU | A | 178 | 18.756 | 5.479 | 17.008 | 1.00 | 34.66 | C |
| ATOM | 1369 | O | LEU | A | 178 | 18.671 | 5.601 | 18.226 | 1.00 | 35.42 | O |
| ATOM | 1370 | CB | LEU | A | 178 | 21.075 | 6.361 | 16.549 | 1.00 | 32.82 | C |
| ATOM | 1371 | CG | LEU | A | 178 | 21.780 | 5.010 | 16.370 | 1.00 | 33.57 | C |
| ATOM | 1372 | CD1 | LEU | A | 178 | 23.276 | 5.239 | 16.127 | 1.00 | 32.26 | C |
| ATOM | 1373 | CD2 | LEU | A | 178 | 21.538 | 4.129 | 17.611 | 1.00 | 30.92 | C |
| ATOM | 1374 | N | GLU | A | 179 | 18.118 | 4.531 | 16.329 | 1.00 | 37.07 | N |
| ATOM | 1375 | CA | GLU | A | 179 | 17.268 | 3.545 | 16.977 | 1.00 | 39.80 | C |
| ATOM | 1376 | C | GLU | A | 179 | 18.028 | 2.253 | 17.216 | 1.00 | 42.53 | C |
| ATOM | 1377 | O | GLU | A | 179 | 18.295 | 1.491 | 16.280 | 1.00 | 42.25 | O |
| ATOM | 1378 | CB | GLU | A | 179 | 16.051 | 3.255 | 16.107 | 1.00 | 42.34 | C |
| ATOM | 1379 | CG | GLU | A | 179 | 14.990 | 2.377 | 16.759 | 1.00 | 47.39 | C |
| ATOM | 1380 | CD | GLU | A | 179 | 14.272 | 3.088 | 17.886 | 1.00 | 51.80 | C |
| ATOM | 1381 | OE1 | GLU | A | 179 | 14.163 | 4.332 | 17.807 | 1.00 | 53.79 | O |
| ATOM | 1382 | OE2 | GLU | A | 179 | 13.805 | 2.414 | 18.837 | 1.00 | 53.63 | O |
| ATOM | 1383 | N | LEU | A | 180 | 18.370 | 2.008 | 18.476 | 1.00 | 44.87 | N |
| ATOM | 1384 | CA | LEU | A | 180 | 19.095 | 0.808 | 18.860 | 1.00 | 47.29 | C |
| ATOM | 1385 | C | LEU | A | 180 | 18.134 | −0.326 | 19.216 | 1.00 | 51.37 | C |
| ATOM | 1386 | O | LEU | A | 180 | 17.260 | −0.174 | 20.075 | 1.00 | 52.32 | O |
| ATOM | 1387 | CB | LEU | A | 180 | 19.993 | 1.103 | 20.060 | 1.00 | 44.12 | C |
| ATOM | 1388 | CG | LEU | A | 180 | 20.766 | −0.097 | 20.608 | 1.00 | 44.50 | C |
| ATOM | 1389 | CD1 | LEU | A | 180 | 21.868 | −0.470 | 19.633 | 1.00 | 42.93 | C |
| ATOM | 1390 | CD2 | LEU | A | 180 | 21.355 | 0.239 | 21.977 | 1.00 | 45.76 | C |
| ATOM | 1391 | N | VAL | A | 181 | 18.289 | −1.459 | 18.543 | 1.00 | 54.80 | N |
| ATOM | 1392 | CA | VAL | A | 181 | 17.454 | −2.619 | 18.821 | 1.00 | 59.13 | C |
| ATOM | 1393 | C | VAL | A | 181 | 18.371 | −3.718 | 19.339 | 1.00 | 61.57 | C |
| ATOM | 1394 | O | VAL | A | 181 | 19.012 | −4.424 | 18.559 | 1.00 | 62.08 | O |
| ATOM | 1395 | CB | VAL | A | 181 | 16.719 | −3.114 | 17.550 | 1.00 | 60.05 | C |
| ATOM | 1396 | CG1 | VAL | A | 181 | 16.053 | −4.457 | 17.819 | 1.00 | 60.71 | C |

TABLE 2-continued

| | | | | | | | | | | |
|---|---|---|---|---|---|---|---|---|---|---|
| ATOM | 1397 | CG2 | VAL | A | 181 | 15.674 | −2.098 | 17.127 | 1.00 | 58.81 | C |
| ATOM | 1398 | N | VAL | A | 182 | 18.444 | −3.848 | 20.660 | 1.00 | 65.09 | N |
| ATOM | 1399 | CA | VAL | A | 182 | 19.298 | −4.857 | 21.275 | 1.00 | 68.86 | C |
| ATOM | 1400 | C | VAL | A | 182 | 18.786 | −6.273 | 21.001 | 1.00 | 70.66 | C |
| ATOM | 1401 | O | VAL | A | 182 | 17.582 | −6.537 | 21.038 | 1.00 | 70.91 | O |
| ATOM | 1402 | CB | VAL | A | 182 | 19.413 | −4.635 | 22.800 | 1.00 | 69.22 | C |
| ATOM | 1403 | CG1 | VAL | A | 182 | 18.081 | −4.884 | 23.464 | 1.00 | 70.10 | C |
| ATOM | 1404 | CG2 | VAL | A | 182 | 20.482 | −5.548 | 23.381 | 1.00 | 70.78 | C |
| ATOM | 1405 | N | THR | A1 | 183 | 19.718 | −7.180 | 20.725 | 1.00 | 72.69 | N |
| ATOM | 1406 | CA | THR | A1 | 183 | 19.386 | −8.566 | 20.422 | 1.00 | 74.52 | C |
| ATOM | 1407 | C | THR | A | 183 | 20.363 | −9.522 | 21.102 | 1.00 | 75.85 | C |
| ATOM | 1408 | O | THR | A | 183 | 21.253 | −10.049 | 20.396 | 1.00 | 77.27 | O |
| ATOM | 1409 | CB | THR | A | 183 | 19.432 | −8.809 | 18.902 | 1.00 | 74.78 | C |
| ATOM | 1410 | OG1 | THR | A | 183 | 18.594 | −7.851 | 18.241 | 1.00 | 74.27 | O |
| ATOM | 1411 | CG2 | THR | A | 183 | 18.961 | −10.216 | 18.572 | 1.00 | 75.05 | C |
| ATOM | 1412 | OXT | THR | A | 183 | 20.238 | −9.723 | 22.331 | 1.00 | 76.42 | O |
| TER | 1413 | | THR | A | 183 | | | | | | |
| ATOM | 1414 | N | GLY | B | 0 | −0.916 | −8.800 | −41.627 | 1.00 | 76.11 | N |
| ATOM | 1415 | CA | GLY | B | 0 | −2.379 | −8.812 | −41.314 | 1.00 | 75.51 | C |
| ATOM | 1416 | C | GLY | B | 0 | −2.653 | −8.476 | −39.863 | 1.00 | 74.69 | C |
| ATOM | 1417 | O | GLY | B | 0 | −3.454 | −7.597 | −39.566 | 1.00 | 74.32 | O |
| ATOM | 1418 | N | GLN | B | 1 | −1.981 | −9.178 | −38.958 | 1.00 | 74.58 | N |
| ATOM | 1419 | CA | GLN | B | 1 | −2.147 | −8.962 | −37.525 | 1.00 | 73.94 | C |
| ATOM | 1420 | C | GLN | B | 1 | −0.879 | −8.352 | −36.940 | 1.00 | 73.10 | C |
| ATOM | 1421 | O | GLN | B | 1 | −0.565 | −8.566 | −35.761 | 1.00 | 72.99 | O |
| ATOM | 1422 | CB | GLN | B | 1 | −2.439 | −10.292 | −36.819 | 1.00 | 75.96 | C |
| ATOM | 1423 | CG | GLN | B | 1 | −3.915 | −10.592 | −36.563 | 1.00 | 79.43 | C |
| ATOM | 1424 | CD | GLN | B | 1 | −4.777 | −10.533 | −37.814 | 1.00 | 81.04 | C |
| ATOM | 1425 | OE1 | GLN | B | 1 | −5.015 | −9.461 | −38.371 | 1.00 | 81.58 | O |
| ATOM | 1426 | NE2 | GLN | B | 1 | −5.251 | −11.694 | −38.260 | 1.00 | 82.82 | N |
| ATOM | 1427 | N | SER | B | 2 | −0.155 | −7.597 | −37.768 | 1.00 | 70.93 | N |
| ATOM | 1428 | CA | SER | B | 2 | 1.090 | −6.955 | −37.346 | 1.00 | 67.32 | C |
| ATOM | 1429 | C | SER | B | 2 | 0.770 | −5.841 | −36.348 | 1.00 | 64.63 | C |
| ATOM | 1430 | O | SER | B | 2 | 0.577 | −4.677 | −36.718 | 1.00 | 62.84 | O |
| ATOM | 1431 | CB | SER | B | 2 | 1.825 | −6.396 | −38.566 | 1.00 | 67.65 | C |
| ATOM | 1432 | OG | SER | B | 2 | 3.224 | −6.354 | −38.342 | 1.00 | 68.54 | O |
| ATOM | 1433 | N | GLY | B | 3 | 0.713 | −6.222 | −35.075 | 1.00 | 61.66 | N |
| ATOM | 1434 | CA | GLY | B | 3 | 0.380 | −5.286 | −34.018 | 1.00 | 57.33 | C |
| ATOM | 1435 | C | GLY | B | 3 | 1.466 | −4.308 | −33.624 | 1.00 | 53.83 | C |
| ATOM | 1436 | O | GLY | B | 3 | 2.539 | −4.281 | −34.230 | 1.00 | 54.15 | O |
| ATOM | 1437 | N | PRO | B | 4 | 1.207 | −3.485 | −32.595 | 1.00 | 50.46 | N |
| ATOM | 1438 | CA | PRO | B | 4 | 2.167 | −2.492 | −32.113 | 1.00 | 49.03 | C |
| ATOM | 1439 | C | PRO | B | 4 | 3.507 | −3.069 | −31.673 | 1.00 | 47.42 | C |
| ATOM | 1440 | O | PRO | B | 4 | 3.577 | −4.099 | −30.994 | 1.00 | 46.75 | O |
| ATOM | 1441 | CB | PRO | B | 4 | 1.415 | −1.807 | −30.967 | 1.00 | 48.16 | C |
| ATOM | 1442 | CG | PRO | B | 4 | 0.471 | −2.867 | −30.499 | 1.00 | 48.05 | C |
| ATOM | 1443 | CD | PRO | B | 4 | −0.022 | −3.453 | −31.784 | 1.00 | 48.13 | C |
| ATOM | 1444 | N | LEU | B | 5 | 4.566 | −2.387 | −32.088 | 1.00 | 44.51 | N |
| ATOM | 1445 | CA | LEU | B | 5 | 5.916 | −2.772 | −31.754 | 1.00 | 42.00 | C |
| ATOM | 1446 | C | LEU | B | 5 | 6.114 | −2.771 | −30.241 | 1.00 | 41.52 | C |
| ATOM | 1447 | O | LEU | B | 5 | 5.443 | −2.035 | −29.511 | 1.00 | 38.34 | O |
| ATOM | 1448 | CB | LEU | B | 5 | 6.896 | −1.805 | −32.416 | 1.00 | 42.25 | C |
| ATOM | 1449 | CG | LEU | B | 5 | 6.739 | −1.786 | −33.934 | 1.00 | 43.15 | C |
| ATOM | 1450 | CD1 | LEU | B | 5 | 7.789 | −0.881 | −34.543 | 1.00 | 44.53 | C |
| ATOM | 1451 | CD2 | LEU | B | 5 | 6.869 | −3.202 | −34.482 | 1.00 | 44.08 | C |
| ATOM | 1452 | N | PRO | B | 6 | 7.043 | −3.607 | −29.752 | 1.00 | 41.71 | N |
| ATOM | 1453 | CA | PRO | B | 6 | 7.337 | −3.709 | −28.315 | 1.00 | 41.67 | C |
| ATOM | 1454 | C | PRO | B | 6 | 7.703 | −2.359 | −27.684 | 1.00 | 42.24 | C |
| ATOM | 1455 | O | PRO | B | 6 | 8.496 | −1.600 | −28.233 | 1.00 | 41.49 | O |
| ATOM | 1456 | CB | PRO | B | 6 | 8.487 | −4.722 | −28.265 | 1.00 | 40.38 | C |
| ATOM | 1457 | CG | PRO | B | 6 | 9.126 | −4.603 | −29.641 | 1.00 | 41.88 | C |
| ATOM | 1458 | CD | PRO | B | 6 | 7.938 | −4.473 | −30.546 | 1.00 | 38.69 | C |
| ATOM | 1459 | N | LYS | B | 7 | 7.120 | −2.073 | −26.525 | 1.00 | 42.93 | N |
| ATOM | 1460 | CA | LYS | B | 7 | 7.357 | −0.814 | −25.831 | 1.00 | 45.34 | C |
| ATOM | 1461 | C | LYS | B | 7 | 8.825 | −0.523 | −25.511 | 1.00 | 44.35 | C |
| ATOM | 1462 | O | LYS | B | 7 | 9.590 | −1.423 | −25.175 | 1.00 | 45.90 | O |
| ATOM | 1463 | CB | LYS | B | 7 | 6.560 | −0.784 | −24.522 | 1.00 | 46.93 | C |
| ATOM | 1464 | CG | LYS | B | 7 | 7.111 | −1.718 | −23.456 | 1.00 | 49.09 | C |
| ATOM | 1465 | CD | LYS | B | 7 | 6.247 | −1.737 | −22.206 | 1.00 | 50.98 | C |
| ATOM | 1466 | CE | LYS | B | 7 | 6.802 | −2.729 | −21.187 | 1.00 | 53.32 | C |
| ATOM | 1467 | NZ | LYS | B | 7 | 6.018 | −2.754 | −19.922 | 1.00 | 54.10 | N |
| ATOM | 1468 | N | PRO | B | 8 | 9.235 | 0.747 | −25.624 | 1.00 | 42.33 | N |
| ATOM | 1469 | CA | PRO | B | 8 | 10.619 | 1.109 | −25.322 | 1.00 | 41.52 | C |
| ATOM | 1470 | C | PRO | B | 8 | 10.749 | 1.295 | −23.819 | 1.00 | 40.88 | C |
| ATOM | 1471 | O | PRO | B | 8 | 9.786 | 1.114 | −23.067 | 1.00 | 40.96 | O |
| ATOM | 1472 | CB | PRO | B | 8 | 10.794 | 2.432 | −26.055 | 1.00 | 40.26 | C |
| ATOM | 1473 | CG | PRO | B | 8 | 9.453 | 3.066 | −25.868 | 1.00 | 41.18 | C |
| ATOM | 1474 | CD | PRO | B | 8 | 8.516 | 1.898 | −26.197 | 1.00 | 43.68 | C |
| ATOM | 1475 | N | SER | B | 9 | 11.946 | 1.657 | −23.386 | 1.00 | 38.78 | N |
| ATOM | 1476 | CA | SER | B | 9 | 12.188 | 1.898 | −21.982 | 1.00 | 37.76 | C |

TABLE 2-continued

| | | | | | | | | | | |
|---|---|---|---|---|---|---|---|---|---|---|
| ATOM | 1477 | C | SER | B | 9 | 12.270 | 3.408 | −21.799 | 1.00 | 35.98 | C |
| ATOM | 1478 | O | SER | B | 9 | 12.630 | 4.141 | −22.723 | 1.00 | 35.63 | O |
| ATOM | 1479 | CB | SER | B | 9 | 13.506 | 1.252 | −21.554 | 1.00 | 37.75 | C |
| ATOM | 1480 | OG | SER | B | 9 | 14.577 | 1.783 | −22.310 | 1.00 | 42.67 | O |
| ATOM | 1481 | N | LEU | B | 10 | 11.915 | 3.866 | −20.610 | 1.00 | 35.05 | N |
| ATOM | 1482 | CA | LEU | B | 10 | 11.970 | 5.278 | −20.282 | 1.00 | 35.79 | C |
| ATOM | 1483 | C | LEU | B | 10 | 12.429 | 5.376 | −18.841 | 1.00 | 37.18 | C |
| ATOM | 1484 | O | LEU | B | 10 | 11.688 | 5.040 | −17.929 | 1.00 | 37.97 | O |
| ATOM | 1485 | CB | LEU | B | 10 | 10.594 | 5.921 | −20.427 | 1.00 | 32.79 | C |
| ATOM | 1486 | CG | LEU | B | 10 | 10.472 | 7.377 | −19.970 | 1.00 | 33.11 | C |
| ATOM | 1487 | CD1 | LEU | B | 10 | 11.563 | 8.255 | −20.627 | 1.00 | 29.06 | C |
| ATOM | 1488 | CD2 | LEU | B | 10 | 9.070 | 7.883 | −20.318 | 1.00 | 31.07 | C |
| ATOM | 1489 | N | GLN | B | 11 | 13.661 | 5.814 | −18.632 | 1.00 | 39.79 | N |
| ATOM | 1490 | CA | GLN | B | 11 | 14.159 | 5.929 | −17.277 | 1.00 | 41.73 | C |
| ATOM | 1491 | C | GLN | B | 11 | 14.713 | 7.310 | −17.001 | 1.00 | 40.82 | C |
| ATOM | 1492 | O | GLN | B | 11 | 14.964 | 8.090 | −17.921 | 1.00 | 40.87 | O |
| ATOM | 1493 | CB | GLN | B | 11 | 15.221 | 4.862 | −17.014 | 1.00 | 45.84 | C |
| ATOM | 1494 | CG | GLN | B | 11 | 16.382 | 4.871 | −17.985 | 1.00 | 53.62 | C |
| ATOM | 1495 | CD | GLN | B | 11 | 17.255 | 3.628 | −17.846 | 1.00 | 58.56 | C |
| ATOM | 1496 | OE1 | GLN | B | 11 | 16.812 | 2.505 | −18.133 | 1.00 | 59.65 | O |
| ATOM | 1497 | NE2 | GLN | B | 11 | 18.501 | 3.820 | −17.401 | 1.00 | 57.80 | N |
| ATOM | 1498 | N | ALA | B | 12 | 14.888 | 7.608 | −15.721 | 1.00 | 39.93 | $$ |
| ATOM | 1499 | CA | ALA | B | 12 | 15.406 | 8.892 | −15.284 | 1.00 | 38.99 | $$ |
| ATOM | 1500 | C | ALA | B | 12 | 16.749 | 8.705 | −14.576 | 1.00 | 39.34 | $$ |
| ATOM | 1501 | O | ALA | B | 12 | 16.870 | 7.912 | −13.637 | 1.00 | 39.09 | $$ |
| ATOM | 1502 | CB | ALA | B | 12 | 14.395 | 9.569 | −14.351 | 1.00 | 34.74 | $$ |
| ATOM | 1503 | N | LEU | B | 13 | 17.756 | 9.437 | −15.034 | 1.00 | 38.76 | $$ |
| ATOM | 1504 | CA | LEU | B | 13 | 19.083 | 9.348 | −14.447 | 1.00 | 39.97 | $$ |
| ATOM | 1505 | C | LEU | B | 13 | 19.455 | 10.673 | −13.801 | 1.00 | 39.10 | $$ |
| ATOM | 1506 | O | LEU | B | 13 | 19.158 | 11.738 | −14.337 | 1.00 | 39.92 | $$ |
| ATOM | 1507 | CB | LEU | B | 13 | 20.109 | 8.991 | −15.523 | 1.00 | 41.41 | $$ |
| ATOM | 1508 | CG | LEU | B | 13 | 19.758 | 7.775 | −16.384 | 1.00 | 44.56 | $$ |
| ATOM | 1509 | CD1 | LEU | B | 13 | 20.621 | 7.750 | −17.635 | 1.00 | 43.42 | $$ |
| ATOM | 1510 | CD2 | LEU | B | 13 | 19.926 | 6.507 | −15.563 | 1.00 | 46.07 | $$ |
| ATOM | 1511 | N | PRO | B | 14 | 20.108 | 10.620 | −12.631 | 1.00 | 37.97 | $$ |
| ATOM | 1512 | CA | PRO | B | 14 | 20.462 | 9.359 | −11.971 | 1.00 | 38.97 | $$ |
| ATOM | 1513 | C | PRO | B | 14 | 19.292 | 8.732 | −11.198 | 1.00 | 40.43 | $$ |
| ATOM | 1514 | O | PRO | B | 14 | 19.406 | 7.598 | −10.723 | 1.00 | 41.67 | $$ |
| ATOM | 1515 | CB | PRO | B | 14 | 21.608 | 9.768 | −11.049 | 1.00 | 35.49 | $$ |
| ATOM | 1516 | CG | PRO | B | 14 | 21.192 | 11.122 | −10.630 | 1.00 | 35.62 | $$ |
| ATOM | 1517 | CD | PRO | B | 14 | 20.702 | 11.764 | −11.920 | 1.00 | 35.91 | $$ |
| ATOM | 1518 | N | SER | B | 15 | 18.175 | 9.458 | −11.082 | 1.00 | 39.35 | $$ |
| ATOM | 1519 | CA | SER | B | 15 | 17.015 | 8.947 | −10.350 | 1.00 | 38.53 | $$ |
| ATOM | 1520 | C | SER | B | 15 | 15.675 | 9.619 | −10.659 | 1.00 | 38.34 | $$ |
| ATOM | 1521 | O | SER | B | 15 | 15.630 | 10.711 | −11.218 | 1.00 | 37.17 | $$ |
| ATOM | 1522 | CB | SER | B | 15 | 17.272 | 9.044 | −8.846 | 1.00 | 36.82 | $$ |
| ATOM | 1523 | OG | SER | B | 15 | 16.127 | 8.649 | −8.107 | 1.00 | 37.33 | $$ |
| ATOM | 1524 | N | SER | B | 16 | 14.590 | 8.946 | −10.267 | 1.00 | 39.07 | $$ |
| ATOM | 1525 | CA | SER | B | 16 | 13.223 | 9.433 | −10.453 | 1.00 | 38.15 | $$ |
| ATOM | 1526 | C | SER | B | 16 | 12.858 | 10.421 | −9.364 | 1.00 | 38.46 | $$ |
| ATOM | 1527 | O | SER | B | 16 | 12.021 | 11.296 | −9.577 | 1.00 | 39.46 | $$ |
| ATOM | 1528 | CB | SER | B | 16 | 12.229 | 8.284 | −10.402 | 1.00 | 39.10 | $$ |
| ATOM | 1529 | OG | SER | B | 16 | 12.401 | 7.417 | −11.500 | 1.00 | 46.01 | $$ |
| ATOM | 1530 | N | LEU | B | 17 | 13.455 | 10.250 | −8.186 | 1.00 | 38.48 | $$ |
| ATOM | 1531 | CA | LEU | B | 17 | 13.222 | 11.151 | −7.059 | 1.00 | 38.73 | $$ |
| ATOM | 1532 | C | LEU | B | 17 | 14.220 | 12.279 | −7.256 | 1.00 | 38.04 | $$ |
| ATOM | 1533 | O | LEU | B | 17 | 15.408 | 12.109 | −6.993 | 1.00 | 38.28 | $$ |
| ATOM | 1534 | CB | LEU | B | 17 | 13.498 | 10.442 | −5.728 | 1.00 | 40.34 | $$ |
| ATOM | 1535 | CG | LEU | B | 17 | 12.443 | 9.501 | −5.143 | 1.00 | 43.65 | $$ |
| ATOM | 1536 | CD1 | LEU | B | 17 | 11.221 | 10.310 | −4.780 | 1.00 | 45.10 | $$ |
| ATOM | 1537 | CD2 | LEU | B | 17 | 12.078 | 8.405 | −6.137 | 1.00 | 44.83 | $$ |
| ATOM | 1538 | N | VAL | B | 18 | 13.734 | 13.429 | −7.713 | 1.00 | 37.92 | $$ |
| ATOM | 1539 | CA | VAL | B | 18 | 14.598 | 14.570 | −8.001 | 1.00 | 36.34 | $$ |
| ATOM | 1540 | C | VAL | B | 18 | 14.317 | 15.800 | −7.161 | 1.00 | 37.48 | $$ |
| ATOM | 1541 | O | VAL | B | 18 | 13.259 | 16.416 | −7.286 | 1.00 | 36.65 | $$ |
| ATOM | 1542 | CB | VAL | B | 18 | 14.465 | 15.005 | −9.486 | 1.00 | 36.96 | $$ |
| ATOM | 1543 | CG1 | VAL | B | 18 | 15.699 | 15.808 | −9.910 | 1.00 | 32.75 | $$ |
| ATOM | 1544 | CG2 | VAL | B | 18 | 14.258 | 13.783 | −10.386 | 1.00 | 35.47 | $$ |
| ATOM | 1545 | N | PRO | B | 19 | 15.269 | 16.185 | −6.294 | 1.00 | 39.40 | $$ |
| ATOM | 1546 | CA | PRO | B | 19 | 15.041 | 17.375 | −5.468 | 1.00 | 38.70 | $$ |
| ATOM | 1547 | C | PRO | B | 19 | 15.056 | 18.604 | −6.352 | 1.00 | 38.08 | $$ |
| ATOM | 1548 | O | PRO | B | 19 | 15.753 | 18.626 | −7.364 | 1.00 | 36.89 | $$ |
| ATOM | 1549 | CB | PRO | B | 19 | 16.203 | 17.343 | −4.473 | 1.00 | 38.32 | $$ |
| ATOM | 1550 | CG | PRO | B | 19 | 17.262 | 16.578 | −5.189 | 1.00 | 40.30 | $$ |
| ATOM | 1551 | CD | PRO | B | 19 | 16.504 | 15.488 | −5.891 | 1.00 | 39.74 | $$ |
| ATOM | 1552 | N | LEU | B | 20 | 14.270 | 19.610 | −5.984 | 1.00 | 37.74 | $$ |
| ATOM | 1553 | CA | LEU | B | 20 | 14.210 | 20.840 | −6.765 | 1.00 | 39.73 | $$ |
| ATOM | 1554 | C | LEU | B | 20 | 15.604 | 21.369 | −7.077 | 1.00 | 41.81 | $$ |
| ATOM | 1555 | O | LEU | B | 20 | 16.548 | 21.184 | −6.303 | 1.00 | 43.28 | $$ |
| ATOM | 1556 | CB | LEU | B | 20 | 13.420 | 21.921 | −6.020 | 1.00 | 37.07 | $$ |

TABLE 2-continued

| | | | | | | | | | | |
|---|---|---|---|---|---|---|---|---|---|---|
| ATOM | 1557 | CG | LEU | B | 20 | 11.990 | 21.551 | −5.633 | 1.00 | 38.86 | $$ |
| ATOM | 1558 | CD1 | LEU | B | 20 | 11.330 | 22.732 | −4.937 | 1.00 | 38.75 | C |
| ATOM | 1559 | CD2 | LEU | B | 20 | 11.203 | 21.153 | −6.876 | 1.00 | 36.95 | C |
| ATOM | 1560 | N | GLU | B | 21 | 15.720 | 22.026 | −8.225 | 1.00 | 42.17 | N |
| ATOM | 1561 | CA | GLU | B | 21 | 16.972 | 22.607 | −8.671 | 1.00 | 42.62 | C |
| ATOM | 1562 | C | GLU | B | 21 | 18.072 | 21.593 | −8.983 | 1.00 | 42.20 | C |
| ATOM | 1563 | O | GLU | B | 21 | 19.183 | 21.973 | −9.346 | 1.00 | 42.95 | O |
| ATOM | 1564 | CB | GLU | B | 21 | 17.460 | 23.629 | −7.643 | 1.00 | 41.87 | C |
| ATOM | 1565 | CG | GLU | B | 21 | 16.467 | 24.759 | −7.405 | 1.00 | 44.41 | C |
| ATOM | 1566 | CD | GLU | B | 21 | 15.918 | 25.345 | −8.702 | 1.00 | 46.18 | C |
| ATOM | 1567 | OE1 | GLU | B | 21 | 16.726 | 25.738 | −9.566 | 1.00 | 47.48 | O |
| ATOM | 1568 | OE2 | GLU | B | 21 | 14.678 | 25.413 | −8.860 | 1.00 | 48.55 | O |
| ATOM | 1569 | N | LYS | B | 22 | 17.775 | 20.308 | −8.841 | 1.00 | 40.59 | N |
| ATOM | 1570 | CA | LYS | B | 22 | 18.769 | 19.290 | −9.161 | 1.00 | 41.63 | C |
| ATOM | 1571 | C | LYS | B | 22 | 18.521 | 18.764 | −10.579 | 1.00 | 40.37 | C |
| ATOM | 1572 | O | LYS | B | 22 | 17.422 | 18.899 | −11.121 | 1.00 | 39.93 | O |
| ATOM | 1573 | CB | LYS | B | 22 | 18.717 | 18.150 | −8.148 | 1.00 | 44.86 | C |
| ATOM | 1574 | CG | LYS | B | 22 | 19.453 | 18.441 | −6.845 | 1.00 | 48.49 | C |
| ATOM | 1575 | CD | LYS | B | 22 | 20.946 | 18.282 | −7.024 | 1.00 | 51.44 | C |
| ATOM | 1576 | CE | LYS | B | 22 | 21.672 | 18.303 | −5.688 | 1.00 | 54.38 | C |
| ATOM | 1577 | NZ | LYS | B | 22 | 23.073 | 17.772 | −5.804 | 1.00 | 55.73 | N |
| ATOM | 1578 | N | PRO | B | 23 | 19.546 | 18.164 | −11.201 | 1.00 | 39.83 | N |
| ATOM | 1579 | CA | PRO | B | 23 | 19.433 | 17.628 | −12.562 | 1.00 | 38.04 | C |
| ATOM | 1580 | C | PRO | B | 23 | 18.791 | 16.255 | −12.718 | 1.00 | 36.68 | C |
| ATOM | 1581 | O | PRO | B | 23 | 18.840 | 15.420 | −11.815 | 1.00 | 35.68 | O |
| ATOM | 1582 | CB | PRO | B | 23 | 20.878 | 17.621 | −13.032 | 1.00 | 35.55 | C |
| ATOM | 1583 | CG | PRO | B | 23 | 21.591 | 17.212 | −11.782 | 1.00 | 37.07 | C |
| ATOM | 1584 | CD | PRO | B | 23 | 20.944 | 18.089 | −10.731 | 1.00 | 38.52 | C |
| ATOM | 1585 | N | VAL | B | 24 | 18.178 | 16.038 | −13.878 | 1.00 | 35.26 | N |
| ATOM | 1586 | CA | VAL | B | 24 | 17.581 | 14.744 | −14.198 | 1.00 | 34.16 | C |
| ATOM | 1587 | C | VAL | B | 24 | 17.541 | 14.553 | −15.697 | 1.00 | 32.06 | C |
| ATOM | 1588 | O | VAL | B | 24 | 17.198 | 15.462 | −16.442 | 1.00 | 32.80 | O |
| ATOM | 1589 | CB | VAL | B | 24 | 16.139 | 14.573 | −13.642 | 1.00 | 35.06 | C |
| ATOM | 1590 | CG1 | VAL | B | 24 | 15.190 | 15.578 | −14.278 | 1.00 | 32.12 | C |
| ATOM | 1591 | CG2 | VAL | B | 24 | 15.666 | 13.141 | −13.910 | 1.00 | 31.10 | C |
| ATOM | 1592 | N | THR | B | 25 | 17.904 | 13.365 | −16.142 | 1.00 | 32.41 | N |
| ATOM | 1593 | CA | THR | B | 25 | 17.901 | 13.074 | −17.566 | 1.00 | 34.56 | C |
| ATOM | 1594 | C | THR | B | 25 | 16.896 | 11.964 | −17.847 | 1.00 | 35.02 | C |
| ATOM | 1595 | O | THR | B | 25 | 16.971 | 10.890 | −17.254 | 1.00 | 35.11 | O |
| ATOM | 1596 | CB | THR | B | 25 | 19.302 | 12.621 | −18.045 | 1.00 | 33.96 | C |
| ATOM | 1597 | OG1 | THR | B | 25 | 20.249 | 13.666 | −17.802 | 1.00 | 37.14 | O |
| ATOM | 1598 | CG2 | THR | B | 25 | 19.292 | 12.303 | −19.523 | 1.00 | 32.40 | C |
| ATOM | 1599 | N | LEU | B | 26 | 15.942 | 12.238 | −18.730 | 1.00 | 35.70 | N |
| ATOM | 1600 | CA | LEU | B | 26 | 14.948 | 11.243 | −19.100 | 1.00 | 37.65 | C |
| ATOM | 1601 | C | LEU | B | 26 | 15.380 | 10.651 | −20.430 | 1.00 | 37.96 | C |
| ATOM | 1602 | O | LEU | B | 26 | 15.529 | 11.360 | −21.416 | 1.00 | 38.81 | O |
| ATOM | 1603 | CB | LEU | B | 26 | 13.560 | 11.871 | −19.211 | 1.00 | 38.89 | C |
| ATOM | 1604 | CG | LEU | B | 26 | 12.853 | 12.207 | −17.893 | 1.00 | 41.77 | C |
| ATOM | 1605 | CD1 | LEU | B | 26 | 13.627 | 13.285 | −17.157 | 1.00 | 43.79 | C |
| ATOM | 1606 | CD2 | LEU | B | 26 | 11.424 | 12.694 | −18.176 | 1.00 | 43.06 | C |
| ATOM | 1607 | N | ARG | B | 27 | 15.589 | 9.342 | −20.440 | 1.00 | 39.90 | N |
| ATOM | 1608 | CA | ARG | B | 27 | 16.047 | 8.634 | −21.624 | 1.00 | 40.88 | C |
| ATOM | 1609 | C | ARG | B | 27 | 15.072 | 7.549 | −22.102 | 1.00 | 41.05 | C |
| ATOM | 1610 | O | ARG | B | 27 | 14.734 | 6.607 | −21.365 | 1.00 | 39.39 | O |
| ATOM | 1611 | CB | ARG | B | 27 | 17.419 | 8.028 | −21.309 | 1.00 | 45.70 | C |
| ATOM | 1612 | CG | ARG | B | 27 | 18.056 | 7.170 | −22.390 | 1.00 | 53.67 | C |
| ATOM | 1613 | CD | ARG | B | 27 | 19.434 | 6.685 | −21.917 | 1.00 | 59.18 | C |
| ATOM | 1614 | NE | ARG | B | 27 | 19.971 | 5.615 | −22.756 | 1.00 | 66.42 | N |
| ATOM | 1615 | CZ | ARG | B | 27 | 21.127 | 4.990 | −22.533 | 1.00 | 68.44 | C |
| ATOM | 1616 | NH1 | ARG | B | 27 | 21.878 | 5.330 | −21.491 | 1.00 | 68.78 | N |
| ATOM | 1617 | NH2 | ARG | B | 27 | 21.530 | 4.021 | −23.350 | 1.00 | 67.63 | N |
| ATOM | 1618 | N | CYS | B | 28 | 14.618 | 7.702 | −23.342 | 1.00 | 39.46 | N |
| ATOM | 1619 | CA | CYS | B | 28 | 13.714 | 6.746 | −23.964 | 1.00 | 40.06 | C |
| ATOM | 1620 | C | CYS | B | 28 | 14.602 | 5.838 | −24.797 | 1.00 | 41.47 | C |
| ATOM | 1621 | O | CYS | B | 28 | 15.423 | 6.314 | −25.578 | 1.00 | 41.30 | O |
| ATOM | 1622 | CB | CYS | B | 28 | 12.719 | 7.468 | −24.870 | 1.00 | 39.09 | C |
| ATOM | 1623 | SG | CYS | B | 28 | 11.419 | 6.413 | −25.592 | 1.00 | 40.76 | S |
| ATOM | 1624 | N | GLN | B | 29 | 14.458 | 4.530 | −24.630 | 1.00 | 45.47 | N |
| ATOM | 1625 | CA | GLN | B | 29 | 15.290 | 3.605 | −25.392 | 1.00 | 47.54 | C |
| ATOM | 1626 | C | GLN | B | 29 | 14.519 | 2.465 | −26.040 | 1.00 | 47.10 | C |
| ATOM | 1627 | O | GLN | B | 29 | 13.830 | 1.700 | −25.371 | 1.00 | 46.86 | O |
| ATOM | 1628 | CB | GLN | B | 29 | 16.389 | 3.021 | −24.502 | 1.00 | 50.07 | C |
| ATOM | 1629 | CG | GLN | B | 29 | 17.316 | 2.063 | −25.241 | 1.00 | 54.22 | C |
| ATOM | 1630 | CD | GLN | B | 29 | 18.168 | 2.759 | −26.291 | 1.00 | 57.28 | C |
| ATOM | 1631 | OE1 | GLN | B | 29 | 19.080 | 3.523 | −25.962 | 1.00 | 60.11 | O |
| ATOM | 1632 | NE2 | GLN | B | 29 | 17.871 | 2.504 | −27.561 | 1.00 | 57.17 | N |
| ATOM | 1633 | N | GLY | B | 30 | 14.644 | 2.365 | −27.356 | 1.00 | 48.10 | N |
| ATOM | 1634 | CA | GLY | B | 30 | 13.984 | 1.302 | −28.087 | 1.00 | 48.88 | C |
| ATOM | 1635 | C | GLY | B | 30 | 15.040 | 0.407 | −28.709 | 1.00 | 48.92 | C |
| ATOM | 1636 | O | GLY | B | 30 | 16.233 | 0.674 | −28.572 | 1.00 | 49.72 | O |

TABLE 2-continued

| | | | | | | | | | | |
|---|---|---|---|---|---|---|---|---|---|---|
| ATOM | 1637 | N | PRO | B | 31 | 14.643 | −0.671 | −29.390 | 1.00 | 49.44 N |
| ATOM | 1638 | CA | PRO | B | 31 | 15.645 | −1.547 | −30.002 | 1.00 | 50.19 C |
| ATOM | 1639 | C | PRO | B | 31 | 16.267 | −0.838 | −31.192 | 1.00 | 51.51 C |
| ATOM | 1640 | O | PRO | B | 31 | 15.819 | 0.242 | −31.576 | 1.00 | 50.81 O |
| ATOM | 1641 | CB | PRO | B | 31 | 14.824 | −2.760 | −30.419 | 1.00 | 49.60 C |
| ATOM | 1642 | CG | PRO | B | 31 | 13.509 | −2.133 | −30.796 | 1.00 | 50.27 C |
| ATOM | 1643 | CD | PRO | B | 31 | 13.278 | −1.154 | −29.665 | 1.00 | 49.39 C |
| ATOM | 1644 | N | PRO | B | 32 | 17.316 | −1.424 | −31.790 | 1.00 | 53.98 N |
| ATOM | 1645 | CA | PRO | B | 32 | 17.918 | −0.748 | −32.945 | 1.00 | 53.80 C |
| ATOM | 1646 | C | PRO | B | 32 | 16.905 | −0.684 | −34.084 | 1.00 | 52.92 C |
| ATOM | 1647 | O | PRO | B | 32 | 16.124 | −1.617 | −34.276 | 1.00 | 53.02 O |
| ATOM | 1648 | CB | PRO | B | 32 | 19.103 | −1.645 | −33.283 | 1.00 | 54.89 C |
| ATOM | 1649 | CG | PRO | B | 32 | 18.580 | −3.016 | −32.917 | 1.00 | 53.63 C |
| ATOM | 1650 | CD | PRO | B | 32 | 17.929 | −2.750 | −31.576 | 1.00 | 52.83 C |
| ATOM | 1651 | N | GLY | B | 33 | 16.904 | 0.420 | −34.824 | 1.00 | 53.07 N |
| ATOM | 1652 | CA | GLY | B | 33 | 15.982 | 0.542 | −35.941 | 1.00 | 52.09 C |
| ATOM | 1653 | C | GLY | B | 33 | 14.884 | 1.571 | −35.766 | 1.00 | 51.47 C |
| ATOM | 1654 | O | GLY | B | 33 | 13.942 | 1.638 | −36.565 | 1.00 | 50.58 O |
| ATOM | 1655 | N | VAL | B | 34 | 14.991 | 2.378 | −34.719 | 1.00 | 50.07 N |
| ATOM | 1656 | CA | VAL | B | 34 | 13.986 | 3.398 | −34.479 | 1.00 | 49.03 C |
| ATOM | 1657 | C | VAL | B | 34 | 14.186 | 4.529 | −35.486 | 1.00 | 48.95 C |
| ATOM | 1658 | O | VAL | B | 34 | 15.314 | 4.948 | −35.751 | 1.00 | 49.29 O |
| ATOM | 1659 | CB | VAL | B | 34 | 14.096 | 3.937 | −33.041 | 1.00 | 49.10 C |
| ATOM | 1660 | CG1 | VAL | | 34 | 13.023 | 4.996 | −32.786 | 1.00 | 49.37 C |
| ATOM | 1661 | CG2 | | | 34 | 13.953 | 2.783 | −32.060 | 1.00 | 46.32 C |
| ATOM | 1662 | N | ASP | B | 35 | 13.092 | 5.001 | −36.071 | 1.00 | 48.43 N |
| ATOM | 1663 | CA | ASP | B | 35 | 13.171 | 6.080 | −37.046 | 1.00 | 46.78 C |
| ATOM | 1664 | C | ASP | B | 35 | 12.760 | 7.363 | −36.379 | 1.00 | 45.10 C |
| ATOM | 1665 | O | ASP | B | 35 | 13.186 | 8.450 | −36.762 | 1.00 | 46.24 O |
| ATOM | 1666 | CB | ASP | B | 35 | 12.226 | 5.835 | −38.223 | 1.00 | 46.93 C |
| ATOM | 1667 | CG | ASP | B | 35 | 12.606 | 4.627 | −39.032 | 1.00 | 46.98 C |
| ATOM | 1668 | OD1 | ASP | B | 35 | 13.821 | 4.383 | −39.186 | 1.00 | 47.82 O |
| ATOM | 1669 | OD2 | ASP | B | 35 | 11.691 | 3.936 | −39.530 | 1.00 | 48.35 O |
| ATOM | 1670 | N | LEU | B | 36 | 11.916 | 7.227 | −35.371 | 1.00 | 44.30 N |
| ATOM | 1671 | CA | LEU | B | 36 | 11.411 | 8.384 | −34.669 | 1.00 | 44.07 C |
| ATOM | 1672 | C | LEU | B | 36 | 11.064 | 8.056 | −33.231 | 1.00 | 43.46 C |
| ATOM | 1673 | O | LEU | B | 36 | 10.439 | 7.036 | −32.936 | 1.00 | 42.25 O |
| ATOM | 1674 | CB | LEU | B | 36 | 10.164 | 8.918 | −35.387 | 1.00 | 43.64 C |
| ATOM | 1675 | CG | LEU | B | 36 | 9.414 | 10.085 | −34.741 | 1.00 | 46.63 C |
| ATOM | 1676 | CD1 | LEU | B | 36 | 10.282 | 11.344 | −34.770 | 1.00 | 45.85 C |
| ATOM | 1677 | CD2 | LEU | B | 36 | 8.104 | 10.321 | −35.482 | 1.00 | 46.87 C |
| ATOM | 1678 | N | TYR | B | 37 | 11.495 | 8.934 | −32.339 | 1.00 | 42.00 N |
| ATOM | 1679 | CA | TYR | B | 37 | 11.207 | 8.796 | −30.932 | 1.00 | 40.65 C |
| ATOM | 1680 | C | TYR | B | 37 | 10.218 | 9.887 | −30.594 | 1.00 | 41.05 C |
| ATOM | 1681 | O | TYR | B | 37 | 10.086 | 10.867 | −31.323 | 1.00 | 42.03 O |
| ATOM | 1682 | CB | TYR | B | 37 | 12.468 | 9.000 | −30.116 | 1.00 | 39.25 C |
| ATOM | 1683 | CG | TYR | B | 37 | 13.257 | 7.744 | −29.893 | 1.00 | 39.18 C |
| ATOM | 1684 | CD1 | TYR | B | 37 | 12.808 | 6.779 | −29.000 | 1.00 | 35.91 C |
| ATOM | 1685 | CD2 | TYR | B | 37 | 14.474 | 7.533 | −30.544 | 1.00 | 36.15 C |
| ATOM | 1686 | CE1 | TYR | B | 37 | 13.547 | 5.638 | −28.750 | 1.00 | 36.56 C |
| ATOM | 1687 | CE2 | TYR | B | 37 | 15.220 | 6.394 | −30.301 | 1.00 | 36.95 C |
| ATOM | 1688 | CZ | TYR | B | 37 | 14.751 | 5.451 | −29.396 | 1.00 | 36.67 C |
| ATOM | 1689 | OH | TYR | B | 37 | 15.501 | 4.337 | −29.102 | 1.00 | 38.70 O |
| ATOM | 1690 | N | ARG | B | 38 | 9.518 | 9.713 | −29.486 | 1.00 | 42.64 N |
| ATOM | 1691 | CA | ARG | B | 38 | 8.555 | 10.703 | −29.042 | 1.00 | 43.15 C |
| ATOM | 1692 | C | ARG | B | 38 | 8.390 | 10.574 | −27.540 | 1.00 | 42.41 C |
| ATOM | 1693 | O | ARG | B | 38 | 7.883 | 9.575 | −27.043 | 1.00 | 44.73 O |
| ATOM | 1694 | CB | ARG | B | 38 | 7.210 | 10.510 | −29.743 | 1.00 | 41.74 C |
| ATOM | 1695 | CG | ARG | B | 38 | 6.157 | 11.497 | −29.280 | 1.00 | 46.02 C |
| ATOM | 1696 | CD | ARG | B | 38 | 4.910 | 11.418 | −30.134 | 1.00 | 48.21 C |
| ATOM | 1697 | NE | ARG | B | 38 | 5.167 | 11.842 | −31.505 | 1.00 | 50.43 N |
| ATOM | 1698 | CZ | ARG | B | 38 | 4.268 | 11.772 | −32.479 | 1.00 | 52.29 C |
| ATOM | 1699 | NH1 | ARG | B | 38 | 3.060 | 11.294 | −32.217 | 1.00 | 53.85 N |
| ATOM | 1700 | NH2 | ARG | B | 38 | 4.572 | 12.174 | −33.706 | 1.00 | 51.92 N |
| ATOM | 1701 | N | LEU | B | 39 | 8.847 | 11.586 | −26.819 | 1.00 | 42.38 N |
| ATOM | 1702 | CA | LEU | B | 39 | 8.751 | 11.593 | −25.371 | 1.00 | 40.18 C |
| ATOM | 1703 | C | LEU | B | 39 | 7.701 | 12.645 | −25.043 | 1.00 | 41.53 C |
| ATOM | 1704 | O | LEU | B | 39 | 7.709 | 13.745 | −25.606 | 1.00 | 41.57 O |
| ATOM | 1705 | CB | LEU | B | 39 | 10.113 | 11.941 | −24.776 | 1.00 | 39.30 C |
| ATOM | 1706 | CG | LEU | B | 39 | 10.251 | 12.235 | −23.285 | 1.00 | 40.62 C |
| ATOM | 1707 | CD1 | LEU | B | 39 | 9.611 | 11.146 | −22.461 | 1.00 | 43.92 C |
| ATOM | 1708 | CD2 | LEU | B | 39 | 11.724 | 12.344 | −22.959 | 1.00 | 43.37 C |
| ATOM | 1709 | N | GLU | B | 40 | 6.791 | 12.311 | −24.139 | 1.00 | 41.64 N |
| ATOM | 1710 | CA | GLU | B | 40 | 5.718 | 13.231 | −23.808 | 1.00 | 42.24 C |
| ATOM | 1711 | C | GLU | B | 40 | 5.378 | 13.309 | −22.329 | 1.00 | 40.88 C |
| ATOM | 1712 | O | GLU | B | 40 | 5.462 | 12.319 | −21.608 | 1.00 | 41.34 O |
| ATOM | 1713 | CB | GLU | B | 40 | 4.472 | 12.819 | −24.601 | 1.00 | 43.82 C |
| ATOM | 1714 | CG | GLU | B | 40 | 3.297 | 13.770 | −24.519 | 1.00 | 49.55 C |
| ATOM | 1715 | CD | GLU | B | 40 | 2.112 | 13.281 | −25.341 | 1.00 | 53.26 C |
| ATOM | 1716 | OE1 | GLU | B | 40 | 2.310 | 12.972 | −26.538 | 1.00 | 53.51 O |

TABLE 2-continued

| | | | | | | | | | | |
|---|---|---|---|---|---|---|---|---|---|---|
| ATOM | 1717 | OE2 | GLU | B | 40 | 0.986 | 13.204 | −24.792 | 1.00 | 54.66 | O |
| ATOM | 1718 | N | LYS | B | 41 | 4.998 | 14.503 | −21.887 | 1.00 | 40.87 | N |
| ATOM | 1719 | CA | LYS | B | 41 | 4.590 | 14.728 | −20.507 | 1.00 | 39.45 | C |
| ATOM | 1720 | C | LYS | B | 41 | 3.071 | 14.652 | −20.572 | 1.00 | 40.15 | C |
| ATOM | 1721 | O | LYS | B | 41 | 2.431 | 15.484 | −21.197 | 1.00 | 42.08 | O |
| ATOM | 1722 | CB | LYS | B | 41 | 5.038 | 16.109 | −20.023 | 1.00 | 37.29 | C |
| ATOM | 1723 | CG | LYS | B | 41 | 4.900 | 16.299 | −18.527 | 1.00 | 36.03 | C |
| ATOM | 1724 | CD | LYS | B | 41 | 5.546 | 17.589 | −18.060 | 1.00 | 37.36 | C |
| ATOM | 1725 | CE | LYS | B | 41 | 5.556 | 17.691 | −16.538 | 1.00 | 36.25 | C |
| ATOM | 1726 | NZ | LYS | B | 41 | 4.183 | 17.550 | −15.956 | 1.00 | 39.49 | N |
| ATOM | 1727 | N | LEU | B | 42 | 2.504 | 13.642 | −19.931 | 1.00 | 41.82 | N |
| ATOM | 1728 | CA | LEU | B | 42 | 1.065 | 13.403 | −19.945 | 1.00 | 42.85 | C |
| ATOM | 1729 | C | LEU | B | 42 | 0.119 | 14.536 | −19.529 | 1.00 | 43.81 | C |
| ATOM | 1730 | O | LEU | B | 42 | −1.001 | 14.612 | −20.027 | 1.00 | 43.08 | O |
| ATOM | 1731 | CB | LEU | B | 42 | 0.757 | 12.156 | −19.105 | 1.00 | 42.65 | C |
| ATOM | 1732 | CG | LEU | B | 42 | 1.490 | 10.869 | −19.514 | 1.00 | 42.87 | C |
| ATOM | 1733 | CD1 | LEU | B | 42 | 0.945 | 9.706 | −18.713 | 1.00 | 43.12 | C |
| ATOM | 1734 | CD2 | LEU | B | 42 | 1.314 | 10.606 | −21.000 | 1.00 | 41.76 | C |
| ATOM | 1735 | N | SER | B | 43 | 0.554 | 15.410 | −18.629 | 1.00 | 44.11 | N |
| ATOM | 1736 | CA | SER | B | 43 | −0.306 | 16.491 | −18.155 | 1.00 | 44.55 | C |
| ATOM | 1737 | C | SER | B | 43 | −0.537 | 17.603 | −19.165 | 1.00 | 46.82 | C |
| ATOM | 1738 | O | SER | B | 43 | −1.557 | 18.296 | −19.113 | 1.00 | 45.47 | O |
| ATOM | 1739 | CB | SER | B | 43 | 0.272 | 17.109 | −16.880 | 1.00 | 44.17 | C |
| ATOM | 1740 | OG | SER | B | 43 | 1.483 | 17.792 | −17.150 | 1.00 | 45.33 | O |
| ATOM | 1741 | N | SER | B | 44 | 0.408 | 17.774 | −20.083 | 1.00 | 48.47 | N |
| ATOM | 1742 | CA | SER | B | 44 | 0.306 | 18.833 | −21.074 | 1.00 | 49.87 | C |
| ATOM | 1743 | C | SER | B | 44 | 0.056 | 18.331 | −22.482 | 1.00 | 51.00 | C |
| ATOM | 1744 | O | SER | B | 44 | −0.318 | 19.105 | −23.357 | 1.00 | 51.61 | O |
| ATOM | 1745 | CB | SER | B | 44 | 1.587 | 19.667 | −21.076 | 1.00 | 50.93 | C |
| ATOM | 1746 | OG | SER | B | 44 | 2.660 | 18.953 | −21.676 | 1.00 | 52.12 | O |
| ATOM | 1747 | N | SER | B | 45 | 0.260 | 17.040 | −22.705 | 1.00 | 53.00 | N |
| ATOM | 1748 | CA | SER | B | 45 | 0.079 | 16.471 | −24.035 | 1.00 | 55.24 | C |
| ATOM | 1749 | C | SER | B | 45 | 1.047 | 17.181 | −24.981 | 1.00 | 56.21 | C |
| ATOM | 1750 | O | SER | B | 45 | 0.763 | 17.368 | −26.165 | 1.00 | 58.19 | O |
| ATOM | 1751 | CB | SER | B | 45 | −1.367 | 16.654 | −24.520 | 1.00 | 55.71 | C |
| ATOM | 1752 | OG | SER | B | 45 | −2.285 | 15.952 | −23.698 | 1.00 | 55.41 | O |
| ATOM | 1753 | N | ARG | B | 46 | 2.183 | 17.598 | −24.432 | 1.00 | 56.13 | N |
| ATOM | 1754 | CA | ARG | B | 46 | 3.226 | 18.263 | −25.205 | 1.00 | 55.10 | C |
| ATOM | 1755 | C | ARG | B | 46 | 4.382 | 17.274 | −25.320 | 1.00 | 52.12 | C |
| ATOM | 1756 | O | ARG | B | 46 | 4.956 | 16.857 | −24.316 | 1.00 | 50.57 | O |
| ATOM | 1757 | CB | ARG | B | 46 | 3.688 | 19.541 | −24.496 | 1.00 | 57.87 | C |
| ATOM | 1758 | CG | ARG | B | 46 | 4.932 | 20.198 | −25.108 | 1.00 | 61.31 | C |
| ATOM | 1759 | CD | ARG | B | 46 | 6.137 | 20.129 | −24.151 | 1.00 | 64.42 | C |
| ATOM | 1760 | NE | ARG | B | 46 | 6.681 | 18.772 | −24.008 | 1.00 | 63.25 | N |
| ATOM | 1761 | CZ | ARG | B | 46 | 7.503 | 18.389 | −23.032 | 1.00 | 61.20 | C |
| ATOM | 1762 | NH1 | ARG | B | 46 | 7.880 | 19.259 | −22.095 | 1.00 | 57.41 | N |
| ATOM | 1763 | NH2 | ARG | B | 46 | 7.956 | 17.140 | −23.006 | 1.00 | 55.99 | N |
| ATOM | 1764 | N | TYR | B | 47 | 4.713 | 16.893 | −26.548 | 1.00 | 50.61 | N |
| ATOM | 1765 | CA | TYR | B | 47 | 5.784 | 15.937 | −26.775 | 1.00 | 46.46 | C |
| ATOM | 1766 | C | TYR | B | 47 | 6.921 | 16.509 | −27.612 | 1.00 | 44.21 | C |
| ATOM | 1767 | O | TYR | B | 47 | 6.802 | 17.582 | −28.195 | 1.00 | 42.05 | O |
| ATOM | 1768 | CB | TYR | B | 47 | 5.216 | 14.696 | −27.455 | 1.00 | 45.94 | C |
| ATOM | 1769 | CG | TYR | B | 47 | 4.728 | 14.952 | −28.853 | 1.00 | 45.67 | C |
| ATOM | 1770 | CD1 | TYR | B | 47 | 5.621 | 15.017 | −29.916 | 1.00 | 46.57 | C |
| ATOM | 1771 | CD2 | TYR | B | 47 | 3.376 | 15.149 | −29.116 | 1.00 | 47.06 | C |
| ATOM | 1772 | CE1 | TYR | B | 47 | 5.189 | 15.271 | −31.205 | 1.00 | 47.71 | C |
| ATOM | 1773 | CE2 | TYR | B | 47 | 2.929 | 15.405 | −30.408 | 1.00 | 46.90 | C |
| ATOM | 1774 | CZ | TYR | B | 47 | 3.843 | 15.465 | −31.447 | 1.00 | 47.09 | C |
| ATOM | 1775 | OH | TYR | B | 47 | 3.429 | 15.731 | −32.733 | 1.00 | 48.36 | O |
| ATOM | 1776 | N | GLN | B | 48 | 8.027 | 15.773 | −27.645 | 1.00 | 43.37 | N |
| ATOM | 1777 | CA | GLN | B | 48 | 9.210 | 16.144 | −28.407 | 1.00 | 41.64 | C |
| ATOM | 1778 | C | GLN | B | 48 | 9.567 | 14.950 | −29.271 | 1.00 | 41.91 | C |
| ATOM | 1779 | O | GLN | B | 48 | 9.104 | 13.837 | −29.014 | 1.00 | 41.10 | O |
| ATOM | 1780 | CB | GLN | B | 48 | 10.385 | 16.457 | −27.473 | 1.00 | 42.45 | C |
| ATOM | 1781 | CG | GLN | B | 48 | 10.825 | 15.293 | −26.581 | 1.00 | 40.39 | C |
| ATOM | 1782 | CD | GLN | B | 48 | 12.050 | 15.633 | −25.751 | 1.00 | 39.63 | C |
| ATOM | 1783 | OE1 | GLN | B | 48 | 12.110 | 16.689 | −25.123 | 1.00 | 39.88 | O |
| ATOM | 1784 | NE2 | GLN | B | 48 | 13.032 | 14.736 | −25.740 | 1.00 | 37.82 | N |
| ATOM | 1785 | N | ASP | B | 49 | 10.401 | 15.177 | −30.279 | 1.00 | 42.14 | N |
| ATOM | 1786 | CA | ASP | B | 49 | 10.804 | 14.106 | −31.179 | 1.00 | 44.17 | C |
| ATOM | 1787 | C | ASP | B | 49 | 12.136 | 13.496 | −30.799 | 1.00 | 43.42 | C |
| ATOM | 1788 | O | ASP | B | 49 | 12.644 | 12.628 | −31.508 | 1.00 | 44.77 | O |
| ATOM | 1789 | CB | ASP | B | 49 | 10.885 | 14.616 | −32.621 | 1.00 | 47.70 | C |
| ATOM | 1790 | CG | ASP | B | 49 | 9.552 | 15.121 | −33.135 | 1.00 | 51.03 | C |
| ATOM | 1791 | OD1 | ASP | B | 49 | 8.561 | 14.357 | −33.072 | 1.00 | 54.50 | O |
| ATOM | 1792 | OD2 | ASP | B | 49 | 9.495 | 16.281 | −33.600 | 1.00 | 53.31 | O |
| ATOM | 1793 | N | GLN | B | 50 | 12.696 | 13.937 | −29.679 | 1.00 | 42.44 | N |
| ATOM | 1794 | CA | GLN | B | 50 | 13.988 | 13.432 | −29.234 | 1.00 | 42.29 | C |
| ATOM | 1795 | C | GLN | B | 50 | 13.847 | 12.397 | −28.120 | 1.00 | 41.76 | C |
| ATOM | 1796 | O | GLN | B | 50 | 12.947 | 12.486 | −27.289 | 1.00 | 40.40 | O |

TABLE 2-continued

| | | | | | | | | | | |
|---|---|---|---|---|---|---|---|---|---|---|
| ATOM | 1797 | CB | GLN | B | 50 | 14.866 | 14.597 | −28.764 | 1.00 | 44.59 | C |
| ATOM | 1798 | CG | GLN | B | 50 | 15.219 | 15.628 | −29.852 | 1.00 | 48.68 | C |
| ATOM | 1799 | CD | GLN | B | 50 | 14.026 | 16.471 | −30.335 | 1.00 | 53.36 | C |
| ATOM | 1800 | OE1 | GLN | B | 50 | 13.284 | 17.060 | −29.535 | 1.00 | 52.68 | O |
| ATOM | 1801 | NE2 | GLN | B | 50 | 13.853 | 16.543 | −31.656 | 1.00 | 55.77 | N |
| ATOM | 1802 | N | ALA | B | 51 | 14.743 | 11.412 | −28.111 | 1.00 | 39.65 | N |
| ATOM | 1803 | CA | ALA | B | 51 | 14.715 | 10.358 | −27.101 | 1.00 | 38.16 | C |
| ATOM | 1804 | C | ALA | B | 51 | 15.130 | 10.840 | −25.708 | 1.00 | 38.77 | C |
| ATOM | 1805 | O | ALA | B | 51 | 14.766 | 10.227 | −24.700 | 1.00 | 38.70 | O |
| ATOM | 1806 | CB | ALA | B | 51 | 15.623 | 9.205 | −27.531 | 1.00 | 35.19 | C |
| ATOM | 1807 | N | VAL | B | 52 | 15.881 | 11.937 | −25.643 | 1.00 | 36.88 | N |
| ATOM | 1808 | CA | VAL | B | 52 | 16.353 | 12.435 | −24.358 | 1.00 | 36.41 | C |
| ATOM | 1809 | C | VAL | B | 52 | 15.849 | 13.807 | −23.933 | 1.00 | 36.63 | C |
| ATOM | 1810 | O | VAL | B | 52 | 15.935 | 14.764 | −24.691 | 1.00 | 38.92 | O |
| ATOM | 1811 | CB | VAL | B | 52 | 17.890 | 12.492 | −24.337 | 1.00 | 36.70 | C |
| ATOM | 1812 | CG1 | VAL | B | 52 | 18.370 | 13.120 | −23.039 | 1.00 | 35.28 | C |
| ATOM | 1813 | CG2 | VAL | B | 52 | 18.460 | 11.107 | −24.503 | 1.00 | 34.89 | C |
| ATOM | 1814 | N | LEU | B | 53 | 15.326 | 13.899 | −22.713 | 1.00 | 35.98 | N |
| ATOM | 1815 | CA | LEU | B | 53 | 14.871 | 15.175 | −22.173 | 1.00 | 35.66 | C |
| ATOM | 1816 | C | LEU | B | 53 | 15.734 | 15.478 | −20.957 | 1.00 | 36.25 | C |
| ATOM | 1817 | O | LEU | B | 53 | 15.617 | 14.817 | −19.924 | 1.00 | 36.96 | O |
| ATOM | 1818 | CB | LEU | B | 53 | 13.391 | 15.128 | −21.760 | 1.00 | 33.43 | C |
| ATOM | 1819 | CG | LEU | B | 53 | 12.897 | 16.300 | −20.887 | 1.00 | 34.36 | C |
| ATOM | 1820 | CD1 | LEU | B | 53 | 13.249 | 17.643 | −21.511 | 1.00 | 30.60 | C |
| ATOM | 1821 | CD2 | LEU | B | 53 | 11.390 | 16.187 | −20.675 | 1.00 | 31.30 | C |
| ATOM | 1822 | N | PHE | B | 54 | 16.613 | 16.467 | −21.083 | 1.00 | 36.44 | N |
| ATOM | 1823 | CA | PHE | B | 54 | 17.483 | 16.846 | −19.975 | 1.00 | 34.55 | C |
| ATOM | 1824 | C | PHE | B | 54 | 16.942 | 18.052 | −19.221 | 1.00 | 34.18 | C |
| ATOM | 1825 | O | PHE | B | 54 | 16.685 | 19.105 | −19.806 | 1.00 | 34.13 | O |
| ATOM | 1826 | CB | PHE | B | 54 | 18.895 | 17.152 | −20.482 | 1.00 | 35.31 | C |
| ATOM | 1827 | CG | PHE | B | 54 | 19.829 | 17.659 | −19.412 | 1.00 | 34.98 | C |
| ATOM | 1828 | CD1 | PHE | B | 54 | 19.986 | 16.961 | −18.217 | 1.00 | 36.58 | C |
| ATOM | 1829 | CD2 | PHE | B | 54 | 20.554 | 18.829 | −19.60 | 1.00 | 36.37 | C |
| ATOM | 1830 | CE1 | PHE | B | 54 | 20.855 | 17.418 | −17.219 | 1.00 | 36.79 | C |
| ATOM | 1831 | CE2 | PHE | B | 54 | 21.427 | 19.302 | −18.617 | 1.00 | 38.09 | C |
| ATOM | 1832 | CZ | PHE | B | 54 | 21.579 | 18.589 | −17.416 | 1.00 | 38.04 | C |
| ATOM | 1833 | N | ILE | B | 55 | 16.769 | 17.880 | −17.915 | 1.00 | 34.15 | N |
| ATOM | 1834 | CA | ILE | B | 55 | 16.283 | 18.932 | −17.028 | 1.00 | 33.65 | C |
| ATOM | 1835 | C | ILE | B | 55 | 17.457 | 19.303 | −16.111 | 1.00 | 35.39 | C |
| ATOM | 1836 | O | ILE | B | 55 | 17.740 | 18.591 | −15.146 | 1.00 | 36.77 | O |
| ATOM | 1837 | CB | ILE | B | 55 | 15.105 | 18.413 | −16.168 | 1.00 | 32.55 | C |
| ATOM | 1838 | CG1 | ILE | B | 55 | 13.906 | 18.086 | −17.062 | 1.00 | 29.44 | C |
| ATOM | 1839 | CG2 | ILE | B | 55 | 14.725 | 19.434 | −15.105 | 1.00 | 32.67 | C |
| ATOM | 1840 | CD1 | ILE | B | 55 | 12.743 | 17.431 | −16.305 | 1.00 | 27.00 | C |
| ATOM | 1841 | N | PRO | B | 56 | 18.163 | 20.411 | −16.406 | 1.00 | 36.87 | N |
| ATOM | 1842 | CA | PRO | B | 56 | 19.304 | 20.833 | −15.581 | 1.00 | 36.83 | C |
| ATOM | 1843 | C | PRO | B | 56 | 18.940 | 21.112 | −14.130 | 1.00 | 37.90 | C |
| ATOM | 1844 | O | PRO | B | 56 | 19.655 | 20.694 | −13.215 | 1.00 | 39.82 | O |
| ATOM | 1845 | CB | PRO | B | 56 | 19.815 | 22.078 | −16.298 | 1.00 | 36.41 | C |
| ATOM | 1846 | CG | PRO | B | 56 | 18.568 | 22.643 | −16.920 | 1.00 | 38.39 | C |
| ATOM | 1847 | CD | PRO | B | 56 | 17.886 | 21.405 | −17.462 | 1.00 | 38.09 | C |
| ATOM | 1848 | N | ALA | B | 57 | 17.830 | 21.817 | −13.922 | 1.00 | 36.40 | N |
| ATOM | 1849 | CA | ALA | B | 57 | 17.364 | 22.137 | −12.576 | 1.00 | 35.59 | C |
| ATOM | 1850 | C | ALA | B | 57 | 15.891 | 21.762 | −12.424 | 1.00 | 34.76 | C |
| ATOM | 1851 | O | ALA | B | 57 | 15.016 | 22.428 | −12.976 | 1.00 | 33.28 | O |
| ATOM | 1852 | CB | ALA | B | 57 | 17.559 | 23.617 | −12.299 | 1.00 | 34.90 | C |
| ATOM | 1853 | N | MET | B | 58 | 15.622 | 20.703 | −11.662 | 1.00 | 35.79 | N |
| ATOM | 1854 | CA | MET | B | 58 | 14.247 | 20.227 | −11.454 | 1.00 | 36.56 | C |
| ATOM | 1855 | C | MET | B | 58 | 13.288 | 21.288 | −10.893 | 1.00 | 34.88 | C |
| ATOM | 1856 | O | MET | B | 58 | 13.566 | 21.928 | −9.880 | 1.00 | 35.56 | O |
| ATOM | 1857 | CB | MET | B | 58 | 14.258 | 18.991 | −10.555 | 1.00 | 34.64 | C |
| ATOM | 1858 | CG | MET | B | 58 | 12.889 | 18.389 | −10.280 | 1.00 | 37.25 | C |
| ATOM | 1859 | SD | MET | B | 58 | 11.953 | 17.858 | −11.735 | 1.00 | 36.75 | S |
| ATOM | 1860 | CE | MET | B | 58 | 12.850 | 16.469 | −12.223 | 1.00 | 38.27 | C |
| ATOM | 1861 | N | LYS | B | 59 | 12.164 | 21.470 | −11.580 | 1.00 | 34.76 | N |
| ATOM | 1862 | CA | LYS | B | 59 | 11.148 | 22.453 | −11.193 | 1.00 | 32.97 | C |
| ATOM | 1863 | C | LYS | B | 59 | 9.856 | 21.722 | −10.846 | 1.00 | 33.46 | C |
| ATOM | 1864 | O | LYS | B | 59 | 9.676 | 20.561 | −11.230 | 1.00 | 33.85 | O |
| ATOM | 1865 | CB | LYS | B | 59 | 10.885 | 23.425 | −12.349 | 1.00 | 31.89 | C |
| ATOM | 1866 | CG | LYS | B | 59 | 12.141 | 24.032 | −12.988 | 1.00 | 31.89 | C |
| ATOM | 1867 | CD | LYS | B | 59 | 12.923 | 24.899 | −12.012 | 1.00 | 30.77 | C |
| ATOM | 1868 | CE | LYS | B | 59 | 14.021 | 25.688 | −12.729 | 1.00 | 31.56 | C |
| ATOM | 1869 | NZ | LYS | B | 59 | 14.875 | 26.493 | −11.794 | 1.00 | 31.88 | N |
| ATOM | 1870 | N | ARG | B | 60 | 8.960 | 22.394 | −10.128 | 1.00 | 32.63 | N |
| ATOM | 1871 | CA | ARG | B | 60 | 7.699 | 21.771 | −9.745 | 1.00 | 32.73 | C |
| ATOM | 1872 | C | ARG | B | 60 | 6.829 | 21.426 | −10.956 | 1.00 | 32.61 | C |
| ATOM | 1873 | O | ARG | B | 60 | 6.119 | 20.423 | −10.962 | 1.00 | 30.60 | O |
| ATOM | 1874 | CB | ARG | B | 60 | 6.906 | 22.698 | −8.827 | 1.00 | 34.46 | C |
| ATOM | 1875 | CG | ARG | B | 60 | 7.532 | 22.962 | −7.477 | 1.00 | 39.36 | C |
| ATOM | 1876 | CD | ARG | B | 60 | 6.600 | 23.818 | −6.646 | 1.00 | 40.85 | C |

TABLE 2-continued

| | | | | | | | | | | | |
|---|---|---|---|---|---|---|---|---|---|---|---|
| ATOM | 1877 | NE | ARG | B | 60 | 6.420 | 25.144 | −7.230 | 1.00 | 43.82 | N |
| ATOM | 1878 | CZ | ARG | B | 60 | 5.268 | 25.811 | −7.240 | 1.00 | 45.46 | C |
| ATOM | 1879 | NH1 | ARG | B | 60 | 4.178 | 25.277 | −6.703 | 1.00 | 46.11 | N |
| ATOM | 1880 | NH2 | ARG | B | 60 | 5.209 | 27.024 | −7.774 | 1.00 | 45.70 | N |
| ATOM | 1881 | N | SER | B | 61 | 6.891 | 22.268 | −11.982 | 1.00 | 32.55 | N |
| ATOM | 1882 | CA | SER | B | 61 | 6.087 | 22.077 | −13.180 | 1.00 | 32.56 | C |
| ATOM | 1883 | C | SER | B | 61 | 6.582 | 20.958 | −14.069 | 1.00 | 33.24 | C |
| ATOM | 1884 | O | SER | B | 61 | 5.876 | 20.531 | −14.977 | 1.00 | 33.15 | O |
| ATOM | 1885 | CB | SER | B | 61 | 6.030 | 23.377 | −13.982 | 1.00 | 32.90 | C |
| ATOM | 1886 | OG | SER | B | 61 | 7.334 | 23.847 | −14.264 | 1.00 | 37.70 | O |
| ATOM | 1887 | N | LEU | B | 62 | 7.794 | 20.479 | −13.812 | 1.00 | 34.16 | N |
| ATOM | 1888 | CA | LEU | B | 62 | 8.351 | 19.406 | −14.623 | 1.00 | 34.43 | C |
| ATOM | 1889 | C | LEU | B | 62 | 8.135 | 18.057 | −13.942 | 1.00 | 34.16 | C |
| ATOM | 1890 | O | LEU | B | 62 | 8.525 | 17.013 | −14.471 | 1.00 | 35.02 | O |
| ATOM | 1891 | CB | LEU | B | 62 | 9.845 | 19.660 | −14.880 | 1.00 | 34.58 | C |
| ATOM | 1892 | CG | LEU | B | 62 | 10.184 | 20.900 | −15.733 | 1.00 | 34.56 | C |
| ATOM | 1893 | CD1 | LEU | B | 62 | 11.690 | 21.212 | −15.675 | 1.00 | 30.95 | C |
| ATOM | 1894 | CD2 | LEU | B | 62 | 9.749 | 20.660 | −17.171 | 1.00 | 30.64 | C |
| ATOM | 1895 | N | ALA | B | 63 | 7.506 | 18.086 | −12.767 | 1.00 | 32.33 | N |
| ATOM | 1896 | CA | ALA | B | 63 | 7.219 | 16.863 | −12.016 | 1.00 | 31.38 | C |
| ATOM | 1897 | C | ALA | B | 63 | 5.962 | 16.280 | −12.620 | 1.00 | 29.97 | C |
| ATOM | 1898 | O | ALA | B | 63 | 5.098 | 17.024 | −13.064 | 1.00 | 29.65 | O |
| ATOM | 1899 | CB | ALA | B | 63 | 6.990 | 17.180 | −10.546 | 1.00 | 29.71 | C |
| ATOM | 1900 | N | GLY | B | 64 | 5.856 | 14.958 | −12.649 | 1.00 | 30.09 | N |
| ATOM | 1901 | CA | GLY | B | 64 | 4.669 | 14.352 | −13.230 | 1.00 | 31.03 | C |
| ATOM | 1902 | C | GLY | B | 64 | 4.907 | 13.063 | −13.992 | 1.00 | 30.84 | C |
| ATOM | 1903 | O | GLY | B | 64 | 5.973 | 12.470 | −13.893 | 1.00 | 31.57 | O |
| ATOM | 1904 | N | ARG | B | 65 | 3.904 | 12.629 | −14.751 | 1.00 | 32.11 | N |
| ATOM | 1905 | CA | ARG | B | 65 | 3.989 | 11.394 | −15.524 | 1.00 | 32.82 | C |
| ATOM | 1906 | C | ARG | B | 65 | 4.507 | 11.616 | −16.939 | 1.00 | 32.28 | C |
| ATOM | 1907 | O | ARG | B | 65 | 4.125 | 12.570 | −17.615 | 1.00 | 30.19 | O |
| ATOM | 1908 | CB | ARG | B | 65 | 2.607 | 10.723 | −15.619 | 1.00 | 36.40 | C |
| ATOM | 1909 | CG | ARG | B | 65 | 1.953 | 10.363 | −14.288 | 1.00 | 43.71 | C |
| ATOM | 1910 | CD | ARG | B | 65 | 0.496 | 9.916 | −14.485 | 1.00 | 49.91 | C |
| ATOM | 1911 | NE | ARG | B | 65 | −0.343 | 10.939 | −15.132 | 1.00 | 55.98 | N |
| ATOM | 1912 | CZ | ARG | B | 65 | −0.729 | 12.085 | −14.568 | 1.00 | 56.48 | C |
| ATOM | 1913 | NH1 | ARG | B | 65 | −0.363 | 12.381 | −13.329 | 1.00 | 56.81 | N |
| ATOM | 1914 | NH2 | ARG | B | 65 | −1.476 | 12.946 | −15.247 | 1.00 | 57.34 | N |
| ATOM | 1915 | N | TYR | B | 66 | 5.375 | 10.719 | −17.389 | 1.00 | 32.29 | N |
| ATOM | 1916 | CA | TYR | B | 66 | 5.912 | 10.792 | −18.744 | 1.00 | 32.24 | C |
| ATOM | 1917 | C | TYR | B | 66 | 5.839 | 9.410 | −19.380 | 1.00 | 32.50 | C |
| ATOM | 1918 | O | TYR | B | 66 | 5.912 | 8.386 | −18.696 | 1.00 | 33.19 | O |
| ATOM | 1919 | CB | TYR | B | 66 | 7.382 | 11.242 | −18.758 | 1.00 | 32.18 | C |
| ATOM | 1920 | CG | TYR | B | 66 | 7.638 | 12.669 | −18.340 | 1.00 | 31.72 | C |
| ATOM | 1921 | CD1 | TYR | B | 66 | 7.489 | 13.063 | −17.018 | 1.00 | 31.85 | C |
| ATOM | 1922 | CD2 | TYR | B | 66 | 8.077 | 13.622 | −19.268 | 1.00 | 33.40 | C |
| ATOM | 1923 | CE1 | TYR | B | 66 | 7.775 | 14.368 | −16.619 | 1.00 | 33.39 | C |
| ATOM | 1924 | CE2 | TYR | B | 66 | 8.368 | 14.932 | −18.877 | 1.00 | 31.83 | C |
| ATOM | 1925 | CZ | TYR | B | 66 | 8.219 | 15.292 | −17.552 | 1.00 | 32.95 | C |
| ATOM | 1926 | OH | TYR | B | 66 | 8.548 | 16.561 | −17.137 | 1.00 | 32.82 | O |
| ATOM | 1927 | N | ARG | B | 67 | 5.677 | 9.396 | −20.693 | 1.00 | 32.57 | N |
| ATOM | 1928 | CA | ARG | B | 67 | 5.645 | 8.163 | −21.463 | 1.00 | 33.51 | C |
| ATOM | 1929 | C | ARG | B | 67 | 6.338 | 8.503 | −22.768 | 1.00 | 32.98 | C |
| ATOM | 1930 | O | ARG | B | 67 | 6.443 | 9.672 | −23.144 | 1.00 | 30.51 | O |
| ATOM | 1931 | CB | ARG | B | 67 | 4.211 | 7.697 | −21.759 | 1.00 | 36.41 | C |
| ATOM | 1932 | CG | ARG | B | 67 | 3.528 | 6.892 | −20.655 | 1.00 | 40.33 | C |
| ATOM | 1933 | CD | ARG | B | 67 | 2.127 | 6.458 | −21.102 | 1.00 | 42.99 | C |
| ATOM | 1934 | NE | ARG | B | 67 | 1.357 | 5.757 | −20.070 | 1.00 | 44.99 | N |
| ATOM | 1935 | CZ | ARG | B | 67 | 1.556 | 4.492 | −19.700 | 1.00 | 47.59 | C |
| ATOM | 1936 | NH1 | ARG | B | 67 | 2.507 | 3.761 | −20.265 | 1.00 | 48.09 | N |
| ATOM | 1937 | NH2 | ARG | B | 67 | 0.789 | 3.947 | −18.770 | 1.00 | 49.44 | N |
| ATOM | 1938 | N | CYS | B | 68 | 6.842 | 7.483 | −23.441 | 1.00 | 32.89 | N |
| ATOM | 1939 | CA | CYS | B | 68 | 7.485 | 7.690 | −24.713 | 1.00 | 34.04 | C |
| ATOM | 1940 | C | CYS | B | 68 | 7.179 | 6.484 | −25.575 | 1.00 | 33.22 | C |
| ATOM | 1941 | O | CYS | B | 68 | 6.887 | 5.400 | −25.074 | 1.00 | 31.84 | O |
| ATOM | 1942 | CB | CYS | B | 68 | 8.995 | 7.892 | −24.545 | 1.00 | 34.86 | C |
| ATOM | 1943 | SG | CYS | B | 68 | 9.988 | 6.416 | −24.149 | 1.00 | 43.06 | S |
| ATOM | 1944 | N | SER | B | 69 | 7.201 | 6.698 | −26.881 | 1.00 | 34.40 | N |
| ATOM | 1945 | CA | SER | B | 69 | 6.933 | 5.642 | −27.834 | 1.00 | 34.47 | C |
| ATOM | 1946 | C | SER | B | 69 | 7.866 | 5.916 | −28.993 | 1.00 | 34.78 | C |
| ATOM | 1947 | O | SER | B | 69 | 8.552 | 6.937 | −29.009 | 1.00 | 34.49 | O |
| ATOM | 1948 | CB | SER | B | 69 | 5.471 | 5.697 | −28.279 | 1.00 | 31.93 | C |
| ATOM | 1949 | OG | SER | B | 69 | 4.608 | 5.634 | −27.157 | 1.00 | 33.17 | O |
| ATOM | 1950 | N | TYR | B | 70 | 7.918 | 5.001 | −29.946 | 1.00 | 34.98 | N |
| ATOM | 1951 | CA | TYR | B | 70 | 8.782 | 5.192 | −31.089 | 1.00 | 35.39 | C |
| ATOM | 1952 | C | TYR | B | 70 | 8.123 | 4.556 | −32.284 | 1.00 | 36.41 | C |
| ATOM | 1953 | O | TYR | B | 70 | 7.224 | 3.723 | −32.147 | 1.00 | 35.28 | O |
| ATOM | 1954 | CB | TYR | B | 70 | 10.153 | 4.556 | −30.845 | 1.00 | 37.00 | C |
| ATOM | 1955 | CG | TYR | B | 70 | 10.122 | 3.045 | −30.765 | 1.00 | 37.11 | C |
| ATOM | 1956 | CD1 | TYR | B | 70 | 10.076 | 2.264 | −31.918 | 1.00 | 34.86 | C |

TABLE 2-continued

| | | | | | | | | | | |
|---|---|---|---|---|---|---|---|---|---|---|
| ATOM | 1957 | CD2 | TYR | B | 70 | 10.105 | 2.398 | −29.533 | 1.00 | 36.05 | C |
| ATOM | 1958 | CE1 | TYR | B | 70 | 10.009 | 0.878 | −31.844 | 1.00 | 33.88 | C |
| ATOM | 1959 | CE2 | TYR | B | 70 | 10.041 | 1.017 | −29.452 | 1.00 | 36.63 | C |
| ATOM | 1960 | CZ | TYR | B | 70 | 9.990 | 0.260 | −30.612 | 1.00 | 34.87 | C |
| ATOM | 1961 | OH | TYR | B | 70 | 9.887 | −1.113 | −30.523 | 1.00 | 37.10 | O |
| ATOM | 1962 | N | GLN | B | 71 | 8.581 | 4.962 | −33.457 | 1.00 | 37.92 | N |
| ATOM | 1963 | CA | GLN | B | 71 | 8.052 | 4.451 | −34.700 | 1.00 | 40.43 | C |
| ATOM | 1964 | C | GLN | B | 71 | 9.158 | 3.841 | −35.552 | 1.00 | 41.44 | C |
| ATOM | 1965 | O | GLN | B | 71 | 10.226 | 4.437 | −35.730 | 1.00 | 40.57 | O |
| ATOM | 1966 | CB | GLN | B | 71 | 7.372 | 5.584 | −35.469 | 1.00 | 40.85 | C |
| ATOM | 1967 | CG | GLN | B | 71 | 6.785 | 5.164 | −36.792 | 1.00 | 42.20 | C |
| ATOM | 1968 | CD | GLN | B | 71 | 6.223 | 6.331 | −37.563 | 1.00 | 43.75 | C |
| ATOM | 1969 | OE1 | GLN | B | 71 | 6.877 | 7.367 | −37.719 | 1.00 | 46.07 | O |
| ATOM | 1970 | NE2 | GLN | B | 71 | 5.009 | 6.171 | −38.064 | 1.00 | 43.24 | N |
| ATOM | 1971 | N | ASN | B | 72 | 8.891 | 2.638 | −36.052 | 1.00 | 42.82 | N |
| ATOM | 1972 | CA | ASN | B | 72 | 9.811 | 1.921 | −36.926 | 1.00 | 45.36 | C |
| ATOM | 1973 | C | ASN | B | 72 | 8.975 | 1.573 | −38.153 | 1.00 | 46.67 | C |
| ATOM | 1974 | O | ASN | B | 72 | 8.005 | 0.816 | −38.059 | 1.00 | 46.38 | O |
| ATOM | 1975 | CB | ASN | B | 72 | 10.330 | 0.645 | −36.262 | 1.00 | 46.04 | C |
| ATOM | 1976 | CG | ASN | B | 72 | 11.345 | −0.087 | −37.129 | 1.00 | 50.17 | C |
| ATOM | 1977 | OD1 | ASN | B | 72 | 11.935 | −1.089 | −36.715 | 1.00 | 52.09 | O |
| ATOM | 1978 | ND2 | ASN | B | 72 | 11.553 | 0.413 | −38.343 | 1.00 | 51.01 | N |
| ATOM | 1979 | N | GLY | B | 73 | 9.350 | 2.124 | −39.302 | 1.00 | 46.34 | N |
| ATOM | 1980 | CA | GLY | B | 73 | 8.573 | 1.890 | −40.499 | 1.00 | 49.02 | C |
| ATOM | 1981 | C | GLY | B | 73 | 7.321 | 2.736 | −40.346 | 1.00 | 50.74 | C |
| ATOM | 1982 | O | GLY | B | 73 | 7.393 | 3.907 | −39.965 | 1.00 | 51.62 | O |
| ATOM | 1983 | N | SER | B | 74 | 6.163 | 2.163 | −40.635 | 1.00 | 51.85 | N |
| ATOM | 1984 | CA | SER | B | 74 | 4.921 | 2.913 | −40.482 | 1.00 | 52.68 | C |
| ATOM | 1985 | C | SER | B | 74 | 4.220 | 2.420 | −39.221 | 1.00 | 50.54 | C |
| ATOM | 1986 | O | SER | B | 74 | 3.030 | 2.658 | −39.020 | 1.00 | 50.61 | O |
| ATOM | 1987 | CB | SER | B | 74 | 4.024 | 2.726 | −41.717 | 1.00 | 52.89 | C |
| ATOM | 1988 | OG | SER | B | 74 | 3.963 | 1.365 | −42.102 | 1.00 | 54.68 | O |
| ATOM | 1989 | N | LEU | B | 75 | 4.987 | 1.744 | −38.368 | 1.00 | 48.26 | N |
| ATOM | 1990 | CA | LEU | B | 75 | 4.470 | 1.191 | −37.122 | 1.00 | 46.98 | C |
| ATOM | 1991 | C | LEU | B | 75 | 4.938 | 1.889 | −35.846 | 1.00 | 46.67 | C |
| ATOM | 1992 | O | LEU | B | 75 | 6.131 | 2.149 | −35.659 | 1.00 | 46.73 | O |
| ATOM | 1993 | CB | LEU | B | 75 | 4.822 | −0.295 | −37.032 | 1.00 | 44.75 | C |
| ATOM | 1994 | CG | LEU | B | 75 | 3.725 | −1.280 | −37.442 | 1.00 | 45.29 | C |
| ATOM | 1995 | CD1 | LEU | B | 75 | 3.090 | −0.844 | −38.756 | 1.00 | 46.02 | C |
| ATOM | 1996 | CD2 | LEU | B | 75 | 4.322 | −2.675 | −37.553 | 1.00 | 44.02 | C |
| ATOM | 1997 | N | TRP | B | 76 | 3.977 | 2.197 | −34.975 | 1.00 | 44.73 | N |
| ATOM | 1998 | CA | TRP | B | 76 | 4.266 | 2.818 | −33.689 | 1.00 | 41.77 | C |
| ATOM | 1999 | C | TRP | B | 76 | 4.319 | 1.694 | −32.671 | 1.00 | 40.76 | C |
| ATOM | 2000 | O | TRP | B | 76 | 3.655 | 0.668 | −32.827 | 1.00 | 41.45 | O |
| ATOM | 2001 | CB | TRP | B | 76 | 3.179 | 3.823 | −33.293 | 1.00 | 41.00 | C |
| ATOM | 2002 | CG | TRP | B | 76 | 3.394 | 5.185 | −33.889 | 1.00 | 43.16 | C |
| ATOM | 2003 | CD1 | TRP | B | 76 | 2.787 | 5.700 | −34.997 | 1.00 | 43.36 | C |
| ATOM | 2004 | CD2 | TRP | B | 76 | 4.338 | 6.177 | −33.453 | 1.00 | 41.30 | C |
| ATOM | 2005 | NE1 | TRP | B | 76 | 3.295 | 6.945 | −35.280 | 1.00 | 42.94 | N |
| ATOM | 2006 | CE2 | TRP | B | 76 | 4.249 | 7.262 | −34.350 | 1.00 | 41.74 | C |
| ATOM | 2007 | CE3 | TRP | B | 76 | 5.251 | 6.250 | −32.395 | 1.00 | 40.40 | C |
| ATOM | 2008 | CZ2 | TRP | B | 76 | 5.041 | 8.412 | −34.225 | 1.00 | 43.00 | C |
| ATOM | 2009 | CZ3 | TRP | B | 76 | 6.040 | 7.392 | −32.268 | 1.00 | 43.40 | C |
| ATOM | 2010 | CH2 | TRP | B | 76 | 5.927 | 8.459 | −33.183 | 1.00 | 43.59 | C |
| ATOM | 2011 | N | SER | B | 77 | 5.118 | 1.880 | −31.634 | 1.00 | 38.46 | N |
| ATOM | 2012 | CA | SER | B | 77 | 5.261 | 0.867 | −30.608 | 1.00 | 38.11 | C |
| ATOM | 2013 | C | SER | B | 77 | 4.255 | 1.112 | −29.496 | 1.00 | 38.45 | C |
| ATOM | 2014 | O | SER | B | 77 | 3.501 | 2.095 | −29.525 | 1.00 | 38.99 | O |
| ATOM | 2015 | CB | SER | B | 77 | 6.657 | 0.941 | −30.012 | 1.00 | 37.04 | C |
| ATOM | 2016 | OG | SER | B | 77 | 6.788 | 2.155 | −29.288 | 1.00 | 37.48 | O |
| ATOM | 2017 | N | LEU | B | 78 | 4.245 | 0.209 | −28.520 | 1.00 | 36.00 | N |
| ATOM | 2018 | CA | LEU | B | 78 | 3.377 | 0.368 | −27.371 | 1.00 | 35.64 | C |
| ATOM | 2019 | C | LEU | B | 78 | 4.073 | 1.446 | −26.570 | 1.00 | 37.10 | C |
| ATOM | 2020 | O | LEU | B | 78 | 5.282 | 1.655 | −26.712 | 1.00 | 38.40 | O |
| ATOM | 2021 | CB | LEU | B | 78 | 3.320 | −0.910 | −26.525 | 1.00 | 33.61 | C |
| ATOM | 2022 | CG | LEU | B | 78 | 2.457 | −2.096 | −26.977 | 1.00 | 34.02 | C |
| ATOM | 2023 | CD1 | LEU | B | 78 | 2.614 | −3.244 | −25.983 | 1.00 | 31.24 | C |
| ATOM | 2024 | CD2 | LEU | B | 78 | 0.998 | −1.670 | −27.067 | 1.00 | 28.27 | C |
| ATOM | 2025 | N | PRO | B | 79 | 3.327 | 2.167 | −25.732 | 1.00 | 36.74 | N |
| ATOM | 2026 | CA | PRO | B | 79 | 4.002 | 3.200 | −24.952 | 1.00 | 37.06 | C |
| ATOM | 2027 | C | PRO | B | 79 | 4.833 | 2.545 | −23.841 | 1.00 | 37.13 | C |
| ATOM | 2028 | O | PRO | B | 79 | 4.528 | 1.442 | −23.394 | 1.00 | 36.87 | O |
| ATOM | 2029 | CB | PRO | B | 79 | 2.836 | 4.031 | −24.417 | 1.00 | 36.14 | C |
| ATOM | 2030 | CG | PRO | B | 79 | 1.767 | 3.012 | −24.243 | 1.00 | 37.20 | C |
| ATOM | 2031 | CD | PRO | B | 79 | 1.873 | 2.202 | −25.515 | 1.00 | 35.23 | C |
| ATOM | 2032 | N | SER | B | 80 | 5.893 | 3.216 | −23.414 | 1.00 | 37.03 | N |
| ATOM | 2033 | CA | SER | B | 80 | 6.739 | 2.686 | −22.351 | 1.00 | 36.95 | C |
| ATOM | 2034 | C | SER | B | 80 | 5.910 | 2.754 | −21.088 | 1.00 | 37.13 | C |
| ATOM | 2035 | O | SER | B | 80 | 4.862 | 3.406 | −21.077 | 1.00 | 37.41 | O |
| ATOM | 2036 | CB | SER | B | 80 | 7.977 | 3.571 | −22.167 | 1.00 | 37.23 | C |

TABLE 2-continued

| | | | | | | | | | | |
|---|---|---|---|---|---|---|---|---|---|---|
| ATOM | 2037 | OG | SER | B | 80 | 7.618 | 4.829 | −21.610 | 1.00 | 34.55 | O |
| ATOM | 2038 | N | ASP | B | 81 | 6.364 | 2.099 | −20.024 | 1.00 | 36.59 | N |
| ATOM | 2039 | CA | ASP | B | 81 | 5.635 | 2.184 | −18.764 | 1.00 | 37.87 | C |
| ATOM | 2040 | C | ASP | B | 81 | 5.724 | 3.660 | −18.391 | 1.00 | 39.02 | C |
| ATOM | 2041 | O | ASP | B | 81 | 6.663 | 4.352 | −18.800 | 1.00 | 40.86 | O |
| ATOM | 2042 | CB | ASP | B | 81 | 6.293 | 1.328 | −17.679 | 1.00 | 37.52 | C |
| ATOM | 2043 | CG | ASP | B | 81 | 6.361 | −0.140 | −18.054 | 1.00 | 38.73 | C |
| ATOM | 2044 | OD1 | ASP | B | 81 | 5.379 | −0.663 | −18.631 | 1.00 | 36.87 | O |
| ATOM | 2045 | OD2 | ASP | B | 81 | 7.399 | −0.770 | −17.762 | 1.00 | 40.96 | O |
| ATOM | 2046 | N | GLN | B | 82 | 4.762 | 4.173 | −17.642 | 1.00 | 38.65 | N |
| ATOM | 2047 | CA | GLN | B | 82 | 4.852 | 5.578 | −17.305 | 1.00 | 41.64 | C |
| ATOM | 2048 | C | GLN | B | 82 | 5.951 | 5.853 | −16.282 | 1.00 | 40.81 | C |
| ATOM | 2049 | O | GLN | B | 82 | 6.064 | 5.173 | −15.259 | 1.00 | 38.29 | O |
| ATOM | 2050 | CB | GLN | B | 82 | 3.516 | 6.114 | −16.776 | 1.00 | 44.48 | C |
| ATOM | 2051 | CG | GLN | B | 82 | 2.954 | 5.354 | −15.596 | 1.00 | 50.45 | C |
| ATOM | 2052 | CD | GLN | B | 82 | 1.951 | 6.174 | −14.813 | 1.00 | 54.07 | C |
| ATOM | 2053 | OE1 | GLN | B | 82 | 1.178 | 6.950 | −15.386 | 1.00 | 57.55 | O |
| ATOM | 2054 | NE2 | GLN | B | 82 | 1.949 | 6.001 | −13.494 | 1.00 | 55.77 | N |
| ATOM | 2055 | N | LEU | B | 83 | 6.776 | 6.842 | −16.593 | 1.00 | 39.74 | N |
| ATOM | 2056 | CA | LEU | B | 83 | 7.832 | 7.260 | −15.694 | 1.00 | 40.28 | C |
| ATOM | 2057 | C | LEU | B | 83 | 7.196 | 8.305 | −14.787 | 1.00 | 40.26 | C |
| ATOM | 2058 | O | LEU | B | 83 | 6.693 | 9.328 | −15.261 | 1.00 | 40.58 | O |
| ATOM | 2059 | CB | LEU | B | 83 | 8.981 | 7.901 | −16.468 | 1.00 | 41.25 | C |
| ATOM | 2060 | CG | LEU | B | 83 | 10.058 | 8.563 | −15.610 | 1.00 | 41.81 | C |
| ATOM | 2061 | CD1 | LEU | B | 83 | 10.890 | 7.510 | −14.897 | 1.00 | 42.53 | C |
| ATOM | 2062 | CD2 | LEU | B | 83 | 10.938 | 9.403 | −16.495 | 1.00 | 43.98 | C |
| ATOM | 2063 | N | GLU | B | 84 | 7.188 | 8.046 | −13.489 | 1.00 | 38.89 | N |
| ATOM | 2064 | CA | GLU | B | 84 | 6.619 | 9.008 | −12.566 | 1.00 | 40.60 | C |
| ATOM | 2065 | C | GLU | B | 84 | 7.735 | 9.887 | −12.005 | 1.00 | 38.36 | C |
| ATOM | 2066 | O | GLU | B | 84 | 8.443 | 9.489 | −11.078 | 1.00 | 37.30 | O |
| ATOM | 2067 | CB | GLU | B | 84 | 5.857 | 8.270 | −11.464 | 1.00 | 43.46 | C |
| ATOM | 2068 | CG | GLU | B | 84 | 4.727 | 7.424 | −12.046 | 1.00 | 48.78 | C |
| ATOM | 2069 | CD | GLU | B | 84 | 3.884 | 6.731 | −10.997 | 1.00 | 51.88 | C |
| ATOM | 2070 | OE1 | GLU | B | 84 | 3.354 | 7.424 | −10.100 | 1.00 | 53.57 | O |
| ATOM | 2071 | OE2 | GLU | B | 84 | 3.741 | 5.493 | −11.081 | 1.00 | 53.36 | O |
| ATOM | 2072 | N | LEU | B | 85 | 7.898 | 11.071 | −12.601 | 1.00 | 35.07 | N |
| ATOM | 2073 | CA | LEU | B | 85 | 8.928 | 12.020 | −12.191 | 1.00 | 33.81 | C |
| ATOM | 2074 | C | LEU | B | 85 | 8.505 | 12.827 | −10.962 | 1.00 | 34.27 | C |
| ATOM | 2075 | O | LEU | B | 85 | 7.646 | 13.710 | −11.033 | 1.00 | 33.16 | O |
| ATOM | 2076 | CB | LEU | B | 85 | 9.274 | 12.968 | −13.343 | 1.00 | 31.31 | C |
| ATOM | 2077 | CG | LEU | B | 85 | 10.539 | 13.812 | −13.121 | 1.00 | 31.62 | C |
| ATOM | 2078 | CD1 | LEU | B | 85 | 11.728 | 12.874 | −12.900 | 1.00 | 29.49 | C |
| ATOM | 2079 | CD2 | LEU | B | 85 | 10.803 | 14.724 | −14.316 | 1.00 | 27.08 | C |
| ATOM | 2080 | N | VAL | B | 86 | 9.140 | 12.518 | −9.838 | 1.00 | 34.91 | N |
| ATOM | 2081 | CA | VAL | B | 86 | 8.848 | 13.164 | −8.570 | 1.00 | 34.42 | C |
| ATOM | 2082 | C | VAL | B | 86 | 9.847 | 14.257 | −8.235 | 1.00 | 35.16 | C |
| ATOM | 2083 | O | VAL | B | 86 | 11.047 | 14.111 | −8.459 | 1.00 | 36.25 | O |
| ATOM | 2084 | CB | VAL | B | 86 | 8.854 | 12.127 | −7.418 | 1.00 | 34.56 | C |
| ATOM | 2085 | CG1 | VAL | B | 86 | 8.622 | 12.814 | −6.088 | 1.00 | 34.59 | C |
| ATOM | 2086 | CG2 | VAL | B | 86 | 7.794 | 11.071 | −7.667 | 1.00 | 32.20 | C |
| ATOM | 2087 | N | ALA | B | 87 | 9.328 | 15.357 | −7.699 | 1.00 | 35.57 | N |
| ATOM | 2088 | CA | ALA | B | 87 | 10.138 | 16.493 | −7.287 | 1.00 | 33.90 | C |
| ATOM | 2089 | C | ALA | B | 87 | 10.167 | 16.489 | −5.764 | 1.00 | 35.74 | C |
| ATOM | 2090 | O | ALA | B | 87 | 9.118 | 16.429 | −5.125 | 1.00 | 36.03 | O |
| ATOM | 2091 | CB | ALA | B | 87 | 9.511 | 17.793 | −7.794 | 1.00 | 31.72 | C |
| ATOM | 2092 | N | THR | B | 88 | 11.354 | 16.526 | −5.168 | 1.00 | 37.16 | N |
| ATOM | 2093 | CA | THR | B | 88 | 11.410 | 16.543 | −3.709 | 1.00 | 36.85 | C |
| ATOM | 2094 | C | THR | B | 88 | 11.909 | 17.903 | −3.251 | 1.00 | 37.13 | C |
| ATOM | 2095 | O | THR | B | 88 | 12.505 | 18.651 | −4.035 | 1.00 | 38.01 | O |
| ATOM | 2096 | CB | THR | B | 88 | 12.341 | 15.440 | −3.121 | 1.00 | 36.62 | C |
| ATOM | 2097 | OG1 | THR | B | 88 | 13.708 | 15.793 | −3.346 | 1.00 | 35.45 | O |
| ATOM | 2098 | CG2 | THR | B | 88 | 12.052 | 14.088 | −3.748 | 1.00 | 31.60 | C |
| ATOM | 2099 | N | GLY | B | 89 | 11.657 | 18.210 | −1.981 | 1.00 | 37.81 | N |
| ATOM | 2100 | CA | GLY | B | 89 | 12.062 | 19.480 | −1.410 | 1.00 | 36.33 | C |
| ATOM | 2101 | C | GLY | B | 89 | 11.000 | 20.529 | −1.674 | 1.00 | 36.04 | C |
| ATOM | 2102 | O | GLY | B | 89 | 11.243 | 21.722 | −1.546 | 1.00 | 35.58 | O |
| ATOM | 2103 | N | VAL | B | 90 | 9.809 | 20.085 | −2.042 | 1.00 | 36.69 | N |
| ATOM | 2104 | CA | VAL | B | 90 | 8.728 | 21.018 | −2.339 | 1.00 | 39.65 | C |
| ATOM | 2105 | C | VAL | B | 90 | 8.102 | 21.536 | −1.054 | 1.00 | 41.20 | C |
| ATOM | 2106 | O | VAL | B | 90 | 7.410 | 22.551 | −1.057 | 1.00 | 41.81 | O |
| ATOM | 2107 | CB | VAL | B | 90 | 7.622 | 20.343 | −3.186 | 1.00 | 37.77 | C |
| ATOM | 2108 | CG1 | VAL | B | 90 | 6.570 | 21.360 | −3.577 | 1.00 | 35.16 | C |
| ATOM | 2109 | CG2 | VAL | B | 90 | 8.234 | 19.694 | −4.411 | 1.00 | 36.57 | C |
| ATOM | 2110 | N | PHE | B | 91 | 8.354 | 20.835 | 0.045 | 1.00 | 42.11 | N |
| ATOM | 2111 | CA | PHE | B | 91 | 7.784 | 21.218 | 1.330 | 1.00 | 42.29 | C |
| ATOM | 2112 | C | PHE | B | 91 | 8.768 | 20.972 | 2.465 | 1.00 | 42.73 | C |
| ATOM | 2113 | O | PHE | B | 91 | 9.805 | 20.324 | 2.273 | 1.00 | 41.46 | O |
| ATOM | 2114 | CB | PHE | B | 91 | 6.519 | 20.400 | 1.590 | 1.00 | 42.07 | C |
| ATOM | 2115 | CG | PHE | B | 91 | 5.524 | 20.445 | 0.468 | 1.00 | 40.04 | C |
| ATOM | 2116 | CD1 | PHE | B | 91 | 4.788 | 21.603 | 0.216 | 1.00 | 40.06 | C |

TABLE 2-continued

| | | | | | | | | | | |
|---|---|---|---|---|---|---|---|---|---|---|
| ATOM | 2117 | CD2 | PHE | B | 91 | 5.303 | 19.321 | −0.319 | 1.00 | 38.76 | C |
| ATOM | 2118 | CE1 | PHE | B | 91 | 3.835 | 21.637 | −0.808 | 1.00 | 39.59 | C |
| ATOM | 2119 | CE2 | PHE | B | 91 | 4.359 | 19.340 | −1.340 | 1.00 | 38.83 | C |
| ATOM | 2120 | CZ | PHE | B | 91 | 3.622 | 20.500 | −1.586 | 1.00 | 40.01 | C |
| ATOM | 2121 | N | ALA | B | 92 | 8.434 | 21.483 | 3.649 | 1.00 | 41.81 | N |
| ATOM | 2122 | CA | ALA | B | 92 | 9.286 | 21.281 | 4.816 | 1.00 | 40.93 | C |
| ATOM | 2123 | C | ALA | B | 92 | 9.356 | 19.782 | 5.073 | 1.00 | 39.54 | C |
| ATOM | 2124 | O | ALA | B | 92 | 8.374 | 19.066 | 4.887 | 1.00 | 40.28 | O |
| ATOM | 2125 | CB | ALA | B | 92 | 8.712 | 21.996 | 6.024 | 1.00 | 37.55 | C |
| ATOM | 2126 | N | LYS | B | 93 | 10.520 | 19.308 | 5.487 | 1.00 | 39.15 | N |
| ATOM | 2127 | CA | LYS | B | 93 | 10.700 | 17.890 | 5.747 | 1.00 | 40.51 | C |
| ATOM | 2128 | C | LYS | B | 93 | 9.899 | 17.395 | 6.948 | 1.00 | 39.57 | C |
| ATOM | 2129 | O | LYS | B | 93 | 9.662 | 18.133 | 7.902 | 1.00 | 40.61 | O |
| ATOM | 2130 | CB | LYS | B | 93 | 12.183 | 17.585 | 5.969 | 1.00 | 40.33 | C |
| ATOM | 2131 | CG | LYS | B | 93 | 12.757 | 18.184 | 7.235 | 1.00 | 39.37 | C |
| ATOM | 2132 | CD | LYS | B | 93 | 14.257 | 18.005 | 7.277 | 1.00 | 40.32 | C |
| ATOM | 2133 | CE | LYS | B | 93 | 14.855 | 18.769 | 8.440 | 1.00 | 43.72 | C |
| ATOM | 2134 | NZ | LYS | B | 93 | 16.343 | 18.828 | 8.367 | 1.00 | 46.76 | N |
| ATOM | 2135 | N | PRO | B | 94 | 9.436 | 16.141 | 6.895 | 1.00 | 38.93 | N |
| ATOM | 2136 | CA | PRO | B | 94 | 8.673 | 15.613 | 8.028 | 1.00 | 39.13 | C |
| ATOM | 2137 | C | PRO | B | 94 | 9.698 | 15.041 | 9.025 | 1.00 | 40.61 | C |
| ATOM | 2138 | O | PRO | B | 94 | 10.908 | 15.110 | 8.780 | 1.00 | 41.35 | O |
| ATOM | 2139 | CB | PRO | B | 94 | 7.802 | 14.543 | 7.377 | 1.00 | 37.90 | C |
| ATOM | 2140 | CG | PRO | B | 94 | 8.711 | 14.000 | 6.292 | 1.00 | 36.34 | C |
| ATOM | 2141 | CD | PRO | B | 94 | 9.371 | 15.237 | 5.729 | 1.00 | 36.07 | C |
| ATOM | 2142 | N | SER | B | 95 | 9.239 | 14.498 | 10.147 | 1.00 | 40.91 | N |
| ATOM | 2143 | CA | SER | B | 95 | 10.175 | 13.929 | 11.106 | 1.00 | 40.87 | C |
| ATOM | 2144 | C | SER | B | 95 | 9.938 | 12.427 | 11.201 | 1.00 | 39.68 | C |
| ATOM | 2145 | O | SER | B | 95 | 8.799 | 11.965 | 11.168 | 1.00 | 39.79 | O |
| ATOM | 2146 | CB | SER | B | 95 | 10.010 | 14.582 | 12.480 | 1.00 | 42.95 | C |
| ATOM | 2147 | OG | SER | B | 95 | 8.742 | 14.280 | 13.036 | 1.00 | 48.73 | O |
| ATOM | 2148 | N | LEU | B | 96 | 11.027 | 11.675 | 11.299 | 1.00 | 38.33 | N |
| ATOM | 2149 | CA | LEU | B | 96 | 10.968 | 10.227 | 11.389 | 1.00 | 39.19 | C |
| ATOM | 2150 | C | LEU | B | 96 | 11.433 | 9.799 | 12.783 | 1.00 | 41.03 | C |
| ATOM | 2151 | O | LEU | B | 96 | 12.472 | 10.245 | 13.268 | 1.00 | 41.11 | O |
| ATOM | 2152 | CB | LEU | B | 96 | 11.862 | 9.609 | 10.306 | 1.00 | 37.60 | C |
| ATOM | 2153 | CG | LEU | B | 96 | 11.863 | 8.091 | 10.140 | 1.00 | 36.31 | C |
| ATOM | 2154 | CD1 | LEU | B | 96 | 10.435 | 7.585 | 10.042 | 1.00 | 37.12 | C |
| ATOM | 2155 | CD2 | LEU | B | 96 | 12.656 | 7.717 | 8.903 | 1.00 | 33.31 | C |
| ATOM | 2156 | N | SER | B | 97 | 10.656 | 8.932 | 13.422 | 1.00 | 41.91 | N |
| ATOM | 2157 | CA | SER | B | 97 | 10.968 | 8.472 | 14.766 | 1.00 | 44.55 | C |
| ATOM | 2158 | C | SER | B | 97 | 10.405 | 7.080 | 14.948 | 1.00 | 45.76 | C |
| ATOM | 2159 | O | SER | B | 97 | 9.621 | 6.619 | 14.121 | 1.00 | 47.36 | O |
| ATOM | 2160 | CB | SER | B | 97 | 10.317 | 9.396 | 15.787 | 1.00 | 44.68 | C |
| ATOM | 2161 | OG | SER | B | 97 | 8.903 | 9.355 | 15.646 | 1.00 | 45.41 | O |
| ATOM | 2162 | N | ALA | B | 98 | 10.788 | 6.420 | 16.036 | 1.00 | 46.70 | N |
| ATOM | 2163 | CA | ALA | B | 98 | 10.304 | 5.077 | 16.307 | 1.00 | 49.73 | C |
| ATOM | 2164 | C | ALA | B | 98 | 9.039 | 5.130 | 17.140 | 1.00 | 53.40 | C |
| ATOM | 2165 | O | ALA | B | 98 | 8.696 | 6.231 | 17.626 | 1.00 | 56.05 | O |
| ATOM | 2166 | CB | ALA | B | 98 | 11.354 | 4.284 | 17.032 | 1.00 | 49.94 | C |
| ATOM | 2167 | N | GLY | B | 108 | 13.701 | −7.552 | 15.288 | 1.00 | 75.24 | N |
| ATOM | 2168 | CA | GLY | B | 108 | 12.736 | −8.586 | 14.808 | 1.00 | 74.51 | C |
| ATOM | 2169 | C | GLY | B | 108 | 11.605 | −7.989 | 13.993 | 1.00 | 74.31 | C |
| ATOM | 2170 | O | GLY | B | 108 | 11.044 | −8.649 | 13.118 | 1.00 | 74.74 | O |
| ATOM | 2171 | N | ASP | B | 109 | 11.272 | −6.734 | 14.284 | 1.00 | 73.60 | N |
| ATOM | 2172 | CA | ASP | B | 109 | 10.204 | −6.024 | 13.588 | 1.00 | 72.12 | C |
| ATOM | 2173 | C | ASP | B | 109 | 10.015 | −4.675 | 14.278 | 1.00 | 70.41 | C |
| ATOM | 2174 | O | ASP | B | 109 | 9.642 | −4.620 | 15.452 | 1.00 | 69.80 | O |
| ATOM | 2175 | CB | ASP | B | 109 | 8.897 | −6.826 | 13.651 | 1.00 | 73.57 | C |
| ATOM | 2176 | CG | ASP | B | 109 | 7.915 | −6.434 | 12.558 | 1.00 | 75.12 | C |
| ATOM | 2177 | OD1 | ASP | B | 109 | 7.655 | −5.221 | 12.406 | 1.00 | 76.59 | O |
| ATOM | 2178 | OD2 | ASP | B | 109 | 7.402 | −7.336 | 11.852 | 1.00 | 74.69 | O |
| ATOM | 2179 | N | VAL | B | 110 | 10.270 | −3.590 | 13.549 | 1.00 | 67.99 | N |
| ATOM | 2180 | CA | VAL | B | 110 | 10.143 | −2.247 | 14.112 | 1.00 | 65.35 | C |
| ATOM | 2181 | C | VAL | B | 110 | 9.127 | −1.369 | 13.383 | 1.00 | 63.44 | C |
| ATOM | 2182 | O | VAL | B | 110 | 8.923 | −1.505 | 12.179 | 1.00 | 63.89 | O |
| ATOM | 2183 | CB | VAL | B | 110 | 11.508 | −1.528 | 14.106 | 1.00 | 64.02 | C |
| ATOM | 2184 | CG1 | VAL | B | 110 | 11.396 | −0.187 | 14.797 | 1.00 | 63.71 | C |
| ATOM | 2185 | CG2 | VAL | B | 110 | 12.543 | −2.389 | 14.798 | 1.00 | 65.11 | C |
| ATOM | 2186 | N | THR | B | 111 | 8.485 | −0.472 | 14.124 | 1.00 | 61.16 | N |
| ATOM | 2187 | CA | THR | B | 111 | 7.506 | 0.437 | 13.541 | 1.00 | 59.52 | C |
| ATOM | 2188 | C | THR | B | 111 | 7.966 | 1.883 | 13.682 | 1.00 | 59.20 | C |
| ATOM | 2189 | O | THR | B | 111 | 8.264 | 2.349 | 14.781 | 1.00 | 58.49 | O |
| ATOM | 2190 | CB | THR | B | 111 | 6.130 | 0.300 | 14.212 | 1.00 | 58.72 | C |
| ATOM | 2191 | OG1 | THR | B | 111 | 5.587 | −0.995 | 13.937 | 1.00 | 58.87 | O |
| ATOM | 2192 | CG2 | THR | B | 111 | 5.184 | 1.358 | 13.686 | 1.00 | 57.77 | C |
| ATOM | 2193 | N | LEU | B | 112 | 8.022 | 2.586 | 12.556 | 1.00 | 58.66 | N |
| ATOM | 2194 | CA | LEU | B | 112 | 8.442 | 3.980 | 12.536 | 1.00 | 57.70 | C |
| ATOM | 2195 | C | LEU | B | 112 | 7.248 | 4.837 | 12.144 | 1.00 | 57.95 | C |
| ATOM | 2196 | O | LEU | B | 112 | 6.329 | 4.366 | 11.474 | 1.00 | 58.52 | O |

TABLE 2-continued

| | | | | | | | | | | |
|---|---|---|---|---|---|---|---|---|---|---|
| ATOM | 2197 | CB | LEU | B | 112 | 9.561 | 4.175 | 11.515 | 1.00 | 55.80 | C |
| ATOM | 2198 | CG | LEU | B | 112 | 10.679 | 3.134 | 11.567 | 1.00 | 53.88 | C |
| ATOM | 2199 | CD1 | LEU | B | 112 | 11.682 | 3.405 | 10.466 | 1.00 | 51.07 | C |
| ATOM | 2200 | CD2 | LEU | B | 112 | 11.343 | 3.173 | 12.929 | 1.00 | 53.84 | C |
| ATOM | 2201 | N | GLN | B | 113 | 7.252 | 6.092 | 12.569 | 1.00 | 57.73 | N |
| ATOM | 2202 | CA | GLN | B | 113 | 6.158 | 6.985 | 12.229 | 1.00 | 57.58 | C |
| ATOM | 2203 | C | GLN | B | 113 | 6.705 | 8.244 | 11.571 | 1.00 | 56.64 | C |
| ATOM | 2204 | O | GLN | B | 113 | 7.596 | 8.908 | 12.104 | 1.00 | 55.57 | O |
| ATOM | 2205 | CB | GLN | B | 113 | 5.343 | 7.347 | 13.474 | 1.00 | 59.03 | C |
| ATOM | 2206 | CG | GLN | B | 113 | 6.048 | 8.255 | 14.459 | 1.00 | 62.63 | C |
| ATOM | 2207 | CD | GLN | B | 113 | 5.119 | 8.747 | 15.558 | 1.00 | 64.92 | C |
| ATOM | 2208 | OE1 | GLN | B | 113 | 3.991 | 9.175 | 15.291 | 1.00 | 65.46 | O |
| ATOM | 2209 | NE2 | GLN | B | 113 | 5.594 | 8.702 | 16.801 | 1.00 | 65.15 | N |
| ATOM | 2210 | N | CYS | B | 114 | 6.177 | 8.553 | 10.394 | 1.00 | 56.49 | N |
| ATOM | 2211 | CA | CYS | B | 114 | 6.602 | 9.729 | 9.655 | 1.00 | 57.78 | C |
| ATOM | 2212 | C | CYS | B | 114 | 5.614 | 10.837 | 9.992 | 1.00 | 58.72 | C |
| ATOM | 2213 | O | CYS | B | 114 | 4.463 | 10.812 | 9.561 | 1.00 | 58.27 | O |
| ATOM | 2214 | CB | CYS | B | 114 | 6.604 | 9.427 | 8.154 | 1.00 | 55.50 | C |
| ATOM | 2215 | SG | CYS | B | 114 | 7.363 | 10.705 | 7.099 | 1.00 | 55.13 | S |
| ATOM | 2216 | N | GLN | B | 115 | 6.075 | 11.802 | 10.777 | 1.00 | 60.98 | N |
| ATOM | 2217 | CA | GLN | B | 115 | 5.234 | 12.906 | 11.211 | 1.00 | 64.67 | C |
| ATOM | 2218 | C | GLN | B | 115 | 5.429 | 14.172 | 10.398 | 1.00 | 65.95 | C |
| ATOM | 2219 | O | GLN | B | 115 | 6.535 | 14.708 | 10.316 | 1.00 | 65.63 | O |
| ATOM | 2220 | CB | GLN | B | 115 | 5.495 | 13.193 | 12.691 | 1.00 | 66.32 | C |
| ATOM | 2221 | CG | GLN | B | 115 | 4.862 | 14.467 | 13.209 | 1.00 | 71.16 | C |
| ATOM | 2222 | CD | GLN | B | 115 | 4.994 | 14.604 | 14.715 | 1.00 | 73.92 | C |
| ATOM | 2223 | OE1 | GLN | B | 115 | 4.430 | 13.810 | 15.471 | 1.00 | 74.83 | O |
| ATOM | 2224 | NE2 | GLN | B | 115 | 5.747 | 15.609 | 15.159 | 1.00 | 75.68 | N |
| ATOM | 2225 | N | THR | B | 116 | 4.333 | 14.645 | 9.810 | 1.00 | 68.24 | N |
| ATOM | 2226 | CA | THR | B | 116 | 4.333 | 15.851 | 8.990 | 1.00 | 70.06 | C |
| ATOM | 2227 | C | THR | B | 116 | 3.323 | 16.858 | 9.525 | 1.00 | 72.02 | C |
| ATOM | 2228 | O | THR | B | 116 | 2.468 | 16.501 | 10.331 | 1.00 | 72.98 | O |
| ATOM | 2229 | CB | THR | B | 116 | 3.969 | 15.519 | 7.545 | 1.00 | 70.02 | C |
| ATOM | 2230 | OG1 | THR | B | 116 | 3.854 | 16.734 | 6.795 | 1.00 | 71.00 | O |
| ATOM | 2231 | CG2 | THR | B | 116 | 2.657 | 14.746 | 7.493 | 1.00 | 68.51 | C |
| ATOM | 2232 | N | ARG | B | 117 | 3.405 | 18.105 | 9.064 | 1.00 | 74.47 | N |
| ATOM | 2233 | CA | ARG | B | 117 | 2.495 | 19.151 | 9.536 | 1.00 | 76.88 | C |
| ATOM | 2234 | C | ARG | B | 117 | 1.445 | 19.654 | 8.542 | 1.00 | 77.42 | C |
| ATOM | 2235 | O | ARG | B | 117 | 0.332 | 19.993 | 8.940 | 1.00 | 77.95 | O |
| ATOM | 2236 | CB | ARG | B | 117 | 3.297 | 20.355 | 10.052 | 1.00 | 78.20 | C |
| ATOM | 2237 | CG | ARG | B | 117 | 4.175 | 20.054 | 11.258 | 1.00 | 80.53 | C |
| ATOM | 2238 | CD | ARG | B | 117 | 4.908 | 21.293 | 11.761 | 1.00 | 82.19 | C |
| ATOM | 2239 | NE | ARG | B | 117 | 4.001 | 22.290 | 12.327 | 1.00 | 84.35 | N |
| ATOM | 2240 | CZ | ARG | B | 117 | 4.398 | 23.422 | 12.904 | 1.00 | 85.06 | C |
| ATOM | 2241 | NH1 | ARG | B | 117 | 5.692 | 23.706 | 12.994 | 1.00 | 85.22 | N |
| ATOM | 2242 | NH2 | ARG | B | 117 | 3.503 | 24.270 | 13.396 | 1.00 | 84.53 | N |
| ATOM | 2243 | N | TYR | B | 118 | 1.793 | 19.711 | 7.260 | 1.00 | 78.09 | N |
| ATOM | 2244 | CA | TYR | B | 118 | 0.868 | 20.207 | 6.237 | 1.00 | 78.10 | C |
| ATOM | 2245 | C | TYR | B | 118 | −0.444 | 19.433 | 6.116 | 1.00 | 77.33 | C |
| ATOM | 2246 | O | TYR | B | 118 | −1.312 | 19.795 | 5.318 | 1.00 | 77.27 | O |
| ATOM | 2247 | CB | TYR | B | 118 | 1.535 | 20.214 | 4.859 | 1.00 | 79.28 | C |
| ATOM | 2248 | CG | TYR | B | 118 | 2.735 | 21.122 | 4.710 | 1.00 | 79.72 | C |
| ATOM | 2249 | CD1 | TYR | B | 118 | 4.012 | 20.695 | 5.075 | 1.00 | 78.94 | C |
| ATOM | 2250 | CD2 | TYR | B | 118 | 2.599 | 22.396 | 4.156 | 1.00 | 79.35 | C |
| ATOM | 2251 | CE1 | TYR | B | 118 | 5.123 | 21.511 | 4.881 | 1.00 | 79.38 | C |
| ATOM | 2252 | CE2 | TYR | B | 118 | 3.702 | 23.218 | 3.962 | 1.00 | 78.91 | C |
| ATOM | 2253 | CZ | TYR | B | 118 | 4.960 | 22.770 | 4.322 | 1.00 | 78.85 | C |
| ATOM | 2254 | OH | TYR | B | 118 | 6.053 | 23.572 | 4.098 | 1.00 | 78.76 | O |
| ATOM | 2255 | N | GLY | B | 119 | −0.591 | 18.365 | 6.887 | 1.00 | 76.06 | N |
| ATOM | 2256 | CA | GLY | B | 119 | −1.812 | 17.588 | 6.801 | 1.00 | 74.06 | C |
| ATOM | 2257 | C | GLY | B | 119 | −1.867 | 16.717 | 5.553 | 1.00 | 72.49 | C |
| ATOM | 2258 | O | GLY | B | 119 | −2.952 | 16.405 | 5.057 | 1.00 | 73.00 | O |
| ATOM | 2259 | N | PHE | B | 120 | −0.703 | 16.330 | 5.035 | 1.00 | 68.91 | N |
| ATOM | 2260 | CA | PHE | B | 120 | −0.655 | 15.477 | 3.857 | 1.00 | 64.91 | C |
| ATOM | 2261 | C | PHE | B | 120 | −1.249 | 14.140 | 4.264 | 1.00 | 62.81 | C |
| ATOM | 2262 | O | PHE | B | 120 | −1.474 | 13.900 | 5.444 | 1.00 | 62.60 | O |
| ATOM | 2263 | CB | PHE | B | 120 | 0.789 | 15.278 | 3.388 | 1.00 | 64.62 | C |
| ATOM | 2264 | CG | PHE | B | 120 | 1.462 | 16.538 | 2.919 | 1.00 | 63.89 | C |
| ATOM | 2265 | CD1 | PHE | B | 120 | 0.940 | 17.272 | 1.859 | 1.00 | 64.15 | C |
| ATOM | 2266 | CD2 | PHE | B | 120 | 2.627 | 16.986 | 3.530 | 1.00 | 63.97 | C |
| ATOM | 2267 | CE1 | PHE | B | 120 | 1.574 | 18.440 | 1.415 | 1.00 | 64.33 | C |
| ATOM | 2268 | CE2 | PHE | B | 120 | 3.267 | 18.149 | 3.094 | 1.00 | 63.89 | C |
| ATOM | 2269 | CZ | PHE | B | 120 | 2.739 | 18.878 | 2.035 | 1.00 | 62.57 | C |
| ATOM | 2270 | N | ASP | B | 121 | −1.498 | 13.270 | 3.291 | 1.00 | 61.19 | N |
| ATOM | 2271 | CA | ASP | B | 121 | −2.073 | 11.956 | 3.569 | 1.00 | 59.12 | C |
| ATOM | 2272 | C | ASP | B | 121 | −1.234 | 10.838 | 2.952 | 1.00 | 56.90 | C |
| ATOM | 2273 | O | ASP | B | 121 | −1.655 | 9.683 | 2.898 | 1.00 | 54.60 | O |
| ATOM | 2274 | CB | ASP | B | 121 | −3.504 | 11.885 | 3.022 | 1.00 | 61.18 | C |
| ATOM | 2275 | CG | ASP | B | 121 | −3.558 | 11.961 | 1.504 | 1.00 | 63.60 | C |
| ATOM | 2276 | OD1 | ASP | B | 121 | −3.103 | 12.982 | 0.936 | 1.00 | 63.05 | O |

TABLE 2-continued

| | | | | | | | | | | |
|---|---|---|---|---|---|---|---|---|---|---|
| ATOM | 2277 | OD2 | ASP | B | 121 | −4.059 | 10.993 | 0.881 | 1.00 | 64.96 | O |
| ATOM | 2278 | N | GLN | B | 122 | −0.042 | 11.188 | 2.484 | 1.00 | 55.50 | N |
| ATOM | 2279 | CA | GLN | B | 122 | 0.838 | 10.208 | 1.871 | 1.00 | 54.56 | C |
| ATOM | 2280 | C | GLN | B | 122 | 2.232 | 10.240 | 2.482 | 1.00 | 52.30 | C |
| ATOM | 2281 | O | GLN | B | 122 | 2.706 | 11.284 | 2.932 | 1.00 | 50.06 | O |
| ATOM | 2282 | CB | GLN | B | 122 | 0.907 | 10.447 | 0.364 | 1.00 | 57.21 | C |
| ATOM | 2283 | CG | GLN | B | 122 | −0.393 | 10.136 | −0.355 | 1.00 | 60.08 | C |
| ATOM | 2284 | CD | GLN | B | 122 | −0.762 | 8.671 | −0.250 | 1.00 | 62.43 | C |
| ATOM | 2285 | OE1 | GLN | B | 122 | −0.039 | 7.802 | −0.741 | 1.00 | 65.28 | O |
| ATOM | 2286 | NE2 | GLN | B | 122 | −1.884 | 8.388 | 0.397 | 1.00 | 63.42 | N |
| ATOM | 2287 | N | PHE | B | 123 | 2.878 | 9.077 | 2.493 | 1.00 | 51.09 | N |
| ATOM | 2288 | CA | PHE | B | 123 | 4.210 | 8.923 | 3.060 | 1.00 | 49.61 | C |
| ATOM | 2289 | C | PHE | B | 123 | 5.015 | 7.895 | 2.285 | 1.00 | 48.55 | C |
| ATOM | 2290 | O | PHE | B | 123 | 4.475 | 6.928 | 1.747 | 1.00 | 48.32 | O |
| ATOM | 2291 | CB | PHE | B | 123 | 4.108 | 8.472 | 4.523 | 1.00 | 50.13 | C |
| ATOM | 2292 | CG | PHE | B | 123 | 3.297 | 9.394 | 5.381 | 1.00 | 52.48 | C |
| ATOM | 2293 | CD1 | PHE | B | 123 | 3.866 | 10.547 | 5.919 | 1.00 | 52.56 | C |
| ATOM | 2294 | CD2 | PHE | B | 123 | 1.937 | 9.148 | 5.598 | 1.00 | 52.92 | C |
| ATOM | 2295 | CE1 | PHE | B | 123 | 3.095 | 11.448 | 6.661 | 1.00 | 54.57 | C |
| ATOM | 2296 | CE2 | PHE | B | 123 | 1.154 | 10.042 | 6.337 | 1.00 | 52.34 | C |
| ATOM | 2297 | CZ | PHE | B | 123 | 1.732 | 11.192 | 6.869 | 1.00 | 54.45 | C |
| ATOM | 2298 | N | ALA | B | 124 | 6.318 | 8.114 | 2.233 | 1.00 | 46.36 | N |
| ATOM | 2299 | CA | ALA | B | 124 | 7.212 | 7.201 | 1.558 | 1.00 | 45.13 | C |
| ATOM | 2300 | C | ALA | B | 124 | 8.424 | 7.053 | 2.456 | 1.00 | 44.69 | C |
| ATOM | 2301 | O | ALA | B | 124 | 9.012 | 8.041 | 2.878 | 1.00 | 42.23 | O |
| ATOM | 2302 | CB | ALA | B | 124 | 7.622 | 7.761 | 0.210 | 1.00 | 45.17 | C |
| ATOM | 2303 | N | LEU | B | 125 | 8.782 | 5.817 | 2.761 | 1.00 | 46.55 | N |
| ATOM | 2304 | CA | LEU | B | 125 | 9.937 | 5.557 | 3.597 | 1.00 | 50.41 | C |
| ATOM | 2305 | C | LEU | B | 125 | 10.875 | 4.653 | 2.827 | 1.00 | 52.56 | C |
| ATOM | 2306 | O | LEU | B | 125 | 10.426 | 3.739 | 2.141 | 1.00 | 51.97 | O |
| ATOM | 2307 | CB | LEU | B | 125 | 9.512 | 4.870 | 4.896 | 1.00 | 51.57 | C |
| ATOM | 2308 | CG | LEU | B | 125 | 10.645 | 4.374 | 5.801 | 1.00 | 52.38 | C |
| ATOM | 2309 | CD1 | LEU | B | 125 | 11.447 | 5.558 | 6.322 | 1.00 | 51.80 | C |
| ATOM | 2310 | CD2 | LEU | B | 125 | 10.063 | 3.570 | 6.953 | 1.00 | 53.36 | C |
| ATOM | 2311 | N | TYR | B | 126 | 12.175 | 4.911 | 2.923 | 1.00 | 56.58 | N |
| ATOM | 2312 | CA | TYR | B | 126 | 13.142 | 4.070 | 2.231 | 1.00 | 60.64 | C |
| ATOM | 2313 | C | TYR | B | 126 | 14.460 | 3.904 | 2.981 | 1.00 | 62.55 | C |
| ATOM | 2314 | O | TYR | B | 126 | 14.962 | 4.842 | 3.612 | 1.00 | 61.18 | O |
| ATOM | 2315 | CB | TYR | B | 126 | 13.436 | 4.619 | 0.836 | 1.00 | 62.95 | C |
| ATOM | 2316 | CG | TYR | B | 126 | 14.407 | 5.774 | 0.820 | 1.00 | 65.41 | C |
| ATOM | 2317 | CD1 | TYR | B | 126 | 14.010 | 7.047 | 1.216 | 1.00 | 66.39 | C |
| ATOM | 2318 | CD2 | TYR | B | 126 | 15.725 | 5.594 | 0.396 | 1.00 | 67.29 | C |
| ATOM | 2319 | CE1 | TYR | B | 126 | 14.900 | 8.119 | 1.186 | 1.00 | 68.96 | C |
| ATOM | 2320 | CE2 | TYR | B | 126 | 16.628 | 6.659 | 0.364 | 1.00 | 68.89 | C |
| ATOM | 2321 | CZ | TYR | B | 126 | 16.208 | 7.920 | 0.759 | 1.00 | 69.43 | C |
| ATOM | 2322 | OH | TYR | B | 126 | 17.083 | 8.984 | 0.730 | 1.00 | 69.26 | O |
| ATOM | 2323 | N | LYS | B | 127 | 15.006 | 2.693 | 2.901 | 1.00 | 64.83 | N |
| ATOM | 2324 | CA | LYS | B | 127 | 16.276 | 2.359 | 3.532 | 1.00 | 66.32 | C |
| ATOM | 2325 | C | LYS | B | 127 | 17.350 | 2.556 | 2.478 | 1.00 | 67.01 | C |
| ATOM | 2326 | O | LYS | B | 127 | 17.279 | 1.962 | 1.407 | 1.00 | 67.56 | O |
| ATOM | 2327 | CB | LYS | B | 127 | 16.284 | 0.900 | 4.004 | 1.00 | 66.39 | C |
| ATOM | 2328 | CG | LYS | B | 127 | 17.655 | 0.419 | 4.474 | 1.00 | 67.65 | C |
| ATOM | 2329 | CD | LYS | B | 127 | 17.631 | −0.983 | 5.092 | 1.00 | 68.47 | C |
| ATOM | 2330 | CE | LYS | B | 127 | 17.443 | −2.094 | 4.058 | 1.00 | 68.91 | C |
| ATOM | 2331 | NZ | LYS | B | 127 | 16.052 | −2.202 | 3.538 | 1.00 | 68.36 | N |
| ATOM | 2332 | N | GLU | B | 128 | 18.335 | 3.394 | 2.772 | 1.00 | 68.42 | N |
| ATOM | 2333 | CA | GLU | B | 128 | 19.403 | 3.636 | 1.817 | 1.00 | 71.11 | C |
| ATOM | 2334 | C | GLU | B | 128 | 20.000 | 2.322 | 1.333 | 1.00 | 72.28 | C |
| ATOM | 2335 | O | GLU | B | 128 | 20.013 | 1.328 | 2.061 | 1.00 | 72.79 | O |
| ATOM | 2336 | CB | GLU | B | 128 | 20.491 | 4.508 | 2.443 | 1.00 | 71.72 | C |
| ATOM | 2337 | CG | GLU | B | 128 | 20.117 | 5.970 | 2.518 | 1.00 | 73.98 | C |
| ATOM | 2338 | CD | GLU | B | 128 | 21.265 | 6.833 | 2.980 | 1.00 | 76.25 | C |
| ATOM | 2339 | OE1 | GLU | B | 128 | 21.639 | 6.740 | 4.166 | 1.00 | 78.76 | O |
| ATOM | 2340 | OE2 | GLU | B | 128 | 21.799 | 7.605 | 2.155 | 1.00 | 78.48 | O |
| ATOM | 2341 | N | GLY | B | 129 | 20.474 | 2.314 | 0.093 | 1.00 | 73.11 | N |
| ATOM | 2342 | CA | GLY | B | 129 | 21.063 | 1.107 | −0.444 | 1.00 | 75.33 | C |
| ATOM | 2343 | C | GLY | B | 129 | 22.200 | 0.656 | 0.450 | 1.00 | 76.68 | C |
| ATOM | 2344 | O | GLY | B | 129 | 22.065 | −0.409 | 1.092 | 1.00 | 76.52 | O |
| ATOM | 2345 | N | GLU | B | 138 | 18.544 | −0.856 | −0.673 | 1.00 | 87.47 | N |
| ATOM | 2346 | CA | GLU | B | 138 | 17.299 | −0.092 | −0.962 | 1.00 | 87.34 | C |
| ATOM | 2347 | C | GLU | B | 138 | 16.053 | −0.869 | −0.567 | 1.00 | 86.98 | C |
| ATOM | 2348 | O | GLU | B | 138 | 16.069 | −2.096 | −0.491 | 1.00 | 86.52 | O |
| ATOM | 2349 | CB | GLU | B | 138 | 17.220 | 0.256 | −2.451 | 1.00 | 88.42 | C |
| ATOM | 2350 | CG | GLU | B | 138 | 18.197 | 1.335 | −2.916 | 1.00 | 89.86 | C |
| ATOM | 2351 | CD | GLU | B | 138 | 17.929 | 2.689 | −2.278 | 1.00 | 90.34 | C |
| ATOM | 2352 | OE1 | GLU | B | 138 | 18.166 | 2.828 | −1.061 | 1.00 | 91.72 | O |
| ATOM | 2353 | OE2 | GLU | B | 138 | 17.476 | 3.611 | −2.989 | 1.00 | 89.89 | O |
| ATOM | 2354 | N | ARG | B | 139 | 14.977 | −0.133 | −0.316 | 1.00 | 87.81 | N |
| ATOM | 2355 | CA | ARG | B | 139 | 13.691 | −0.711 | 0.062 | 1.00 | 88.91 | C |
| ATOM | 2356 | C | ARG | B | 139 | 12.697 | 0.428 | 0.320 | 1.00 | 88.59 | C |

TABLE 2-continued

| | | | | | | | | | | |
|---|---|---|---|---|---|---|---|---|---|---|
| ATOM | 2357 | O | ARG | B | 139 | 12.943 | 1.297 | 1.161 | 1.00 | 88.32 | O |
| ATOM | 2358 | CB | ARG | B | 139 | 13.834 | −1.568 | 1.327 | 1.00 | 90.06 | C |
| ATOM | 2359 | CG | ARG | B | 139 | 12.765 | −2.650 | 1.472 | 1.00 | 91.68 | C |
| ATOM | 2360 | CD | ARG | B | 139 | 13.006 | −3.796 | 0.487 | 1.00 | 94.06 | C |
| ATOM | 2361 | NE | ARG | B | 139 | 14.241 | −4.524 | 0.790 | 1.00 | 95.28 | N |
| ATOM | 2362 | CZ | ARG | B | 139 | 14.792 | −5.442 | −0.002 | 1.00 | 95.04 | C |
| ATOM | 2363 | NH1 | ARG | B | 139 | 14.223 | −5.755 | −1.161 | 1.00 | 94.72 | N |
| ATOM | 2364 | NH2 | ARG | B | 139 | 15.912 | −6.049 | 0.368 | 1.00 | 94.22 | N |
| ATOM | 2365 | N | TRP | B | 140 | 11.581 | 0.426 | −0.406 | 1.00 | 87.94 | N |
| ATOM | 2366 | CA | TRP | B | 140 | 10.569 | 1.464 | −0.241 | 1.00 | 87.04 | C |
| ATOM | 2367 | C | TRP | B | 140 | 9.289 | 0.993 | 0.439 | 1.00 | 86.95 | C |
| ATOM | 2368 | O | TRP | B | 140 | 8.877 | −0.161 | 0.309 | 1.00 | 86.63 | O |
| ATOM | 2369 | CB | TRP | B | 140 | 10.222 | 2.094 | −1.593 | 1.00 | 86.32 | C |
| ATOM | 2370 | CG | TRP | B | 140 | 11.308 | 2.959 | −2.121 | 1.00 | 86.48 | C |
| ATOM | 2371 | CD1 | TRP | B | 140 | 12.441 | 2.552 | −2.763 | 1.00 | 86.74 | C |
| ATOM | 2372 | CD2 | TRP | B | 140 | 11.404 | 4.384 | −1.995 | 1.00 | 86.21 | C |
| ATOM | 2373 | NE1 | TRP | B | 140 | 13.240 | 3.637 | −3.043 | 1.00 | 87.45 | N |
| ATOM | 2374 | CE2 | TRP | B | 140 | 12.626 | 4.773 | −2.582 | 1.00 | 86.40 | C |
| ATOM | 2375 | CE3 | TRP | B | 140 | 10.576 | 5.369 | −1.440 | 1.00 | 85.13 | C |
| ATOM | 2376 | CZ2 | TRP | B | 140 | 13.042 | 6.108 | −2.630 | 1.00 | 85.50 | C |
| ATOM | 2377 | CZ3 | TRP | B | 140 | 10.990 | 6.694 | −1.487 | 1.00 | 84.34 | C |
| ATOM | 2378 | CH2 | TRP | B | 140 | 12.212 | 7.050 | −2.078 | 1.00 | 84.74 | C |
| ATOM | 2379 | N | TYR | B | 141 | 8.667 | 1.912 | 1.169 | 1.00 | 87.34 | N |
| ATOM | 2380 | CA | TYR | B | 141 | 7.431 | 1.641 | 1.884 | 1.00 | 87.91 | C |
| ATOM | 2381 | C | TYR | B | 141 | 6.530 | 2.864 | 1.738 | 1.00 | 88.25 | C |
| ATOM | 2382 | O | TYR | B | 141 | 6.791 | 3.910 | 2.328 | 1.00 | 88.34 | O |
| ATOM | 2383 | CB | TYR | B | 141 | 7.725 | 1.392 | 3.368 | 1.00 | 88.48 | C |
| ATOM | 2384 | CG | TYR | B | 141 | 8.876 | 0.439 | 3.626 | 1.00 | 89.00 | C |
| ATOM | 2385 | CD1 | TYR | B | 141 | 8.768 | −0.919 | 3.329 | 1.00 | 89.23 | C |
| ATOM | 2386 | CD2 | TYR | B | 141 | 10.079 | 0.902 | 4.158 | 1.00 | 89.28 | C |
| ATOM | 2387 | CE1 | TYR | B | 141 | 9.831 | −1.794 | 3.556 | 1.00 | 89.63 | C |
| ATOM | 2388 | CE2 | TYR | B | 141 | 11.148 | 0.037 | 4.388 | 1.00 | 90.09 | C |
| ATOM | 2389 | CZ | TYR | B | 141 | 11.017 | −1.309 | 4.086 | 1.00 | 89.71 | C |
| ATOM | 2390 | OH | TYR | B | 141 | 12.070 | −2.166 | 4.318 | 1.00 | 88.28 | O |
| ATOM | 2391 | N | ARG | B | 142 | 5.481 | 2.733 | 0.935 | 1.00 | 88.77 | N |
| ATOM | 2392 | CA | ARG | B | 142 | 4.537 | 3.824 | 0.718 | 1.00 | 89.75 | C |
| ATOM | 2393 | C | ARG | B | 142 | 3.271 | 3.491 | 1.501 | 1.00 | 89.26 | C |
| ATOM | 2394 | O | ARG | B | 142 | 2.796 | 2.357 | 1.451 | 1.00 | 89.80 | O |
| ATOM | 2395 | CB | ARG | B | 142 | 4.226 | 3.956 | −0.781 | 1.00 | 90.55 | C |
| ATOM | 2396 | CG | ARG | B | 142 | 3.288 | 5.104 | −1.157 | 1.00 | 91.87 | C |
| ATOM | 2397 | CD | ARG | B | 142 | 3.154 | 5.212 | −2.678 | 1.00 | 93.89 | C |
| ATOM | 2398 | NE | ARG | B | 142 | 2.209 | 6.245 | −3.106 | 1.00 | 95.91 | N |
| ATOM | 2399 | CZ | ARG | B | 142 | 1.988 | 6.582 | −4.378 | 1.00 | 96.11 | C |
| ATOM | 2400 | NH1 | ARG | B | 142 | 2.645 | 5.967 | −5.355 | 1.00 | 95.67 | N |
| ATOM | 2401 | NH2 | ARG | B | 142 | 1.115 | 7.536 | −4.676 | 1.00 | 94.93 | N |
| ATOM | 2402 | N | ALA | B | 143 | 2.732 | 4.467 | 2.230 | 1.00 | 88.27 | N |
| ATOM | 2403 | CA | ALA | B | 143 | 1.528 | 4.232 | 3.021 | 1.00 | 87.48 | C |
| ATOM | 2404 | C | ALA | B | 143 | 0.684 | 5.481 | 3.234 | 1.00 | 87.63 | C |
| ATOM | 2405 | O | ALA | B | 143 | 1.203 | 6.595 | 3.309 | 1.00 | 88.01 | O |
| ATOM | 2406 | CB | ALA | B | 143 | 1.905 | 3.631 | 4.370 | 1.00 | 86.74 | C |
| ATOM | 2407 | N | SER | B | 144 | −0.627 | 5.279 | 3.341 | 1.00 | 87.89 | N |
| ATOM | 2408 | CA | SER | B | 144 | −1.567 | 6.376 | 3.555 | 1.00 | 87.52 | C |
| ATOM | 2409 | C | SER | B | 144 | −1.827 | 6.567 | 5.046 | 1.00 | 86.55 | C |
| ATOM | 2410 | O | SER | B | 144 | −2.926 | 6.945 | 5.450 | 1.00 | 86.03 | O |
| ATOM | 2411 | CB | SER | B | 144 | −2.888 | 6.086 | 2.833 | 1.00 | 88.06 | C |
| ATOM | 2412 | OG | SER | B | 144 | −3.463 | 4.871 | 3.283 | 1.00 | 87.49 | O |
| ATOM | 2413 | N | PHE | B | 145 | −0.804 | 6.297 | 5.854 | 1.00 | 86.49 | N |
| ATOM | 2414 | CA | PHE | B | 145 | −0.883 | 6.425 | 7.309 | 1.00 | 85.93 | C |
| ATOM | 2415 | C | PHE | B | 145 | 0.514 | 6.758 | 7.843 | 1.00 | 84.38 | C |
| ATOM | 2416 | O | PHE | B | 145 | 1.487 | 6.066 | 7.543 | 1.00 | 84.38 | O |
| ATOM | 2417 | CB | PHE | B | 145 | −1.382 | 5.113 | 7.922 | 1.00 | 87.31 | C |
| ATOM | 2418 | CG | PHE | B | 145 | −1.945 | 5.262 | 9.309 | 1.00 | 88.85 | C |
| ATOM | 2419 | CD1 | PHE | B | 145 | −3.053 | 6.075 | 9.539 | 1.00 | 89.43 | C |
| ATOM | 2420 | CD2 | PHE | B | 145 | −1.382 | 4.576 | 10.382 | 1.00 | 89.20 | C |
| ATOM | 2421 | CE1 | PHE | B | 145 | −3.594 | 6.204 | 10.819 | 1.00 | 90.00 | C |
| ATOM | 2422 | CE2 | PHE | B | 145 | −1.914 | 4.696 | 11.667 | 1.00 | 89.91 | C |
| ATOM | 2423 | CZ | PHE | B | 145 | −3.023 | 5.512 | 11.886 | 1.00 | 90.23 | C |
| ATOM | 2424 | N | PRO | B | 146 | 0.625 | 7.817 | 8.658 | 1.00 | 82.85 | N |
| ATOM | 2425 | CA | PRO | B | 146 | 1.899 | 8.259 | 9.236 | 1.00 | 81.70 | C |
| ATOM | 2426 | C | PRO | B | 146 | 2.651 | 7.227 | 10.072 | 1.00 | 81.46 | C |
| ATOM | 2427 | O | PRO | B | 146 | 3.711 | 7.522 | 10.616 | 1.00 | 81.44 | O |
| ATOM | 2428 | CB | PRO | B | 146 | 1.491 | 9.475 | 10.058 | 1.00 | 81.64 | C |
| ATOM | 2429 | CG | PRO | B | 146 | 0.122 | 9.094 | 10.535 | 1.00 | 82.01 | C |
| ATOM | 2430 | CD | PRO | B | 146 | −0.504 | 8.538 | 9.275 | 1.00 | 82.72 | C |
| ATOM | 2431 | N | ILE | B | 147 | 2.111 | 6.016 | 10.167 | 1.00 | 81.59 | N |
| ATOM | 2432 | CA | ILE | B | 147 | 2.738 | 4.963 | 10.961 | 1.00 | 81.02 | C |
| ATOM | 2433 | C | ILE | B | 147 | 3.025 | 3.697 | 10.151 | 1.00 | 80.57 | C |
| ATOM | 2434 | O | ILE | B | 147 | 2.122 | 2.907 | 9.873 | 1.00 | 79.81 | O |
| ATOM | 2435 | CB | ILE | B | 147 | 1.844 | 4.608 | 12.167 | 1.00 | 81.33 | C |
| ATOM | 2436 | CG1 | ILE | B | 147 | 1.638 | 5.857 | 13.034 | 1.00 | 80.74 | C |

TABLE 2-continued

| | | | | | | | | | | |
|---|---|---|---|---|---|---|---|---|---|---|
| ATOM | 2437 | CG2 | ILE | B | 147 | 2.473 | 3.481 | 12.972 | 1.00 | 81.16 | C |
| ATOM | 2438 | CD1 | ILE | B | 147 | 0.615 | 5.689 | 14.134 | 1.00 | 80.93 | C |
| ATOM | 2439 | N | ILE | B | 148 | 4.292 | 3.510 | 9.788 | 1.00 | 79.81 | N |
| ATOM | 2440 | CA | ILE | B | 148 | 4.712 | 2.355 | 8.999 | 1.00 | 79.33 | C |
| ATOM | 2441 | C | ILE | B | 148 | 5.495 | 1.366 | 9.848 | 1.00 | 79.72 | C |
| ATOM | 2442 | O | ILE | B | 148 | 6.289 | 1.754 | 10.703 | 1.00 | 79.94 | O |
| ATOM | 2443 | CB | ILE | B | 148 | 5.615 | 2.765 | 7.821 | 1.00 | 78.84 | C |
| ATOM | 2444 | CG1 | ILE | B | 148 | 4.964 | 3.891 | 7.012 | 1.00 | 79.43 | C |
| ATOM | 2445 | CG2 | ILE | B | 148 | 5.860 | 1.566 | 6.929 | 1.00 | 78.71 | C |
| ATOM | 2446 | CD1 | ILE | B | 148 | 5.017 | 5.255 | 7.673 | 1.00 | 79.07 | C |
| ATOM | 2447 | N | THR | B | 149 | 5.278 | 0.083 | 9.596 | 1.00 | 80.09 | N |
| ATOM | 2448 | CA | THR | B | 149 | 5.960 | −0.961 | 10.346 | 1.00 | 81.16 | C |
| ATOM | 2449 | C | THR | B | 149 | 6.799 | −1.860 | 9.456 | 1.00 | 81.33 | C |
| ATOM | 2450 | O | THR | B | 149 | 6.270 | −2.715 | 8.750 | 1.00 | 81.76 | O |
| ATOM | 2451 | CB | THR | B | 149 | 4.956 | −1.839 | 11.106 | 1.00 | 81.77 | C |
| ATOM | 2452 | OG1 | THR | B | 149 | 5.595 | −3.061 | 11.498 | 1.00 | 81.59 | O |
| ATOM | 2453 | CG2 | THR | B | 149 | 3.749 | −2.147 | 10.230 | 1.00 | 82.30 | C |
| ATOM | 2454 | N | VAL | B | 150 | 8.111 | −1.668 | 9.493 | 1.00 | 81.96 | N |
| ATOM | 2455 | CA | VAL | B | 150 | 9.009 | −2.480 | 8.687 | 1.00 | 82.78 | C |
| ATOM | 2456 | C | VAL | B | 150 | 9.020 | −3.905 | 9.236 | 1.00 | 83.55 | C |
| ATOM | 2457 | O | VAL | B | 150 | 9.272 | −4.124 | 10.423 | 1.00 | 82.97 | O |
| ATOM | 2458 | CB | VAL | B | 150 | 10.442 | −1.910 | 8.706 | 1.00 | 82.49 | C |
| ATOM | 2459 | CG1 | VAL | B | 150 | 11.322 | −2.681 | 7.734 | 1.00 | 83.19 | C |
| ATOM | 2460 | CG2 | VAL | B | 150 | 10.417 | −0.437 | 8.343 | 1.00 | 82.51 | C |
| ATOM | 2461 | N | THR | B | 151 | 8.735 | −4.868 | 8.363 | 1.00 | 84.78 | N |
| ATOM | 2462 | CA | THR | B | 151 | 8.698 | −6.278 | 8.741 | 1.00 | 86.28 | C |
| ATOM | 2463 | C | THR | B | 151 | 10.064 | −6.781 | 9.204 | 1.00 | 86.77 | C |
| ATOM | 2464 | O | THR | B | 151 | 10.280 | −7.005 | 10.394 | 1.00 | 87.05 | O |
| ATOM | 2465 | CB | THR | B | 151 | 8.198 | −7.152 | 7.558 | 1.00 | 86.55 | C |
| ATOM | 2466 | OG1 | THR | B | 151 | 6.832 | −6.821 | 7.264 | 1.00 | 86.20 | O |
| ATOM | 2467 | CG2 | THR | B | 151 | 8.294 | −8.634 | 7.900 | 1.00 | 86.38 | C |
| ATOM | 2468 | N | ALA | B | 152 | 10.985 | −6.957 | 8.263 | 1.00 | 87.52 | N |
| ATOM | 2469 | CA | ALA | B | 152 | 12.324 | −7.428 | 8.596 | 1.00 | 88.38 | C |
| ATOM | 2470 | C | ALA | B | 152 | 13.181 | −6.287 | 9.144 | 1.00 | 88.56 | C |
| ATOM | 2471 | O | ALA | B | 152 | 13.654 | −5.432 | 8.390 | 1.00 | 88.93 | O |
| ATOM | 2472 | CB | ALA | B | 152 | 12.984 | −8.035 | 7.360 | 1.00 | 89.22 | C |
| ATOM | 2473 | N | ALA | B | 153 | 13.372 | −6.276 | 10.461 | 1.00 | 88.08 | N |
| ATOM | 2474 | CA | ALA | B | 153 | 14.174 | −5.246 | 11.118 | 1.00 | 87.52 | C |
| ATOM | 2475 | C | ALA | B | 153 | 15.626 | −5.295 | 10.634 | 1.00 | 86.96 | C |
| ATOM | 2476 | O | ALA | B | 153 | 16.496 | −5.853 | 11.310 | 1.00 | 87.57 | O |
| ATOM | 2477 | CB | ALA | B | 153 | 14.117 | −5.431 | 12.636 | 1.00 | 86.62 | C |
| ATOM | 2478 | N | HIS | B | 154 | 15.879 | −4.709 | 9.463 | 1.00 | 85.74 | N |
| ATOM | 2479 | CA | HIS | B | 154 | 17.222 | −4.682 | 8.883 | 1.00 | 83.38 | C |
| ATOM | 2480 | C | HIS | B | 154 | 17.975 | −3.386 | 9.138 | 1.00 | 80.11 | C |
| ATOM | 2481 | O | HIS | B | 154 | 17.567 | −2.312 | 8.683 | 1.00 | 78.84 | O |
| ATOM | 2482 | CB | HIS | B | 154 | 17.168 | −4.931 | 7.373 | 1.00 | 85.43 | C |
| ATOM | 2483 | CG | HIS | B | 154 | 17.206 | −6.378 | 7.000 | 1.00 | 88.44 | C |
| ATOM | 2484 | ND1 | HIS | B | 154 | 18.181 | −7.236 | 7.461 | 1.00 | 88.59 | N |
| ATOM | 2485 | CD2 | HIS | B | 154 | 16.397 | −7.117 | 6.203 | 1.00 | 89.73 | |
| ATOM | 2486 | CE1 | HIS | B | 154 | 17.972 | −8.443 | 6.964 | 1.00 | 89.87 | C |
| ATOM | 2487 | NE2 | HIS | B | 154 | 16.896 | −8.398 | 6.198 | 1.00 | 90.21 | N |
| ATOM | 2488 | N | SER | B | 155 | 19.082 | −3.506 | 9.864 | 1.00 | 76.22 | N |
| ATOM | 2489 | CA | SER | B | 155 | 19.926 | −2.367 | 10.189 | 1.00 | 72.58 | C |
| ATOM | 2490 | C | SER | B | 155 | 20.132 | −1.521 | 8.934 | 1.00 | 69.83 | C |
| ATOM | 2491 | O | SER | B | 155 | 20.286 | −2.056 | 7.838 | 1.00 | 69.56 | O |
| ATOM | 2492 | CB | SER | B | 155 | 21.272 | −2.862 | 10.726 | 1.00 | 72.09 | C |
| ATOM | 2493 | OG | SER | B | 155 | 22.115 | −1.785 | 11.083 | 1.00 | 72.22 | O |
| ATOM | 2494 | N | GLY | B | 156 | 20.120 | −0.202 | 9.098 | 1.00 | 66.92 | N |
| ATOM | 2495 | CA | GLY | B | 156 | 20.302 | 0.690 | 7.968 | 1.00 | 62.64 | C |
| ATOM | 2496 | C | GLY | B | 156 | 19.869 | 2.111 | 8.280 | 1.00 | 60.32 | C |
| ATOM | 2497 | O | GLY | B | 156 | 19.441 | 2.411 | 9.397 | 1.00 | 58.49 | O |
| ATOM | 2498 | N | THR | B | 157 | 19.974 | 2.986 | 7.284 | 1.00 | 58.09 | N |
| ATOM | 2499 | CA | THR | B | 157 | 19.606 | 4.390 | 7.435 | 1.00 | 56.19 | C |
| ATOM | 2500 | C | THR | B | 157 | 18.276 | 4.704 | 6.750 | 1.00 | 54.12 | C |
| ATOM | 2501 | O | THR | B | 157 | 18.150 | 4.557 | 5.540 | 1.00 | 54.88 | O |
| ATOM | 2502 | CB | THR | B | 157 | 20.694 | 5.288 | 6.839 | 1.00 | 57.02 | C |
| ATOM | 2503 | OG1 | THR | B | 157 | 21.952 | 4.968 | 7.448 | 1.00 | 56.76 | O |
| ATOM | 2504 | CG2 | THR | B | 157 | 20.369 | 6.759 | 7.077 | 1.00 | 58.21 | C |
| ATOM | 2505 | N | TYR | B | 158 | 17.294 | 5.150 | 7.528 | 1.00 | 52.00 | N |
| ATOM | 2506 | CA | TYR | B | 158 | 15.969 | 5.465 | 6.996 | 1.00 | 49.14 | C |
| ATOM | 2507 | C | TYR | B | 158 | 15.676 | 6.951 | 6.859 | 1.00 | 47.44 | C |
| ATOM | 2508 | O | TYR | B | 158 | 16.245 | 7.779 | 7.564 | 1.00 | 47.07 | O |
| ATOM | 2509 | CB | TYR | B | 158 | 14.882 | 4.839 | 7.874 | 1.00 | 49.72 | C |
| ATOM | 2510 | CG | TYR | B | 158 | 14.882 | 3.336 | 7.859 | 1.00 | 50.84 | C |
| ATOM | 2511 | CD1 | TYR | B | 158 | 15.852 | 2.611 | 8.544 | 1.00 | 52.22 | C |
| ATOM | 2512 | CD2 | TYR | B | 158 | 13.933 | 2.634 | 7.123 | 1.00 | 52.04 | C |
| ATOM | 2513 | CE1 | TYR | B | 158 | 15.877 | 1.222 | 8.494 | 1.00 | 54.89 | C |
| ATOM | 2514 | CE2 | TYR | B | 158 | 13.946 | 1.246 | 7.063 | 1.00 | 54.25 | C |
| ATOM | 2515 | CZ | TYR | B | 158 | 14.917 | 0.548 | 7.749 | 1.00 | 55.04 | C |
| ATOM | 2516 | OH | TYR | B | 158 | 14.928 | −0.822 | 7.695 | 1.00 | 57.75 | O |

TABLE 2-continued

| | | | | | | | | | | |
|---|---|---|---|---|---|---|---|---|---|---|
| ATOM | 2517 | N | ARG | B | 159 | 14.767 | 7.265 | 5.941 | 1.00 | 46.94 | N |
| ATOM | 2518 | CA | ARG | B | 159 | 14.323 | 8.632 | 5.675 | 1.00 | 45.63 | C |
| ATOM | 2519 | C | ARG | B | 159 | 12.920 | 8.559 | 5.084 | 1.00 | 44.13 | C |
| ATOM | 2520 | O | ARG | B | 159 | 12.595 | 7.607 | 4.371 | 1.00 | 43.49 | O |
| ATOM | 2521 | CB | ARG | B | 159 | 15.242 | 9.324 | 4.670 | 1.00 | 45.56 | C |
| ATOM | 2522 | CG | ARG | B | 159 | 16.644 | 9.597 | 5.155 | 1.00 | 46.50 | C |
| ATOM | 2523 | CD | ARG | B | 159 | 17.364 | 10.519 | 4.174 | 1.00 | 49.75 | C |
| ATOM | 2524 | NE | ARG | B | 159 | 18.726 | 10.830 | 4.603 | 1.00 | 51.91 | N |
| ATOM | 2525 | CZ | ARG | B | 159 | 19.765 | 10.011 | 4.465 | 1.00 | 52.43 | C |
| ATOM | 2526 | NH1 | ARG | B | 159 | 19.613 | 8.817 | 3.902 | 1.00 | 51.18 | N |
| ATOM | 2527 | NH2 | ARG | B | 159 | 20.960 | 10.387 | 4.895 | 1.00 | 53.56 | N |
| ATOM | 2528 | N | CYS | B | 160 | 12.086 | 9.548 | 5.378 | 1.00 | 43.33 | N |
| ATOM | 2529 | CA | CYS | B | 160 | 10.732 | 9.545 | 4.831 | 1.00 | 44.94 | C |
| ATOM | 2530 | C | CYS | B | 160 | 10.326 | 10.876 | 4.202 | 1.00 | 43.33 | C |
| ATOM | 2531 | O | CYS | B | 160 | 10.880 | 11.930 | 4.525 | 1.00 | 43.44 | O |
| ATOM | 2532 | CB | CYS | B | 160 | 9.703 | 9.141 | 5.902 | 1.00 | 46.41 | C |
| ATOM | 2533 | SG | CYS | B | 160 | 9.366 | 10.355 | 7.226 | 1.00 | 52.39 | S |
| ATOM | 2534 | N | TYR | B | 161 | 9.365 | 10.801 | 3.286 | 1.00 | 41.73 | N |
| ATOM | 2535 | CA | TYR | B | 161 | 8.839 | 11.965 | 2.596 | 1.00 | 39.63 | C |
| ATOM | 2536 | C | TYR | B | 161 | 7.351 | 12.001 | 2.850 | 1.00 | 40.18 | C |
| ATOM | 2537 | O | TYR | B | 161 | 6.725 | 10.957 | 3.009 | 1.00 | 39.82 | O |
| ATOM | 2538 | CB | TYR | B | 161 | 9.057 | 11.858 | 1.090 | 1.00 | 39.03 | C |
| ATOM | 2539 | CG | TYR | B | 161 | 10.497 | 11.771 | 0.660 | 1.00 | 38.99 | C |
| ATOM | 2540 | CD1 | TYR | B | 161 | 11.183 | 10.555 | 0.668 | 1.00 | 37.63 | C |
| ATOM | 2541 | CD2 | TYR | B | 161 | 11.167 | 12.901 | 0.206 | 1.00 | 39.46 | C |
| ATOM | 2542 | CE1 | TYR | B | 161 | 12.498 | 10.473 | 0.222 | 1.00 | 36.81 | C |
| ATOM | 2543 | CE2 | TYR | B | 161 | 12.478 | 12.831 | −0.238 | 1.00 | 37.86 | C |
| ATOM | 2544 | CZ | TYR | B | 161 | 13.136 | 11.619 | −0.233 | 1.00 | 37.50 | C |
| ATOM | 2545 | OH | TYR | B | 161 | 14.424 | 11.570 | −0.709 | 1.00 | 36.65 | O |
| ATOM | 2546 | N | SER | B | 162 | 6.781 | 13.199 | 2.880 | 1.00 | 41.15 | N |
| ATOM | 2547 | CA | SER | B | 162 | 5.346 | 13.342 | 3.090 | 1.00 | 43.48 | C |
| ATOM | 2548 | C | SER | B | 162 | 4.745 | 14.129 | 1.931 | 1.00 | 42.91 | C |
| ATOM | 2549 | O | SER | B | 162 | 5.370 | 15.050 | 1.407 | 1.00 | 40.58 | O |
| ATOM | 2550 | CB | SER | B | 162 | 5.070 | 14.075 | 4.403 | 1.00 | 46.71 | C |
| ATOM | 2551 | OG | SER | B | 162 | 5.590 | 15.398 | 4.365 | 1.00 | 51.20 | O |
| ATOM | 2552 | N | PHE | B | 163 | 3.536 | 13.758 | 1.526 | 1.00 | 43.64 | N |
| ATOM | 2553 | CA | PHE | B | 163 | 2.869 | 14.454 | 0.430 | 1.00 | 44.70 | C |
| ATOM | 2554 | C | PHE | B | 163 | 1.368 | 14.227 | 0.367 | 1.00 | 45.43 | C |
| ATOM | 2555 | O | PHE | B | 163 | 0.823 | 13.359 | 1.056 | 1.00 | 44.79 | O |
| ATOM | 2556 | CB | PHE | B | 163 | 3.483 | 14.070 | −0.919 | 1.00 | 41.44 | C |
| ATOM | 2557 | CG | PHE | B | 163 | 3.301 | 12.632 | −1.288 | 1.00 | 39.30 | C |
| ATOM | 2558 | CD1 | PHE | B | 163 | 4.122 | 11.650 | −0.744 | 1.00 | 40.03 | C |
| ATOM | 2559 | CD2 | PHE | B | 163 | 2.356 | 12.262 | −2.239 | 1.00 | 38.32 | C |
| ATOM | 2560 | CE1 | PHE | B | 163 | 4.014 | 10.318 | −1.152 | 1.00 | 37.22 | C |
| ATOM | 2561 | CE2 | PHE | B | 163 | 2.238 | 10.936 | −2.654 | 1.00 | 38.32 | C |
| ATOM | 2562 | CZ | PHE | B | 163 | 3.073 | 9.962 | −2.108 | 1.00 | 39.30 | C |
| ATOM | 2563 | N | SER | B | 164 | 0.714 | 15.017 | −0.482 | 1.00 | 46.61 | N |
| ATOM | 2564 | CA | SER | B | 164 | −0.731 | 14.950 | −0.669 | 1.00 | 48.10 | C |
| ATOM | 2565 | C | SER | B | 164 | −1.077 | 14.101 | −1.887 | 1.00 | 47.89 | C |
| ATOM | 2566 | O | SER | B | 164 | −0.418 | 14.187 | −2.925 | 1.00 | 47.44 | O |
| ATOM | 2567 | CB | SER | B | 164 | −1.292 | 16.368 | −0.835 | 1.00 | 48.78 | C |
| ATOM | 2568 | OG | SER | B | 164 | −2.708 | 16.372 | −0.864 | 1.00 | 49.70 | O |
| ATOM | 2569 | N | SER | B | 165 | −2.106 | 13.272 | −1.755 | 1.00 | 48.17 | N |
| ATOM | 2570 | CA | SER | B | 165 | −2.530 | 12.413 | −2.860 | 1.00 | 49.84 | C |
| ATOM | 2571 | C | SER | B | 165 | −3.166 | 13.248 | −3.976 | 1.00 | 50.03 | C |
| ATOM | 2572 | O | SER | B | 165 | −3.491 | 12.736 | −5.045 | 1.00 | 47.95 | O |
| ATOM | 2573 | CB | SER | B | 165 | −3.526 | 11.357 | −2.358 | 1.00 | 50.70 | C |
| ATOM | 2574 | OG | SER | B | 165 | −4.639 | 11.957 | −1.712 | 1.00 | 50.39 | O |
| ATOM | 2575 | N | ARG | B | 166 | −3.330 | 14.538 | −3.715 | 1.00 | 51.93 | N |
| ATOM | 2576 | CA | ARG | B | 166 | −3.914 | 15.453 | −4.682 | 1.00 | 55.40 | C |
| ATOM | 2577 | C | ARG | B | 166 | −2.841 | 15.895 | −5.684 | 1.00 | 55.13 | C |
| ATOM | 2578 | O | ARG | B | 166 | −3.151 | 16.278 | −6.813 | 1.00 | 54.44 | O |
| ATOM | 2579 | CB | ARG | B | 166 | −4.496 | 16.663 | −3.953 | 1.00 | 58.95 | C |
| ATOM | 2580 | CG | ARG | B | 166 | −5.592 | 17.369 | −4.715 | 1.00 | 63.83 | C |
| ATOM | 2581 | CD | ARG | B | 166 | −6.269 | 18.414 | −3.844 | 1.00 | 68.76 | C |
| ATOM | 2582 | NE | ARG | B | 166 | −6.811 | 17.843 | −2.610 | 1.00 | 72.15 | N |
| ATOM | 2583 | CZ | ARG | B | 166 | −7.672 | 18.472 | −1.813 | 1.00 | 73.13 | C |
| ATOM | 2584 | NH1 | ARG | B | 166 | −8.091 | 19.696 | −2.123 | 1.00 | 71.81 | N |
| ATOM | 2585 | NH2 | ARG | B | 166 | −8.121 | 17.878 | −0.711 | 1.00 | 71.54 | N |
| ATOM | 2586 | N | ASP | B | 167 | −1.586 | 15.834 | −5.243 | 1.00 | 53.13 | N |
| ATOM | 2587 | CA | ASP | B | 167 | −0.405 | 16.181 | −6.038 | 1.00 | 51.71 | C |
| ATOM | 2588 | C | ASP | B | 167 | 0.643 | 15.151 | −5.638 | 1.00 | 50.05 | C |
| ATOM | 2589 | O | ASP | B | 167 | 1.678 | 15.484 | −5.052 | 1.00 | 50.09 | O |
| ATOM | 2590 | CB | ASP | B | 167 | 0.099 | 17.573 | −5.677 | 1.00 | 55.27 | C |
| ATOM | 2591 | CG | ASP | B | 167 | −0.703 | 18.670 | −6.329 | 1.00 | 59.46 | C |
| ATOM | 2592 | OD1 | ASP | B | 167 | −1.948 | 18.638 | −6.224 | 1.00 | 62.23 | O |
| ATOM | 2593 | OD2 | ASP | B | 167 | −0.082 | 19.567 | −6.943 | 1.00 | 61.70 | O |
| ATOM | 2594 | N | PRO | B | 168 | 0.384 | 13.878 | −5.959 | 1.00 | 47.64 | N |
| ATOM | 2595 | CA | PRO | B | 168 | 1.255 | 12.743 | −5.650 | 1.00 | 45.81 | C |
| ATOM | 2596 | C | PRO | B | 168 | 2.683 | 12.775 | −6.188 | 1.00 | 45.38 | C |

TABLE 2-continued

| | | | | | | | | | | |
|---|---|---|---|---|---|---|---|---|---|---|
| ATOM | 2597 | O | PRO | B | 168 | 3.450 | 11.844 | −5.932 | 1.00 | 45.41 | O |
| ATOM | 2598 | CB | PRO | B | 168 | 0.465 | 11.560 | −6.191 | 1.00 | 45.14 | C |
| ATOM | 2599 | CG | PRO | B | 168 | −0.221 | 12.153 | −7.386 | 1.00 | 43.86 | C |
| ATOM | 2600 | CD | PRO | B | 168 | −0.712 | 13.466 | −6.859 | 1.00 | 45.33 | C |
| ATOM | 2601 | N | TYR | B | 169 | 3.041 | 13.833 | −6.918 | 1.00 | 43.61 | N |
| ATOM | 2602 | CA | TYR | B | 169 | 4.377 | 13.939 | −7.495 | 1.00 | 41.62 | C |
| ATOM | 2603 | C | TYR | B | 169 | 5.192 | 15.101 | −6.956 | 1.00 | 42.03 | C |
| ATOM | 2604 | O | TYR | B | 169 | 6.338 | 15.310 | −7.374 | 1.00 | 41.65 | O |
| ATOM | 2605 | CB | TYR | B | 169 | 4.287 | 14.030 | −9.015 | 1.00 | 41.17 | C |
| ATOM | 2606 | CG | TYR | B | 169 | 3.497 | 12.897 | −9.627 | 1.00 | 41.33 | C |
| ATOM | 2607 | CD1 | TYR | B | 169 | 3.858 | 11.574 | −9.399 | 1.00 | 41.81 | C |
| ATOM | 2608 | CD2 | TYR | B | 169 | 2.364 | 13.146 | −10.397 | 1.00 | 41.00 | C |
| ATOM | 2609 | CE1 | TYR | B | 169 | 3.107 | 10.524 | −9.920 | 1.00 | 43.58 | C |
| ATOM | 2610 | CE2 | TYR | B | 169 | 1.606 | 12.103 | −10.924 | 1.00 | 41.15 | C |
| ATOM | 2611 | CZ | TYR | B | 169 | 1.981 | 10.795 | −10.680 | 1.00 | 42.13 | C |
| ATOM | 2612 | OH | TYR | B | 169 | 1.233 | 9.753 | −11.185 | 1.00 | 42.73 | O |
| ATOM | 2613 | N | LEU | B | 170 | 4.597 | 15.860 | −6.040 | 1.00 | 40.59 | N |
| ATOM | 2614 | CA | LEU | B | 170 | 5.288 | 16.976 | −5.404 | 1.00 | 41.48 | C |
| ATOM | 2615 | C | LEU | B | 170 | 5.542 | 16.540 | −3.965 | 1.00 | 41.75 | C |
| ATOM | 2616 | O | LEU | B | 170 | 4.629 | 16.563 | −3.134 | 1.00 | 43.88 | O |
| ATOM | 2617 | CB | LEU | B | 170 | 4.433 | 18.242 | −5.412 | 1.00 | 41.02 | C |
| ATOM | 2618 | CG | LEU | B | 170 | 4.092 | 18.867 | −6.767 | 1.00 | 42.48 | C |
| ATOM | 2619 | CD1 | LEU | B | 170 | 3.473 | 20.244 | −6.530 | 1.00 | 40.89 | C |
| ATOM | 2620 | CD2 | LEU | B | 170 | 5.346 | 18.987 | −7.624 | 1.00 | 39.31 | C |
| ATOM | 2621 | N | TRP | B | 171 | 6.779 | 16.134 | −3.679 | 1.00 | 39.70 | N |
| ATOM | 2622 | CA | TRP | B | 171 | 7.153 | 15.657 | −2.348 | 1.00 | 37.80 | C |
| ATOM | 2623 | C | TRP | B | 171 | 7.946 | 16.653 | −1.509 | 1.00 | 37.65 | C |
| ATOM | 2624 | O | TRP | B | 171 | 8.649 | 17.528 | −2.028 | 1.00 | 37.20 | O |
| ATOM | 2625 | CB | TRP | B | 171 | 7.973 | 14.370 | −2.463 | 1.00 | 35.99 | C |
| ATOM | 2626 | CG | TRP | B | 171 | 7.223 | 13.148 | −2.939 | 1.00 | 35.37 | C |
| ATOM | 2627 | CD1 | TRP | B | 171 | 5.992 | 13.101 | −3.543 | 1.00 | 33.72 | C |
| ATOM | 2628 | CD2 | TRP | B | 171 | 7.700 | 11.795 | −2.898 | 1.00 | 34.98 | C |
| ATOM | 2629 | NE1 | TRP | B | 171 | 5.681 | 11.801 | −3.880 | 1.00 | 32.40 | N |
| ATOM | 2630 | CE2 | TRP | B | 171 | 6.712 | 10.983 | −3.495 | 1.00 | 33.28 | C |
| ATOM | 2631 | CE3 | TRP | B | 171 | 8.871 | 11.194 | −2.414 | 1.00 | 33.28 | C |
| ATOM | 2632 | CZ2 | TRP | B | 171 | 6.860 | 9.604 | −3.618 | 1.00 | 33.96 | C |
| ATOM | 2633 | CZ3 | TRP | B | 171 | 9.016 | 9.825 | −2.538 | 1.00 | 33.23 | C |
| ATOM | 2634 | CH2 | TRP | B | 171 | 8.017 | 9.044 | −3.135 | 1.00 | 34.26 | C |
| ATOM | 2635 | N | SER | B | 172 | 7.839 | 16.492 | −0.195 | 1.00 | 36.76 | N |
| ATOM | 2636 | CA | SER | B | 172 | 8.549 | 17.344 | 0.750 | 1.00 | 36.21 | C |
| ATOM | 2637 | C | SER | B | 172 | 10.035 | 17.028 | 0.711 | 1.00 | 34.22 | C |
| ATOM | 2638 | O | SER | B | 172 | 10.479 | 16.161 | −0.035 | 1.00 | 32.71 | O |
| ATOM | 2639 | CB | SER | B | 172 | 8.048 | 17.075 | 2.163 | 1.00 | 36.67 | C |
| ATOM | 2640 | OG | SER | B | 172 | 8.421 | 15.765 | 2.561 | 1.00 | 38.14 | O |
| ATOM | 2641 | N | ALA | B | 173 | 10.802 | 17.747 | 1.518 | 1.00 | 35.35 | N |
| ATOM | 2642 | CA | ALA | B | 173 | 12.229 | 17.482 | 1.619 | 1.00 | 36.59 | C |
| ATOM | 2643 | C | ALA | B | 173 | 12.273 | 16.230 | 2.479 | 1.00 | 36.92 | C |
| ATOM | 2644 | O | ALA | B | 173 | 11.375 | 15.997 | 3.292 | 1.00 | 36.79 | O |
| ATOM | 2645 | CB | ALA | B | 173 | 12.947 | 18.626 | 2.326 | 1.00 | 35.55 | C |
| ATOM | 2646 | N | PRO | B | 174 | 13.299 | 15.394 | 2.299 | 1.00 | 37.01 | N |
| ATOM | 2647 | CA | PRO | B | 174 | 13.398 | 14.172 | 3.097 | 1.00 | 37.67 | C |
| ATOM | 2648 | C | PRO | B | 174 | 13.560 | 14.509 | 4.567 | 1.00 | 38.39 | C |
| ATOM | 2649 | O | PRO | B | 174 | 14.076 | 15.574 | 4.915 | 1.00 | 39.36 | O |
| ATOM | 2650 | CB | PRO | B | 174 | 14.643 | 13.497 | 2.534 | 1.00 | 38.05 | C |
| ATOM | 2651 | CG | PRO | B | 174 | 15.501 | 14.666 | 2.171 | 1.00 | 37.71 | C |
| ATOM | 2652 | CD | PRO | B | 174 | 14.504 | 15.578 | 1.475 | 1.00 | 38.40 | C |
| ATOM | 2653 | N | SER | B | 175 | 13.111 | 13.607 | 5.429 | 1.00 | 37.76 | N |
| ATOM | 2654 | CA | SER | B | 175 | 13.246 | 13.814 | 6.865 | 1.00 | 38.89 | C |
| ATOM | 2655 | C | SER | B | 175 | 14.708 | 13.581 | 7.233 | 1.00 | 37.67 | C |
| ATOM | 2656 | O | SER | B | 175 | 15.474 | 13.029 | 6.438 | 1.00 | 37.63 | O |
| ATOM | 2657 | CB | SER | B | 175 | 12.400 | 12.797 | 7.621 | 1.00 | 39.16 | C |
| ATOM | 2658 | OG | SER | B | 175 | 12.895 | 11.490 | 7.361 | 1.00 | 41.30 | O |
| ATOM | 2659 | N | ASP | B | 176 | 15.102 | 14.010 | 8.427 | 1.00 | 38.07 | N |
| ATOM | 2660 | CA | ASP | B | 176 | 16.464 | 13.757 | 8.881 | 1.00 | 38.39 | C |
| ATOM | 2661 | C | ASP | B | 176 | 16.540 | 12.235 | 8.949 | 1.00 | 37.45 | C |
| ATOM | 2662 | O | ASP | B | 176 | 15.556 | 11.570 | 9.266 | 1.00 | 36.92 | O |
| ATOM | 2663 | CB | ASP | B | 176 | 16.711 | 14.342 | 10.274 | 1.00 | 38.96 | C |
| ATOM | 2664 | CG | ASP | B | 176 | 16.723 | 15.853 | 10.277 | 1.00 | 41.25 | C |
| ATOM | 2665 | OD1 | ASP | B | 176 | 17.423 | 16.435 | 9.423 | 1.00 | 44.24 | O |
| ATOM | 2666 | OD2 | ASP | B | 176 | 16.041 | 16.457 | 11.132 | 1.00 | 40.46 | O |
| ATOM | 2667 | N | PRO | B | 177 | 17.710 | 11.662 | 8.655 | 1.00 | 37.29 | N |
| ATOM | 2668 | CA | PRO | B | 177 | 17.836 | 10.205 | 8.697 | 1.00 | 35.33 | C |
| ATOM | 2669 | C | PRO | B | 177 | 17.708 | 9.631 | 10.100 | 1.00 | 34.97 | C |
| ATOM | 2670 | O | PRO | B | 177 | 18.153 | 10.232 | 11.070 | 1.00 | 32.31 | O |
| ATOM | 2671 | CB | PRO | B | 177 | 19.217 | 9.973 | 8.099 | 1.00 | 36.66 | C |
| ATOM | 2672 | CG | PRO | B | 177 | 19.984 | 11.159 | 8.608 | 1.00 | 34.54 | C |
| ATOM | 2673 | CD | PRO | B | 177 | 19.017 | 12.309 | 8.437 | 1.00 | 35.30 | C |
| ATOM | 2674 | N | LEU | B | 178 | 17.067 | 8.474 | 10.194 | 1.00 | 35.63 | N |
| ATOM | 2675 | CA | LEU | B | 178 | 16.914 | 7.776 | 11.461 | 1.00 | 36.55 | C |
| ATOM | 2676 | C | LEU | B | 178 | 17.749 | 6.524 | 11.266 | 1.00 | 38.19 | C |

TABLE 2-continued

| | | | | | | | | | | |
|---|---|---|---|---|---|---|---|---|---|---|
| ATOM | 2677 | O | LEU | B | 178 | 17.414 | 5.676 | 10.435 | 1.00 | 38.99 | O |
| ATOM | 2678 | CB | LEU | B | 178 | 15.452 | 7.390 | 11.708 | 1.00 | 36.81 | C |
| ATOM | 2679 | CG | LEU | B | 178 | 15.126 | 6.590 | 12.979 | 1.00 | 36.90 | C |
| ATOM | 2680 | CD1 | LEU | B | 178 | 13.619 | 6.569 | 13.202 | 1.00 | 37.36 | C |
| ATOM | 2681 | CD2 | LEU | B | 178 | 15.663 | 5.172 | 12.864 | 1.00 | 35.47 | C |
| ATOM | 2682 | N | GLU | B | 179 | 18.838 | 6.407 | 12.015 | 1.00 | 38.87 | N |
| ATOM | 2683 | CA | GLU | B | 179 | 19.712 | 5.249 | 11.883 | 1.00 | 39.46 | C |
| ATOM | 2684 | C | GLU | B | 179 | 19.207 | 4.050 | 12.677 | 1.00 | 39.46 | C |
| ATOM | 2685 | O | GLU | B | 179 | 19.209 | 4.054 | 13.906 | 1.00 | 39.73 | O |
| ATOM | 2686 | CB | GLU | B | 179 | 21.117 | 5.610 | 12.348 | 1.00 | 42.21 | C |
| ATOM | 2687 | CG | GLU | B | 179 | 22.182 | 4.631 | 11.898 | 1.00 | 47.32 | C |
| ATOM | 2688 | CD | GLU | B | 179 | 22.362 | 4.635 | 10.394 | 1.00 | 50.57 | C |
| ATOM | 2689 | OE1 | GLU | B | 179 | 22.500 | 5.740 | 9.823 | 1.00 | 50.52 | O |
| ATOM | 2690 | OE2 | GLU | B | 179 | 22.374 | 3.540 | 9.786 | 1.00 | 53.02 | O |
| ATOM | 2691 | N | LEU | B | 180 | 18.763 | 3.020 | 11.975 | 1.00 | 39.19 | N |
| ATOM | 2692 | CA | LEU | B | 180 | 18.283 | 1.827 | 12.641 | 1.00 | 38.79 | C |
| ATOM | 2693 | C | LEU | B | 180 | 19.466 | 0.886 | 12.811 | 1.00 | 41.64 | C |
| ATOM | 2694 | O | LEU | B | 180 | 20.148 | 0.562 | 11.843 | 1.00 | 43.68 | O |
| ATOM | 2695 | CB | LEU | B | 180 | 17.208 | 1.142 | 11.801 | 1.00 | 37.03 | C |
| ATOM | 2696 | CG | LEU | B | 180 | 16.705 | −0.200 | 12.339 | 1.00 | 39.04 | C |
| ATOM | 2697 | CD1 | LEU | B | 180 | 15.938 | 0.022 | 13.632 | 1.00 | 38.67 | C |
| ATOM | 2698 | CD2 | LEU | B | 180 | 15.817 | −0.879 | 11.307 | 1.00 | 39.98 | C |
| ATOM | 2699 | N | VAL | B | 181 | 19.723 | 0.442 | 14.032 | 1.00 | 43.73 | N |
| ATOM | 2700 | CA | VAL | B | 181 | 20.833 | −0.473 | 14.239 | 1.00 | 46.11 | C |
| ATOM | 2701 | C | VAL | B | 181 | 20.473 | −1.639 | 15.167 | 1.00 | 48.00 | C |
| ATOM | 2702 | O | VAL | B | 181 | 20.251 | −1.462 | 16.365 | 1.00 | 47.48 | O |
| ATOM | 2703 | CB | VAL | B | 181 | 22.074 | 0.290 | 14.747 | 1.00 | 44.36 | C |
| ATOM | 2704 | CG1 | VAL | B | 181 | 21.670 | 1.291 | 15.794 | 1.00 | 44.70 | C |
| ATOM | 2705 | CG2 | VAL | B | 181 | 23.099 | −0.687 | 15.286 | 1.00 | 45.60 | C |
| ATOM | 2706 | N | VAL | B | 182 | 20.399 | −2.833 | 14.583 | 1.00 | 50.37 | N |
| ATOM | 2707 | CA | VAL | B | 182 | 20.056 | −4.038 | 15.326 | 1.00 | 54.73 | C |
| ATOM | 2708 | C | VAL | B | 182 | 21.298 | −4.827 | 15.725 | 1.00 | 56.59 | C |
| ATOM | 2709 | O | VAL | B | 182 | 22.177 | −5.101 | 14.901 | 1.00 | 57.26 | O |
| ATOM | 2710 | CB | VAL | B | 182 | 19.108 | −4.962 | 14.507 | 1.00 | 55.51 | C |
| ATOM | 2711 | CG1 | VAL | B | 182 | 19.645 | −5.152 | 13.102 | 1.00 | 58.24 | C |
| ATOM | 2712 | CG2 | VAL | B | 182 | 18.983 | −6.317 | 15.189 | 1.00 | 55.52 | C |
| ATOM | 2713 | N | THR | B | 183 | 21.357 | −5.189 | 17.001 | 1.00 | 58.09 | N |
| ATOM | 2714 | CA | THR | B | 183 | 22.482 | −5.940 | 17.537 | 1.00 | 60.50 | C |
| ATOM | 2715 | C | THR | B | 183 | 22.185 | −7.445 | 17.610 | 1.00 | 61.32 | C |
| ATOM | 2716 | O | THR | B | 183 | 22.345 | −8.038 | 18.698 | 1.00 | 63.07 | O |
| ATOM | 2717 | CB | THR | B | 183 | 22.850 | −5.411 | 18.941 | 1.00 | 60.64 | C |
| ATOM | 2718 | OG1 | THR | B | 183 | 21.683 | −5.414 | 19.773 | 1.00 | 60.72 | O |
| ATOM | 2719 | CG2 | THR | B | 183 | 23.393 | −3.990 | 18.849 | 1.00 | 59.96 | C |
| ATOM | 2720 | OXT | THR | B | 183 | 21.804 | −8.022 | 16.569 | 1.00 | 60.88 | O |
| TER | 2721 | | THR | B | 183 | | | | | | |
| HETATM | 2722 | S | SO4 | | 203 | 27.448 | 30.064 | 35.300 | 1.00 | 67.63 | S |
| HETATM | 2723 | O1 | SO4 | | 203 | 27.917 | 28.680 | 35.471 | 1.00 | 69.01 | O |
| HETATM | 2724 | O2 | SO4 | | 203 | 26.041 | 30.164 | 35.740 | 1.00 | 68.17 | O |
| HETATM | 2725 | O3 | SO4 | | 203 | 28.286 | 30.956 | 36.127 | 1.00 | 66.05 | O |
| HETATM | 2726 | O4 | SO4 | | 203 | 27.541 | 30.442 | 33.876 | 1.00 | 65.80 | O |
| HETATM | 2727 | S | SO4 | | 204 | 17.095 | 36.631 | 37.561 | 1.00 | 89.60 | S |
| HETATM | 2728 | O1 | SO4 | | 204 | 18.070 | 36.485 | 36.461 | 1.00 | 89.38 | O |
| HETATM | 2729 | O2 | SO4 | | 204 | 17.623 | 35.965 | 38.768 | 1.00 | 87.90 | O |
| HETATM | 2730 | O3 | SO4 | | 204 | 16.884 | 38.070 | 37.829 | 1.00 | 89.18 | O |
| HETATM | 2731 | O4 | SO4 | | 204 | 15.812 | 36.007 | 37.180 | 1.00 | 88.34 | O |
| HETATM | 2732 | CL | CL | | 205 | 0.622 | 14.858 | −13.729 | 1.00 | 48.19 | C |
| HETATM | 2733 | O1 | CRY | | 201 | 8.494 | 26.546 | −13.798 | 1.00 | 61.77 | O |
| HETATM | 2734 | O2 | CRY | | 201 | 6.980 | 25.532 | −10.933 | 1.00 | 58.36 | O |
| HETATM | 2735 | O3 | CRY | | 201 | 9.339 | 25.778 | −9.263 | 1.00 | 57.45 | O |
| HETATM | 2736 | C1 | CRY | | 201 | 7.989 | 27.017 | −12.560 | 1.00 | 59.96 | C |
| HETATM | 2737 | C2 | CRY | | 201 | 8.219 | 26.015 | −11.426 | 1.00 | 58.27 | C |
| HETATM | 2738 | C3 | CRY | | 201 | 9.033 | 26.676 | −10.326 | 1.00 | 57.99 | C |
| HETATM | 2739 | O1 | CRY | | 202 | 22.596 | 19.139 | 32.420 | 1.00 | 74.69 | O |
| HETATM | 2740 | O2 | CRY | | 202 | 22.195 | 15.532 | 32.582 | 1.00 | 74.29 | O |
| HETATM | 2741 | O3 | CRY | | 202 | 19.369 | 16.082 | 32.439 | 1.00 | 74.07 | O |
| HETATM | 2742 | C1 | CRY | | 202 | 22.671 | 17.818 | 31.896 | 1.00 | 75.74 | C |
| HETATM | 2743 | C2 | CRY | | 202 | 21.676 | 16.857 | 32.567 | 1.00 | 74.89 | C |
| HETATM | 2744 | C3 | CRY | | 202 | 20.351 | 16.912 | 31.832 | 1.00 | 75.05 | C |
| HETATM | 2745 | O | HOH | | 1 | 9.345 | 35.972 | 36.041 | 1.00 | 49.87 | O |
| HETATM | 2746 | O | HOH | | 2 | 29.477 | 29.132 | 31.866 | 1.00 | 39.19 | O |
| HETATM | 2747 | O | HOH | | 3 | 19.793 | 14.003 | −6.560 | 1.00 | 50.40 | O |
| HETATM | 2748 | O | HOH | | 4 | 3.634 | 7.951 | −26.066 | 1.00 | 48.23 | O |
| HETATM | 2749 | O | HOH | | 5 | 21.577 | 24.558 | 14.056 | 1.00 | 51.29 | O |
| HETATM | 2750 | O | HOH | | 6 | 20.673 | 30.352 | 51.927 | 1.00 | 27.82 | O |
| HETATM | 2751 | O | HOH | | 7 | 20.713 | 13.953 | −15.139 | 1.00 | 31.87 | O |
| HETATM | 2752 | O | HOH | | 8 | 2.444 | 2.099 | −16.613 | 1.00 | 43.60 | O |
| HETATM | 2753 | O | HOH | | 9 | 1.078 | 1.378 | −35.388 | 1.00 | 33.34 | O |
| HETATM | 2754 | O | HOH | | 10 | 8.708 | 25.978 | −17.078 | 1.00 | 50.29 | O |
| HETATM | 2755 | O | HOH | | 11 | 11.777 | 22.999 | 2.803 | 1.00 | 50.81 | O |
| HETATM | 2756 | O | HOH | | 12 | −1.565 | 8.014 | −21.599 | 1.00 | 58.93 | O |

TABLE 2-continued

| | | | | | | | | | |
|---|---|---|---|---|---|---|---|---|---|
| HETATM | 2757 | O | HOH | 13 | 0.913 | 8.830 | −24.759 | 1.00 | 47.61 O |
| HETATM | 2758 | O | HOH | 14 | 28.087 | 30.051 | 45.339 | 1.00 | 35.99 O |
| HETATM | 2759 | O | HOH | 15 | 18.475 | 13.354 | 4.405 | 1.00 | 38.26 O |
| HETATM | 2760 | O | HOH | 16 | 14.005 | 18.288 | 25.649 | 1.00 | 44.08 O |
| HETATM | 2761 | O | HOH | 17 | 22.120 | 21.625 | 13.143 | 1.00 | 46.12 O |
| HETATM | 2762 | O | HOH | 18 | 25.578 | 4.080 | 12.461 | 1.00 | 46.48 O |
| HETATM | 2763 | O | HOH | 19 | 16.696 | 18.298 | 51.473 | 1.00 | 34.69 O |
| HETATM | 2764 | O | HOH | 20 | 16.065 | 20.866 | 19.361 | 1.00 | 32.66 O |
| HETATM | 2765 | O | HOH | 21 | 14.927 | 16.895 | 20.392 | 1.00 | 41.92 O |
| HETATM | 2766 | O | HOH | 22 | 15.199 | 43.247 | 49.855 | 1.00 | 69.19 O |
| HETATM | 2767 | O | HOH | 23 | 11.592 | 11.810 | −38.128 | 1.00 | 64.49 O |
| HETATM | 2768 | O | HOH | 24 | 29.391 | 33.117 | 33.755 | 1.00 | 37.74 O |
| HETATM | 2769 | O | HOH | 25 | 18.865 | 32.204 | 59.266 | 1.00 | 39.13 O |
| HETATM | 2770 | O | HOH | 26 | 21.302 | 11.936 | 0.261 | 1.00 | 72.54 O |
| HETATM | 2771 | O | HOH | 27 | 27.812 | 5.521 | 9.687 | 1.00 | 52.88 O |
| HETATM | 2772 | O | HOH | 28 | 12.963 | 20.941 | 5.215 | 1.00 | 52.75 O |
| HETATM | 2773 | O | HOH | 29 | 29.083 | 24.701 | 38.577 | 1.00 | 65.83 O |
| HETATM | 2774 | O | HOH | 30 | 16.555 | 11.924 | −4.419 | 1.00 | 46.70 O |
| HETATM | 2775 | O | HOH | 31 | 18.831 | 20.610 | 39.628 | 1.00 | 37.46 O |
| HETATM | 2776 | O | HOH | 32 | 8.629 | 5.970 | −12.408 | 1.00 | 45.59 O |
| HETATM | 2777 | O | HOH | 33 | 19.170 | 16.184 | 47.559 | 1.00 | 57.57 O |
| HETATM | 2778 | O | HOH | 34 | 10.757 | 23.307 | 42.419 | 1.00 | 35.08 O |
| HETATM | 2779 | O | HOH | 35 | 23.584 | 14.112 | −14.334 | 1.00 | 51.67 O |
| HETATM | 2780 | O | HOH | 36 | 13.341 | 38.357 | 36.930 | 1.00 | 46.55 O |
| HETATM | 2781 | O | HOH | 37 | 17.751 | 12.572 | −11.035 | 1.00 | 37.79 O |
| HETATM | 2782 | O | HOH | 38 | 27.123 | 2.637 | 30.993 | 1.00 | 52.80 O |
| HETATM | 2783 | O | HOH | 39 | 22.781 | 27.082 | 14.239 | 1.00 | 49.68 O |
| HETATM | 2784 | O | HOH | 40 | 33.837 | 2.899 | 12.534 | 1.00 | 42.25 O |
| HETATM | 2785 | O | HOH | 41 | 26.665 | 36.131 | 23.687 | 1.00 | 52.46 O |
| HETATM | 2786 | O | HOH | 42 | 6.541 | 33.983 | 42.116 | 1.00 | 56.94 O |
| HETATM | 2787 | O | HOH | 43 | 21.407 | 20.886 | −1.230 | 1.00 | 47.27 O |
| HETATM | 2788 | O | HOH | 44 | 22.534 | 2.711 | −21.085 | 1.00 | 54.19 O |
| HETATM | 2789 | O | HOH | 45 | −1.055 | 18.564 | −12.432 | 1.00 | 50.37 O |
| HETATM | 2790 | O | HOH | 46 | 17.195 | 11.052 | −30.319 | 1.00 | 37.25 O |
| HETATM | 2791 | O | HOH | 47 | 22.773 | 21.850 | 47.235 | 1.00 | 41.52 O |
| HETATM | 2792 | O | HOH | 48 | 30.408 | 22.549 | 34.895 | 1.00 | 52.22 O |
| HETATM | 2793 | O | HOH | 49 | 4.125 | 20.975 | −18.103 | 1.00 | 46.93 O |
| HETATM | 2794 | O | HOH | 50 | −1.611 | 21.121 | 2.063 | 1.00 | 53.12 O |
| HETATM | 2795 | O | HOH | 51 | 24.397 | 15.163 | 10.642 | 1.00 | 42.65 O |
| HETATM | 2796 | O | HOH | 52 | 20.020 | 19.587 | 51.778 | 1.00 | 45.69 O |
| HETATM | 2797 | O | HOH | 53 | 14.697 | 5.748 | −9.674 | 1.00 | 41.66 O |
| HETATM | 2798 | O | HOH | 54 | 27.831 | 27.970 | 29.867 | 1.00 | 33.90 O |
| HETATM | 2799 | O | HOH | 55 | 13.676 | 10.838 | −33.233 | 1.00 | 34.24 O |
| HETATM | 2800 | O | HOH | 56 | 23.207 | 20.593 | 10.696 | 1.00 | 45.13 O |
| HETATM | 2801 | O | HOH | 57 | −2.683 | 6.783 | −18.369 | 1.00 | 66.64 O |
| HETATM | 2802 | O | HOH | 58 | 11.623 | 40.422 | 43.131 | 1.00 | 43.32 O |
| HETATM | 2803 | O | HOH | 59 | 14.028 | 23.139 | 18.371 | 1.00 | 63.51 O |
| HETATM | 2804 | O | HOH | 60 | 14.159 | 18.446 | −25.758 | 1.00 | 58.73 O |
| HETATM | 2805 | O | HOH | 61 | 10.698 | 20.528 | −25.480 | 1.00 | 68.18 O |
| HETATM | 2806 | O | HOH | 62 | 3.987 | 8.914 | −6.190 | 1.00 | 56.87 O |
| HETATM | 2807 | O | HOH | 63 | 9.046 | 4.439 | −17.164 | 1.00 | 33.61 O |
| HETATM | 2808 | O | HOH | 64 | 15.572 | 15.955 | 26.055 | 1.00 | 54.13 O |
| HETATM | 2809 | O | HOH | 65 | 14.765 | 14.388 | 13.517 | 1.00 | 49.30 O |
| HETATM | 2810 | O | HOH | 66 | 21.516 | 15.358 | 8.600 | 1.00 | 38.76 O |
| HETATM | 2811 | O | HOH | 67 | 15.186 | 13.626 | −2.068 | 1.00 | 40.17 O |
| HETATM | 2812 | O | HOH | 68 | 15.486 | −2.827 | 26.343 | 1.00 | 53.38 O |
| HETATM | 2813 | O | HOH | 69 | 15.530 | 22.799 | −15.739 | 1.00 | 38.93 O |
| HETATM | 2814 | O | HOH | 70 | 17.145 | 15.805 | 21.705 | 1.00 | 52.06 O |
| HETATM | 2815 | O | HOH | 71 | 14.137 | 11.634 | 11.877 | 1.00 | 38.80 O |
| HETATM | 2816 | O | HOH | 72 | 12.665 | 11.118 | 26.076 | 1.00 | 48.60 O |
| HETATM | 2817 | O | HOH | 73 | 17.385 | 21.388 | 45.846 | 1.00 | 38.81 O |
| HETATM | 2818 | O | HOH | 74 | 28.611 | 20.108 | 34.705 | 1.00 | 58.52 O |
| HETATM | 2819 | O | HOH | 75 | 23.192 | 21.527 | −8.071 | 1.00 | 56.38 O |
| HETATM | 2820 | O | HOH | 76 | 20.826 | 15.112 | −9.585 | 1.00 | 38.08 O |
| HETATM | 2821 | O | HOH | 77 | 17.464 | 15.250 | 14.230 | 1.00 | 51.91 O |
| HETATM | 2822 | O | HOH | 78 | 1.295 | 11.432 | −29.725 | 1.00 | 59.93 O |
| HETATM | 2823 | O | HOH | 79 | 10.556 | 10.787 | 29.467 | 1.00 | 52.79 O |
| HETATM | 2824 | O | HOH | 80 | 23.540 | 24.190 | 46.289 | 1.00 | 31.37 O |
| HETATM | 2825 | O | HOH | 81 | 24.176 | 11.097 | −12.886 | 1.00 | 63.38 O |
| HETATM | 2826 | O | HOH | 82 | 19.791 | 21.221 | 37.227 | 1.00 | 37.15 O |
| HETATM | 2827 | O | HOH | 83 | 14.614 | 20.920 | 36.628 | 1.00 | 30.32 O |
| HETATM | 2828 | O | HOH | 84 | 21.408 | 17.270 | 46.517 | 1.00 | 58.01 O |
| HETATM | 2829 | O | HOH | 85 | 22.190 | 23.220 | 50.321 | 1.00 | 43.16 O |
| HETATM | 2830 | O | HOH | 86 | 18.149 | 13.017 | −8.335 | 1.00 | 39.78 O |
| HETATM | 2831 | O | HOH | 87 | 27.271 | 20.790 | 31.675 | 1.00 | 45.02 O |
| HETATM | 2832 | O | HOH | 88 | 12.253 | 19.174 | 17.551 | 1.00 | 46.46 O |
| HETATM | 2833 | O | HOH | 89 | 18.108 | 17.291 | 1.907 | 1.00 | 48.10 O |
| HETATM | 2834 | O | HOH | 90 | 17.148 | 15.903 | −0.509 | 1.00 | 48.37 O |
| HETATM | 2835 | O | HOH | 91 | 32.390 | 26.731 | 34.200 | 1.00 | 52.46 O |
| HETATM | 2836 | O | HOH | 92 | 20.733 | 25.649 | 66.071 | 1.00 | 55.95 O |

TABLE 2-continued

| | | | | | | | | | |
|---|---|---|---|---|---|---|---|---|---|
| HETATM | 2837 | O | HOH | 93 | 18.109 | 13.559 | −0.549 | 1.00 | 55.88 | O |
| HETATM | 2838 | O | HOH | 94 | 17.988 | 24.631 | −3.754 | 1.00 | 51.13 | O |
| HETATM | 2839 | O | HOH | 95 | 11.147 | 25.599 | 7.464 | 1.00 | 54.03 | O |
| HETATM | 2840 | O | HOH | 96 | 0.669 | 20.153 | −14.220 | 1.00 | 61.13 | O |
| HETATM | 2841 | O | HOH | 97 | 23.423 | 16.822 | 7.820 | 1.00 | 47.11 | O |
| HETATM | 2842 | O | HOH | 98 | 4.169 | 28.368 | 47.401 | 1.00 | 49.11 | O |
| HETATM | 2843 | O | HOH | 99 | 17.907 | 22.480 | 19.908 | 1.00 | 25.19 | O |
| HETATM | 2844 | O | HOH | 100 | 18.913 | 18.483 | −1.892 | 1.00 | 42.00 | O |
| HETATM | 2845 | O | HOH | 101 | 29.430 | 25.548 | 35.765 | 1.00 | 52.14 | O |
| HETATM | 2846 | O | HOH | 102 | 7.533 | 37.946 | 49.399 | 1.00 | 47.42 | O |
| HETATM | 2847 | O | HOH | 103 | 4.559 | −5.686 | −35.297 | 1.00 | 33.47 | O |
| HETATM | 2848 | O | HOH | 104 | 16.365 | 21.287 | 43.112 | 1.00 | 37.52 | O |
| HETATM | 2849 | O | HOH | 105 | 12.647 | 22.707 | 26.991 | 1.00 | 40.89 | O |
| HETATM | 2850 | O | HOH | 106 | 17.387 | 8.577 | −4.168 | 1.00 | 58.00 | O |
| HETATM | 2851 | O | HOH | 107 | 19.144 | 38.706 | 55.887 | 1.00 | 54.56 | O |
| HETATM | 2852 | O | HOH | 108 | 29.881 | −10.278 | 30.643 | 1.00 | 59.44 | O |
| HETATM | 2853 | O | HOH | 109 | 27.905 | 36.586 | 33.075 | 1.00 | 72.69 | O |
| HETATM | 2854 | O | HOH | 110 | 15.881 | 4.099 | −21.160 | 1.00 | 46.82 | O |
| HETATM | 2855 | O | HOH | 111 | 25.849 | −5.581 | 21.859 | 1.00 | 64.80 | O |
| HETATM | 2856 | O | HOH | 112 | 35.376 | 10.168 | 11.497 | 1.00 | 64.49 | O |
| HETATM | 2857 | O | HOH | 113 | 6.943 | 38.954 | 37.146 | 1.00 | 58.18 | O |
| HETATM | 2858 | O | HOH | 114 | 13.626 | 21.235 | 15.770 | 1.00 | 57.55 | O |
| HETATM | 2859 | O | HOH | 115 | 20.479 | 9.262 | 11.648 | 1.00 | 34.66 | O |
| HETATM | 2860 | O | HOH | 116 | 33.288 | 14.468 | 17.531 | 1.00 | 44.57 | O |
| HETATM | 2861 | O | HOH | 117 | 1.569 | 15.732 | −8.368 | 1.00 | 32.82 | O |
| HETATM | 2862 | O | HOH | 118 | 27.694 | 8.889 | 31.895 | 1.00 | 42.30 | O |
| HETATM | 2863 | O | HOH | 119 | 15.732 | 20.157 | −2.274 | 1.00 | 46.93 | O |
| HETATM | 2864 | O | HOH | 120 | −3.393 | 16.381 | 1.929 | 1.00 | 44.37 | O |
| HETATM | 2865 | O | HOH | 121 | 1.833 | 16.793 | −2.687 | 1.00 | 35.38 | O |
| HETATM | 2866 | O | HOH | 122 | 27.991 | −4.809 | 19.258 | 1.00 | 51.85 | O |
| HETATM | 2867 | O | HOH | 123 | −3.494 | 13.598 | −9.407 | 1.00 | 60.31 | O |
| HETATM | 2868 | O | HOH | 124 | 12.591 | 16.103 | 21.706 | 1.00 | 53.70 | O |
| HETATM | 2869 | O | HOH | 125 | 8.516 | 0.694 | −20.459 | 1.00 | 38.88 | O |
| HETATM | 2870 | O | HOH | 126 | 8.891 | 36.072 | 47.904 | 1.00 | 47.38 | O |
| HETATM | 2871 | O | HOH | 127 | 4.793 | −6.174 | −27.894 | 1.00 | 54.09 | O |
| HETATM | 2872 | O | HOH | 128 | 12.115 | 36.278 | 31.925 | 1.00 | 44.39 | O |
| HETATM | 2873 | O | HOH | 129 | 12.645 | 38.231 | 34.367 | 1.00 | 47.38 | O |
| HETATM | 2874 | O | HOH | 130 | −0.374 | 1.306 | −18.286 | 1.00 | 43.50 | O |
| HETATM | 2875 | O | HOH | 131 | 1.435 | −5.901 | −28.903 | 1.00 | 59.12 | O |
| HETATM | 2876 | O | HOH | 132 | 3.606 | −4.066 | −21.697 | 1.00 | 53.36 | O |
| HETATM | 2877 | O | HOH | 133 | 7.722 | 6.537 | −6.384 | 1.00 | 59.86 | O |
| HETATM | 2878 | O | HOH | 134 | 32.764 | −3.214 | 23.681 | 1.00 | 66.32 | O |
| HETATM | 2879 | O | HOH | 135 | 11.444 | 29.479 | 68.519 | 1.00 | 52.15 | O |
| HETATM | 2880 | O | HOH | 136 | 17.708 | 32.932 | 21.066 | 1.00 | 46.20 | O |
| HETATM | 2881 | O | HOH | 137 | 24.356 | 8.033 | 11.474 | 1.00 | 42.27 | O |
| HETATM | 2882 | O | HOH | 138 | 37.871 | 32.641 | 28.378 | 1.00 | 53.68 | O |
| HETATM | 2883 | O | HOH | 139 | 22.791 | 4.294 | −18.714 | 1.00 | 42.79 | O |
| HETATM | 2884 | O | HOH | 140 | 20.508 | 17.110 | 50.703 | 1.00 | 45.09 | O |
| HETATM | 2885 | O | HOH | 141 | 12.008 | 41.980 | 48.992 | 1.00 | 69.99 | O |
| HETATM | 2886 | O | HOH | 142 | 7.076 | 34.223 | 23.515 | 1.00 | 56.38 | O |
| HETATM | 2887 | O | HOH | 143 | 13.346 | 5.425 | −13.549 | 1.00 | 48.33 | O |
| HETATM | 2888 | O | HOH | 144 | 1.946 | 8.698 | −30.959 | 1.00 | 63.85 | O |
| HETATM | 2889 | O | HOH | 145 | 12.922 | 22.533 | 7.109 | 1.00 | 54.73 | O |
| HETATM | 2890 | O | HOH | 146 | 8.710 | −2.537 | −38.383 | 1.00 | 58.89 | O |
| HETATM | 2891 | O | HOH | 147 | 21.767 | 5.803 | 32.948 | 1.00 | 61.52 | O |
| HETATM | 2892 | O | HOH | 148 | 24.812 | 6.711 | −18.661 | 1.00 | 52.13 | O |
| HETATM | 2893 | O | HOH | 149 | 4.802 | 23.746 | 32.504 | 1.00 | 63.10 | O |
| HETATM | 2894 | O | HOH | 150 | −5.626 | 7.875 | 1.548 | 1.00 | 48.19 | O |
| HETATM | 2895 | O | HOH | 151 | 10.718 | 37.270 | 24.721 | 1.00 | 53.57 | O |
| HETATM | 2896 | O | HOH | 152 | 26.659 | −2.956 | 16.507 | 1.00 | 53.28 | O |
| HETATM | 2897 | O | HOH | 153 | 16.908 | 13.134 | −34.370 | 1.00 | 56.42 | O |
| HETATM | 2898 | O | HOH | 154 | 30.127 | 23.186 | 11.723 | 1.00 | 54.72 | O |
| HETATM | 2899 | O | HOH | 155 | 17.814 | 37.129 | 57.927 | 1.00 | 53.40 | O |
| HETATM | 2900 | O | HOH | 156 | 34.904 | −1.525 | 23.222 | 1.00 | 44.82 | O |
| HETATM | 2901 | O | HOH | 157 | 0.630 | 3.969 | 19.265 | 1.00 | 64.63 | O |
| HETATM | 2902 | O | HOH | 158 | 2.852 | 8.449 | 18.136 | 1.00 | 46.43 | O |
| HETATM | 2903 | O | HOH | 159 | 10.548 | 5.464 | −6.260 | 1.00 | 59.31 | O |
| HETATM | 2904 | O | HOH | 160 | 17.519 | 20.643 | −22.015 | 1.00 | 27.50 | O |
| HETATM | 2905 | O | HOH | 161 | 5.642 | 20.599 | 31.550 | 1.00 | 49.79 | O |
| HETATM | 2906 | O | HOH | 162 | 6.127 | 11.707 | 32.248 | 1.00 | 64.27 | O |
| HETATM | 2907 | O | HOH | 163 | 13.295 | 17.527 | 37.772 | 1.00 | 57.93 | O |
| HETATM | 2908 | O | HOH | 164 | 23.610 | 22.112 | 6.595 | 1.00 | 58.06 | O |
| HETATM | 2909 | O | HOH | 165 | 9.245 | 37.107 | 32.386 | 1.00 | 46.35 | O |
| HETATM | 2910 | O | HOH | 166 | 11.302 | 16.597 | 35.016 | 1.00 | 47.51 | O |
| HETATM | 2911 | O | HOH | 167 | 39.408 | 19.148 | 22.624 | 1.00 | 67.29 | O |
| HETATM | 2912 | O | HOH | 168 | 13.285 | 13.827 | 23.371 | 1.00 | 53.16 | O |
| HETATM | 2913 | O | HOH | 169 | 35.794 | 0.803 | 12.173 | 1.00 | 48.76 | O |
| HETATM | 2914 | O | HOH | 170 | 26.327 | 23.228 | 39.153 | 1.00 | 53.68 | O |
| HETATM | 2915 | O | HOH | 171 | −2.607 | 11.697 | −24.443 | 1.00 | 59.86 | O |
| HETATM | 2916 | O | HOH | 172 | −0.424 | 3.799 | −22.256 | 1.00 | 49.47 | O |

TABLE 2-continued

| HETATM | 2917 | O | HOH | 173 | 17.815 | 12.725 | −28.023 | 1.00 | 46.50 | O |
| --- | --- | --- | --- | --- | --- | --- | --- | --- | --- | --- |
| HETATM | 2918 | O | HOH | 174 | 0.000 | 22.643 | 52.435 | 1.00 | 29.85 | O |
| HETATM | 2919 | O | HOH | 175 | 0.000 | 22.643 | 0.783 | 1.00 | 19.44 | O |
| HETATM | 2920 | O | HOH | 176 | 0.000 | 0.000 | 14.870 | 1.00 | 19.44 | O |
| HETATM | 2921 | O | HOH | 177 | 0.000 | 0.000 | −33.652 | 1.00 | 22.06 | O |
| END | | | | | | | | | | |

What is claimed:

1. A crystal comprising a collagen binding domain of human glycoprotein VI (GPVI), wherein the collagen binding domain of human GPVI comprises the amino acid sequence of SEQ ID NO: 1 and an N-terminal glycine, wherein the crystal has orthorhombic space group symmetry $P2_12_12$ and unit cell dimensions of a=114.06 Angstroms, b=45.29 Angstroms, and c=75.13 Angstroms, with a unit cell variability of 5% in all dimensions.

2. The crystal according to claim 1, wherein the human glycoprotein VI (GPVI) collagen binding domain is in a dimeric form.

3. The crystal according to claim 1, wherein the crystal diffracts X-rays for determination of atomic coordinates to provide resolution of from 20.0 Angstroms to 2.4 Angstroms.

4. The crystal according to claim 1, wherein the human glycoprotein VI (GPVI) collagen binding domain of the crystal has a three-dimensional structure comprising main chain and side chain atoms and atomic coordinates set forth in Table 2 plus or minus a root mean square deviation for the main chain atoms of not more than 3.0 Angstroms.

5. The crystal according to claim 4, wherein the three-dimensional structure comprises the atomic coordinates set forth in Table 2 plus or minus a root mean square deviation for the main chain atoms of not more than 2.0 Angstroms.

6. The crystal according to claim 4, wherein the three-dimensional structure comprises the atomic coordinates set forth in Table 2 plus or minus a root mean square deviation for the main chain atoms of not more than 1.0 Angstrom.

7. The crystal according to claim 4, wherein the three-dimensional structure comprises the atomic coordinates set forth in Table 2 plus or minus a root mean square deviation for the main chain atoms of not more than 0.50 Angstrom.

8. The crystal according to claim 4, wherein the three-dimensional structure comprises the atomic coordinates set forth in Table 2.

* * * * *

UNITED STATES PATENT AND TRADEMARK OFFICE
CERTIFICATE OF CORRECTION

PATENT NO. : 8,084,577 B2  
APPLICATION NO. : 12/294581  
DATED : December 27, 2011  
INVENTOR(S) : Andrew B. Herr and Katsunori Horii Page 1 of 1

It is certified that error appears in the above-identified patent and that said Letters Patent is hereby corrected as shown below:

Col. 91, Claim 1, Line 66, "...(GPVI)." should read --...(GPVI),--

Signed and Sealed this  
Twenty-eighth Day of August, 2012

David J. Kappos  
*Director of the United States Patent and Trademark Office*

SEQUENCE LISTING

<160> NUMBER OF SEQ ID NOS: 4

<210> SEQ ID NO 1
<211> LENGTH: 183
<212> TYPE: PRT
<213> ORGANISM: homo sapiens

<400> SEQUENCE: 1

```
Gln Ser Gly Pro Leu Pro Lys Pro Ser Leu Gln Ala Leu Pro Ser Ser
 1               5                  10                  15

Leu Val Pro Leu Glu Lys Pro Val Thr Leu Arg Cys Gln Gly Pro Pro
             20                  25                  30

Gly Val Asp Leu Tyr Arg Leu Glu Lys Leu Ser Ser Ser Arg Tyr Gln
         35                  40                  45

Asp Gln Ala Val Leu Phe Ile Pro Ala Met Lys Arg Ser Leu Ala Gly
     50                  55                  60

Arg Tyr Arg Cys Ser Tyr Gln Asn Gly Ser Leu Trp Ser Leu Pro Ser
 65                  70                  75                  80

Asp Gln Leu Glu Leu Val Ala Thr Gly Val Phe Ala Lys Pro Ser Leu
                 85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr
            180
```

<210> SEQ ID NO 2
<211> LENGTH: 338
<212> TYPE: PRT
<213> ORGANISM: Homo sapiens

<400> SEQUENCE: 2

```
Met Ser Pro Ser Pro Thr Ala Leu Phe Cys Leu Gly Leu Cys Leu Gly
 1               5                  10                  15

Arg Val Pro Ala Gln Ser Gly Pro Leu Pro Lys Pro Ser Leu Gln Ala
             20                  25                  30

Leu Pro Ser Ser Leu Val Pro Leu Glu Lys Pro Val Thr Leu Arg Cys
         35                  40                  45

Gln Gly Pro Pro Gly Val Asp Leu Tyr Arg Leu Glu Asp Leu Ser Ser
     50                  55                  60
```

```
Ser Arg Tyr Gln Asp Gln Ala Val Leu Phe Ile Pro Ala Met Lys Arg
 65                  70                  75                  80

Ser Leu Ala Gly Arg Tyr Arg Cys Ser Tyr Gln Asn Gly Ser Leu Trp
                 85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Gln Thr Arg Tyr Gly Phe Asp Gln Phe Ala Leu
    130                 135                 140

Tyr Lys Glu Gly Asp Pro Ala Pro Tyr Lys Asn Pro Glu Arg Trp Tyr
145                 150                 155                 160

Arg Ala Ser Phe Pro Ile Ile Thr Val Thr Ala Ala His Ser Gly Arg
                165                 170                 175

Tyr Arg Cys Tyr Ser Phe Ser Ser Arg Asp Pro Tyr Leu Trp Ser Ala
            180                 185                 190

Pro Ser Asp Pro Leu Glu Leu Val Val Thr Gly Thr Ser Val Thr Pro
        195                 200                 205

Ser Arg Leu Pro Thr Glu Pro Pro Ser Ser Val Ala Glu Phe Ser Glu
210                 215                 220

Ala Thr Ala Glu Leu Thr Val Ser Phe Thr Asn Lys Val Phe Thr Thr
225                 230                 235                 240

Glu Thr Ser Arg Ser Ile Thr Thr Ser Pro Lys Glu Ser Asp Ser Pro
                245                 250                 255

Ala Gly Pro Ala Arg Gln Tyr Tyr Thr Lys Gly Asn Leu Val Arg Ile
            260                 265                 270

Cys Leu Gly Ala Val Ile Leu Ile Ile Leu Ala Gly Phe Leu Ala Glu
        275                 280                 285

Asp Trp His Ser Arg Arg Lys Arg Leu Arg His Arg Gly Arg Ala Val
    290                 295                 300

Gln Arg Pro Leu Pro Pro Leu Pro Pro Leu Pro Gln Thr Arg Lys Ser
305                 310                 315                 320

His Gly Gly Gln Asp Gly Gly Arg Gln Asp Val His Ser Arg Gly Leu
                325                 330                 335

Cys Ser

<210> SEQ ID NO 3
<211> LENGTH: 43
<212> TYPE: DNA
<213> ORGANISM: Homo sapiens

<400> SEQUENCE: 3
caccgaaaac ctgtattttc agggccagag tggaccgctc ccc       43

<210> SEQ ID NO 4
<211> LENGTH: 33
<212> TYPE: DNA
<213> ORGANISM: Homo sapiens

<400> SEQUENCE: 4
ctatgtgacc acaagctcca gcgggtcgct ggg       33
```